(12) United States Patent
Patz, Jr. et al.

(10) Patent No.: US 11,897,946 B2
(45) Date of Patent: *Feb. 13, 2024

(54) METHODS OF INHIBITING COMPLEMENT FACTOR H (CFH) COMPRISING ADMINISTERING AN ANTIBODY THAT BINDS CFH

(71) Applicant: Duke University, Durham, NC (US)

(72) Inventors: Edward F. Patz, Jr., Durham, NC (US); Michael J. Campa, Durham, NC (US); Elizabeth Gottlin, Durham, NC (US); Barton F. Haynes, Durham, NC (US); Hua-Xin Liao, Durham, NC (US); M. Anthony Moody, Durham, NC (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/458,019

(22) Filed: Aug. 26, 2021

(65) Prior Publication Data

US 2021/0395353 A1    Dec. 23, 2021

Related U.S. Application Data

(60) Division of application No. 16/196,758, filed on Nov. 20, 2018, now Pat. No. 11,136,380, which is a continuation of application No. 14/895,963, filed as application No. PCT/US2014/041441 on Jun. 7, 2014, now Pat. No. 10,183,988.

(60) Provisional application No. 61/926,539, filed on Jan. 13, 2014, provisional application No. 61/832,434, filed on Jun. 7, 2013.

(51) Int. Cl.
*A61K 39/395* (2006.01)
*C07K 16/18* (2006.01)
*C07K 14/72* (2006.01)
*G01N 33/68* (2006.01)
*A61K 45/06* (2006.01)
*C07K 16/28* (2006.01)
*A61K 39/00* (2006.01)

(52) U.S. Cl.
CPC .......... *C07K 16/18* (2013.01); *A61K 39/3955* (2013.01); *A61K 45/06* (2013.01); *C07K 14/72* (2013.01); *G01N 33/6872* (2013.01); *G01N 33/6878* (2013.01); *A61K 2039/505* (2013.01); *A61K 2039/507* (2013.01); *C07K 16/2863* (2013.01); *C07K 2317/21* (2013.01); *C07K 2317/33* (2013.01); *C07K 2317/34* (2013.01); *C07K 2317/51* (2013.01); *C07K 2317/565* (2013.01); *C07K 2317/73* (2013.01); *C07K 2317/734* (2013.01); *C07K 2317/76* (2013.01); *C07K 2317/92* (2013.01); *G01N 2333/4716* (2013.01)

(58) Field of Classification Search
None
See application file for complete search history.

(56) References Cited

U.S. PATENT DOCUMENTS

| 4,526,938 A | 7/1985 | Churchill et al. |
| 4,554,101 A | 11/1985 | Hopp |
| 4,704,692 A | 11/1987 | Ladner |
| 4,816,567 A | 3/1989 | Cabilly et al. |
| 4,873,316 A | 10/1989 | Meade et al. |
| 4,880,078 A | 11/1989 | Inoue et al. |
| 4,946,778 A | 8/1990 | Ladner et al. |
| 5,128,326 A | 7/1992 | Balazs et al. |
| 5,223,409 A | 6/1993 | Ladner et al. |
| 5,225,539 A | 7/1993 | Winter |
| 5,258,498 A | 11/1993 | Huston et al. |
| 5,290,540 A | 3/1994 | Prince et al. |
| 5,304,489 A | 4/1994 | Rosen |
| 5,403,484 A | 4/1995 | Ladner et al. |
| 5,427,908 A | 6/1995 | Dower et al. |
| 5,480,792 A | 1/1996 | Buechler et al. |
| 5,516,637 A | 5/1996 | Huang et al. |
| 5,525,524 A | 6/1996 | Buechler et al. |
| 5,530,101 A | 6/1996 | Queen et al. |
| 5,565,362 A | 10/1996 | Rosen |
| 5,571,698 A | 11/1996 | Ladner et al. |
| 5,580,717 A | 12/1996 | Dower et al. |
| 5,585,089 A | 12/1996 | Queen et al. |
| 5,627,052 A | 5/1997 | Schrader |
| 5,658,727 A | 8/1997 | Barbas et al. |
| 5,679,377 A | 10/1997 | Bernstein et al. |
| 5,679,526 A | 10/1997 | Buechler et al. |
| 5,693,762 A | 12/1997 | Queen et al. |
| 5,698,426 A | 12/1997 | Huse |
| 5,714,352 A | 2/1998 | Jakobovits |

(Continued)

FOREIGN PATENT DOCUMENTS

| EP | 404097 A2 | 12/1990 |
| WO | WO 1990002809 A1 | 3/1990 |

(Continued)

OTHER PUBLICATIONS

Canada Patent Office Action for Application No. 2,914,566 dated Mar. 18, 2022 (8 pages).

(Continued)

*Primary Examiner* — Maher M Haddad
(74) *Attorney, Agent, or Firm* — Michael Best & Friedrich LLP

(57) ABSTRACT

Disclosed herein are Complement factor H (CFH) inhibitors, such as anti-CFH antibodies and small molecules, and methods of using said inhibitors.

17 Claims, 18 Drawing Sheets
Specification includes a Sequence Listing.

(56) References Cited

U.S. PATENT DOCUMENTS

| | | |
|---|---|---|
| 5,723,323 A | 3/1998 | Kauffman et al. |
| 5,733,743 A | 3/1998 | Johnson et al. |
| 5,750,753 A | 5/1998 | Kimae et al. |
| 5,763,192 A | 6/1998 | Kauffman et al. |
| 5,766,886 A | 6/1998 | Studnicka et al. |
| 5,770,429 A | 6/1998 | Lonberg et al. |
| 5,814,476 A | 6/1998 | Kauffman et al. |
| 5,780,225 A | 7/1998 | Wigler et al. |
| 5,817,483 A | 10/1998 | Kauffman et al. |
| 5,821,047 A | 10/1998 | Garrand et al. |
| 5,824,514 A | 10/1998 | Kauffman et al. |
| 5,824,799 A | 10/1998 | Buechler et al. |
| 5,827,690 A | 10/1998 | Meade et al. |
| 5,833,985 A | 11/1998 | Ball et al. |
| 5,837,243 A | 11/1998 | Deo et al. |
| 5,849,992 A | 12/1998 | Meade et al. |
| 5,851,776 A | 12/1998 | Valkirs |
| 5,855,913 A | 1/1999 | Hanes et al. |
| 5,874,064 A | 2/1999 | Edwards et al. |
| 5,885,527 A | 3/1999 | Buechler |
| 5,912,015 A | 6/1999 | Bernstein et al. |
| 5,916,597 A | 6/1999 | Lee et al. |
| 5,916,771 A | 6/1999 | Hori et al. |
| 5,922,615 A | 7/1999 | Nowakowski et al. |
| 5,922,845 A | 7/1999 | Deo et al. |
| 5,934,272 A | 8/1999 | Buechler et al. |
| 5,939,272 A | 8/1999 | Lloyd et al. |
| 5,939,598 A | 8/1999 | Kucherlapati et al. |
| 5,947,124 A | 9/1999 | Buechler et al. |
| 5,969,108 A | 10/1999 | McCafferty et al. |
| 5,976,862 A | 11/1999 | Kauffman et al. |
| 5,985,309 A | 11/1999 | Edwards et al. |
| 5,985,320 A | 11/1999 | Edwards et al. |
| 5,985,579 A | 11/1999 | Buechler et al. |
| 5,985,615 A | 11/1999 | Jakobovits et al. |
| 5,989,463 A | 11/1999 | Tracy et al. |
| 5,994,616 A | 11/1999 | Rosen |
| 5,998,209 A | 12/1999 | Jokobovits et al. |
| 6,017,517 A | 1/2000 | Park |
| 6,019,944 A | 2/2000 | Buechler |
| 6,019,968 A | 2/2000 | Platz et al. |
| 6,075,181 A | 6/2000 | Kucherlapati et al. |
| 6,091,001 A | 7/2000 | Jakobovits et al. |
| 6,096,311 A | 8/2000 | Fanger et al. |
| 6,111,166 A | 8/2000 | van de Winkel |
| 6,113,855 A | 9/2000 | Buechler |
| 6,114,598 A | 9/2000 | Kucherlapati et al. |
| 6,130,364 A | 10/2000 | Jakobovits et al. |
| 6,143,576 A | 11/2000 | Buechler |
| 6,180,370 B1 | 1/2001 | Queen et al. |
| 6,204,023 B1 | 3/2001 | Robinson et al. |
| 6,270,765 B1 | 8/2001 | Deo et al. |
| 6,303,755 B1 | 10/2001 | Deo et al. |
| 6,365,116 B1 | 4/2002 | Barham et al. |
| 6,410,690 B1 | 6/2002 | Deo et al. |
| 6,632,926 B1 | 10/2003 | Chen et al. |
| 6,660,843 B1 | 12/2003 | Feige et al. |
| 6,682,928 B2 | 1/2004 | Keler et al. |
| 6,699,658 B1 | 3/2004 | Wittrup et al. |
| 6,914,128 B1 | 7/2005 | Salfeld et al. |
| 6,984,720 B1 | 1/2006 | Korman et al. |
| 10,183,988 B2 * | 1/2019 | Patz, Jr. ............ A61K 39/3955 |
| 10,865,238 B1 | 12/2020 | Patz, Jr. et al. |
| 11,136,380 B2 * | 10/2021 | Patz, Jr. ............ A61K 39/3955 |
| 2003/0186374 A1 | 10/2003 | Hufton et al. |
| 2006/0104968 A1 | 5/2006 | Bookbinder et al. |
| 2007/0020647 A1 | 1/2007 | Hageman et al. |
| 2009/0269338 A1 | 10/2009 | Huang et al. |
| 2011/0229497 A1 | 9/2011 | Thurman et al. |
| 2012/0003225 A1 | 1/2012 | Patz, Jr. et al. |
| 2015/0147323 A1 | 5/2015 | Thurman et al. |
| 2016/0311893 A1 | 10/2016 | Patz, Jr. et al. |
| 2019/0127484 A1 | 5/2019 | Schwaeble et al. |
| 2020/0363411 A1 | 11/2020 | Shih et al. |

FOREIGN PATENT DOCUMENTS

| | | |
|---|---|---|
| WO | WO 1991005548 A1 | 5/1991 |
| WO | WO 1991010737 A1 | 7/1991 |
| WO | WO 1991010741 A1 | 7/1991 |
| WO | WO 1991017271 A1 | 11/1991 |
| WO | WO 1992001047 A1 | 1/1992 |
| WO | WO 1992002551 A1 | 2/1992 |
| WO | WO 1992009690 A2 | 6/1992 |
| WO | WO 1992015679 A1 | 7/1992 |
| WO | WO 1992018619 A1 | 10/1992 |
| WO | WO 1992019244 A2 | 11/1992 |
| WO | WO 1992020791 A1 | 11/1992 |
| WO | WO 1992022324 A1 | 12/1992 |
| WO | WO 1993001288 A1 | 1/1993 |
| WO | WO 1993011161 A1 | 6/1993 |
| WO | WO 1993011236 A1 | 6/1993 |
| WO | WO 1994002602 A1 | 2/1994 |
| WO | WO 1995015982 A2 | 6/1995 |
| WO | WO 1995020401 A1 | 8/1995 |
| WO | WO 1996020698 A2 | 7/1996 |
| WO | WO 1996033735 A1 | 10/1996 |
| WO | WO 1996034096 A1 | 10/1996 |
| WO | WO 1997029131 A1 | 8/1997 |
| WO | WO 1997032572 A2 | 9/1997 |
| WO | WO 1997044013 A1 | 11/1997 |
| WO | WO 1998016654 A1 | 4/1998 |
| WO | WO 1998024893 A2 | 6/1998 |
| WO | WO 1998031346 A1 | 7/1998 |
| WO | WO 1998031700 A1 | 7/1998 |
| WO | WO 1998050433 A2 | 11/1998 |
| WO | WO 1999015154 A1 | 4/1999 |
| WO | WO 1999020253 A1 | 4/1999 |
| WO | WO 1999025044 A1 | 5/1999 |
| WO | WO 1999045031 A2 | 9/1999 |
| WO | WO 1999053049 A1 | 10/1999 |
| WO | WO 1999066903 A2 | 12/1999 |
| WO | WO 2000009560 A2 | 2/2000 |
| WO | WO 2000037504 A2 | 6/2000 |
| WO | WO 2000056772 A1 | 9/2000 |
| WO | WO 2001058956 A2 | 8/2001 |
| WO | WO 2002002773 A2 | 1/2002 |
| WO | WO 2004078140 A2 | 9/2004 |
| WO | 2006122825 A2 | 11/2006 |
| WO | WO 2009137832 A2 | 11/2009 |

OTHER PUBLICATIONS

1 United States Patent Office Action for U.S. Appl. No. 17/076,042 dated Aug. 26, 2022 (8 pages).

Adams et al., "Phenix: a comprehensive Python-based system for macromolecular structure solution," Acta Crystallogr. D Biol. Crystallogr., 2010, 66, 213-221.

Ajona et al., "Down-Regulation of Human Complement Factor H Sensitizes Non-Small Cell Lung Cancer Cells to Complement Attack and Reduces In Vivo Tumor Growth" (2007) J Immunol 178, 5991-8.

Ajona et al: "Expression of Complement Factor H by Lung Cancer Cells: Effects on the Activation of the Alternative Pathway of Complement", Cancer Research, vol. 64, No. 17, Sep. 1, 2004, pp. 6310-6318.

Alam et al., "Differential reactivity of germ line allelic variants of a broadly neutralizing HIV-1 antibody to a gp41 fusion intermediate conformation," J Virol, 2011, 85, 11725-11731.

Alam et al., "Human immunodeficiency virus type 1 gp41 antibodies that mask membrane proximal region epitopes: antibody binding kinetics, induction, and potential for regulation in acute infection," J Virol, 2008, 82, 115-125.

Ames et al., "Conversion of murine Fabs isolated from a combinatorial phage display library to full length immunoglobulins" J. Immunol. Methods, 184:177-186 (1995).

Amornsiripanitch et al., "Complement Factor H Autoantibodies are Associated with Early Stage NSCLC" (2010) Clinical Cancer Research 16, 3226-3231.

Babcook et al., "A novel strategy for generating monoclonal antibodies from single, isolated lymphocytes producing antibodies of

(56) References Cited

OTHER PUBLICATIONS defined specificities" Proc. Natl. Acad. Sci. USA, 93: 7843-7848 (1996).
Barbas et al., "Assembly of combinatorial antibody libraries on phage surfaces: The gene III site" Proc. Natl. Acad. Sci. USA, 88:7978-7982 (1991).
Barbas et al., "In vitro evolution of a neutralizing human antibody to human immunodeficiency virus type 1 to enhance affinity and broaden strain cross-reactivity" Proc. Nat. Acad. Sci. USA, 91: 3809-3813 (1994).
Better et al., "*Escherichia coli* secretion of an active chimeric antibody fragment" Science, 240: 1041-1043 (1988).
Bigner et al., "Characterization of the epidermal growth factor receptor in human glioma cell lines and xenografts," Cancer Res., 1990, 50, 8017-8022.
Bird et al., "Single-chain antigen-binding proteins" Science 242: 423-426 (1988).
Blanc et al., "Overall Neutralization of Complement Factor H by Autoantibodies in the Acute Phase of the Autoimmune Form of Atypical Hemolytic Uremic Syndrome" (2012) J Immunol 189, 3528-37.
Bonsignori et al., "Antibody-Dependent Cellular Cytotoxicity-Mediating Antibodies from an HIV-1 Vaccine Efficacy Trial Target Multiple Epitopes and Preferentially Use the VH1 Gene Family" (2012) J Virol 86(21): 11521-11532.
Brinkmann et al., "Phage display of disulfide-stabilized Fv fragments" J. Immunol. Methods, 182: 41-50 (1995).
Buchwald et al., "Long-term, continuous intravenous heparin administration by an implantable infusion pump in ambulatory patients with recurrent venous thrombosis", 1980, Surgery 88:507-516.
Burton et al., "Human antibodies from Combinatorial Libraries" Advances in Immunology, 57: 191-280 (1994).
Bushey R J et al: "A Therapeutic Antibody for Cancer, Derived from Single Human B Cells", Cell Reports, vol. 15, No. 7, May 17, 2016, pp. 1505-1513.
Campa J et al: "Complement Factor H Antibodies from Lung Cancer Patients Induce Complement-Dependent Lysis of Tumor Cells, Suggesting a Novel Immunotherapeutic Strategy", Cancer Immunology Research, vol. 3, No. 12, Dec. 1, 2015, published online Jul. 27, 2015, pp. 1325-1332.
Carroll, M. V. & Sim, R. B., "Complement in health and disease" (2011) Adv Drug Deliv Rev 63, 965-75.
Ceccarell et al., "The redox state of the lung cancer microenvironment depends on the levels of thioredoxin expressed by tumor cells and affects tumor progression and response to prooxidants" (2008) Int J Cancer 123, 1770-8.
Chen et al., "Enhancement and destruction of antibody function by somatic mutation: unequal occurrence is controlled by V gene combinatorial associations," EMBO J., 14: 2784-2794, 1995.
Chothia et al., "Canonical structures for the hypervariable regions of immunoglobulins," J. Mol. Biol., 1987, 196: 901-917.
Chothia et al., "Conformations of immunoglobulin hypervariable regions," Nature, 1989, 342: 877-883.
Clackson et al., "Making antibody fragments using phage display libraries" Nature, 352: 624-628 (1991).
Cleek et al., 1997, "Biodegradable Polymeric Carriers for a bFGF Antibody for Cardiovascular Application," Pro. Int'l. Symp. Control. Rel. Bioact. Mater. 24:853-854.
Colman, "Effects of amino acid sequence changes on antibody-antigen interactions," Research in Immunology 145: 33-36, 1994.
Conrad et al., "Compartment-specific accumulation of recombinant immunoglobulins in plant cells: an essential tool for antibody production and immunomodulation of physiological functions and pathogen activity" (1998) Plant Mol. Biol. 38:101-109.
Cramer et al., "Transgenic plants for therapeutic proteins: linking upstream and downstream strategies" (1999) Curr. Top. Microbiol. Immunol. 240:95-118.
Cui et al., "Human complement factor H is a novel diagnostic marker for lung adenocarcinoma," Int J Oncol, 2011, 39:161-8.

D'Angelo et al., "Many Routes to an Antibody Heavy-Chain CDR3: Necessary, Yet Insufficient, for Specific Binding," Frontiers in Immunology, 2018, vol. 9, Article 395 13 pages.
Disis et al., "Cancer vaccines targeting the HER2/neu oncogenic protein" (2001) Semin Oncol 28, 12-20.
Dragon-Durey et al., "Anti-Factor H Autoantibody-Associated Hemolytic Uremic Syndrome: Review of Literature of the Autoimmune Form of HUS" (2010) Semin Thromb Hemost 36, 633-40.
During et al., "Controlled release of dopamine from a polymeric brain implant: In vivo characterization" 1989, Ann. Neurol. 25:351.
Emsley et al., "Features and development of Coot," Acta Crystallogr. D Biol. Crystallogr., 2010, 66, 486-501.
Eren et al., "Human monoclonal antibodies specific to hepatitis B virus generated in a human/mouse radiation chimera: the Trimera system" (1998) Immunol. 93:154-161.
Ferreira et al., "Complement control protein factor H: the good, the bad, and the inadequate," Mol. Immunol., 2010, 47, 2187-2197.
Ferreira et al., "Critical Role of the C-Terminal Domains of Factor H in Regulating Complement Activation at Cell Surfaces" (2006) J Immunol 177, 6308-16.
Ferreira et al., "The binding of factor H to a complex of physiological polyanions and C3b on cells is impaired in atypical hemolytic uremic syndrome," J Immunol, 2009, 182:7009-18.
Firlej et al., "Thrombospondin-1 triggers cell migration and development of advanced prostate tumors," Cancer Res, 2011, 71:7649-58.
Fuchs et al., "Targeting Recombinant Antibodies to the Surface of *Escherichia coli*: Fusion to a Peptidoglycan Associated Lipoprotein" Bio/Technology, 9: 1369-1372 (1991).
Funaro et al., "Generation of potent neutralizing human monoclonal antibodies against cytomegalovirus infection from immune B cells" BMC Biotechnology, 2008(8):85.
Gajewski et al., "Innate and adaptive immune cells in the tumor microenvironment," Nature immunology, 2013, 14:1014-22.
Gancz et al., "A Role for the NF-kB Pathway in Cell Protection from Complement-Dependent Cytotoxicity," J Immunol, 2012, 189:860-6.
Gancz et al., "Involvement of the c-jun N-terminal kinases JNK1 and JNK2 in complement-mediated cell death," Mol Immunol, 2009, 47:310-7.
Garg et al., "Danger signalling during cancer cell death: origins, plasticity and regulation," Cell Death Differ, 2014, 21:26-38.
Garrard et al., "FAB Assembly and Enrichment in a Monovalent Phage Display System" Bio/Technology, 9: 1373-1377 (1991).
Goodson, Medical Applications of Controlled Release, supra, vol. 2, pp. 115-138 (1984).
Gottlin et al., "Isolation of Novel EGFR-Specific VHH Domains" Journal of Biomolecular Screening, 14:77-85 (2009).
Gram et al., "In vitro selection and affinity maturation of antibodies from a naïve combinatorial immunoglobulin library" Proc. Natl. Acad. Sci. USA, 89: 3576-3580 (1992).
Gray et al., "Isolation of a Monoclonal Antibody That Targets the Alpha-2 Helix of gp120 and Represents the Initial Autologous Neutralizing-Antibody Response in an HIV-1 Subtype C-Infected Individual" (2011) J Virol 85(15): 7719-7729.
Gray et al., "Secretion capture and report web: use of affinity derivatized agarose microdroplets for the selection of hybridoma cells" (1995) J. Imm. Meth. 182:155-163.
Green et al., "Antigen-specific human monoclonal antibodies from mice engineered with human Ig heavy and light chain YACs" Nature Genetics, 7: 13-21 (1994).
Green et al., "Regulation of B Cell Development by Variable Gene Complexity in Mice Reconstituted with Human Immunoglobulin Yeast Artificial Chromosomes" J. Exp. Med., 188: 483-495 (1998).
Griffiths et al., "Human anti-self antibodies with high specificity from phage display libraries" EMBO J., 12: 725-734 (1993).
Guo et al., "Emmprin (CD147), an inducer of matrix metalloproteinase synthesis, also binds interstitial collagenase to the tumor cell surface," Cancer Res, 2000, 60:888-91.
Hanes et al., "In vitro selection and evolution of functional proteins by using ribosome display" (1997) Proc. Natl. Acad. Sci. USA, 94:4937-4942.

(56) References Cited

OTHER PUBLICATIONS

Hanes et al., "Ribosome display efficiently selects and evolves high-affinity antibodies in vitro from immune libraries" (1998) Proc. Natl. Acad. Sci. USA, 95:14130-14135.

Hawkins et al., "Selection of phage antibodies by binding affinity: Mimicking affinity maturation" J. Mol. Biol., 226: 889-896 (1992).

Hay et al., "Bacteriophage cloning and *Escherichia coli* expression of a human IgM Fab" Hum. Antibod. Hybridomas, 3: 81-85(1992).

Herbert et al., "Structural and functional characterization of the product of disease-related factor H gene conversion," Biochemistry, 2012, 51, 1874-1884.

Hofer et al., "Complement factor H-antibody-associated hemolytic uremic syndrome: pathogenesis, clinical presentation, and treatment," Semin. Thromb. Hemost., 2014, 40, 431-443.

Holliger et al., "Diabodies: Small bivalent and bispecific antibody fragments" Proc. Natl. Acad. Sci. USA, 90(14): 6444-6448 (1993).

Hood et al., "Molecular Farming of Industrial Proteins from Transgenic Maize" Adv. Exp. Med. Biol. (1999) 464:127-147.

Hoogenboom et al., "Multi-subunit proteins on the surface of filamentous phage: methodologies for displaying antibody (Fab) heavy and light chains" Nucl. Acids Res., 19: 4133-4137 (1991).

Hörl et al., "Reduction of complement factor H binding to CLL cells improves the induction of rituximab-mediated complement-dependent cytotoxicity," Leukemia, 2013, 27:2200-8.

Howard et al., "Intracerebral drug delivery in rats with lesion-induced memory deficits" 1989, J. Neurosurg. 7 1:105.

Hsu et al., "Complement activation mediates cetuximab inhibition of non-small cell lung cancer tumor growth in vivo," Mol Cancer, 2010, 9:139.

Hu et al., "Human CD59 inhibitor sensitizes rituximab-resistant lymphoma cells to complement-mediated cytolysis," Cancer Res, 2011, 71:2298-307.

Huang et al., "Crystal structure of the calcium-stabilized human factor IX Gia domain bound to a conformation-specific anti-factor IX antibody," J. Biol. Chem., 2004, 279, 14338-14346.

Huck et al., "Sequence of a human immunoglobulin gamma 3 heavy chain constant region gene: comparison with the other human Cγ genes," Nucleic Acids Res., 1986, 14, 1779-1789.

Huse et al., "Generation of a large combinatorial library of the immunoglobulin repertoire in phage lambda" Science, 246: 1275-1281 (1989).

Huston et al., "Protein engineering of antibody binding sites: Recovery of specific activity in an anti digoxin single-chain Fv analogue produced in *Escherichia coli*" PNAS USA 85: 5879-5883 (1988).

Huston et al., "Protein engineering of single-chain Fv analogs and fusion proteins" Methods in Enzymology, 203: 46-88 (1991).

Iikuni et al., "Leptin and Inflammation," Curr Immunol Rev, 2008, 4:70-9.

Jackson et al., "In vitro antibody maturation. Improvement of a high affinity, neutralizing antibody against IL-1 beta" J. Immunol., 154(7): 3310-3319 (1995).

Jager et al., "Antibodies and vaccines—hope or illusion?" (2005) Breast 14, 631-5.

Jeanne et al., "Original insights on thrombospondin-1-related antireceptor strategies in cancer," Front Pharmacol, 2015, 6:252.

Jimenez-Reinoso et al., "Complement in basic processes of the cell," Mol Immunol 2016.

Jokiranta et al., "Analysis of the recognition mechanism of the alternative pathway of complement by monoclonal anti-factor H antibodies: evidence for multiple interactions between H and surface bound C3b," FEBS Letters, 1996, 393(2-3):297-302.

Jozsi M et al: "The C-terminus of complement factor H is essential for host cell protection", Molecular Immunology, Pergamon, GB, vol. 44, No. 10, Apr. 2007, pp. 2697-2706.

Junnikkala et al., "Exceptional Resistance of Human H2 Glioblastoma Cells to Complement-Mediated Killing by Expression and Utilization of Factor H and Factor H-Like Protein 1" (2000) J Immunol 164, 6075-81.

Kajander et al., "Dual interaction of factor H with C3d and glycosaminoglycans in host-nonhost discrimination by complement" (2011) Proc Natl Acad Sci U S A 108, 2897-902.

Kaneko et al., "Growth characteristics and drug responses of a murine lung carcinoma in vitro and in vivo," Cancer Res., 1978, 38, 2084-2090.

Kaufman et al., "Growth-Dependent Expression of Dihydrofolate Reductase mRNA from Modular cDNA Genes" J. Mol. Biol., 159: 601-621 (1982).

Kenny et al., "Production of monoclonal antibodies using a secretion capture report Web" (1995) Bio/Technol. 13:787-790.

Kepler et al., "Reconstructing a B-Cell Clonal Lineage. II. Mutation, Selection, and Affinity Maturation," Front. Immunol., 2014, 5, 170.

Kepler, "Reconstructing a B-cell clonal lineage. I. Statistical inference of unobserved ancestors," F1000Research, 2013, 2, 103.

Kepp et al., "Consensus guidelines for the detection of immunogenic cell death," Oncoimmunology, 2014, 3:e955691.

Kettleborough et al., "Isolation of tumor cell-specific single-chain Fv from immunized mice using phage-antibody libraries and the re-construction of whole antibodies from these antibody fragments" Eur. J. Immunol., 24: 952-958 (1994).

Klos et al., "The role of the anaphylatoxins in health and disease," Mol. Immunol., 2009, 46, 2753-2766.

Koski et al., "Cytolysis of nucleated cells by complement: cell death displays multi-hit characteristics," Proc. Natl. Acad. Sci. USA, 1983, 80, 3816-3820.

Krysko et al., "Immunogenic cell death and DAMPs in cancer therapy," Nat Rev Cancer, 2012, 12:860-75.

Kunik et al., "Paratome: an online tool for systematic identification of antigen-binding regions in antibodies based on sequence or structure," Nucleic Acids Res. 2012, W521-4.

Kunik et al., "Structural Consensus among Antibodies Defines the Antigen Binding Site," PLoS Comput Biol, 2012, 8(2): e1002388.

Kussie et al., "A Single Engineered Amino Acid Substitution Changes Antibody Fine Specificity," J. Immunol. 152: 146-152, 1994.

Kwon et al., "Adipokines mediate inflammation and insulin resistance," Front Endocrinol (Lausanne), 2013, 4:71.

Kyte et al., "A Simple Method for Displaying the Hydropathic Character of a Protein," J. Mol. Biol. 157:105-132 (1982).

Lam et al., 1997, "Microencapsulation of Recombinant Humanized Monoclonal Antibody for Local Delivery," Proc. Int'l. Symp. Control Rel. Bioact. Mater. 24:759-760.

Langer et al., "Chemical and Physical Structure of Polymers as Carriers for Controlled Release of Bioactive Agents: A Review" 1983, J., Macromol. Sci. Rev. Macromol. Chem. 23:61-126.

Langer, "New methods of drug delivery" (1990), Science 249:1527-1533.

Lederman et al., "A single amino acid substitution in a common african allele of the CD4 molecule ablates binding of the monoclonal antibody, OKT4," Molecular Immunology 28: 1171-1181, 1991.

Levy et al., "Inhibition of calcification of bioprosthetic heart valves by local controlled-release diphosphonate" 1985, Science 228:190-2.

Li et al., "The EMBL-EBI bioinformatics web and programmatic tools framework," Nucleic Acids Research, 2015, 43(W1):W580-W584.

Li et al., "β-Endorphin omission analogs: dissociation of immunoreactivity from other biological activities," PNAS 77: 3211-3214, 1980.

Liao et al., "Co-evolution of a broadly neutralizing HIV-1 antibody and founder virus," 2013, Nature 496, 469-476.

Liao et al., "High-throughput isolation of immunoglobulin genes from single human B cells and expression as monoclonal antibodies" (2009) J Virol Methods 158(1-2): 171-179.

Liao et al., "Initial antibodies binding to HIV-1 gp41 in acutely infected subjects are polyreactive and highly mutated," J. Exp. Med., 2011, 208, 2237-2249.

Liao et al., "Vaccine induction of antibodies against a structurally heterogeneous site of immune pressure within HIV-1 envelope protein variable regions 1 and 2." (2013) Immunity 38(1): 176-186.

(56) References Cited

OTHER PUBLICATIONS

Lo et al., "Adipsin is an adipokine that improves B cell function in diabetes," Cell, 2014, 158:41-53.
Lovell et al., "Structure validation by Cα geometry: φ,ψ and Cβ deviation," Proteins, 2003, 50, 437-450.
MacCallum, "Antibody-antigen interactions: contact analysis and binding site topography," J. Mol. Biol., 1996, 262(5): 732-745.
Makou et al., "Functional anatomy of complement factor H," Biochemistry, 2013, 52, 3949-3962.
Malia et al., "Crystal structure of human germline antibody 3-23/B3," Mol. Immunol., 2011, 48, 1586-1588.
Mamidi et al., "Neutralization of membrane complement regulators improves complement-dependent effector functions of therapeutic anticancer antibodies targeting leukemic cells," Oncoimmunology, 2015, 4:e979688.
Marks et al., "By-Passing Immunization: Building High Affinity Human Antibodies by Chain Shuffling" BioTechnology, 10: 779-783 (1992).
McCafferty et al., "Phage antibodies: filamentous phage displaying antibody variable domains" Nature 348: 552-554 (1990).
McWilliam et al., "Analysis Tool Web Services from the EMBL-EBI," Nucleic Acids Res., 2013, 41:W597-W600.
Mendez et al., "Functional transplant of megabase human immunoglobulin loci recapitulates human antibody response in mice" Nature Genetics, 15: 146-156 (1997).
Milstein et al., "Hybrid hybridomas and their use in immunohistochemistry" Nature, 305(5934): 537-540 (1983).
Moody et al., "HIV-1 gp120 Vaccine Induces Affinity Maturation in both New and Persistent Antibody Clonal Lineages" (2012) J Virol 86(14): 7496-7507.
Morgan et al., "Structural analysis of the C-terminal region (modules 18-20) of complement regulator factor H (FH)," PLoS ONE, 2012, 7, e32187.
Morgan et al., "Structural basis for engagement by complement factor H of C3b on a self surface" (2011) Nat Struct Mol Biol 18, 463-70.
Morris et al., "Isolation of a Human Anti-HIV gp41 Membrane Proximal Region Neutralizing Antibody by Antigen-Specific Single B Cell Sorting" (2011) PLoS ONE 6(9): e23532 1-10.
Moyer et al., "Screening for lung cancer: U.S. Preventive Services Task Force recommendation statement," Ann Intern Med, 2014, 160:330-8.
Moynihan et al., "Eradication of large established tumors in mice by combination immunotherapy that engages innate and adaptive immune responses," Nat Med, 2016, 22:1402-10.
Mullinax et al., "Expression of a heterodimeric Fab antibody protein in one cloning step" BioTechniques, 12(6): 864-869 (1992).
Nguyen et al., "Production of Human Monoclonal Antibodies in SCID Mouse" (1997) Microbiol. Immunol. 41:901-907.
Nicely et al., "Crystal structure of a non-neutralizing antibody to the HIV-1 gp41 membrane-proximal external region," Nat. Struct. Mol. Biol., 2010, 17, 1492-1494.
Ning et al., 1996, "Intratumoral Radioimmunotherapy of a Human Colon Cancer Xenograft Using a Sustained-Release Gel," Radiotherapy & Oncology 39:179-189.
Ollert M W et al: "Classical Complement Pathway Activation on Nucleated Cells. Role of Factor H in the Control of Deposited C3B" , The Journal of Immunology, The American Association of Immunologists, US, Nov. 15, 1995, vol. 155, Issue 10, pp. 4955-4962.
Oppermann et al., "The C-terminus of complement regulator Factor H mediates target recognition: evidence for a compact conformation of the native protein" (2006) Clin Exp Immunol 144, 342-52.
Otwinowski et al., "Processing of X-ray diffraction data collected in oscillation model," Methods Enzymol., 1997, 276, 307-326.
Padlan, "Identification of specificity-determining residues in antibodies," FASEB J., 1995, 9: 133-139.
Park et al., "The therapeutic effect of anti-HER2/neu antibody depends on both innate and adaptive immunity," Cancer cell, 2010, 18:160-70.

Peng et al., "Dendritic cell function in allostimulation is modulated by C5aR signaling," J Immunol, 2009, 183:6058-68.
Perkins et al., "Complement factor H-ligand interactions: self-association, multivalency and dissociation constants." (2012) Immunobiology 217, 281-97.
Persic et al., "An integrated vector system for the eukaryotic expression of antibodies or their fragments after selection from phage display libraries." Gene, 187: 9-18 (1997).
Powell et al., "Gel Microdroplets and Flow Cytometry: Rapid Determination of Antibody Secretion by Individual Cells Within a Cell Population" (1990) Biotechnol. 8:333-337.
Prodinger W M et al: "The C-terminus of factor H: monoclonal antibodies inhibit heparin binding and identify epitopes common to factor H and factor H-related proteins", The Biochemical Journal, Apr. 1, 1998, vol. 331, pp. 41-47.
Prof Andrew C R Martin's Group; "Antibodies;" http://www.bioinf.org.uk/abs/#cdrid ; printed Jul. 3, 2020.
Prof Andrew CR Martin's Group; "Antibody Information" http://www.bioinf.org.uk/abs/info.html#cdrdef ; printed Jul. 3, 2020.
Rakhmilevich et al., "Effective Combination of Innate and Adaptive Immunotherapeutic Approaches in a Mouse Melanoma Model," J Immunol, 2017, 198:1575-84.
Reuschenbach et al., "A systematic review of humoral immune responses against tumor antigens" (2009) Cancer Immunol Immunother 58, 1535-44.
Roberts, "RNA-peptide fusions for the in vitro selection of peptides and proteins" Proc. Natl. Acad. Sci. USA, 94: 12297-12302 (1997).
Rodriguez et al., "The human complement factor H: functional roles, genetic variations and disease associations" (2004) Mol Immunol 41, 355-67.
Rudikoff et al., "Single amino acid substitution altering antigen-binding specificity," Proc Natl Acad Sci USA 79: 1979-1983, 1982.
Saltzman et al., "Transport rates of proteins in porous materials with known microgeometry" Biophys. J. 55:163-171 (1989).
Sandhu et al., "The Use of SCID Mice in Biotechnology and as a Model for Human Disease" (1996) Crit. Rev. Biotechnol. 16:95-118.
Saudek et al., "A Preliminary Trial of the Programmable Implantable Medication System for Insulin Delivery" 1989, N. Engl. J. Med. 321:574-579.
Sawai et al., "Direct production of the Fab fragment derived from the sperm immobilizing antibody using polymerase chain reaction and cDNA expression vectors" Am. J. Reprod. Immunol., 34: 26-34 (1995).
Schier et al., "Identification of functional and structural amino-acid residues by parsimonious mutagenesis" Gene, 169: 147-155 (1995).
Schmidt et al., "A new map of glycosaminoglycan and C3b binding sites on factor H" (2008) J Immunol 181, 2610-9.
Schmidt et al., "Translational mini-review series on complement factor H: structural and functional correlations for factor H" (2008) Clin Exp Immunol 151, 14-24.
Sefton, 1987, "Implantable pumps," CRC Crit Ref., Biomed Eng., vol. 14:201.
Shu et al., "Secretion of a single-gene-encoded immunoglobulin from myeloma cells" Proc. Natl. Acad. Sci. USA, 90: 7995-7999 (1993).
Sievers et al., "Fast, scalable generation of high-quality protein multiple sequence alignments using Clustal Omega," Molecular Systems Biology, 2011, 7:539.
Skerra et al., "Assembly of a functional immunoglobulin Fv fragment in *Escherichia coli*" Science, 240: 1038-1041 (1988).
Slootstra et al., "Structural aspects of antibody-antigen interaction revealed through small random peptide libraries" Mol Divers (1996) 1:87-96.
Song et al., 1995, "Antibody Mediated Lung Targeting of Long-Circulating Emulsions, " PDA Journal of Pharmaceutical Science & Technology 50:372-397.
Staerz et al., "Hybrid antibodies can target sites for attack by T cells" Nature, 314(6012): 628-631 (1985).
Steenbakkers et al., "Efficient generation of monoclonal antibodies from preselected antigen specific B cells" (1994) Molec. Biol. Reports 19:125-134 (1994).

(56) References Cited

OTHER PUBLICATIONS

Strainic et al., "Locally produced complement fragments C5a and C3a provide both costimulatory and survival signals to naive CD4+ T cells," Immunity, 2008, 28:425-35.
Strausberg et al., "Generation and initial analysis of more than 15,000 full-length human and mouse cDNA sequences," Proc. Natl. Acad. Sci., 2002, USA 99, 16899-16903.
Surace et al., "Complement is a central mediator of radiotherapy-induced tumor-specific immunity and clinical response," Immunity, 2015, 42, 767-777.
Svasti et al., The complete amino acid sequence of a mouse kappa light chain. Biochem. J., 1972, 128, 427-444.
Terwilliger et al., "Iterative model building, structure refinement and density modification with the Phenix AutoBuild wizard," Acta Crystallogr. D Biol. Crystallogr., 2008, 64, 61-69.
Thiele et al., "Link between macrophage migration inhibitory factor and cellular redox regulation" (2005) Antioxid Redox Signal 7, 1234-48.
Urlaub et al., "Isolation of Chinese hamster cell mutants deficient in dihydrofolate reductase activity" Proc. Natl. Acad. Sci. USA, 77: 4216-4220 (1980).
Varsano et al., "Human lung cancer cell lines express cell membrane complement inhibitory proteins and are extremely resistant to complement-mediated lysis; a comparison with normal human respiratory epithelium in vitro, and an insight into mechanism(s) of resistance" (1998) Clin Exp Immunol 113, 173-82.
Wai Wong et al., "The role of immunoglobulin superfamily cell adhesion molecules in cancer metastasis," Int J Cell Biol, 2012, 2012:340296.
Wen et al., "Limiting dilution assay for human B cells based on their activation by mutant EL4 thymoma cells: total and anti-malaria responder B cell frequencies" (1987) Eur. J. Immunol. 17:887-892.
Wilbur et al., "Rapid Similarity Searches of Nucleic Acid and Protein Data Banks," Proc. Natl. Acad. Sci. USA, 1983, 80, 726-730.
Wilczek et al., "The possible role of factor H in colon cancer resistance to complement attack" (2008) Int J Cancer 122, 2030-7.
Wu et al., "Receptor-mediated in vitro gene transformation by a soluble DNA carrier system" J. Biol. Chem. 262:4429-4432 (1987).
Wu, C., et al., Simultaneous targeting of multiple disease mediators by a dual-variable-domain immunoglobulin Nature Biotechnology, 25(11):1290-1297 (2007).
Yelton et al., "Affinity maturation of the BR96 anti-carcinoma antibody by codon-based mutagenesis" J. Immunol., 155: 1994-2004 (1995).
Zapata et al., "Engineering linear F(ab')2 fragments for efficient production in *Escherichia coli* and enhanced antiproliferative activity" (1995) Protein Eng. 8(10):1057-1062.
Ziporen et al., "Programmed necrotic cell death induced by complement involves a Bid-dependent pathway," J Immunol, 2009, 182:515-21.
International Search Report and Written Opinion for Application No. PCT/US14/41441 dated Jan. 12, 2015 (13 pages).
Partial European Search Report for Application No. 14806951.1 dated Jan. 16, 2017 (9 pages).
Extended European Search Report for Application No. 14806951.1 dated Apr. 21, 2017 (15 pages).
European Patent Office Action for Application No. 14806951.1 dated Apr. 18, 2018 (5 pages).
United States Patent Office Action for U.S. Appl. No. 14/895,963 dated Apr. 26, 2018 (17 pages).
Japanese Patent Office Action for Application No. 2016-518058 dated Jul. 23, 2018 (16 pages, English translation included).
Japanese Patent Office Action for Application No. 2016-518058 dated Mar. 27, 2019 (6 pages, English translation included).
United States Patent Office Notice of Allowance for U.S. Appl. No. 14/895,963 dated Oct. 22, 2018 (8 pages).
Canada Patent Office Action for Application No. 2,914,566 dated Jan. 31, 2020 (7 pages).
European Patent Office Extended Search Report for Application No. 19191054.6 dated Mar. 3, 2020 (12 pages).
United States Patent Office Notice of Allowance for U.S. Appl. No. 15/973,345 dated Jul. 21, 2020 (8 pages).
United States Patent Office Action for U.S. Appl. No. 17/076,042 dated Dec. 9, 2022 (9 pages).
Canadian Patent Office Action for Application No. 2,914,566 dated Jan. 27, 2023 (6 pages).
Edwards et al., "The remarkable flexibility of the human antibody repertoire; isolation of over one thousand different antibodies to a single protein, BLyS," J Mol Biol, 2003, 334(1): 103-118.
Goel et al., "Plasticity within the Antigen-Combining Site May Manifest as Molecular Mimicry in the Humoral Immune Response," J Immunol, 2004, 173(12): 7358-7367.
Janeway, Jr. et al., "Structure of the Antibody Molecule and Immunoglobulin Genes," Immuno Biology, Chapter 3, 1997, 3:1-3:11.
Kanyavuz et al., "Breaking the law: unconventional strategies for antibody diversification," Nat Rev Immunol, 2019, 19(6): 355-368.
Kipriyanov et al., "Generation and production of engineered antibodies," Mol Biotechnol, 2004, 26(1): 39-60.
Lescar et al., "Crystal Struture of a Cross-reaction Complex between Fab F9.13.7 and Guinea Fowl Lysonzyme," Journal of Biological Chemistry, 1995, 270(30): 18067-18076.
Lloyd et al., "Modelling the human immune response: performance of a 1011 human antibody repertoire against a broad panel of therapeutically relevant antigens," Protein Eng Des Sel, 2009, 22(3): 159-168.
United States Patent Office Action for U.S. Appl. No. 17/076,042 dated Oct. 3, 2023 (22 pages).

\* cited by examiner $EC_{50}$ = 0.014356 ug/ml    SCR19-20 Peptide $EC_{50}$ = 0.01525 ug/ml    SCR19-20 Peptide

METHODS OF INHIBITING COMPLEMENT FACTOR H (CFH) COMPRISING ADMINISTERING AN ANTIBODY THAT BINDS CFH

CROSS REFERENCE TO RELATED APPLICATIONS

This application is a divisional of U.S. patent application Ser. No. 16/196,758, filed on Nov. 20, 2018, which is a continuation of U.S. patent application Ser. No. 14/895,963, filed Dec. 4, 2015, which is a national stage filing under 35 U.S.C. § 371 of International Patent Application No. PCT/US2014/041441, filed Jun. 7, 2014, which claims the benefit of priority to U.S. Provisional Application No. 61/832,434, filed Jun. 7, 2013, and U.S. Provisional Application No. 61/926,539, filed Jan. 13, 2014, each of which are incorporated by reference in its entirety.

REFERENCE TO SEQUENCE LISTING

This application is filed with a Computer Readable Form of a Sequence Listing in accord with 37 C.F.R. § 1.821(c). The text file submitted by EFS, "028193-9163-US04_sequence_listing_25-AUG-20201_ST25.txt," was created on Aug. 25, 2021, contains 132 sequences, has a file size of 109 Kbytes, and is hereby incorporated by reference in its entirety.

TECHNICAL FIELD

The present disclosure relates to Complement factor H (CFH), in particular CFH inhibitors, such as anti-CFH antibodies and small molecules, and methods of treating cancer patients using said CFH inhibitors.

BACKGROUND

Lung cancer is a significant public health issue. The majority of tumors are detected at an advanced stage when treatment options are limited and patients require systemic therapy. Even patients with resectable, early stage lung cancer have an almost 50% chance of developing recurrence and at some point need adjuvant treatment. Over the past several years new therapies targeting specific pathways have been introduced and, in select individuals, these produce an initial response. However, almost all patients develop resistance, which is most likely due to tumor heterogeneity and clonal evolution.

While activation of the humoral response against malignant cells has been investigated, humoral immunity per se has not been very well exploited for cancer therapy. Circulating antibodies against over 100 different tumor-associated antigens (TAAs) have been described, but very few are associated with tumor stage or outcome. Certain host antibodies may have the potential for anti-tumor activity, but this ability has not been fully realized for a number of possible reasons, including low concentration or low affinity of antibodies, or ineffective activation of B lymphocytes. There is a clear need for a greater number and wider variety of effective therapies.

SUMMARY

The present invention is directed to an isolated antibody or antibody fragment thereof capable of binding to a reduce form of Complement Factor H (CFH) protein. The isolated antibody or antibody fragment thereof may bind to an epitope within short consensus repeat (SCR) 19 of CFH protein. The epitope may comprise PIDNGDIT (SEQ ID NO: 3). The isolated antibody or antibody fragment may comprise one or more of the following amino acid sequences: SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, and SEQ ID NO:92. The heavy chain may comprise a sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, and SEQ ID NO:82. The light chain may comprise a sequence selected from the group consisting of SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, and SEQ ID NO:92. The isolated antibody or antibody fragment may not cross-react with at least one of systemic lupus erythematosus autoantigens SSA, SSB, sphingomyelin (Sm), ribonucleoprotein (RNP), sclerosis autoantigen (Scl-70), histidine-tRNA ligase (Jo-1), double-stranded DNA (dsDNA), centromere B (CentB), and histones. The isolated antibody or antibody fragment may be selected from the group consisting of a human antibody, an immunoglobulin molecule, a disulfide linked Fv, a monoclonal antibody, an affinity matured, a scFv, a chimeric antibody, a single domain antibody, a CDR-grafted antibody, a diabody, a humanized antibody, a multispecific antibody, a Fab, a dual specific antibody, a DVD, a TVD, a Fab', a bispecific antibody, a F(ab')$_2$, and a Fv. The isolated antibody or antibody fragment may be humanized. The isolated antibody or antibody fragment may comprise a heavy chain immunoglobulin constant domain selected from the group consisting of a human IgM constant domain, a human IgG4 constant domain, a human IgG1 constant domain, a human IgE constant domain, a human IgG2 constant domain, a human igG3 constant domain, and a human IgA constant domain. The isolated antibody or antibody fragment of any one of the preceding claims with the proviso that the isolated antibody or antibody fragment is not an autoantibody.

The present invention is directed to an isolated antibody or antibody fragment thereof capable of binding to complement factor H (CFH) protein. The complement factor H (CFH) protein may be a reduced form of CFH protein. The isolated antibody or antibody fragment thereof may bind to an epitope within short consensus repeat (SCR) 19 of CFH protein. The epitope may comprise PIDNGDIT (SEQ ID NO: 3). The isolated antibody or antibody fragment may comprise one or more of the following amino acid sequences: SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, and SEQ ID NO:92. The heavy chain may comprise a sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, and SEQ ID NO:82. The light chain may comprise a sequence selected from the group consisting of SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, and SEQ ID NO:92. The isolated antibody or antibody fragment may not cross-react with at least one of systemic lupus erythematosus autoantigens SSA, SSB, sphingomyelin (Sm), ribonucleoprotein (RNP), sclerosis autoantigen (Scl-70), histidine-tRNA ligase (Jo-1), double-stranded DNA (dsDNA), centromere B (CentB), and histones. The isolated antibody or antibody fragment may be selected from the group consisting of a human antibody, an immunoglobulin molecule, a disulfide linked Fv, a monoclonal antibody, an affinity matured, a scFv, a chimeric antibody, a single domain antibody, a CDR-grafted antibody, a diabody, a humanized antibody, a multispecific antibody, a Fab, a dual specific antibody, a DVD, a TVD, a Fab', a bispecific antibody, a F(ab')$_2$, and a Fv. The isolated antibody or antibody fragment may be humanized. The isolated antibody or antibody fragment may comprise a heavy chain immunoglobulin constant domain selected from the group consisting of a human IgM constant domain, a human IgG4 constant domain, a human IgG1 constant domain, a human IgE constant domain, a human IgG2 constant domain, a human igG3 constant domain, and a human IgA constant domain. The isolated antibody or antibody fragment of any one of the preceding claims with the proviso that the isolated antibody or antibody fragment is not an autoantibody.

The present invention is directed to an isolated antibody or antibody fragment thereof which immunospecifically binds to Complement Factor H (CFH) protein. The binding of the antibody or antibody fragment to CFH protein is sensitive to the reduced form of CFH protein. The isolated antibody or antibody fragment thereof may bind to an epitope within short consensus repeat (SCR) 19 of CFH protein. The epitope may comprise PIDNGDIT (SEQ ID NO: 3). The isolated antibody or antibody fragment may comprise one or more of the following amino acid sequences: SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, and SEQ ID NO:92. The heavy chain may comprise a sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, and SEQ ID NO:82. The light chain may comprise a sequence selected from the group consisting of SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, and SEQ ID NO:92. The isolated antibody or antibody fragment may not cross-react with at least one of systemic lupus erythematosus autoantigens SSA, SSB, sphingomyelin (Sm), ribonucleoprotein (RNP), sclerosis autoantigen (Scl-70), histidine-tRNA ligase (Jo-1), double-stranded DNA (dsDNA), centromere B (CentB), and histones. The isolated antibody or antibody fragment may be selected from the group consisting of a human antibody, an immunoglobulin molecule, a disulfide linked Fv, a monoclonal antibody, an affinity matured, a scFv, a chimeric antibody, a single domain antibody, a CDR-grafted antibody, a diabody, a humanized antibody, a multispecific antibody, a Fab, a dual specific antibody, a DVD, a TVD, a Fab', a bispecific antibody, a F(ab')$_2$, and a Fv. The isolated antibody or antibody fragment may be humanized. The isolated antibody or antibody fragment may comprise a heavy chain immunoglobulin constant domain selected from the group consisting of a human IgM constant domain, a human IgG4 constant domain, a human IgG1 constant domain, a human IgE constant domain, a human IgG2 constant domain, a human igG3 constant domain, and a human IgA constant domain. The isolated antibody or antibody fragment of any one of the preceding claims with the proviso that the isolated antibody or antibody fragment is not an autoantibody.

The present invention is directed to an isolated antibody or antibody fragment which immunospecifically binds to the complement factor H (CFH) protein. The antibody has an equilibrium dissociation constant ($K_D$) of between about $1.00\times10^{-10}$ M to about $1.00\times10^{-15}$ M. The antibody may have a $K_D$ of $2.46\times10^{-12}$ M. The isolated antibody or antibody fragment may not cross-react with at least one of systemic lupus erythematosus autoantigens SSA, SSB, sphingomyelin (Sm), ribonucleoprotein (RNP), sclerosis autoantigen (Scl-70), histidine-tRNA ligase (Jo-1), double-stranded DNA (dsDNA), centromere B (CentB), and histones. The isolated antibody or antibody fragment may be selected from the group consisting of a human antibody, an immunoglobulin molecule, a disulfide linked Fv, a monoclonal antibody, an affinity matured, a scFv, a chimeric antibody, a single domain antibody, a CDR-grafted antibody, a diabody, a humanized antibody, a multispecific antibody, a Fab, a dual specific antibody, a DVD, a TVD, a Fab', a bispecific antibody, a F(ab')$_2$, and a Fv. The isolated antibody or antibody fragment may be humanized. The isolated antibody or antibody fragment may comprise a heavy chain immunoglobulin constant domain selected from the group consisting of a human IgM constant domain, a human IgG4 constant domain, a human IgG1 constant domain, a human IgE constant domain, a human IgG2 constant domain, a human igG3 constant domain, and a human IgA constant domain. The isolated antibody or antibody fragment of any one of the preceding claims with the proviso that the isolated antibody or antibody fragment is not an autoantibody.

The present invention is directed to an isolated antibody or antibody fragment which immunospecifically binds to the complement factor H (CFH) protein. The antibody has an off-rate ($k_d$) of between about $1.00\times10^{-4}$ s$^{-1}$ to about $1.00\times10^{-9}$ s$^{-1}$. The antibody may have a kd of $5.56\times10^{-7}$ s$^{-1}$. The isolated antibody or antibody fragment may not cross-react with at least one of systemic lupus erythematosus autoantigens SSA, SSB, sphingomyelin (Sm), ribonucleoprotein (RNP), sclerosis autoantigen (Scl-70), histidine-tRNA ligase (Jo-1), double-stranded DNA (dsDNA), centromere B (CentB), and histones. The isolated antibody or antibody fragment may be selected from the group consisting of a human antibody, an immunoglobulin molecule, a disulfide linked Fv, a monoclonal antibody, an affinity matured, a scFv, a chimeric antibody, a single domain antibody, a CDR-grafted antibody, a diabody, a humanized antibody, a multispecific antibody, a Fab, a dual specific antibody, a DVD, a TVD, a Fab', a bispecific antibody, a F(ab')$_2$, and a Fv. The isolated antibody or antibody fragment may be humanized. The isolated antibody or antibody fragment may comprise a heavy chain immunoglobulin constant domain selected from the group consisting of a human IgM constant domain, a human IgG4 constant domain, a human IgG1 constant domain, a human IgE constant domain, a human IgG2 constant domain, a human igG3 constant domain, and a human IgA constant domain. The isolated antibody or antibody fragment of any one of the preceding claims with the proviso that the isolated antibody or antibody fragment is not an autoantibody.

The present invention is directed to an isolated antibody or antibody fragment which immunospecifically binds to the complement factor H (CFH) protein. The antibody has on-rate ($k_a$) of between about $1.00\times10^{3}$/M$^{-1}$s$^{-1}$ to about $1.00\times10^{8}$/M$^{-1}$s$^{-1}$. The antibody may have a $k_a$ of $2.26\times10^{5}$/ M$^{-1}$s$^{-1}$. The isolated antibody or antibody fragment may not cross-react with at least one of systemic lupus erythematosus autoantigens SSA, SSB, sphingomyelin (Sm), ribonucleoprotein (RNP), sclerosis autoantigen (Scl-70), histidine-tRNA ligase (Jo-1), double-stranded DNA (dsDNA), centromere B (CentB), and histones. The isolated antibody or antibody fragment may be selected from the group consisting of a human antibody, an immunoglobulin molecule, a disulfide linked Fv, a monoclonal antibody, an affinity matured, a scFv, a chimeric antibody, a single domain antibody, a CDR-grafted antibody, a diabody, a humanized antibody, a multispecific antibody, a Fab, a dual specific antibody, a DVD, a TVD, a Fab', a bispecific antibody, a F(ab')$_2$, and a Fv. The isolated antibody or antibody fragment may be humanized. The isolated antibody or antibody fragment may comprise a heavy chain immunoglobulin constant domain selected from the group consisting of a human IgM constant domain, a human IgG4 constant domain, a human IgG1 constant domain, a human IgE constant domain, a human IgG2 constant domain, a human igG3 constant domain, and a human IgA constant domain. The isolated antibody or antibody fragment of any one of the preceding claims with the proviso that the isolated antibody or antibody fragment is not an autoantibody.

The present invention is directed to an isolated nucleic acid encoding an antibody or antibody fragment that immunospecifically binds to CFH, a fragment thereof, or a variant thereof.

The isolated nucleic acid comprises a nucleotide sequence that encodes a polypeptide comprising one or more of the of the following amino acid sequences: SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, and SEQ ID NO:92.

The present invention is directed to an isolated nucleic acid comprising a nucleic acid sequence from the group consisting of SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, and SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO: 102, and SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO:111, SEQ ID NO:112, and SEQ ID NO:113.

The present invention is directed to an isolated cell comprising a nucleic acid sequence operatively linked to a promoter. The nucleic acid sequence comprises a coding sequence that encodes a polypeptide comprising one or more of the of the following amino acid sequences: SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, and SEQ ID NO:92. The isolated cell may express an antibody or antibody fragment capable of binding to complement factor H (CFH) protein. The isolated cell may be a eukaryotic cell. The eukaryotic cell may be a mammalian cell.

The present invention is directed to a pharmaceutical composition comprising said isolated antibody or antibody fragment, said isolated nucleic acid, or said isolated cell.

The present invention is directed to a method of treating a subject in need thereof having cancer. The method comprises administering to the subject said isolated antibody or antibody fragment, said isolated nucleic acid, said isolated cell, or said pharmaceutical composition. The cancer may be lung cancer. The cancer may be non-small cell lung carcinoma. The method may further comprise administering an effective amount of at least one of Cetuximab, PERJETA®, or HERCEPTIN®.

The present invention is directed to a method of detecting or measuring Complement Factor H (CFH) in a sample. The method comprises contacting the sample with said isolated antibody or antibody fragment.

The present invention is directed to a method of detecting or measuring a reduced form of Complement Factor H (CFH) in a sample. The method comprises contacting the sample with said isolated antibody or antibody fragment.

The present invention is directed to a method of treating a subject having cancer. The method comprises administering a therapeutic compound, wherein the therapeutic compound binds to short consensus repeat (SCR) 19 of a reduced form of CFH. The therapeutic compound may comprise an antibody or a small molecule. The antibody may comprise said isolated antibody or antibody fragment.

The present invention is directed to a method of increasing complement dependent lysis of a cell. The method comprises administering to the cell said isolated antibody or antibody fragment or said pharmaceutical composition. An effective amount of the isolated antibody or antibody fragment may be administered to the cell. The cell may be a cancer cell. The cancer cell may be a breast cancer cell or a lung cancer cell. The cancer cell may be MCF7 breast cancer cell, SKBR3 breast cancer cell, MDA-MB-231 breast cancer cell, or A549 lung carcinoma cell. The isolated antibody or antibody fragment may comprise a polypeptide sequence having at least one amino acid sequence of SEQ ID NO: 75, 85, 79, or 89. The isolated antibody or antibody fragment may comprise a polypeptide sequence having SEQ ID NOs: 75 and 85. The isolated antibody or antibody fragment may comprise a polypeptide sequence having SEQ ID NOs: 79 and 89.

The present invention is directed to a method of increasing C3b deposition on a cell. The method comprises administering to the cell said isolated antibody or antibody fragment or said pharmaceutical composition. An effective amount of the isolated antibody or antibody fragment may be administered to the cell. The cell may be a cancer cell. The cancer cell may be a breast cancer cell or a lung cancer cell. The cancer cell may be MCF7 breast cancer cell, SKBR3 breast cancer cell, MDA-MB-231 breast cancer cell, or A549 lung carcinoma cell. The isolated antibody or antibody fragment may comprise a polypeptide sequence having at least one amino acid sequence of SEQ ID NO: 75, 85, 79, or 89. The isolated antibody or antibody fragment may comprise a polypeptide sequence having SEQ ID NOs: 75 and 85. The isolated antibody or antibody fragment may comprise a polypeptide sequence having SEQ ID NOs: 79 and 89.

The present invention is directed to a method of inhibiting Complement Factor H (CFH) binding to C3b in a subject or a cell. The method comprises administering to the cell said isolated antibody or antibody fragment or said pharmaceutical composition. An effective amount of the isolated antibody or antibody fragment may be administered to the cell. The cell may be a cancer cell. The cancer cell may be a breast cancer cell or a lung cancer cell. The cancer cell may be MCF7 breast cancer cell, SKBR3 breast cancer cell, MDA-MB-231 breast cancer cell, or A549 lung carcinoma cell. The isolated antibody or antibody fragment may comprise a polypeptide sequence having at least one amino acid sequence of SEQ ID NO: 75, 85, 79, or 89. The isolated antibody or antibody fragment may comprise a polypeptide sequence having SEQ ID NOs: 75 and 85. The isolated antibody or antibody fragment may comprise a polypeptide sequence having SEQ ID NOs: 79 and 89.

The present invention is directed to a method of detecting or measuring complement factor H (CFH) in a sample. The method comprises contacting the sample with said isolated antibody or antibody fragment.

The present invention is directed to a method of detecting or measuring a reduced form of Complement Factor H (CFH) in a sample. The method comprises contacting the sample with said isolated antibody or antibody fragment.

The present invention is directed to a method of inhibiting tumor growth in a subject. The method comprises administering to the subject said isolated antibody or antibody fragment, said isolated nucleic acid, said isolated cell, or said pharmaceutical composition. Lung tumor growth may be inhibited.

The present invention is directed to a kit. The kit comprises said isolated antibody or antibody fragment, said isolated nucleic acid, said isolated cell, or said pharmaceutical composition.

The present invention is directed to a kit for assaying a test sample for Complement Factor H (CFH). The kit comprises said isolated antibody or antibody fragment, said isolated nucleic acid, said isolated cell, or said pharmaceutical composition.

The present invention is directed to a kit for assaying a test sample for a reduce form of Complement Factor H (CFH). The kit comprises said isolated antibody or antibody fragment, said isolated nucleic acid, said isolated cell, or said pharmaceutical composition.

DETAILED DESCRIPTION

Figure 1:
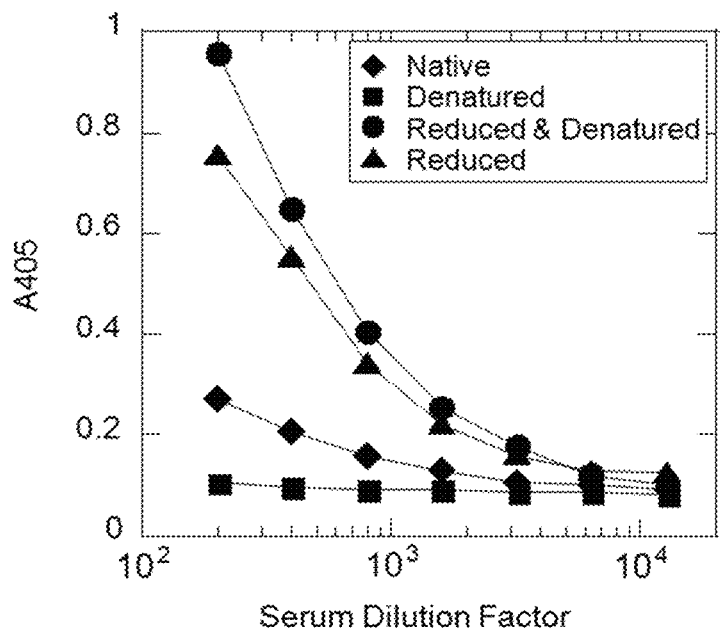
FIG. 1 shows the effect of reduction and denaturation of CFH on autoantibody binding. ELISA plate wells were coated with either native CFH or CFH treated with the reductant TCEP and with or without the denaturant urea. Titration curves were generated using serum from a CFH-antibody positive individual and antibody binding was detected with anti-human IgG-HRP.

The present disclosure is directed to inhibitors of Complement factor H (CFH). In particular, the present disclosure is directed to inhibitors that target an epitope or region in the SCR 19 domain of CFH. This particular epitope or region was discovered by characterizing the humoral immune response in cancer to develop therapeutic agents against lung cancer. Autoantibodies to CFH are associated with early stage, non-metastatic, non-small cell lung cancer (NSCLC). Functional analysis of NSCLC patient autoantibodies to CFH was performed to assess their potential for development into a lung cancer therapeutic that promotes complement dependent tumor cell lysis.

The present disclosure describes antibodies in lung cancer patients that recognize a reduced form of CFH in vitro, which may represent (or mimic) the tumor-bound form of CFH. Anti-CFH antibodies were affinity purified from patient sera and epitope mapped. A common epitope recognized by most of these antibodies was located in a functional domain of CFH that interacts with C3b. Purified CFH autoantibody increased C3b deposition on tumor cells and increased complement dependent lysis of tumor cells. This discovery provides a therapeutic target for cancer treatment.

The present disclosure is also directed to anti-CFH antibodies. In particular, the present disclosure is directed to anti-CFH antibodies that target an epitope or region in the SCR 19 domain of CFH. The present disclosure describes antibodies that recognize a reduced form of CFH in vitro, which may represent (or mimic) the tumor-bound form of CFH. A common epitope recognized by most of these antibodies was located in a functional domain of CFH that interacts with C3b. This discovery provides a therapeutic target for cancer treatment.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "administration" or "administering," as used herein refers to providing, contacting, and/or delivery of the CFH inhibitor by any appropriate route to achieve the desired effect. These agents may be administered to a subject in numerous ways including, but not limited to, orally, ocularly, nasally, intravenously, topically, as aerosols, suppository, etc. and may be used in combination.

"Affinity Matured Antibody" is used herein to refer to an antibody with one or more alterations in one or more CDRs, which result in an improvement in the affinity (i.e., $K_D$, $k_d$ or $k_a$) of the antibody for a target antigen compared to a parent antibody, which does not possess the alteration(s). Exemplary affinity matured antibodies will have nanomolar or even picomolar affinities for the target antigen. Various procedures for producing affinity matured antibodies are known in the art, including the screening of a combinatory antibody library that has been prepared using bio-display. For example, Marks et al., BioTechnology, 10: 779-783 (1992) describes affinity maturation by VH and VL domain shuffling. Random mutagenesis of complementarity determining regions (CDRs) and/or framework residues is described by Barbas et al., *Proc. Nat. Acad. Sci. USA*, 91: 3809-3813 (1994); Schier et al., *Gene*, 169: 147-155 (1995); Yelton et al., *J. Immunol.*, 155: 1994-2004 (1995); Jackson et al., *J. Immunol.*, 154(7): 3310-3319 (1995); and Hawkins et al, *J. Mol. Biol.*, 226: 889-896 (1992). Selective mutation at selective mutagenesis positions and at contact or hypermutation positions with an activity-enhancing amino acid residue is described in U.S. Pat. No. 6,914,128 B1.

"Alternative pathway," also known as "alternative complement pathway," as used herein refers to one of three complement pathways that opsonize and kill target cells. The alternative pathway is triggered when the C3b protein directly binds the target cell. The alternative complement pathway is able to distinguish self from non-self on the basis of the surface expression of complement regulatory proteins which limit the activation of the complement as host-cells do not accumulate cell surface C3b because this is prevented by the complement regulatory proteins. Foreign cells, pathogens and abnormal surfaces generally do not have complement regulatory proteins and thus may become heavily decorated with C3b, which eventually leads to the lysis of the cell.

"Antibody" and "antibodies" as used herein refers to monoclonal antibodies, multispecific antibodies, human antibodies, humanized antibodies (fully or partially humanized), animal antibodies such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies, single-chain Fvs ("scFv"), single chain antibodies, single domain antibodies, such as variable heavy chain domains ("VHH"; also known as "VHH fragments") derived from animals in the Camelidae family (VHH and methods of making them are described in Gottlin et al., *Journal of Biomolecular Screening*, 14:77-85 (2009)) and VNAR fragments, Fab fragments, F(ab') fragments, F(ab')$_2$ fragments, disulfide-linked Fvs ("sdFv"), and anti-idiotypic ("anti-Id") antibodies, dual-domain antibodies, dual variable domain (DVD) or triple variable domain (TVD) antibodies (dual-variable domain immunoglobulins and methods for making them are described in Wu, C., et al., Nature Biotechnology, 25(11):1290-1297 (2007)) and PCT International Application WO 2001/058956, the contents of each of which are herein incorporated by reference), and functionally active epitope-binding fragments of any of the above. In particular, antibodies include immunoglobulin molecules and immunologically active fragments of immunoglobulin molecules, namely, molecules that contain an analyte-binding site. Immunoglobulin molecules can be of any type (for example, IgG, IgE, IgM, IgD, IgA, and IgY), class (for example, IgG1, IgG2, IgG3, IgG4, IgA1, and IgA2), or subclass. For simplicity sake, an antibody against an analyte is frequently referred to herein as being either an "anti-analyte antibody" or merely an "analyte antibody" (e.g., an anti-CFH antibody or a CFH antibody).

"Antibody fragment" as used herein refers to a portion of an intact antibody comprising the antigen-binding site or variable region. The portion does not include the constant heavy chain domains (i.e., CH2, CH3, or CH4, depending on the antibody isotype) of the Fc region of the intact antibody. Examples of antibody fragments include, but are not limited to, Fab fragments, Fab' fragments, Fab'-SH fragments, F(ab')$_2$ fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, single-chain polypeptides containing the three CDRs of the heavy chain variable region, and VHH.

"Autoantibody," "patient antibodies," "patient's CFH autoantibodies" or "patient's CFH antibodies" as used interchangeably herein refers to an immunoglobulin, antigen specific B cell surface receptor (surface immunoglobulin), or antigen specific T cell receptor produced by an individual that is directed against an individual's own self-protein, carbohydrate or nucleic acid.

An "autoantibody to the CFH protein" as used herein refers to an autoantibody capable of reacting with the CFH protein, or with a variant or with a fragment of said protein, provided that said variant or said fragment is functionally equivalent, i.e., susceptible of being recognized by said autoantibody. For example, an autoantibody to the CFH protein may be an IgG or an IgM.

"Binding Constants" are described herein. The term "association rate constant," "$k_{on}$" or "$k_a$" as used herein, refers to the value indicating the binding rate of an antibody to its target antigen or the rate of complex formation between an antibody and antigen as shown by the equation below:

Antibody (Ab)+Antigen (Ag)→Ab-Ag.

The term "dissociation rate constant," "$k_{off}$" or "$k_d$" as used interchangeably herein, refers to the value indicating the dissociation rate of an antibody form its target antigen or separation of Ab-Ag complex over time into free antibody and antigen as shown by the equation below:

Antibody (Ab)+Antigen (Ag)←Ab-Ag.

Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Idaho) can also be used.

The term "effective dosage" or "effective amount" as used interchangeably herein means a dosage of a drug effective for periods of time necessary, to achieve the desired therapeutic result. An effective dosage may be determined by a person skilled in the art and may vary according to factors such as the disease state, age, sex, and weight of the individual, and the ability of the drug to elicit a desired response in the individual. This term as used herein may also refer to an amount effective at bringing about a desired in vivo effect in an animal, mammal, or human, such as reducing and/or inhibiting the function of the estrogen receptor. A therapeutically effective amount may be administered in one or more administrations (e.g., the agent may be given as a preventative treatment or therapeutically at any stage of disease progression, before or after symptoms, and the like), applications or dosages and is not intended to be limited to a particular formulation, combination or administration route. It is within the scope of the present disclosure that the SERM may be administered at various times during the course of treatment of the subject. The times of administration and dosages used will depend on several factors, such as the goal of treatment (e.g., treating v. preventing), condition of the subject, etc. and can be readily determined by one skilled in the art.

The term "equilibrium dissociation constant," "Kd," "$k_d$" or "$K_D$" as used interchangeably, herein, refers to the value obtained by dividing the dissociation rate ($k_{off}$) by the association rate ($k_{on}$). The association rate, the dissociation rate and the equilibrium dissociation constant are used to represent the binding affinity of an antibody to an antigen.

"Binding Protein" is used herein to refer to a monomeric or multimeric protein that binds to and forms a complex with a binding partner, such as, for example, a polypeptide, an antigen, a chemical compound or other molecule, or a substrate of any kind. A binding protein specifically binds a binding partner. Binding proteins include antibodies, as well as antigen-binding fragments thereof and other various forms and derivatives thereof as are known in the art and described herein below and other molecules comprising one or more antigen-binding domains that bind to an antigen molecule or a particular site (epitope) on the antigen molecule. Accordingly, a binding protein includes, but is not limited to, an antibody a tetrameric immunoglobulin, an IgG molecule, an IgG1 molecule, a monoclonal antibody, a chimeric antibody, a CDR-grafted antibody, a humanized antibody, an affinity matured antibody, and fragments of any such antibodies that retain the ability to bind to an antigen.

"Bispecific antibody" is used herein to refer to a full-length antibody that is generated by quadroma technology (see Milstein et al., Nature, 305(5934): 537-540 (1983)), by chemical conjugation of two different monoclonal antibodies (see, Staerz et al., Nature, 314(6012): 628-631 (1985)), or by knob-into-hole or similar approaches, which introduce mutations in the Fc region (see Holliger et al., Proc. Natl. Acad. Sci. USA, 90(14): 6444-6448 (1993)), resulting in multiple different immunoglobulin species of which only one is the functional bispecific antibody. A bispecific antibody binds one antigen (or epitope) on one of its two binding arms (one pair of HC/LC), and binds a different antigen (or epitope) on its second arm (a different pair of HC/LC). By this definition, a bispecific antibody has two distinct antigen-binding arms (in both specificity and CDR sequences), and is monovalent for each antigen to which it binds to.

"C3b" as used herein refers to the larger of two elements formed by the cleavage of complement component 3 (C3) by C3 convertase enzyme complex or by spontaneous cleavage in the blood. C3b covalently bonds to microbial cell surfaces within an organism's body, leading to the production of surface-bound C3-convertase and more C3b components and opsonization of the microbe by macrophages. C3b that is generated from C3 by a C3 convertase enzyme complex in the fluid phase is rapidly inactivated by factor H and factor I. When the internal thioester of C3 reacts with a hydroxyl or amine group of a molecule on the surface of a cell or pathogen, the C3b that is now covalently bound to the surface is protected from factor H-mediated inactivation and may now bind factor B to form C3bB.

"Cancer" or "tumor" as used interchangeably herein refers to the uncontrolled and unregulated growth of abnormal cells in the body. Cancer may invade nearby parts of the body and may also spread to more distant parts of the body through the lymphatic system or bloodstream. "Cancer cell" or "tumor cell" as used interchangeably herein refers to a cell that divides and reproduces abnormally with uncontrolled growth. A cancer cell can break away and travel to other parts of the body and set up another site, referred to as metastasis. Cancer cells or cancerous cells are also called malignant cells. A cancer cell or cancer cell line may originate from a cancer. For examples, a cancer cell line may be A549 cell line ("A549"), which is a human lung adenocarcinoma epithelial cell line.

Cancers may include Adrenocortical Carcinoma, Anal Cancer, Bladder Cancer, Brain Tumor, Breast Cancer, Carcinoid Tumor, Gastrointestinal, Carcinoma of Unknown Primary, Cervical Cancer, Colon Cancer, Endometrial Cancer, Esophageal Cancer, Extrahepatic Bile Duct Cancer, Ewings Family of Tumors (PNET), Extracranial Germ Cell Tumor, Intraocular Melanoma Eye Cancer, Gallbladder Cancer, Gastric Cancer (Stomach), Extragonadal Germ Cell Tumor, Gestational Trophoblastic Tumor, Head and Neck Cancer, Hypopharyngeal Cancer, Islet Cell Carcinoma, Kidney Cancer (renal cell cancer), Laryngeal Cancer, Acute Lymphoblastic Leukemia, Leukemia, Acute Myeloid, Chronic Lymphocytic Leukemia, Chronic Myelogenous Leukemia, Hairy Cell Leukemia, Lip and Oral Cavity Cancer, Liver Cancer, Non-Small Cell Lung Cancer, Small Cell Lung Cancer, AIDS-Related Lymphoma, Central Nervous System (Primary) Lymphoma, Cutaneous T-Cell Lymphoma, Hodgkin's Disease Lymphoma, Non-Hodgkin's Disease Lymphoma, Malignant Mesothelioma, Melanoma, Merkel Cell Carcinoma, Metastatic Squamous Neck Cancer with Occult Primary, Multiple Myeloma and Other Plasma Cell Neoplasms, Mycosis Fungoides, Myelodysplastic Syndrome, Myeloproliferative Disorders, Nasopharyngeal Cancer, euroblastoma, Oral Cancer, Oropharyngeal Cancer, Osteosarcoma, Ovarian Epithelial Cancer, Ovarian Germ Cell Tumor, Pancreatic Cancer, Exocrine, Pancreatic Cancer, Islet Cell Carcinoma, Paranasal Sinus and Nasal Cavity Cancer, Parathyroid Cancer, Penile Cancer, Pituitary Cancer, Plasma Cell Neoplasm, Prostate Cancer, Rhabdomyosarcoma, Rectal Cancer, Renal Cell Cancer (cancer of the kidney), Transitional Cell Renal Pelvis and Ureter, Salivary Gland Cancer, Sezary Syndrome, Skin Cancer, Small Intestine Cancer, Soft Tissue Sarcoma, Testicular Cancer, Malignant Thymoma, Thyroid Cancer, Urethral Cancer, Uterine Cancer, Unusual Cancer of Childhood, Vaginal Cancer, Vulvar Cancer, and Wilms' Tumor.

"Complement Factor H protein," "CFH protein," or "CFH" as used herein refers to a protein of approximately 150 kDa (UniProt P08603) that is a member of the regulators of complement activation family and is a complement control protein. CFH is a large soluble glycoprotein that circulates in human plasma and serves to regulate the alternative pathway of the complement system, ensuring that the complement system is directed towards pathogens or other dangerous material and does not damage host tissue. CFH is a cofactor in the inactivation of C3b by factor I and functions to increase the rate of dissociation of the C3bBb complex (C3 convertase) and the (C3b)NBB complex (C5 convertase) in the alternative complement pathway. CFH binds to glycosaminoglycans that are generally present on host cells but not, normally, on pathogen surfaces.

CFH is composed of 20 short consensus repeats (SCRs), some of which function in cell attachment, while others function to eliminate C3b from the cell surface. The 20 SCRs that comprise CFH are each approximately 60 amino acids long, are arranged head to tail, and contain 4 cysteine residues forming 2 disulfide bonds per module. The C3b binding domain may refer to the part of the CFH that binds to C3b. SCRs 19 and 20 are involved in C3b binding.

"Derivative" of an antibody as used herein may refer to an antibody having one or more modifications to its amino acid sequence when compared to a genuine or parent antibody and exhibit a modified domain structure. The derivative may still be able to adopt the typical domain configuration found in native antibodies, as well as an amino acid sequence, which is able to bind to targets (antigens) with specificity. Typical examples of antibody derivatives are antibodies coupled to other polypeptides, rearranged antibody domains, or fragments of antibodies. The derivative may also comprise at least one further compound, e.g., a protein domain, said protein domain being linked by covalent or non-covalent bonds. The linkage can be based on genetic fusion according to the methods known in the art. The additional domain present in the fusion protein comprising the antibody employed in accordance with the invention may preferably be linked by a flexible linker, advantageously a peptide linker, wherein said peptide linker comprises plural, hydrophilic, peptide-bonded amino acids of a length sufficient to span the distance between the C-terminal end of the further protein domain and the N-terminal end of the antibody or vice versa. The antibody may be linked to an effector molecule having a conformation suitable for biological activity or selective binding to a solid support, a biologically active substance (e.g., a cytokine or growth hormone), a chemical agent, a peptide, a protein, or a drug, for example.

"Dual-specific antibody" is used herein to refer to a full-length antibody that can bind two different antigens (or epitopes) in each of its two binding arms (a pair of HC/LC) (see PCT publication WO 02/02773). Accordingly, a dual-specific binding protein has two identical antigen binding arms, with identical specificity and identical CDR sequences, and is bivalent for each antigen to which it binds.

"Dual variable domain" or "DVD" as used interchangeably herein to refer to two or more antigen binding sites on a binding protein, which may be divalent (two antigen binding sites), tetravalent (four antigen binding sites), or multivalent binding proteins. DVDs may be monospecific, i.e., capable of binding one antigen (or one specific epitope), or multispecific, i.e., capable of binding two or more antigens (i.e., two or more epitopes of the same target antigen molecule or two or more epitopes of different target antigens). A preferred DVD binding protein comprises two heavy chain DVD polypeptides and two light chain DVD polypeptides and is referred to as a "DVD immunoglobulin" or "DVD-Ig." Such a DVD-Ig binding protein is thus tetrameric and reminiscent of an IgG molecule, but provides more antigen binding sites than an IgG molecule. Thus, each half of a tetrameric DVD-Ig molecule is reminiscent of one half of an IgG molecule and comprises a heavy chain DVD polypeptide and a light chain DVD polypeptide, but unlike a pair of heavy and light chains of an IgG molecule that provides a single antigen binding domain, a pair of heavy and light chains of a DVD-Ig provide two or more antigen binding sites.

Each antigen binding site of a DVD-Ig binding protein may be derived from a donor ("parental") monoclonal antibody and thus comprises a heavy chain variable domain (VH) and a light chain variable domain (VL) with a total of six CDRs involved in antigen binding per antigen binding site. Accordingly, a DVD-Ig binding protein that binds two different epitopes (i.e., two different epitopes of two different antigen molecules or two different epitopes of the same antigen molecule) comprises an antigen binding site derived from a first parental monoclonal antibody and an antigen binding site of a second parental monoclonal antibody.

In a preferred embodiment, a DVD-Ig binding protein according to the invention not only binds the same target molecules bound by its parental monoclonal antibodies, but also possesses one or more desirable properties of one or more of its parental monoclonal antibodies. Preferably, such an additional property is an antibody parameter of one or more of the parental monoclonal antibodies. Antibody parameters that may be contributed to a DVD-Ig binding protein from one or more of its parental monoclonal antibodies include, but are not limited to, antigen specificity, antigen affinity, potency, biological function, epitope recognition, protein stability, protein solubility, production efficiency, immunogenicity, pharmacokinetics, bioavailability, tissue cross reactivity, and orthologous antigen binding.

A DVD-Ig binding protein binds at least one epitope of a CFH. Non-limiting examples of a DVD-Ig binding protein include a DVD-Ig binding protein that binds one or more epitopes of CFH, a DVD-Ig binding protein that binds an epitope of a human CFH and an epitope of a CFH of another species (for example, mouse), and a DVD-Ig binding protein that binds an epitope of a human CFH and an epitope of another target molecule.

"Epitope," or "epitopes," or "epitopes of interest" refer to a site(s) on any molecule that is recognized and can bind to a complementary site(s) on its specific binding partner. The molecule and specific binding partner are part of a specific binding pair. For example, an epitope can be on a polypeptide, a protein, a hapten, a carbohydrate antigen (such as, but not limited to, glycolipids, glycoproteins or lipopolysaccharides), or a polysaccharide. Its specific binding partner can be, but is not limited to, an antibody.

"F(ab')$_2$ fragment" as used herein refers to antibodies generated by pepsin digestion of whole IgG antibodies to remove most of the Fc region while leaving intact some of the hinge region. F(ab')$_2$ fragments have two antigen-binding F(ab) portions linked together by disulfide bonds, and therefore are divalent with a molecular weight of about 110 kDa. Divalent antibody fragments (F(ab')$_2$ fragments) are smaller than whole IgG molecules and enable a better penetration into tissue thus facilitating better antigen recognition in immunohistochemistry. The use of F(ab')$_2$ fragments also avoids unspecific binding to Fc receptor on live cells or to Protein A/G. F(ab')$_2$ fragments can both bind and precipitate antigens.

"Framework" (FR) or "Framework sequence" as used herein may mean the remaining sequences of a variable region minus the CDRs. Because the exact definition of a CDR sequence can be determined by different systems (for example, see above), the meaning of a framework sequence is subject to correspondingly different interpretations. The six CDRs (CDR-L1, -L2, and -L3 of light chain and CDR- H1, -H2, and -H3 of heavy chain) also divide the framework regions on the light chain and the heavy chain into four sub-regions (FR1, FR2, FR3, and FR4) on each chain, in which CDR1 is positioned between FR1 and FR2, CDR2 between FR2 and FR3, and CDR3 between FR3 and FR4. Without specifying the particular sub-regions as FR1, FR2, FR3, or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region.

Human heavy chain and light chain FR sequences are known in the art that can be used as heavy chain and light chain "acceptor" framework sequences (or simply, "acceptor" sequences) to humanize a non-human antibody using techniques known in the art. In one embodiment, human heavy chain and light chain acceptor sequences are selected from the framework sequences listed in publicly available databases such as V-base (hypertext transfer protocol:// vbase.mrc-cpe.cam.ac.uk/) or in the international ImMunoGeneTics® (IMGT®) information system (imgt.cines.fr/texts/IMGTrepertoire/LocusGenes/).

"Functional antigen binding site" as used herein may mean a site on a binding protein (e.g., an antibody) that is capable of binding a target antigen. The antigen binding affinity of the antigen binding site may not be as strong as the parent binding protein, e.g., parent antibody, from which the antigen binding site is derived, but the ability to bind antigen must be measurable using any one of a variety of methods known for evaluating protein, e.g., antibody, binding to an antigen. Moreover, the antigen binding affinity of each of the antigen binding sites of a multivalent protein, e.g., multivalent antibody, herein need not be quantitatively the same.

"Humanized antibody" is used herein to describe an antibody that comprises heavy and light chain variable region sequences from a non-human species (e.g., a mouse) but in which at least a portion of the VH and/or VL sequence has been altered to be more "human-like," i.e., more similar to human germLine variable sequences. A "humanized antibody" is an antibody or a variant, derivative, analog, or fragment thereof, which immunospecifically binds to an antigen of interest and which comprises a framework (FR) region having substantially the amino acid sequence of a human antibody and a complementarity determining region (CDR) having substantially the amino acid sequence of a non-human antibody. As used herein, the term "substantially" in the context of a CDR refers to a CDR having an amino acid sequence at least 80%, at least 85%, at least 90%, at least 95%, at least 98%, or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. In an embodiment, a humanized antibody also comprises at least a portion of an immunoglobulin constant region (Fc), typically that of a human immunoglobulin. In some embodiments, a humanized antibody contains the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

A humanized antibody can be selected from any class of immunoglobulins, including IgM, IgG, IgD, IgA, IgY, and IgE, and any isotype, including without limitation IgG1, IgG2, IgG3, and IgG4. A humanized antibody may comprise sequences from more than one class or isotype, and particular constant domains may be selected to optimize desired effector functions using techniques well-known in the art.

The framework regions and CDRs of a humanized antibody need not correspond precisely to the parental sequences, e.g., the donor antibody CDR or the consensus framework may be mutagenized by substitution, insertion, and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (see, e.g., Winnaker, From Genes to Clones (Verlagsgesellschaft, Weinheim, 1987)). A "consensus immunoglobulin sequence" may thus comprise a "consensus framework region(s)" and/or a "consensus CDR(s)." In a family of immunoglobulins, each position in the consensus sequence is occupied by the amino acid occurring most frequently at that position in the family. If two amino acids occur equally frequently, either can be included in the consensus sequence.

"Identical" or "identity," as used herein in the context of two or more polypeptide or polynucleotide sequences, can mean that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation.

"Linking sequence" or "linking peptide sequence" refers to a natural or artificial polypeptide sequence that is connected to one or more polypeptide sequences of interest (e.g., full-length, fragments, etc.). The term "connected" refers to the joining of the linking sequence to the polypeptide sequence of interest. Such polypeptide sequences are preferably joined by one or more peptide bonds. Linking sequences can have a length of from about 4 to about 50 amino acids. Preferably, the length of the linking sequence is from about 6 to about 30 amino acids. Natural linking sequences can be modified by amino acid substitutions, additions, or deletions to create artificial linking sequences. Exemplary linking sequences include, but are not limited to:

(i) Histidine (His) tags, such as a 6× His tag, which has an amino acid sequence of HHHHHH (SEQ ID NO:116), are useful as linking sequences to facilitate the isolation and purification of polypeptides and antibodies of interest; (ii) Enterokinase cleavage sites, like His tags, are used in the isolation and purification of proteins and antibodies of interest. Often, enterokinase cleavage sites are used together with His tags in the isolation and purification of proteins and antibodies of interest. Various enterokinase cleavage sites are known in the art. Examples of enterokinase cleavage sites include, but are not limited to, the amino acid sequence of DDDDK (SEQ ID NO:117) and derivatives thereof (e.g., ADDDDK (SEQ ID NO:118), etc.); (iii) Miscellaneous sequences can be used to link or connect the light and/or heavy chain variable regions of single chain variable region fragments. Examples of other linking sequences can be found in Bird et al., Science 242: 423-426 (1988); Huston et al., PNAS USA 85: 5879-5883 (1988); and McCafferty et al., Nature 348: 552-554 (1990). Linking sequences also can be modified for additional functions, such as attachment of drugs or attachment to solid supports. In the context of the present disclosure, the CFH inhibitor, such as the anti-CFH antibody, for example, can contain a linking sequence, such as a His tag, an enterokinase cleavage site, or both.

"Lung cancer" as used herein refers to cancer that originates in the lung. For example, lung cancer may be cancer of the lung, such as small-cell lung cancer, also known as small-cell lung carcinoma and oat cell cancer, non-small-cell lung carcinoma ("NSCLC"), glandular tumors, carcinoid tumors and undifferentiated carcinomas.

"Non-small-cell lung carcinoma" or "NSCLC" as used interchangeably herein refers to any type of epithelial lung cancer other than small cell lung carcinoma. The three main subtypes of NSCLC are adenocarcinoma, including bronchioloalveolar carcinoma, squamous-cell lung carcinoma, and large-cell lung carcinoma. NSCLCs are relatively insensitive to chemotherapy.

"Monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological properties.

"Multivalent binding protein" is used herein to refer to a binding protein comprising two or more antigen binding sites (also referred to herein as "antigen binding domains"). A multivalent binding protein is preferably engineered to have three or more antigen binding sites, and is generally not a naturally occurring antibody. The term "multispecific binding protein" refers to a binding protein that can bind two or more related or unrelated targets, including a binding protein capable of binding two or more different epitopes of the same target molecule.

"Recombinant antibody" and "recombinant antibodies" refer to antibodies prepared by one or more steps, including cloning nucleic acid sequences encoding all or a part of one or more monoclonal antibodies into an appropriate expression vector by recombinant techniques and subsequently expressing the antibody in an appropriate host cell. The terms include, but are not limited to, recombinantly produced monoclonal antibodies, chimeric antibodies, humanized antibodies (fully or partially humanized), multi-specific or multi-valent structures formed from antibody fragments, bifunctional antibodies, heteroconjugate Abs, DVD-Ig®s, and other antibodies as described in (i) herein. (Dual-variable domain immunoglobulins and methods for making them are described in Wu, C., et al., Nature Biotechnology, 25:1290-1297 (2007)). The term "bifunctional antibody," as used herein, refers to an antibody that comprises a first arm having a specificity for one antigenic site and a second arm having a specificity for a different antigenic site, i.e., the bifunctional antibodies have a dual specificity.

"Sample," "test sample," "specimen," "sample from a subject," and "patient sample" as used herein may be used interchangeable and may be a sample of blood, tissue, urine, serum, plasma, amniotic fluid, cerebrospinal fluid, placental cells or tissue, endothelial cells, leukocytes, or monocytes. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

Any cell type, tissue, or bodily fluid may be utilized to obtain a sample. Such cell types, tissues, and fluid may include sections of tissues such as biopsy and autopsy samples, frozen sections taken for histologic purposes, blood (such as whole blood), plasma, serum, sputum, stool, tears, mucus, saliva, bronchoalveolar lavage (BAL) fluid, hair, skin, red blood cells, platelets, interstitial fluid, ocular lens fluid, cerebral spinal fluid, sweat, nasal fluid, synovial fluid, menses, amniotic fluid, semen, etc. Cell types and tissues may also include lymph fluid, ascetic fluid, gynecological fluid, urine, peritoneal fluid, cerebrospinal fluid, a fluid collected by vaginal rinsing, or a fluid collected by vaginal flushing. A tissue or cell type may be provided by removing a sample of cells from an animal, but can also be accomplished by using previously isolated cells (e.g., isolated by another person, at another time, and/or for another purpose). Archival tissues, such as those having treatment or outcome history, may also be used. Protein or nucleotide isolation and/or purification may not be necessary.

"Small consensus repeat" or "SCR" as used interchangeably herein refers to a structure based on a beta-sandwich arrangement where one face is made up of three beta-strands hydrogen bonded to form a triple stranded region at its center and the other face formed from two separate beta-strands. SCRs are also called complement control protein (CCP) modules and sushi domains. SCRs exist in a wide variety of complement and adhesion proteins. As used herein, "SCR19" refers to short consensus repeat domain 19 and "SCR19-20" refers to short consensus repeat domains 19 and 20, covalently linked to one another as in the parent molecule, CFH.

"Specific binding" or "specifically binding" as used herein may refer to the interaction of an antibody, a protein, or a peptide with a second chemical species, wherein the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A," the presence of a molecule containing epitope A (or free, unlabeled A), in a reaction containing labeled "A" and the antibody, will reduce the amount of labeled A bound to the antibody.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. The subject or patient may be undergoing other forms of treatment.

"Target region" or "molecular target" as used interchangeably herein refers to a region of CFH to which, for example, CFH inhibitors, such as the anti-CFH antibodies, may bind. For example, the target region may include SCR 19 and/or the amino acid sequence of PIDNGDIT (SEQ ID NO:3). The target region may include a 15-mer peptide of GPPP-PIDNGDITSFP (SEQ ID NO:114).

"Treat," "treating" or "treatment" are each used interchangeably herein to describe reversing, alleviating, or inhibiting the progress of a disease, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of an antibody or pharmaceutical composition of the present invention to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

"Variant" is used herein to describe a peptide or polypeptide that differs in amino acid sequence by the insertion, deletion, or conservative substitution of amino acids, but retains at least one biological activity. Representative examples of "biological activity" include the ability to be bound by a specific antibody or to promote an immune response. Variant is also used herein to describe a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree, and distribution of charged regions) is recognized in the art as typically involving a minor change. These minor changes can be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. "Variant" also can be used to refer to an antigenically reactive fragment of an anti-CFH antibody that differs from the corresponding fragment of anti-CFH antibody in amino acid sequence but is still antigenically reactive and can compete with the corresponding fragment of anti-CFH antibody for binding with CFH. "Variant" also can be used to describe a polypeptide or a fragment thereof that has been differentially processed, such as by proteolysis, phosphorylation, or other post-translational modification, yet retains its antigen reactivity.

Unless otherwise defined herein, scientific, and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

CFH Inhibitors

Provided herein are inhibitors for use in methods of treating cancer, such as lung cancer. The inhibitor may be an isolated antibody or a small molecule that specifically binds to CFH, such as a reduced form of CFH, or fragments thereof.

CFH

Complement factor H is one of a class of complement inhibitory factors that protect both normal and tumor cells from attack and destruction by the alternative complement pathway by inactivating C3b, a protein that is essential for formation of a cell lytic complex on a cell surface. The primary function of CFH is to inhibit the alternative pathway of complement-mediated lysis. CFH prevents the deposition of complement protein C3b on the cell surface by (a) acting as a cofactor for complement factor I (CFI), a protease that cleaves C3b, and (b) preventing the formation of and accelerating the decay of the enzyme that forms C3b from its precursor, C3. Deposition of C3b initiates the formation of the cell-lytic membrane attack complex, leading to cell lysis; thus, control of the deposition of C3b on the cell surface by CFH protects against cell lysis. CFH engages with C3b (or degraded C3b, named C3d) on mammalian cell surfaces that contain glycosaminoglycans and sialic acid, as opposed to bacterial surfaces lacking these groups, thus mediating target discrimination. Besides protecting normal host cells, CFH has been shown to protect tumor cells, including those from NSCLC, glioblastoma, and colon cancer cells, from complement attack.

Human CFH may have the following amino acid sequence:

(SEQ ID NO: 1; UniProt P08603)
MRLLAKIICLMLWAICVAEDCNELPPRRNTEILTGSWSDQTYPEGTQATY

KCRPGYRSLGNVIMVCRKGEWVALNPLRKCQKRPCGHPGDTPFGTFTLTG

GNVFEYGVKAVYTCNEGYQLLGEINYRECDTDGWTNDIPICEVVKCLPVT

APENGKIVSSAMEPDREYHFGQAVREVCNSGYKIEGDEEMHCSDDGEWSK

EKPKCVEISCKSPDVINGSPISQKITYKENERFQYKCNMGYEYSERGDAV

CTESGWRPLPSCEEKSCDNPYIPNGDYSPLRIKHRTGDEITYQCRNGFYP

ATRGNTAKCTSTGWIPAPRCTLKPCDYPDIKHGGLYHENMRRPYFPVAVG

KYYSYYCDEHFETPSGSYWDHIHCTQDGWSPAVPCLRKCYFPYLENGYNQ

NYGRKFVQGKSIDVACHPGYALPKAQTTVTCMENGWSPTPRCIRVKTCSK

SSIDIENGFISESQYTYALKEKAKYQCKLGYVTADGETSGSITCGKDGWS

AQPTCIKSCDIPVFMNARTKNDFTWFKLNDTLDYECHDGYESNTGSTTGS

IVCGYNGWSDLPICYERECELPKIDVHLVPDRKKDQYKVGEVLKESCKPG

FTIVGPNSVQCYHEGLSPDLPICKEQVQSCGPPPELLNGNVKEKTKEEYG

HSEVVEYYCNPRELMKGPNKIQCVDGEWTTLPVCIVEESTCGDIPELEHG

WAQLSSPPYYYGDSVEENCSESFTMIGHRSITCIHGVWTQLPQCVAIDKL

KKCKSSNLIILEEHLKNKKEEDHNSNIRYRCRGKEGWIHTVCINGRWDPE

VNCSMAQIQLCPPPPQIPNSHNMTTTLNYRDGEKVSVLCQENYLIQEGEE

ITCKDGRWQSIPLCVEKIPCSQPPQIEHGTINSSRSSQESYAHGTKLSYT

CEGGFRISEENETTCYMGKWSSPPQCEGLPCKSPPEISHGVVAHMSDSYQ

YGEEVTYKCFEGEGIDGPAIAKCLGEKWSHPPSCIKTDCLSLPSFENAIP

MGEKKDVYKAGEQVTYTCATYYKMDGASNVTCINSRWTGRPTCRDTSCVN

PPTVQNAYIVSRQMSKYPSGERVRYQCRSPYEMFGDEEVMCLNGNWTEPP

QCKDSTGKCGPPPPIDNGDITSFPLSVYAPASSVEYQCQNLYQLEGNKRI

TCRNGQWSEPPKCLHPCVISREIMENYNIALRWTAKQKLYSRTGESVEFV

CKRGYRLSSRSHTLRTTCWDGKLEYPTCAKR.

The CFH may be reduced or not reduced.

The human CFH may be a fragment or variant of SEQ ID NO:1. The fragment or variant may be reduced or not reduced form. The fragment of CFH may be between 5 and 1230 amino acids, between 10 and 1000 amino acids, between 10 and 750 amino acids, between 10 and 500 amino acids, between 50 and 400 amino acids, between 60 and 400 amino acids, between 65 and 400 amino acids, between 100 and 400 amino acids, between 150 and 400 amino acids, between 100 and 300 amino acids, or between 200 and 300 amino acids in length. The fragment may comprise a contiguous number of amino acids from SEQ ID NO:1.

The fragment of human CFH may have the following amino acid sequence: GKCGPPPPIDNGDITSFPLSVYAPASSVEYQCQNLYQLEGNKRITCRNGQWSEPPKCLH (SEQ ID NO:2), which correspond to amino acids 1107-1165 of SEQ ID NO:1. The fragment of human CFH may have the following amino acid sequence GPPPPIDNGDITSFP (SEQ ID NO:114).

Reduced Form of CFH

The reduced form of CFH may reveal a cryptic epitope or cryptic target region. This epitope or target region may be revealed only on the surface of tumor cells. CFH may be an autoantigen due to the presentation of the cryptic epitope in the tumor microenvironment. NSCLC tumors exhibit elevated levels of thioredoxin, the disulfide reductase macrophage migration inhibitory factor, and non-protein thiols such as reduced cysteine and glutathione. These factors contribute to the production of a more reducing environment in the tumor than in normal tissues. Thus, the anti-CFH epitope(s) may be hidden and only exposed upon reduction of the protein in the intratumoral space. Alternatively, once the soluble form of CFH binds to the tumor cell, the protein may unfold and bind in a tumor cell-specific conformation so that it becomes antigenic; reduction in vitro may simply put CFH in a conformation that mimics this state.

Target Region

The target region for the CFH inhibitor, such as the anti-CFH antibody, which may be cryptic, may be SCR 19 (SEQ ID NO: 2), which is involved with CFH function. SCR19 contains binding sites for C3b/C3d and polyanions typical of self- or auto-surfaces. SCR19 is a domain that is involved in the host cell-protective function of CFH as it is involved in binding to the C3d portion of C3b. The target region may be an epitope of PIDNGDIT (SEQ ID NO:3), which resides in SCR19. The target region may include the D1119 residue of SEQ ID NO:1, which is also residue 6 of SEQ ID NO:3. The target region may include the 15-mer peptide of GPPPPIDNGDITSFP (SEQ ID NO:114)

CFH-Recognizing Antibodies

The antibody is an antibody that binds to the reduced form of CFH, a fragment thereof, an epitope of CFH, or a variant thereof. The antibody may be a fragment of the anti-CFH antibody or a variant or a derivative thereof. The antibody may be a polyclonal or monoclonal antibody. The antibody may be a chimeric antibody, a single chain antibody, an affinity matured antibody, a human antibody, a humanized antibody, a fully human antibody or an antibody fragment, such as a Fab fragment, or a mixture thereof. Antibody fragments or derivatives may comprise F(ab')$_2$, Fv or scFv fragments. The antibody derivatives can be produced by peptidomimetics. The anti-CFH antibodies may be human-derived antibodies. Further, techniques described or the production of single chain antibodies can be adapted to produce single chain antibodies. The antibody may or may not be generated from a human in vivo immune response. For example, the antibody may or may not be an autoantibody.

The anti-CFH antibodies may be a chimeric anti-CFH or humanized anti-CFH antibody. In one embodiment, both the humanized antibody and chimeric antibody are monovalent. In one embodiment, both the humanized antibody and chimeric antibody comprise a single Fab region linked to an Fc region.

Human antibodies may be derived from phage-display technology or from transgenic mice that express human immunoglobulin genes. The antibody may be generated as a result of a human in vivo immune response and isolated. See, for example, Funaro et al., BMC Biotechnology, 2008 (8):85. Therefore, the antibody may be a product of the human and not animal repertoire. Because it is of human origin, the risks of reactivity against self-antigens may be minimized. Alternatively, standard yeast display libraries and display technologies may be used to select and isolate human anti-CFH antibodies. For example, libraries of naïve human single chain variable fragments (scFv) may be used to select human anti-CFH antibodies. Transgenic animals may be used to express human antibodies.

Humanized antibodies may be antibody molecules from non-human species antibody that binds the desired antigen having one or more complementarity determining regions (CDRs) from the non-human species and framework regions from a human immunoglobulin molecule.

The antibody is distinguishable from known antibodies in that it possesses different biological function(s) than those known in the art.

Epitope

A CFH antibody may immunospecifically bind to a reduced or non-reduced form of any one or more of epitopes within SEQ ID NOs:1-3, 114, or 119-132, a fragment thereof, or a variant thereof. The antibody may immunospecifically recognize and bind at least three amino acids, at least four amino acids, at least five amino acids, at least six amino acids, or at least seven amino acids within the epitope peptide of PIDNGDIT (SEQ ID NO:3) or GPPP-PIDNGDITSFP (SEQ ID NO:14). The antibody may immunospecifically recognize and bind to an epitope that has at least three contiguous amino acids, at least four contiguous amino acids, at least five contiguous amino acids, at least six contiguous amino acids, at least seven contiguous amino acids, at least eight contiguous amino acids, at least nine contiguous amino acids, or at least ten contiguous amino acids of SEQ ID NO: 1 or 2. The contiguous amino acids may include amino acid D1119 of SEQ ID NO:1.

Antibody Binding Characteristics

The antibody may immunospecifically bind to CFH (SEQ ID NO:1), SCR19 (SEQ ID NO:2), the amino acid sequence of PIDNGDIT (SEQ ID NO:3), the amino acid sequence of GPPPPIDNGDITSFP (SEQ ID NO:114), a fragment thereof, or a variant thereof and have an off-rate ($k_d$) of about $1.0 \times 10^{-4}$ s$^{-1}$ or less, about $1.0 \times 10^{-5}$ s$^{-1}$ or less, about $5.0 \times 10^{-6}$ s$^{-1}$ or less, about $1.0 \times 10^{-6}$ s$^{-1}$ or less, about $5.0 \times 10^{-7}$ s$^{-1}$ or less, about $1.0 \times 10^{-7}$ s$^{-1}$ or less, about $5.0 \times 10^{-8}$ s$^{-1}$ or less, about $1.0 \times 10^{-8}$ s$^{-1}$ or less, about $1.0 \times 10^{-9}$ s$^{-1}$ or less, about $1.0 \times 10^{-10}$ s$^{-1}$ or less, about $1.0 \times 10^{-11}$ s$^{-1}$ or less, about $1.0 \times 10^{-12}$ s$^{-1}$ or less, or has a kd ranging from about $1.0 \times 10^{-12}$ s$^{-1}$ to about $1.0 \times 10^{-4}$ s$^{-1}$, about $1.0 \times 10^{-12}$ s$^{-1}$ to about $1.0 \times 10^{-5}$ s$^{-1}$, about $1.0 \times 10^{-12}$ s$^{-1}$ to about $1.0 \times 10^{-6}$ s$^{-1}$, about $1.0 \times 10^{-12}$ s$^{-1}$ to about $1.0 \times 10^{-7}$ s$^{-1}$, about $1.0 \times 10^{-12}$ s$^{-1}$ to about $1.0 \times 10^{-8}$ s$^{-1}$, about $1.0 \times 10^{-12}$ s$^{-1}$ to about $1.0 \times 10^{-9}$ s$^{-1}$, about $1.0 \times 10^{-12}$ s$^{-1}$ to about $1.0 \times 10^{-10}$ s$^{-1}$, about $1.0 \times 10^{-10}$ s$^{-1}$ to about $1.0 \times 10^{-4}$ s$^{-1}$, about $1.0 \times 10^{-10}$ s$^{-1}$ to about $1.0 \times 10^{-5}$ s$^{-1}$, about $1.0 \times 10^{-10}$ s$^{-1}$ to about $1.0 \times 10^{-6}$ s$^{-1}$, about $1.0 \times 10^{-10}$ s$^{-1}$ to about $1.0 \times 10^{-7}$ s$^{-1}$, about $1.0 \times 10^{-10}$ s$^{-1}$ to about $1.0 \times 10^{-8}$ s$^{-1}$, about $1.0 \times 10^{-8}$ s$^{-1}$ to about $1.0 \times 10^{-4}$ s$^{-1}$, about $1.0 \times 10^{-8}$ s$^{-1}$ to about $1.0 \times 10^{-5}$ s$^{-1}$, about $1.0 \times 10^{-8}$ s$^{-1}$ to about $1.0 \times 10^{-6}$ s$^{-1}$, about $1.0 \times 10^{-8}$ s$^{-1}$ to about $1.0 \times 10^{-7}$ s$^{-1}$, about $1.0 \times 10^{-7}$ s$^{-1}$ to about $1.0 \times 10^{-4}$ s$^{-1}$, about $1.0 \times 10^{-7}$ s$^{-1}$ to about $1.0 \times 10^{-5}$ s$^{-1}$, or about $1.0 \times 10^{-7}$ s$^{-1}$ to about $1.0 \times 10^{-6}$ s$^{-1}$. The fragment may be SEQ ID NO:114 or SEQ ID NO:115.

The antibody may immunospecifically bind to CFH (SEQ ID NO:1), SCR19 (SEQ ID NO:2), the amino acid sequence of PIDNGDIT (SEQ ID NO:3), the amino acid sequence of GPPPPIDNGDITSFP (SEQ ID NO:114), a fragment thereof, or a variant thereof and have an on-rate ($k_a$) of at least about $1.0 \times 10^{3}$ M$^{-1}$s$^{-1}$, at least about $1.0 \times 10^{4}$ M$^{-1}$s$^{-1}$, at least about $5.0 \times 10^{4}$ M$^{-1}$s$^{-1}$, at least about $1.0 \times 10^{5}$ M$^{-1}$s$^{-1}$, at least about $2.0 \times 10^{5}$ M$^{-1}$s$^{-1}$, at least about $3.0 \times 10^{5}$ M$^{-1}$s$^{-1}$, at least about $4.0 \times 10^{5}$ M$^{-1}$s$^{-1}$, at least about $5.0 \times 10^{5}$ M$^{-1}$s$^{-1}$, least about $6.0 \times 10^{5}$ M$^{-1}$s$^{-1}$, at least about $1.0 \times 10^{6}$ M$^{-1}$s$^{-1}$, at least about $1.0 \times 10^{7}$ M$^{-1}$s$^{-1}$, at least about $1.0 \times 10^{8}$ M$^{-1}$s$^{-1}$, or has a $k_a$ ranging from about $1.0 \times 10^{3}$ M$^{-1}$s$^{-1}$ to about $1.0 \times 10^{8}$ M$^{-1}$s$^{-1}$, about $1.0 \times 10^{4}$ M$^{-1}$s$^{-1}$ to about $1.0 \times 10^{8}$ M$^{-1}$s$^{-1}$, about $1.0 \times 10^{5}$ M$^{-1}$s$^{-1}$ to about $1.0 \times 10^{8}$ M$^{-1}$s$^{-1}$, about $1.0 \times 10^{6}$ M$^{-1}$s$^{-1}$ to about $1.0 \times 10^{8}$ M$^{-1}$s$^{-1}$, about $1.0 \times 10^{7}$ M$^{-1}$s$^{-1}$ to about $1.0 \times 10^{8}$ M$^{-1}$s$^{-1}$, about $1.0 \times 10^{3}$ M$^{-1}$s$^{-1}$ to about $1.0 \times 10^{7}$ M$^{-1}$s$^{-1}$, about $1.0 \times 10^{4}$ M$^{-1}$s$^{-1}$ to about $1.0 \times 10^{7}$ M$^{-1}$s$^{-1}$, about $1.0 \times 10^{5}$ M$^{-1}$s$^{-1}$ to about $1.0 \times 10^{7}$ M$^{-1}$s$^{-1}$, about $1.0 \times 10^{6}$ M$^{-1}$s$^{-1}$ to about $1.0 \times 10^{7}$ M$^{-1}$s$^{-1}$, about $1.0 \times 10^{4}$ M$^{-1}$s$^{-1}$ to about $1.0 \times 10^{7}$ M$^{-1}$s$^{-1}$, about $1.0 \times 10^{4}$ M$^{-1}$s$^{-1}$ to about $1.0 \times 10^{6}$ M$^{-1}$s$^{-1}$, about $1.0 \times 10^{4}$ M$^{-1}$s$^{-1}$ to about $1.0 \times 10^{5}$ M$^{-1}$s$^{-1}$, about $1.0 \times 10^{5}$ M$^{-1}$s$^{-1}$ to about $1.0 \times 10^{7}$ M$^{-1}$s$^{-1}$, or about $1.0 \times 10^{5}$ M$^{-1}$s$^{-1}$ to about $1.0 \times 10^{6}$ M$^{-1}$s$^{-1}$. The fragment may be SEQ ID NO:114 or SEQ ID NO:115.

The antibody may immunospecifically bind to CFH (SEQ ID NO:1), SCR19 (SEQ ID NO:2), the amino acid sequence of PIDNGDIT (SEQ ID NO:3), the amino acid sequence of GPPPPIDNGDITSFP (SEQ ID NO:114), a fragment thereof, or a variant thereof and have an affinity ($K_D$) of at least about $1.0 \times 10^{-15}$ M, at least about $1.0 \times 10^{-14}$ M, at least about $1.0 \times 10^{-13}$ M, at least about $1.5 \times 10^{-13}$ M, at least about $1.0 \times 10^{-12}$ M, at least about $1.6 \times 10^{-12}$ M, at least about $1.7 \times 10^{-12}$ M, at least about $1.8 \times 10^{-12}$ M, at least about $1.9 \times 10^{-12}$ M, at least about $2.0 \times 10^{-12}$ M, at least about $2.1 \times 10^{-12}$ M, at least about $2.2 \times 10^{-12}$ M, at least about $2.3 \times 10^{-12}$ M, at least about $2.4 \times 10^{-12}$ M, at least about $2.5 \times 10^{-12}$ M, at least about $2.6 \times 10^{-12}$ M, at least about $2.7 \times 10^{-12}$ M, at least about $2.8 \times 10^{-12}$ M, at least about $2.9 \times 10^{-12}$ M, at least about $3.0 \times 10^{-12}$ M, at least about $5.0 \times 10^{-12}$ M, at about least $1.0 \times 10^{-11}$ M, at least about $1.5 \times 10^{-11}$ M, at least about $5.0 \times 10^{-11}$ M, at least about $1.0 \times 10^{-10}$ M, at least about $5.0 \times 10^{-10}$ M, at least about $1.0 \times 10^{-9}$ M, or has a KD ranging from about $1.0 \times 10^{-15}$ M to about $1.0 \times 10^{-9}$ M, about $1.0 \times 10^{-15}$ M to about $1.0 \times 10^{-10}$ M, about $1.0 \times 10^{-15}$ M to about $1.0 \times 10^{-11}$ M, about $1.0 \times 10^{-15}$ M to about $1.0 \times 10^{-12}$ M, about $1.0 \times 10^{-15}$ M to about $1.0 \times 10^{-13}$ M, about $1.0 \times 10^{-14}$ M to about $1.0 \times 10^{-9}$ M, about $1.0 \times 10^{-14}$ M to about $1.0 \times 10^{-10}$ M, about $1.0 \times 10^{-14}$ M to about $1.0 \times 10^{-11}$ M, about $1.0 \times 10^{-14}$ M to about $1.0 \times 10^{-12}$ M, about $1.0 \times 10^{-14}$ M to about $1.0 \times 10^{-13}$ M, about $1.0 \times 10^{-13}$ M to about $1.0 \times 10^{-9}$ M, about $1.0 \times 10^{-13}$ M to about $1.0 \times 10^{-10}$ M, about $1.0 \times 10^{-13}$ M to about $1.0 \times 10^{-11}$ M, about $1.0 \times 10^{-13}$ M to about $1.0 \times 10^{-12}$ M, about $1.0 \times 10^{-12}$ M to about $1.0 \times 10^{-9}$ M, about $1.0 \times 10^{-12}$ M to about $1.0 \times 10^{-10}$ M, or about $1.0 \times 10^{-12}$ M to about $1.0 \times 10^{-11}$ M. The fragment may be SEQ ID NO:114 or SEQ ID NO:115.

The binding of the antibody to CFH may be sensitive to the reduced form of CFH. An antibody that is sensitive to the reduced form of CFH means that the antibody's binding affinity to CFH changes depending on whether the CFH is in the reduced form or not reduced form. For example, an antibody whose binding is sensitive to the CFH being in the reduced form or not reduced form may have lower binding affinity to CFH if the CFH is not in the reduced form. Alternatively, an antibody whose binding is sensitive to the CFH being in the reduced form or not reduced form may have lower binding affinity to CFH if the CFH is in the reduced form. An antibody that is insensitive to the CFH being in the reduced form or not reduced form means that the antibody's binding affinity to CFH does not change if the CFH is in the reduced form or not reduced form.

Heavy and Light Chain Sequences

The antibody may immunospecifically bind to CFH (SEQ ID NO:1), SCR19 (SEQ ID NO:2), the amino acid sequence of PIDNGDIT (SEQ ID NO:3), the amino acid sequence of GPPPPIDNGDITSFP (SEQ ID NO: 114), a fragment thereof, or a variant thereof and comprise a variable heavy chain (VH) and/or variable light chain (VL) shown in Tables 1 and 2. The antibody may have a HCDR3 region as indicated by the underlined amino acid residues in Tables 1 and 2. The light chain of the antibody may be a kappa chain (VLK) or a lambda chain (VLL).

TABLE 1

| Protein | Region | SEQ ID NO. | Sequence |
|---|---|---|---|
| H007970 | (VH) | 4 | LVESGGGVVQPGRSLRLSCAASGLTFSFYNFHWVRQTPGKGLEWVAGISYD ATRTNYAGSVTGRFTISRDNSKKMLYLQMSSLGPQDTAVYHCARDRSDGQL HKVAFDSWGQGALVTVSS |
| H007955 | (VH) | 5 | LVESGGGVVRPGRSLRLSCVASGFTFNAYGMHWVRQGPGKGLEWLAVISYE GKTVYYADSVKDRFTISRDNSRNTVSLHLNNLRGEDTAVYYCAKGSASAAV LQHWGQGTLVSVTS |
| H007957 | (VH) | 6 | LVESGGGVVPPGKSLRLSCAASGFTFSLYGIHWVRQAPGKGLEWVAVISYD GNTKYYTDSVKGRFTISRDNAKNTIYLQMNSLRLDDTAVYYCAKGAANSAT FDFWGRGTMVTVSS |
| H007958 | (VH) | 7 | LVESGGGVVPPGKSLRLSCAASGFTFSLYGIHWVRQAPGKGLEWVAVISYD GNTKYYTDSVKGRFTISRDNAKNTIYLQMNSLRLDDTAVYYCAKGAANSAT FDFWGRGTMVTVSS |
| H007963 | (VH) | 8 | LVESGGGVVPPGKSLRLSCAASGFTFSLYGIHWVRQAPGKGLEWVAVISYD GNTKYYTDSVKGRFTISRDNAKNTIYLQMNSLRLDDTAVYYCAKGAANSAT FDFWGRGTMVTVSS |
| H007982 | (VH) | 9 | LVESGGGVVPPGKSLRLSCAASGFTFSLYGIHWVRQAPGKGLEWVAVISYD GNTKYYTDSVKGRFTISRDNAKNTIYLQMNSLRLDDTAVYYCAKGAANSAT FDFWGRGTMVTVSS |
| H007960 | (VH) | 10 | LVESGGGVVQPGKSLRLSCVASGFSFSTYGMHWVRQAPGKGLEWVAVMSFD GKTKYYADSVKGRFTISRDNPKNTLYLQMNSLRSEDTAVYYCAKGGAAAAV FDSWGPGILLTVSS |
| H007967 | (VH) | 11 | LVESGGGVVQPGKSLRLSCVASGFSFSTYGMHWVRQAPGKGLEWVAVMSFD GKTKYYADSVKGRFTISRDNPKNTLYLQMNSLRSEDTAVYYCAKGGAAAAV FDSWGPGILLTVSS |
| H007964 | (VH) | 12 | LVESGGGVVQPGRSLRLSCAASGVTFSRYGMHWVRQAPGKGLEWVAVISYD EKTKYYADSVKGRFTISRDNSKNTLFLHMNRLRYEDTAVYYCAKGASSGAY FDYWGQGTLVTVSS |
| H007979 | (VH) | 13 | LVESGGGVVQPGKSLRLSCVASGFTFSTYGMHWVRQAPGKGLEWVAVMSFD GKTKYYADSVKGRFTISRDNPKNTLYLQMNSLRSEDTAVYYCAKGGAAAAV FDSWGQGILLTVSS |
| H007961 | (VH) | 14 | LVESGGGVVQPGKSLRLSCVASGFTFSSYGMHWVRQAPGKGLEWVAVMSFD GKTKYYADSVKGRFTISRDNPKNTLYLQMNSLRSEDTAVYYCAKGGAAAAV FDSWGQGILLTVSS |
| H007965 | (VH) | 15 | LVESGGGVVQPGKSLRLSCVASGFTFSSYGMHWVRQAPGKGLEWVAVMSFD GKTKYYADSVKGRFTISRDNPKNTLYLQMNSLRSEDTAVYYCAKGGAAAAV FDSWGQGILLTVSS |
| H007968 | (VH) | 16 | LVESGGGVVQPGRSLRLSCAASGFTFSRYGMHWVRQAPGKGLEWVAVMSYD GSTKYYADSVKGRFAISRDNPKNTLFLQMNSLRPDDTAVYYCAKGGAAAAV MDVWGKGTTVTVSS |
| H007971 | (VH) | 17 | LVESGGGVVQPGRSLRLSCAASGFTFSRYGMHWVRQAPGKGLEWVAVMSYD GSTKYYADSVKGRFAISRDNPKNTLFLQMNSLRPDDTAVYYCAKGGAAAAV MDVWGKGTTVTVSS |
| H007983 | (VH) | 18 | EVQLVESGGGVVQPGRSLRLSCAASGFTFNRFGMHWVRQRQVPGKGLEWVA VISYDDNTKYYADSVKGRFTISRDNNKSTLYLQMSSLRVEDTAVYFCAKGS TAAAVLDYWGQGTLVTVSS |
| H007962 | (VH) | 19 | LVESGGGLVQPGGSLRLSCAASGFTFSSYEMNWVRQAPGKGLEWVSYISSS GSTIYYADSVKGRFTISRDNAKNSLYLQMNSLRAEDTAVYYCARVEQLAPS PYMDVWGKGTTVTVSS |
| H007966 | (VH) | 20 | QVQLVQSGAEVKKPGESLKIS~KGSGYSFTSYWIGWVRQMPGKGLEWMGII YPGDSDTRYSPSFQGQVTISADKSISTAYLQWSSLKASDTAMYYCARRGLR GAYYYYGMDVWGQGTTVTVSS |
| K006004 | (VL$_K$) | 21 | MTQSPDSLTLSLGERATINCRSSRTVLYRSNNKNYLAWYQHKPGQPPKLLM SWASTRETGVPDRFSGSGSGTHFTLTITSLQPEDVAVYYCQQYYSPPWTFG QGTKVEIR |

TABLE 1-continued

| Protein | Region | SEQ ID NO. | Sequence |
|---|---|---|---|
| K005989 | (VL_K) | 22 | MTQSPGSLAVSLGSRATINCKSSRSLLYRSNNKNYLAWYQQKPGQSPRLLI YWASSRESGVPDRFSGGGSTSFTLTISSLQAEDVAVYYCQQYFNPPWTFG QGTKVEIK |
| K005991 | (VL_K) | 23 | MTQSPDSLTLSLGERATINCRSSRTVLYRSNNKNYLAWYQHKPGQPPKLLM SWASTRETGVPDRFSGSGSGTHFTLTITSLQPEDVAVYYCQQYYSPPWTFG QGTKVEIR |
| K005992 | (VL_K) | 24 | MTQSPDSLTLSLGERATINCRSSRTVLYRSNNKNYLAWYQHKPGQPPKLLM SWASTRETGVPDRFSGSGSGTHFTLTITSLQPEDVAVYYCQQYYSPPWTFG QGTKVEIR |
| K005998 | (VL_K) | 25 | MTQSPDSLTLSLGERATINCRSSRTVLYRSNNKNYLAWYQHKPGQPPKLLM SWASTRETGVPDRFSGSGSGTHFTLTITSLQPEDVAVYYCQQYYSPPWTFG QGTKVEIR |
| K006018 | (VL_K) | 26 | MTQSPDSLTLSLGERATINCRSSRTVLYRSNNKNYLAWYQHKPGQPPKLLM SWASTRETGVPDRFSGSGSGTHFTLTITSLQPEDVAVYYCQQYYSPPWTFG QGTKVEIR |
| K005994 | (VL_K) | 27 | MTQSPNSLAVSLGGRATINCKASQSILYRSNNKNYLAWYQHKAGQPPKLLI YWASTRESGVPERFSGSGSRTDFTLTINGLQAEDVAVYYCQQYYNPPWTFG QGTKVEIK |
| K006002 | (VL_K) | 28 | MTQSPNSLAVSLGGRATINCKASQSILYRSNNKNYLAWYQHKAGQPPKLLI YWASTRESGVPERFSGSGSRTDFTLTINGLQAEDVAVYYCQQYYNPPWTFG QGTKVEIK |
| K005999 | (VL_K) | 29 | MTQSPDSLAVSLGERATIKCKSSQSVLYSSNNKNYLAWYQHKPGQPPKVLV YWASTRESGVPDRFSGSGSGTDFTLTISSLQAEDVAVYYCQQYYNPPWTFG QGTKVAIK |
| K006015 | (VL_K) | 30 | MTQSPNSLAVSLGGRATINCKTSQSILYRSNNKNYLAWYQHKPGQPPKLLI YWASTRESRVPDRFSGSGSRTDFTLTISGLQAEDVAVYYCQQYYNPPWTFG QGTKVEIK |
| K005995 | (VL_K) | 31 | MTQSPNSLAVSLGGRATINCKTSQSILYRSNNKNYLAWYQHKSGQPPKLLI YWASTRESGVPDRFSGSGSRTDFTLTISGLQAEDVAVYYCQQYYNPPWTFG QGTKVEIK |
| K006000 | (VL_K) | 32 | MTQSPNSLAVSLGGRATINCKTSQSILYRSNNKNYLAWYQHKSGQPPKLLI YWASTRESGVPDRFSGSGSRTDFTLTISGLQAEDVAVYYCQQYYNPPWTFG QGTKVEIK |
| K006003 | (VL_K) | 33 | MTQSPDSLTVSLGERATISCKSSQRLLYSSNNKNYLAWYQQKPGQPPKLLM YWASTRESGVPDRFSGSGSGTDFSLTISSLQAEDVAVYYCQQYYNPPWTFG QGTKVEVK |
| K006005 | (VL_K) | 34 | MTQSPDSLTVSLGERATISCKSSQRLLYSSNNKNYLAWYQQKPGQPPKLLM YWASTRESGVPDRFSGSGSGTDFSLTISSLQAEDVAVYYCQQYYNPPWTFG QGTKVEVK |
| K006019 | (VL_K) | 35 | DIVMTQSPDSLTLSLGERATINCKSSQSLFYRSNNKSYLAWYQQKPGQPPK LLIYWASVRESGVPDRFTGSGSVTDFTLTISSLRAEDVAVYYCQQYFTTPL TFGGGTKVAIK |
| K005996 | (VL_K) | 36 | MTQSLDSLTVSLGERATINCKSSQSLLYTSNNKNYLAWYQQKSGQPPKLLI YWASIRDSGVPDRFSGSGSATDFTLTINNLQAEDVAVYFCQQYYKTPLTFG GGTKVEVR |
| K006001 | (VL_K) | 37 | DIQXTQSPSTLSASVGDRVTITCRASQSISSWLAWYQQKPGKAPKLLIYKA SSLESGVPSRFSGSGSGTEFTLTISSLQPDDFATYYCQQYNSYSWTFGQGT KVEIK |

TABLE 2

| Protein | Region | SEQ ID NO. | Sequence |
|---|---|---|---|
| pH007970 | (VH) | 72 | LVESGGGVVQPGRSLRLSCAASGLTFSFYNFHWVRQTPGKGLEWVAGISYD ATRTNYAGSVTGRFTISRDNSKKMLYLQMSSLGPQDTAVYHCARDRSDGQL HKVAFDSWGQGALVTVSS |
| pH007955 | (VH) | 73 | LVESGGGVVRPGRSLRLSCVASGFTFNAYGMHWVRQGPGKGLEWLAVISYE GKTVYYADSVKDRFTISRDNSRNTVSLHLNNLRGEDTAVYYCAKGSASAAV LQHWGQGTLVSVTS |

TABLE 2-continued

| Protein Region | SEQ ID NO. | Sequence |
| --- | --- | --- |
| pH007957 (VH) | 74 | LVESGGGVVPPGKSLRLSCAASGFTFSLYGIHWVRQAPGKGLEWVAVISYD<br>GNTKYYTDSVKGRFTISRDNAKNTIYLQMNSLRLDDTAVYYCAKGAANSAT<br>FDFWGRGTMVTSS |
| pH007960 (VH) | 75 | LVESGGGVVQPGKSLRLSCVASGFSFSTYGMHWVRQAPGKGLEWVAVMSFD<br>GKTKYYADSVKGRFTISRDNPKNTLYLQMNSLRSEDTAVYYCAKGGAAAAV<br>FDSWGPGILLTVSS |
| pH007964 (VH) | 76 | LVESGGGVVQPGRSLRLSCAASGVTFSRYGMHWVRQAPGKGLEWVAVISYD<br>EKTKYYADSVKGRFTISRDNSKNTLFLHMNRLRYEDTAVYYCAKGASSGAY<br>FDYWGQGTLVTSS |
| pH007979 (VH) | 77 | LVESGGGVVQPGKSLRLSCVASGFTFSTYGMHWVRQAPGKGLEWVAVMSFD<br>GKTKYYADSVKGRFTISRDNPKNTLYLQMNSLRSEDTAVYYCAKGGAAAAV<br>FDSWGQGILLTVSS |
| pH007961 (VH) | 78 | LVESGGGVVQPGKSLRLSCVASGFTFSSYGMHWVRQAPGKGLEWVAVMSFD<br>GKTKYYADSVKGRFTISRDNPKNTLYLQMNSLRSEDTAVYYCAKGGAAAAV<br>FDSWGQGILLTVSS |
| pH007968 (VH) | 79 | LVESGGGVVQPGRSLRLSCAASGFTFSRYGMHWVRQAPGKGLEWVAVMSYD<br>GSTKYYADSVKGRFAISRDNPKNTLFLQMNSLRPDDTAVYYCAKGGAAAAV<br>MDVWGKGTTVTSS |
| pH007983 (VH) | 80 | EVQLVESGGGVVQPGRSLRLSCAASGFTFNRFGMHWVRQRVPGKGLEWVA<br>VISYDDNTKYYADSVKGRFTISRDNNKSTLYLQMSSLRVEDTAVYFCAKGS<br>TAAAVLDYWGQGTLVTSS |
| pH007962 (VH) | 81 | LVESGGGLVQPGGSLRLSCAASGFTFSSYEMNWVRQAPGKGLEWVSYISSS<br>GSTIYYADSVKGRFTISRDNAKNSLYLQMNSLRAEDTAVYYCARVEQLAPS<br>PYMDVWGQGTTVTSS |
| pH007966 (VH) | 82 | QVQLVQSGAEVKKPGESLKISCKGSGYSFTSYWIGWVRQMPGKGLEWMGII<br>YPGDSDTRYSPSFQGQVTISADKSISTAYLQWSSLKASDTAMYYCARRGLR<br>GAYYYYGMDVWGQGTTVTSS |
| pK005991_6004 (VL$_K$) | 83 | MTQSPDSLTLSLGERATINCRSSRTVLYRSNNKNYLAWYQHKPGQPPKLLM<br>SWASTRETGVPDRFSGSGSGTHFTLTITSLQPEDVAVYYCQQYYSPPWTFG<br>QGTKVEIR |
| pK005989 (VL$_K$) | 84 | MTQSPGSLAVSLGSRATINCKSSRSLLYRSNNKNYLAWYQQKPGQSPRLLI<br>YWASSRESGPVDRFSGGGSGTSFTLTISSLQAEDVAVYYCQQYFNPPWTFG<br>QGTKVEIK |
| pK005994 (VL$_K$) | 85 | MTQSPNSLAVSLGGRATINCKASQSILYRSNNKNYLAWYQHKAGQPPKLLI<br>YWASTRESGVPERFSGSGSRTDFTLTINGLQAEDVAVYYCQQYYNPPWTFG<br>QGTKVEIK |
| pK005999 (VL$_K$) | 86 | MTQSPDSLAVSLGERATIKCKSSQSVLYSSNNKNYLAWYQHKPGQPPKVLV<br>YWASTRESGVPDRFSGSGSGTDFTLTISSLQAEDVAVYYCQQYYNPPWTFG<br>QGTKVAIK |
| pK006015 (VL$_K$) | 87 | MTQSPNSLAVSLGGRATINCKTSQSILYRSNNKNYLAWYQHKPGQPPKLLI<br>YWASTRESRVPDRFSGSGSRTDFTLTISGLQAEDVAVYYCQQYYNPPWTFG<br>QGTKVEIK |
| pK005995 (VL$_K$) | 88 | MTQSPNSLAVSLGGRATINCKTSQSILYRSNNKNYLAWYQHKSGQPPKLLI<br>YWASTRESGVPDRFSGSGSRTDFTLTISGLQAEDVAVYYCQQYYNPPWTFG<br>QGTKVEIK |
| pK006003 (VL$_K$) | 89 | MTQSPDSLTVSLGERATISCKSSQRLLYSSNNKNYLAWYQQKPGQPPKLLM<br>YWASTRESGVPDRFSGSGSGTDFSLTISSLQAEDVAVYYCQQYYNPPWTFG<br>QGTKVEVK |
| pK006019 (VL$_K$) | 90 | DIVMTQSPDSLTLSLGERATINCKSSQSLFYRSNNKSYLAWYQQKPGQPPK<br>LLIYWASVRESGVPDRFTGSGSVTDFTLTISSLRAEDVAVYYCQQYFTTPL<br>TFGGGTKVAIK |
| pK005996 (VL$_K$) | 91 | MTQSLDSLTVSLGERATINCKSSQSLLYTSNNKNYLAWYQQKSGQPPKLLI<br>YWASIRDSGVPDRFSGSGSATDFTLTINNLQAEDVAVYFCQQYYKTPLTFG<br>GGTKVEVR |
| pK006001 (VL$_K$) | 92 | DIQXTQSPSTLSASVGDRVTITCRASQSISSWLAWYQQKPGKAPKLLIYKA<br>SSLESGVPSRFSGSGSGTEFTLTISSLQPDDFATYYCQQYNSYSWTFGQGT<br>KVEIK |

The antibody or variant or derivative thereof may contain one or more amino acid sequences that are greater than 95%, 90%, 85%, 80%, 75%, 70%, 65%, 60%, 55%, or 50% identical to one or more of SEQ ID NOs:4-31. The antibody or variant or derivative thereof may be encoded by one or more nucleic acid sequences that are greater than 95%, 90%, 85%, 80%, 75%, 70%, 65%, 60%, 55%, or 50% identical to one or more of SEQ ID NOs:32-48. Polypeptide homology and identity can be determined, for example, by the algorithm described in the report: Wilbur, W. J. and Lipman, D. J., *Proc. Nat. Acad. Sci. USA* 80, 726-30 (1983). The herein described antibody, variant, or derivative thereof may be encoded by a nucleic acid that hybridizes under stringent conditions with the complement of one or more of SEQ ID NOs:32-48. The herein described antibody, variant, or derivative thereof may be encoded by a nucleic acid that hybridizes under stringent conditions with the complement of one or more nucleic acids that encode one or more of SEQ ID NOs:4-31.

The antibody may be an IgG, IgE, IgM, IgD, IgA, and IgY molecule class (for example, IgG1, IgG2, IgG3, IgG4, IgA1, and IgA2) or subclass.

Nucleotide Sequences

Provided herein is an isolated nucleic acid encoding an antibody that immunospecifically binds to CFH, a fragment thereof, or a variant thereof. The isolated nucleic acid may comprise a nucleotide sequence that hybridizes, under stringent conditions, to the nucleic acid molecule that encodes an antibody comprising a heavy chain or light chain sequence, as shown in Table 1 and 2. The isolated nucleic acid may comprise a nucleotide sequence, as shown in Tables 3 and 4.

TABLE 3

| Nucleotide | SEQ ID NO. | Sequence |
| --- | --- | --- |
| H007970 (VH) | 38 | GAGGTgCAGCTGGTGGAGTCTGGGGGAGGCGTGGTCCAGCCTGGGAGGTCC CTGAGACTCTCCTGCGCAGCCTCTGGACTCACCTTCAGTTTCTATAATTTC CACTGGGTCCGCCAGACTCCAGGCAAGGGGCTGGAGTGGGTGGCAGGCATC TCATACGATGCAACCAGGACGAACTACGCAGGCTCGTCACGGGCCGATTCA CCATTTCCAGAGACAATTCCAAGAAAATGCTGTATCTGCAAATGAGCAGCC TGGGACCTCAAGACACGGCTGTATATCATTGTGCGAGAGATCGTTCTGACG GGCAACTGCATAAAGTGGCTTTTGACTCCTGGGGCCAGGGAGCCCTGGTCA CCGTCTCATCA |
| H007955 (VH) | 39 | GAGGTgCAGCTGGTGGAGTCTGGGGGAGGCGTGGTCCGGCCTGGGCGGTCC CTGAGACTCTCCTGTGTTGCCTCTGGTTTCACCTTCAATGCTTATGGCATG CATTGGGTCCGCCAGGGTCCAGGCAAGGGCCTTGAGTGGCTGGCGGTCATT TCATATGAAGGAAAGACTGTTTATTATGCAGATTCCGTTAAGGACCGTTTC ACCATCTCCAGAGACAATTCCAGGAACACGGTGTCTCTACATCTGAACAAC CTGAGAGGTGAGGACACGGCTGTCTATTACTGTGCGAAGGGGTCGGCTTCA GCAGCAGTCCTCCAACACTGGGGTCAGGGCACCCTGGTCAGCGTCACGTCA |
| H007957 (VH) | 40 | GAGGTgCAGCTGGTGGAGTCTGGGGGAGGCGTGGTCCCGCCTGGGAAGTCC CTGAGACTCTCCTGTGCAGCCTCTGGATTCACCTTCAGTCTCTATGGCATA CACTGGGTCCGCCAGGCTCCCGGCAAGGGACTGGAGTGGGTGGCAGTTATC TCATATGATGGAAATACTAAATACTATACAGACTCTGTAAAGGGTCGATTC ACCATCTCCAGAGACAATGCCAAGAACACAATTTATCTGCAAATGAACAGT CTAAGACTTGACGACACGGCTGTTTATTACTGTGCGAAAGGAGCGGCGAAT AGCGCTACTTTTGATTTCTGGGGCCGAGGGACAATGGTCACCGTCTCTTCA |
| H007958 (VH) | 41 | GAGGTgCAGCTGGTGGAGTCTGGGGGAGGCGTGGTCCCGCCTGGGAAGTCC CTGAGACTCTCCTGTGCAGCCTCTGGATTCACCTTCAGTCTCTATGGCATA CACTGGGTCCGCCAGGCTCCCGGCAAGGGACTGGAGTGGGTGGCAGTTATC TCATATGATGGAAATACTAAATACTATACAGACTCTGTAAAGGGTCGATTC ACCATCTCCAGAGACAATGCCAAGAACACAATTTATCTGCAAATGAACAGT CTAAGACTTGACGACACGGCTGTTTATTACTGTGCGAAAGGAGCGGCGAAT AGCGCTACTTTTGATTTCTGGGGCCGAGGGACAATGGTCACCGTCTCTTCA |
| H007963 (VH) | 42 | GAGGTgCAGCTGGTGGAGTCTGGGGGAGGCGTGGTCCCGCCTGGGAAGTCC CTGAGACTCTCCTGTGCAGCCTCTGGATTCACCTTCAGTCTCTATGGCATA CACTGGGTCCGCCAGGCTCCCGGCAAGGGACTGGAGTGGGTGGCAGTTATC TCATATGATGGAAATACTAAATACTATACAGACTCTGTAAAGGGTCGATTC ACCATCTCCAGAGACAATGCCAAGAACACAATTTATCTGCAAATGAACAGT CTAAGACTTGACGACACGGCTGTTTATTACTGTGCGAAAGGAGCGGCGAAT AGCGCTACTTTTGATTTCTGGGGCCGAGGGACAATGGTCACCGTCTCTTCA |
| H007982 (VH) | 43 | GAGGTgCAGCTGGTGGAGTCTGGGGGAGGCGTGGTCCCGCCTGGGAAGTCC CTGAGACTCTCCTGTGCAGCCTCTGGATTCACCTTCAGTCTCTATGGCATA CACTGGGTCCGCCAGGCTCCCGGCAAGGGACTGGAGTGGGTGGCAGTTATC TCATATGATGGAAATACTAAATACTATACAGACTCTGTAAAGGGTCGATTC ACCATCTCCAGAGACAATGCCAAGAACACAATTTATCTGCAAATGAACAGT CTAAGACTTGACGACACGGCTGTTTATTACTGTGCGAAAGGAGCGGCGAAT AGCGCTACTTTTGATTTCTGGGGCCGAGGGACAATGGTCACCGTCTCTTCA |
| H007960 (VH) | 44 | GAGGTgCAGCTGGTGGAGTCTGGGGGAGGCGTGGTCCAGCCTGGAAAGTCT CTGAGACTCTCCTGTGTAGCCTCTGGATTCAGCTTCAGTACTTATGGCATG CACTGGGTCCGCCAGGCTCCAGGCAAGGGGCTGGAGTGGGTGGCGGTTATG TCATTTGATGGAAAGACTAAATACTATGCAGACTCCGTGAAGGGCCGATTC ACCATCTCCAGAGACAATCCCAAGAACACACTATATCTGCAA |

TABLE 3-continued

| Nucleotide | SEQ ID NO. | Sequence |
| --- | --- | --- |
| H007967 (VH) | 45 | GAGGTgCAGCTGGTGGAGTCTGGGGGAGGCGTGGTCCAGCCTGGAAAGTCT<br>CTGAGACTCTCCTGTGTAGCCTCTGGATTCAGCTTCAGTACTTATGGCATG<br>CACTGGGTCCGCCAGGCTCCAGGCAAGGGGCTGGAGTGGGTGGCGGTTATG<br>TCATTTGATGGAAAGACTAAATACTATGCAGACTCCGTGAAGGGCCGATTC<br>ACCATCTCCAGAGACAATCCCAAGAACACACTATATCTGCAAATGAACAGC<br>CTGAGAAGCGAAGACACGGCTGTGTATTATTGTGCGAAGGGGGTGCAGCA<br>GCGGCCGTCTTTGACTCCTGGGGCCCGGGAATACTGCTCACCGTCTCCTCA |
| H007964 (VH) | 46 | GAGGTgCAGCTGGTGGAGTCTGGGGGAGGCGTGGTCCAGCCTGGGAGGTCC<br>CTAAGACTCTCCTGTGCAGCCTCTGGAGTCACCTTCAGTAGATATGGCATG<br>CACTGGGTCCGCCAGGCTCCAGGCAAGGGGCTGGAGTGGGTGGCAGTTATA<br>TCATATGATGAAAGACTAAATACTATGCAGACTCCGTGAAGGGCCGATTC<br>ACCATCTCCAGAGACAATTCCAAGAACACACTGTTTCTGCACATGAACAGA<br>CTGAGATATGAGGACACGGCTGTATATTATTGTGCGAAAGGGGCCAGTAGC<br>GGTGCGTACTTTGACTACTGGGGCCAGGGTACCCTGGTCACCGTCTCCTCA |
| H007979 (VH) | 47 | GAGGTgCAGCTGGTGGAGTCTGGGGGAGGCGTGGTCCAGCCTGGAAAGTCT<br>CTGAGACTCTCCTGTGTAGCCTCTGGATTCACCTTCAGTACTTATGGCATG<br>CACTGGGTCCGCCAGGCTCCAGGCAAGGGGCTGGAGTGGGTGGCAGTTATG<br>TCATTTGATGGAAAGACTAAATACTATGCAGACTCCGTGAAGGGCCGATTC<br>ACCATCTCCAGAGACAATCCCAAGAACACACTATATCTGCAAATGAACAGC<br>CTGAGAAGCGAAGACACGGCTGTGTATTATTGTGCGAAGGGGGTGCAGCA<br>GCGGCCGTCTTTGACTCCTGGGGCCAGGGAATACTGCTCACCGTCTCCTCA |
| H007961 (VH) | 48 | GAGGTgCAGCTGGTGGAGTCTGGGGGAGGCGTGGTCCAGCCTGGAAAGTCT<br>CTGAGACTCTCCTGTGTAGCCTCTGGATTCACCTTCAGTAGTTATGGCATG<br>CACTGGGTCCGCCAGGCTCCGGGCAAGGGGCTGGAGTGGGTGGCGGTTATG<br>TCATTTGATGGAAAGACTAAATACTATGCAGACTCCGTGAAGGGCCGATTC<br>ACCATCTCCAGAGACAACCCCAAGAACACACTATATCTGCAAATGAACAGC<br>CTGAGAAGCGAAGACACGGCTGTCTATTATTGTGCGAAGGGGGTGCAGCA<br>GCGGCCGTCTTTGACTCCTGGGGCCAGGGAATACTGCTCACCGTCTCCTCA |
| H007965 (VH) | 49 | GAGGTgCAGCTGGTGGAGTCTGGGGGAGGCGTGGTCCAGCCTGGAAAGTCT<br>CTGAGACTCTCCTGTGTAGCCTCTGGATTCACCTTCAGTAGTTATGGCATG<br>CACTGGGTCCGCCAGGCTCCGGGCAAGGGGCTGGAGTGGGTGGCGGTTATG<br>TCATTTGATGGAAAGACTAAATACTATGCAGACTCCGTGAAGGGCCGATTC<br>ACCATCTCCAGAGACAACCCCAAGAACACACTATATCTGCAAATGAACAGC<br>CTGAGAAGCGAAGACACGGCTGTCTATTATTGTGCGAAGGGGGTGCAGCA<br>GCGGCCGTCTTTGACTCCTGGGGCCAGGGAATACTGCTCACCGTCTCCTCA |
| H007968 (VH) | 50 | GAGGTgCAGCTGGTGGAGTCTGGGGGAGGCGTGGTCCAGCCTGGGAGGTCC<br>CTGAGACTCTCCTGTGCAGCCTCTGGATTCACCTTCAGTAGATATGGCATG<br>CACTGGGTCCGCCAGGCTCCAGGCAAGGGGCTGGAGTGGGTGGCAGTTATG<br>TCATATGATGGAAGTACTAAATACTATGCAGACTCCGTGAAGGGCCGCTTC<br>GCCATCTCCAGAGACAATCCCAAGAACACGCTATTTCTGCAAATGAACAGC<br>CTGAGACCTGACGACACGGCTGTATATTACTGTGCGAAAGGGGGGCGGCA<br>8CAGCTGTCATGGACGTCTGGGGCAAAGGGACCACGGTCACCGTCTCCTCA |
| H007971 (VH) | 51 | GAGGTgCAGCTGGTGGAGTCTGGGGGAGGCGTGGTCCAGCCTGGGAGGTCC<br>CTGAGACTCTCCTGTGCAGCCTCTGGATTCACCTTCAGTAGATATGGCATG<br>CACTGGGTCCGCCAGGCTCCAGGCAAGGGGCTGGAGTGGGTGGCAGTTATG<br>TCATATGATGGAAGTACTAAATACTATGCAGACTCCGTGAAGGGCCGCTTC<br>GCCATCTCCAGAGACAATCCCAAGAACACGCTATTTCTGCAAATGAACAGC<br>CTGAGACCTGACGACACGGCTGTATATTACTGTGCGAAAGGGGGGCGGCA<br>GCAGCTGTCATGGACGTCTGGGGCAAAGGGACCACGGTCACCGTCTCCTCA |
| H007983 (VH) | 52 | GAGGTGCAGCTGGTGGAGTCTGGGGGAGGCGTGGTCCAGCCTGGGAGGTCC<br>CTGAGACTCTCCTGTGCAGCCTCTGGATTCACCTTCAATAGGTTTGGCATG<br>CACTGGGTCCGCCAGCGCCAGGTTCCAGGCAAGGGGCTGGAGTGGGTGGCA<br>GTTATCTCATATGACGACAACACTAAATATTATGCGGACTCCGTGAAGGGC<br>CGTTTCACCATCTCCAGAGACAATAACAAGAGCACTCTCTATCTGCAAATG<br>AGCAGCCTGAGAGTTGAGGACACGGCTGTCTATTTCTGTGCGAAGGGGTCG<br>ACAGCGGCAGCTGTTCTTGACTACTGGGGCCAGGGAACCCTTGTCACCGTC<br>TCCTCA |
| H007962 (VH) | 53 | GAGGTgCAGCTGGTGGAGTCTGGGGGAGGCTTGGTACAGCCTGGAGGGTCC<br>CTGAGACTCTCCTGTGCAGCCTCTGGATTCACCTTCAGTAGTTATGAAATG<br>AACTGGGTCCGCCAGGCTCCAGGGAAGGGGCTGGAGTGGGTTTCATACATT<br>AGTAGTAGTGGTAGTACCATATACTACGCAGACTCTGTGAAGGGCCGATTC<br>ACCATCTCCAGAGACAACGCCAAGAACTCACTGTATCTGCAAATGAACAGC<br>CTGAGAGCCGAGGACACGGCTGTTTATTACTGTGCGAGAGTAGAGCAGCTC<br>GCCCCCTCCCCCTACATGGACGTCTGGGGCAAAGGGACCACGGTCACCGTC<br>TCCTCA |
| H007966 (VH) | 54 | CAGGTGCAGCTGGTGCAGTCTGGGGCAGAGGTGAAAAAGCCCGGGGAGTCT<br>CTGAAGATCTCCTGTAAGGGTTCTGGATACAGCTTTACCAGCTACTGGATC<br>GGCTGGGTGCGCCAGATGCCCGGGAAAGGCCTGGAGTGGATGGGGATCATC |

TABLE 3-continued

| Nucleotide | SEQ ID NO. | Sequence |
|---|---|---|
| | | TATCCTGGTGACTCTGATACCAGATACAGCCCGTCCTTCCAAGGCCAGGTC<br>ACCATCTCAGCCGACAAGTCCATCAGCACCGCCTACCTGCAGTGGAGCAGC<br>CTGAAGGCCTCGGACACCGCCATGTATTACTGTGCGAGACGGGGTCTTCGA<br>GGGGCCTACTACTACTACTACGGTATGGACGTCTGGGGCCAAGGGACCACG<br>GTCACCGTCTCCTCA |
| K006004 (VL$_K$) | 55 | GACATCGTGATGACCCAGTCTCCAGACTCCCTGACTCTGTCTCTGGGCGAG<br>AGGGCCACCATCAACTGCAGATCCAGCCGGACTGTTTTATACAGGTCCAAC<br>AATAAAAATTACTTAGCTTGGTATCAACATAAACCAGGACAGCCTCCTAAG<br>TTGCTCATGTCCTGGGCATCTACCCGGGAAACCGGGGTCCCTGACCGATTC<br>AGTGGCAGCGGTTCTGGGACACATTTCACTCTCACCATCACCAGCCTGCAG<br>CCTGAAGATGTGGCAGTTTATTACTGTCAACAGTATTATAGTCCTCCGTGG<br>ACGTTCGGCCAAGGGACCAAGGTGGAAATCAGA |
| K005989 (VL$_K$) | 56 | GACATCGTGATGACCCAGTCTCCAGGCTCCCTGGCTGTGTCTCTGGGCTCG<br>AGGGCCACCATCAACTGCAAGTCCAGCCGGAGTCTTTTATACAGGTCCAAC<br>AATAAGAATTATTTAGCTTGGTATCAACAGAAACCAGGACAGTCTCCTCGG<br>CTTCTCATTTATTGGGCATCTTCCCGGGAATCCGGGGTCCCTGACCGATTC<br>AGTGGCGGCGGGTCTGGGACAAGTTTCACTCTCACCATCAGC |
| K005991 (VL$_K$) | 57 | GACATCGTGATGACCCAGTCTCCAGACTCCCTGACTCTGTCTCTGGGCGAG<br>AGGGCCACCATCAACTGCAGATCCAGCCGGACTGTTTTATACAGGTCCAAC<br>AATAAAAATTACTTAGCTTGGTATCAACATAAACCAGGACAGCCTCCTAAG<br>TTGCTCATGTCCTGGGCATCTACCCGGGAAACCGGGGTCCCTGACCGATTC<br>AGTGGCAGCGGTTCTGGGACACATTTCACTCTCACCATCACCAGCCTGCAG<br>CCTGAAGATGTGGCAGTTTATTACTGTCAACAGTATTATAGTCCTCCGTGG<br>ACGTTCGGCCAAGGGACCAAGGTGGAAATCAGA |
| K005992 (VL$_K$) | 58 | GACATCGTGATGACCCAGTCTCCAGACTCCCTGACTCTGTCTCTGGGCGAG<br>AGGGCCACCATCAACTGCAGATCCAGCCGGACTGTTTTATACAGGTCCAAC<br>AATAAAAATTACTTAGCTTGGTATCAACATAAACCAGGACAGCCTCCTAAG<br>TTGCTCATGTCCTGGGCATCTACCCGGGAAACCGGGGTCCCTGACCGATTC<br>AGTGGCAGCGGTTCTGGGACACATTTCACTCTCACCATCACCAGCCTGCAG<br>CCTGAAGATGTGGCAGTTTATTACTGTCAACAGTATTATAGTCCTCCGTGG<br>ACGTTCGGCCAAGGGACCAAGGTGGAAATCAGA |
| K005998 (VL$_K$) | 59 | GACATCGTGATGACCCAGTCTCCAGACTCCCTGACTCTGTCTCTGGGCGAG<br>AGGGCCACCATCAACTGCAGATCCAGCCGGACTGTTTTATACAGGTCCAAC<br>AATAAAAATTACTTAGCTTGGTATCAACATAAACCAGGACAGCCTCCTAAG<br>TTGCTCATGTCCTGGGCATCTACCCGGGAAACCGGGGTCCCTGACCGATTC<br>AGTGGCAGCGGTTCTGGGACACATTTCACTCTCACCATCACCAGCCTGCAG<br>CCTGAAGATGTGGCAGTTTATTACTGTCAACAGTATTATAGTCCTCCGTGG<br>ACGTTCGGCCAAGGGACCAAGGTGGAAATCAGA |
| K006018 (VL$_K$) | 60 | GACATCGTGATGACCCAGTCTCCAGACTCCCTGACTCTGTCTCTGGGCGAG<br>AGGGCCACCATCAACTGCAGATCCAGCCGGACTGTTTTATACAGGTCCAAC<br>AATAAAAATTACTTAGCTTGGTATCAACATAAACCAGGACAGCCTCCTAAG<br>TTGCTCATGTCCTGGGCATCTACCCGGGAAACCGGGGTCCCTGACCGATTC<br>AGTGGCAGCGGTTCTGGGACACATTTCACTCTCACCATCACCAGCCTGCAG<br>CCTGAAGATGTGGCAGTTTATTACTGTCAACAGTATTATAGTCCTCCGTGG<br>ACGTTCGGCCAAGGGACCAAGGTGGAAATCAGA |
| K005994 (VL$_K$) | 61 | GACATCGTGATGACCCAGTCTCCAAACTCCCTGGCTGTGTCTCTGGGCGGG<br>AGGGCCACCATCAACTGCAAGGCCAGCCAGAGTATTTTATACAGGTCCAAC<br>AATAAGAACTATTTAGCTTGGTACCAACATAAAGCAGGACAGCCTCCCAAG<br>CTGCTCATTTACTGGGCATCTACCCGGGAATCCGGGGTCCCTGAGCGATTC<br>AGTGGCAGCGGGTCTAGGACAGATTTCACTCTCACCATCAACGGCCTGCAG<br>GCTGAAGATGTGGCAGTTTATTACTGTCAGCAATATTATAATCCTCCGTGG<br>ACGTTCGGCCAAGGGACCAAGGTGGAAATCAAA |
| K006002 (VL$_K$) | 62 | GACATCGTGATGACCCAGTCTCCAAACTCCCTGGCTGTGTCTCTGGGCGGG<br>AGGGCCACCATCAACTGCAAGGCCAGCCAGAGTATTTTATACAGGTCCAAC<br>AATAAGAACTATTTAGCTTGGTACCAACATAAAGCAGGACAGCCTCCCAAG<br>CTGCTCATTTACTGGGCATCTACCCGGGAATCCGGGGTCCCTGAGCGATTC<br>AGTGGCAGCGGGTCTAGGACAGATTTCACTCTCACCATCAACGCCTGCAG<br>GCTGAAGATGTGGCAGTTTATTACTGTCAGCAATATTATAATCCTCCGTGG<br>ACGTTCGGCCAAGGGACCAAGGTGGAAATCAAA |
| K005999 (VL$_K$) | 63 | GACATCGTGATGACCCAGTCTCCAGACTCCCTGGCTGTGTCTCTGGGCGAG<br>AGGGCCACCATCAAGTGCAAGTCCAGCCAGAGTGTCTTGTACAGCTCCAAC<br>AATAAGAACTACTTAGCTTGGTACCAGCATAAACCAGGACAGCCTCCTAAG<br>GTACTCGTTTACTGGGCATCCACCCGGGAATCCGGGGTCCCTGACCGATTC<br>AGTGGCAGCGGGTCTGGGACAGATTTCACTCTCACCATCAGCAGCCTGCAG<br>GCTGAAGATGTGGCAGTTTATTACTGTCAACAATATTATAATCCTCCGTGG<br>ACGTTCGGCCAAGGGACCAAGGTAGCAATCAAG |

TABLE 3-continued

| Nucleotide | SEQ ID NO. | Sequence |
|---|---|---|
| K006015 (VL$_K$) | 64 | GACATCGTGATGACCCAGTCTCCAAACTCCCTGGCTGTGTCTCTGGGCGGG<br>AGGGCCACCATCAACTGCAAGACCAGCCAGAGTATTTTATACAGGTCCAAC<br>AATAAGAACTACTTAGCTTGGTACCAGCATAAACCAGGACAGCCTCCCAAG<br>CTGCTCATTTACTGGGCATCTACCCGGGAATCCAGGGTCCCTGACCGATTC<br>AGTGGCAGCGGGTCTAGGACAGATTTCACTCTCACCATCAGCGGCCTGCAG<br>GCTGAAGATGTGGCAGTTTATTACTGTCAGCAATATTATAATCCTCCGTGG<br>ACGTTCGGCCAGGGGACCAAGGTGGAAATCAAA |
| K005995 (VL$_K$) | 65 | GACATCGTGATGACCCAGTCTCCAAACTCCCTGGCTGTGTCTCTGGGCGGG<br>AGGGCCACCATCAACTGCAAGACCAGCCAGAGTATTTTATACAGGTCCAAC<br>AATAAGAACTACTTAGCTTGGTACCAGCATAAATCAGGACAGCCTCCCAAG<br>CTGCTCATTTACTGGGCATCTACCCGGGAATCCGGGGTCCCTGACCGATTC<br>AGTGGCAGCGGGTCTAGGACAGATTTCACTCTCACCATCAGCGGCCTGCAG<br>GCTGAAGATGTGGCAGTTTATTACTGTCAGCAATATTATAATCCTCCGTGG<br>ACGTTCGGCCAAGGGACCAAGGTGGAAATCAAA |
| K006000 (VL$_K$) | 66 | GACATCGTGATGACCCAGTCTCCAAACTCCCTGGCTGTGTCTCTGGGCGGG<br>AGGGCCACCATCAACTGCAAGACCAGCCAGAGTATTTTATACAGGTCCAAC<br>AATAAGAACTACTTAGCTTGGTACCAGCATAAATCAGGACAGCCTCCCAAG<br>CTGCTCATTTACTGGGCATCTACCCGGGAATCCGGGGTCCCTGACCGATTC<br>AGTGGCAGCGGGTCTAGGACAGATTTCACTCTCACCATCAGCGGCCTGCAG<br>GCTGAAGATGTGGCAGTTTATTACTGTCAGCAATATTATAATCCTCCGTGG<br>ACGTTCGGCCAAGGGACCAAGGTGGAAATCAAA |
| K006003 (VL$_K$) | 67 | GACATCGTGATGACCCAGTCTCCGGACTCCCTGACTGTGTCTCTGGGCGAG<br>AGGGCCACCATCAGCTGCAAGTCCAGCCAGCGTCTTTTGTATAGGTCCAAC<br>AATAAGAACTACTTAGCTTGGTACCAGCAGAAACCTGGACAGCCTCCTAAA<br>CTGCTCATGTACTGGGCGTCCACCCGGGAATCCGGGGTCCCTGACCGATTC<br>AGTGGCAGCGGGTCTGGGACAGATTTCTCTCTCACCATCAGCAGCCTGCAG<br>GCTGAAGATGTGGCAGTTTATTACTGTCAGCAATATTATAATCCTCCCTGG<br>ACGTTCGGCCAAGGGACCAAGGTGGAAGTCAAA |
| K006005 (VL$_K$) | 68 | GACATCGTGATGACCCAGTCTCCGGACTCCCTGACTGTGTCTCTGGGCGAG<br>AGGGCCACCATCAGCTGCAAGTCCAGCCAGCGTCTTTTGTATAGTTCCAAC<br>AATAAGAACTACTTAGCTTGGTACCAGCAGAAACCTGGACAGCCTCCTAAA<br>CTGCTCATGTACTGGGCGTCCACCCGGGAATCCGGGGTCCCTGACCGATTC<br>AGTGGCAGCGGGTCTGGGACAGATTTCTCTCTCACCATCAGCAGCCTGCAG<br>GCTGAAGATGTGGCAGTTTATTACTGTCAGCAATATTATAATCCTCCCTGG<br>ACGTTCGGCCAAGGGACCAAGGTGGAAGTCAAA |
| K006019 (VL$_K$) | 69 | GACATCGTGATGACCCAGTCTCCAGATTCCCTGACTCTGTCTCTGGGCGAG<br>AGGGCCACCATCAACTGCAAGTCCAGCCAGAGTCTGTTTTACAGGTCCAAC<br>AATAAGAGCTACTTAGCTTGGTATCAGCAAAAACCAGGGCAGCCTCCTAAA<br>CTGCTCATTTACTGGGCCTCTGTCCGGGAATCCGGGGTCCCTGACCGATTC<br>ACTGGCAGCGGGTCTGTAACAGATTTCACTCTCACCATCAGCAGCCTGCGG<br>GCTGAGGATGTGGCTGTTTATTATTGTCAACAGTATTTTACTACTCCTCTC<br>ACTTTCGGCGGGGGGACCAAGGTGGCGATCAAA |
| K005996 (VL$_K$) | 70 | GACATCGTGATGACCCAGTCTCTAGACTCCCTGACTGTGTCTCTGGGCGAG<br>AGGGCCACCATCAACTGCAAGTCCAGCCAGAGTCTTTTATACACCTCCAAC<br>AATAAGAATTACTTAGCTTGGTACCAGCAGAAATCAGGACAGCCTCCTAAG<br>TTACTCATTTACTGGGCGTCTATTCGGGATTCCGGGGTCCCTGACCGATTC<br>AGTGGCAGCGGGTCTGCGACAGATTTCACTCTCACCATCAACAACCTGCAG<br>GCTGAAGATGTGGCAGTTTACTTCTGTCAGCAATATTACAAGACTCCTCTC<br>ACTTTCGGCGGGGGGACCAAGGTGGAGGTCAGA |
| K006001 (VL$_K$) | 71 | GACATCCAGWTGACCCAGTCTCCTTCCACCCTGTCTGCATCTGTAGGAGAC<br>AGAGTCACCATCACTTGCCGGGCCAGTCAGAGTATTAGTAGCTGGTTGGCC<br>TGGTATCAGCAGAAACCAGGGAAAGCCCCTAAGCTCCTGATCTATAAGGCG<br>TCTAGTTTAGAAAGTGGGGTCCCATCAAGGTTCAGCGGCAGTGGATCTGGG<br>ACAGAATTCACTCTCACCATCAGCAGCCTGCAGCCTGATGATTTTGCAACT<br>TATTACTGCCAACAGTATAATAGTTATTCTTGGACGTTCGGCCAAGGGACC<br>AAGGTGGAAATCAAA |

TABLE 4

| Nucleotide | SEQ ID NO. | Sequence |
|---|---|---|
| pH007970 (VH) | 93 | GAGGTgCAGCTGGTGGAGTCTGGGGGAGGCGTGGTCCAGCCTGGGAGGTCC<br>CTGAGACTCTCCTGCGCAGCCTCTGGACTCACCTTCAGTTTCTATAATTTC<br>CACTGGGTCCGCCAGACTCCAGGCAAGGGGCTGGAGTGGGTGGCAGGCATC<br>TCATACGATGCAACCAGGACGAACTACGCAGGCTCCGTGACGGGCCGATTC<br>ACCATTTCCAGAGACAATTCCAAGAAAATGCTGTATCTGCAAATGAGCAGC<br>CTGGGACCTCAAGACACGGCTGTATATCATTGTGCGAGAGATCGTTCTGAC |

TABLE 4-continued

| Nucleotide | SEQ ID NO. | Sequence |
|---|---|---|
| | | GGGCAACTGCATAAAGTGGCTTTTGACTCCTGGGGCCAGGGAGCCCTGGTC<br>ACCGTCTCATCA |
| pH007955 (VH) | 94 | GAGGTgCAGCTGGTGGAGTCTGGGGGAGGCGTGGTCCGGCCTGGGCGGTCC<br>CTGAGACTCTCCTGTGTTGCCTCTGGTTTCACCTTCAATGCTTATGGCATG<br>CATTGGGTCCGCCAGGGTCCAGGCAAGGGCCTTGAGTGGCTGGCGGTCATT<br>TCATATGAAGGAAAGACTGTTTATTATGCAGATTCCGTTAAGGACCGTTTC<br>ACCATCTCCAGAGACAATTCCAGGAACACGGTGTCTCTACATCTGAACAAC<br>CTGAGAGGTGAGGACACGGCTGTCTATTACTGTGCAAGGGGTCGGCTTCA<br>GCAGCAGTCCTCCAACACTGGGGTCAGGGCACCCTGGTCAGCGTCACGTCA |
| pH007957 (VH) | 95 | GAGGTgCAGCTGGTGGAGTCTGGGGGAGGCGTGGTCCCGCCTGGGAAGTCC<br>CTGAGACTCTCCTGTGCAGCCTCTGGATTCACCTTCAGTCTCTATGGCATA<br>CACTGGGTCCGCCAGGCTCCCGGCAAGGGACTGGAGTGGGTGGCAGTTATC<br>TCATATGATGGAAATACTAAATACTATACAGACTCTGTAAAGGGTCGATTC<br>ACCATCTCCAGAGACAATGCCAAGAACACAATTTATCTGCAAATGAACAGT<br>CTAAGACTTGACGACACGGCTGTTTATTACTGTGCAAAGGAGCGGCGAAT<br>AGCGCTACTTTTGATTTCTGGGGCCGAGGGACAATGGTCACCGTCTCTTCA |
| pH007960 (VH) | 96 | GAGGTgCAGCTGGTGGAGTCTGGGGGAGGCGTGGTCCAGCCTGGAAAGTCT<br>CTGAGACTCTCCTGTGTAGCCTCTGGATTCAGCTTCAGTACTTATGGCATG<br>CACTGGGTCCGCCAGGCTCCAGGCAAGGGGCTGGAGTGGGTGGCGGTTATG<br>TCATTTGATGGAAAGACTAAATACTATGCAGACTCCGTGAAGGGCCGATTC<br>ACCATCTCCAGAGACAATCCCAAGAACACACTATATCTGCAAATGAACAGC<br>CTGAGAAGCGAAGACACGGCTGTGTATTATTGTGCGAAGGGGGGTGCAGCA<br>GCGGCCGTCTTTGACTCCTGGGGCCCGGGAATACTGCTCACCGTCTCCTCA |
| pH007964 (VH) | 97 | GAGGTgCAGCTGGTGGAGTCTGGGGGAGGCGTGGTCCAGCCTGGGAGGTCC<br>CTAAGACTCTCCTGTGCAGCCTCTGGAGTCACCTTCAGTAGATATGGCATG<br>CACTGGGTCCGCCAGGCTCCAGGCAAGGGGCTGGAGTGGGTGGCAGTTATA<br>TCATATGATGAAAGACTAAATACTATGCAGACTCCGTGAAGGGCCGATTC<br>ACCATCTCCAGAGACAATTCCAAGAACACACTGTTTCTGCACATGAACAGA<br>CTGAGATATGAGGACACGGCTGTATATTATTGTGCGAAAGGGGCCAGTAGC<br>GGTGCGTACTTTGACTACTGGGGCCAGGGTACCCTGGTCACCGTCTCCTCA |
| pH007979 (VH) | 98 | GAGGTgCAGCTGGTGGAGTCTGGGGGAGGCGTGGTCCAGCCTGGAAAGTCT<br>CTGAGACTCTCCTGTGTAGCCTCTGGATTCACCTTCAGTACTTATGGCATG<br>CACTGGGTCCGCCAGGCTCCAGGCAAGGGGCTGGAGTGGGTGGCAGTTATG<br>TCATTTGATGGAAAGACTAAATACTATGCAGACTCCGTGAAGGGCCGATTC<br>ACCATCTCCAGAGACAATCCCAAGAACACACTATATCTGCAAATGAACAGC<br>CTGAGAAGCGAAGACACGGCTGTGTATTATTGTGCGAAGGGGGGTGCAGCA<br>GCGGCCGTCTTTGACTCCTGGGGCCAGGGAATACTGCTCACCGTCTCCTCA |
| pH007961 (VH) | 99 | GAGGTgCAGCTGGTGGAGTCTGGGGGAGGCGTGGTCCAGCCTGGAAAGTCT<br>CTGAGACTCTCCTGTGTAGCCTCTGGATTCACCTTCAGTAGTTATGGCATG<br>CACTGGGTCCGCCAGGCTCCGGGCAAGGGGCTGGAGTGGGTGGCGGTTATG<br>TCATTTGATGGAAAGACTAAATACTATGCAGACTCCGTGAAGGGCCGATTC<br>ACCATCTCCAGAGACAACCCCAAGAACACACTATATCTGCAAATGAACAGC<br>CTGAGAAGCGAAGACACGGCTGTCTATTATTGTGCGAAGGGGGTGCAGCA<br>GCGGCCGTCTTTGACTCCTGGGGCCAGGGAATACTGCTCACCGTCTCCTCA |
| pH007968 (VH) | 100 | GAGGTgCAGCTGGTGGAGTCTGGGGGAGGCGTGGTCCAGCCTGGGAGGTCC<br>CTGAGACTCTCCTGTGCAGCCTCTGGATTCACCTTCAGTAGATATGGCATG<br>CACTGGGTCCGCCAGGCTCCAGGCAAGGGGCTGGAGTGGGTGGCAGTTATG<br>TCATATGATGGAAGTACTAAATACTATGCAGACTCCGTGAAGGGCCGCTTC<br>GCCATCTCCAGAGACAATCCCAAGAACACGCTATTTCTGCAAATGAACAGC<br>CTGAGACCTGACGACACGGCTGTATATTACTGTGCGAAGGGGGGGCGGCA<br>GCAGCTGTCATGGACGTCTGGGGCAAAGGGACCACGGTCACCGTCTCCTCA |
| pH007983 (VH) | 101 | GAGGTGCAGCTGGTGGAGTCTGGGGGAGGCGTGGTCCAGCCTGGGAGGTCC<br>CTGAGACTCTCCTGTGCAGCCTCTGGATTCACCTTCAATAGGTTTGGCATG<br>CACTGGGTCCGCCAGCGCCAGGTTCAGGCAAGGGGCTGGAGTGGGTGGCA<br>GTTATCTCATATGACGACAACACTAAATATTATGCGGACTCCGTGAAGGGC<br>CGTTTCACCATCTCCAGAGACAATAACAAGAGCACTCTCTATCTGCAAATG<br>AGCAGCCTGAGAGTTGAGGACACGGCTGTCTATTTCTGTGCGAAGGGGTCG<br>ACAGCGGCAGCTGTTCTTGACTACTGGGGCCAGGGAACCCTTGTCACCGTC<br>TCCTCA |
| pH007962 (VH) | 102 | GAGGTgCAGCTGGTGAGTCTGGGGGAGGCTTGGTACAGCCTGGAGGGTCC<br>CTGAGACTCTCCTGTGCAGCCTCTGGATTCACCTTCAGTAGTTATGAAATG<br>AACTGGGTCCGCCAGGCTCCAGGGAAGGGGCTGGAGTGGGTTTCATACATT<br>AGTAGTAGTGGTAGTACCATATACTACGCAGACTCTGTGAAGGGCCGATTC<br>ACCATCTCCAGAGACAACGCCAAGAACTCACTGTATCTGCAAATGAACAGC<br>CTGAGAGCCGAGGACACGGCTGTTTATTACTGTGCGAGAGTAGAGCAGCTC<br>GCCCCCTCCCCCTACATGGACGTCTGGGGCAAAGGGACCACGGTCACCGTC<br>TCCTCA |

TABLE 4-continued

| Nucleotide | SEQ ID NO. | Sequence |
| --- | --- | --- |
| pH007966 (VH) | 103 | CAGGTGCAGCTGGTGCAGTCTGGGGCAGAGGTGAAAAAGCCCGGGGAGTCT<br>CTGAAGATCTCCTGTAAGGGTTCTGGATACAGCTTTACCAGCTACTGGATC<br>GGCTGGGTGCGCCAGATGCCCGGGAAAGGCCTGGAGTGGATGGGGATCATC<br>TATCCTGGTGACTCTGATACCAGATACAGCCCGTCCTTCCAAGGCCAGGTC<br>ACCATCTCAGCCGACAAGTCCATCAGCACCGCCTACCTGCAGTGGAGCAGC<br>CTGAAGGCCTCGGACACCGCCATGTATTACTGTGCGAGACGGGGTCTTCGA<br>GGGGCCTACTACTACTACTACGGTATGGACGTCTGGGGCCAAGGGACCACG<br>GTCACCGTCTCCTCA |
| pK005991_6004 (VL$_K$) | 104 | GACATCGTGATGACCCAGTCTCCAGACTCCCTGACTCTGTCTCTGGGCGAG<br>AGGGCCACCATCAACTGCAGATCCAGCCGGACTGTTTTATACAGGTCCAAC<br>AATAAAAATTACTTAGCTTGGTATCAACATAAACCAGGACAGCCTCCTAAG<br>TTGCTCATGTCCTGGGCATCTACCCGGGAAACCGGGGTCCCTGACCGATTC<br>AGTGGCAGCGGTTCTGGGACACATTTCACTCTCACCATCACCAGCCTGCAG<br>CCTGAAGATGTGGCAGTTTATTACTGTCAACAGTATTATAGTCCTCCGTGG<br>ACGTTCGGCCAAGGGACCAAGGTGGAAATCAGA |
| pK005989 (VL$_K$) | 105 | GACATCGTGATGACCCAGTCTCCAGGCTCCCTGGCTGTGTCTCTGGGCTCG<br>AGGGCCACCATCAACTGCAAGTCCAGCCGGAGTCTTTTATACAGGTCCAAC<br>AATAAGAATTATTTAGCTTGGTATCAACAGAAACCAGGACAGTCTCCTCGG<br>CTTCTCATTTATTGGGCATCTTCCCGGGAATCCGGGGTCCCTGACCGATTC<br>AGTGGCGGCGGGTCTGGGACAAGTTTCACTCTCACCATCAGCAGCCTGCAG<br>GCTGAAGATGTGGCAGTTTATTACTGTCAGCAATATTTTAATCCTCCGTGG<br>ACGTTCGGCCAAGGGACCAAGGTGGAGATCAAA |
| pK005994 (VL$_K$) | 106 | GACATCGTGATGACCCAGTCTCCAAACTCCCTGGCTGTGTCTCTGGGCGGG<br>AGGGCCACCATCAACTGCAAGGCCAGCCAGAGTATTTTATACAGGTCCAAC<br>AATAAGAACTATTTAGCTTGGTACCAACATAAAGCAGGACAGCCTCCCAAG<br>CTGCTCATTTACTGGGCATCTACCCGGGAATCCGGGGTCCCTGAGCGATTC<br>AGTGGCAGCGGGTCTAGGACAGATTTCACTCTCACCATCAACGGCCTGCAG<br>GCTGAAGATGTGGCAGTTTATTACTGTCAGCAATATTATAATCCTCCGTGG<br>ACGTTCGGCCAAGGGACCAAGGTGGAAATCAAA |
| pK005999 (VL$_K$) | 107 | GACATCGTGATGACCCAGTCTCCAGACTCCCTGGCTGTGTCTCTGGGCGAG<br>AGGGCCACCATCAAGTGCAAGTCCAGCCAGAGTGTCTTGTACAGCTCCAAC<br>AATAAGAACTACTTAGCTTGGTACCAGCATAAACCAGGACAGCCTCCTAAG<br>GTACTCGTTTACTGGGCATCCACCCGGGAATCCGGGGTCCCTGACCGATTC<br>AGTGGCAGCGGGTCTGGGACAGATTTCACTCTCACCATCAGCAGCCTGCAG<br>GCTGAAGATGTGGCAGTTTATTACTGTCAACAATATTATAATCCTCCGTGG<br>ACGTTCGGCCAAGGGACCAAGGTAGCAATCAAG |
| pK006015 (VL$_K$) | 108 | GACATCGTGATGACCCAGTCTCCAAACTCCCTGGCTGTGTCTCTGGGCGGG<br>AGGGCCACCATCAACTGCAAGACCAGCCAGAGTTTTATACAGGTCCAAC<br>AATAAGAACTACTTAGCTTGGTACCAGCATAAACCAGGACAGCCTCCCAAG<br>CTGCTCATTTACTGGGCATCTACCCGGGAATCCAGGGTCCCTGACCGATTC<br>AGTGGCAGCGGGTCTAGGACAGATTTCACTCTCACCATCAGCGGCCTGCAG<br>GCTGAAGATGTGGCAGTTTATTACTGTCAGCAATATTATAATCCTCCGTGG<br>ACGTTCGGCCAGGGGACCAAGGTGGAAATCAAA |
| pK005995 (VL$_K$) | 109 | GACATCGTGATGACCCAGTCTCCAAACTCCCTGGCTGTGTCTCTGGGCGGG<br>AGGGCCACCATCAACTGCAAGACCAGCCAGAGTATTTTATACAGGTCCAAC<br>AATAAGAACTACTTAGCTTGGTACCAGCATAAATCAGGACAGCCTCCCAAG<br>CTGCTCATTTACTGGGCATCTACCCGGGAATCCGGGGTCCCTGACCGATTC<br>AGTGGCAGCGGGTCTAGGACAGATTTCACTCTCACCATCAGCGGCCTGCAG<br>GCTGAAGATGTGGCAGTTTATTACTGTCAGCAATATTATAATCCTCCGTGG<br>ACGTTCGGCCAAGGGACCAAGGTGGAAATCAAA |
| pK006003 (VL$_K$) | 110 | GACATCGTGATGACCCAGTCTCCGGACTCCCTGACTGTGTCTCTGGGCGAG<br>AGGGCCACCATCAGCTGCAAGTCCAGCCAGCGTCTTTTGTATAGTTCCAAC<br>AATAAGAACTACTTAGCTTGGTACCAGCAGAAACCTGGACAGCCTCCTAAA<br>CTGCTCATGTACTGGGCGTCCACCCGGGAATCCGGGGTCCCTGACCGATTC<br>AGTGGCAGCGGGTCTGGGACAGATTCTCTCTCACCATCAGCAGCCTGCAG<br>GCTGAAGATGTGGCAGTTTATTACTGTCAGCAATATTATAATCCTCCCTGG<br>ACGTTCGGCCAAGGGACCAAGGTGGAAGTCAAA |
| pK006019 (VL$_K$) | 111 | GACATCGTGATGACCCAGTCTCCAGATTCCCTGACTCTGTCTCTGGGCGAG<br>AGGGCCACCATCAACTGCAAGTCCAGCCAGAGTCTGTTTTACAGGTCCAAC<br>AATAAGAGCTACTTAGCTTGGTATCAGCAAAAACCAGGGCAGCCTCCTAAA<br>CTGCTCATTTACTGGGCCTCTGTCCGGGAATCCGGGGTCCCTGACCGATTC<br>ACTGGCAGCGGGTCTGTAACAGATTTCACTCTCACCATCAGCAGCCTGCGG<br>GCTGAGGATGTGGCTGTTTATTATTGTCAACAGTATTTTACTACTCCTCTC<br>ACTTTCGGCGGGGGGACCAAGGTGGCGATCAAA |
| pK005996 (VL$_K$) | 112 | GACATCGTGATGACCCAGTCTCTAGACTCCCTGACTGTGTCTCTGGGCGAG<br>AGGGCCACCATCAACTGCAAGTCCAGCCAGAGTCTTTTATACACCTCCAAC<br>AATAAGAATTACTTAGCTTGGTACCAGCAGAAATCAGGACAGCCTCCTAAG<br>TTACTCATTTACTGGGCGTCTATTCGGATTCCGGGGTCCCTGACCGATTC |

TABLE 4-continued

| Nucleotide | SEQ ID NO. | Sequence |
|---|---|---|
| | | AGTGGCAGCGGGTCTGCGACAGATTTCACTCTCACCATCAACAACCTGCAG<br>GCTGAAGATGTGGCAGTTTACTTCTGTCAGCAATATTACAAGACTCCTCTC<br>ACTTTCGGCGGGGGGACCAAGGTGGAGGTCAGA |
| pK006001 (VL$_K$) | 113 | GACATCCAGWTGACCCAGTCTCCTTCCACCCTGTCTGCATCTGTAGGAGAC<br>AGAGTCACCATCACTTGCCGGGCCAGTCAGAGTATTAGTAGCTGGTTGGCC<br>TGGTATCAGCAGAAACCAGGGAAAGCCCCTAAGCTCCTGATCTATAAGGCG<br>TCTAGTTTAGAAAGTGGGGTCCCATCAAGGTTCAGCGGCAGTGGATCTGGG<br>ACAGAATTCACTCTCACCATCAGCAGCCTGCAGCCTGATGATTTTGCAACT<br>TATTACTGCCAACAGTATAATAGTTATTCTTGGACGTTCGGCCAAGGGACC<br>AAGGTGGAAATCAAA |

Antibody Preparation/Production

Antibodies may be prepared by any of a variety of techniques. In general, antibodies can be produced by cell culture techniques, including the generation of monoclonal antibodies via conventional techniques, or via transfection of antibody genes, heavy chains, and/or light chains into suitable bacterial or mammalian cell hosts, in order to allow for the production of antibodies, wherein the antibodies may be recombinant. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Exemplary mammalian host cells for expressing the recombinant antibodies of the invention include Chinese Hamster Ovary (CHO cells) (including dhfr-CHO cells, described in Urlaub and Chasin, Proc. Natl. Acad. Sci. USA, 77: 4216-4220 (1980)), used with a DHFR selectable marker, e.g., as described in Kaufman and Sharp, J. Mol. Biol., 159: 601-621 (1982), NS0 myeloma cells, COS cells, HEK 293T cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention (i.e., binds human CFH) and the other heavy and light chain are specific for an antigen other than human CFH by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells, and recover the antibody from the culture medium. Still further, the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

Methods of preparing monoclonal antibodies involve the preparation of immortal cell lines capable of producing antibodies having the desired specificity. Such cell lines may be produced from spleen cells obtained from an immunized animal. The animal may be immunized with CFH or a fragment and/or variant thereof. For example, any of SEQ ID NOs:1-3 or 119-132, or a variant of SEQ ID NOs:1-3 or 119-132 may be used to immunize the animal. The immunizing antigen may be reduced or not reduced. The spleen cells may then be immortalized by, for example, fusion with a myeloma cell fusion partner. A variety of fusion techniques may be employed. For example, the spleen cells and myeloma cells may be combined with a nonionic detergent for a few minutes and then plated at low density on a selective medium that supports that growth of hybrid cells, but not myeloma cells. One such technique uses hypoxanthine, aminopterin, thymidine (HAT) selection. Another technique includes eletrofusion. After a sufficient time, usually about 1 to 2 weeks, colonies of hybrids are observed. Single colonies are selected and their culture supernatants tested for binding activity against the polypeptide. Hybridomas having high reactivity and specificity may be used.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. Affinity chromatography is an example of a method that can be used in a process to purify the antibodies.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment, which comprises both antigen-binding sites.

The Fv fragment can be produced by preferential proteolytic cleavage of an IgM, and on rare occasions IgG or IgA immunoglobulin molecules. The Fv fragment may be derived using recombinant techniques. The Fv fragment includes a non-covalent VH::VL heterodimer including an antigen-binding site that retains much of the antigen recognition and binding capabilities of the native antibody molecule.

The antibody, antibody fragment, or derivative may comprise a heavy chain and a light chain complementarity determining region ("CDR") set, respectively interposed between a heavy chain and a light chain framework ("FR") set which provide support to the CDRs and define the spatial relationship of the CDRs relative to each other. The DR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region. A polypeptide comprising a single CDR, (e.g., a CDR1, CDR2, or CDR3) may be referred to as a "molecular recognition unit." Crystallographic analyses of antigen-antibody complexes have demonstrated that the amino acid residues of CDRs form extensive contact with bound antigen, wherein the most extensive antigen contact is with the heavy chain CDR3. Thus, the molecular recognition units may be primarily responsible for the specificity of an antigen-binding site. In general, the CDR residues are directly and most substantially involved in influencing antigen binding.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, yeast or the like, display library); e.g., as available from various commercial vendors such as Cambridge Antibody Technologies (Cambridgeshire, UK), MorphoSys (Martinsried/Planegg, Del.), Biovation (Aberdeen, Scotland, UK) Biolnvent (Lund, Sweden), using methods known in the art. See U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1997) *Microbiol. Immunol.* 41:901-907; Sandhu et al. (1996) *Crit. Rev. Biotechnol.* 16:95-118; Eren et al. (1998) *Immunol.* 93:154-161) that are capable of producing a repertoire of human antibodies, as known in the art and/or as described herein. Such techniques, include, but are not limited to, ribosome display (Hanes et al. (1997) *Proc. Natl. Acad. Sci. USA,* 94:4937-4942; Hanes et al. (1998) *Proc. Natl. Acad. Sci. USA,* 95:14130-14135); single cell antibody producing technologies (e.g., selected lymphocyte antibody method ("SLAM") (U.S. Pat. No. 5,627,052, Wen et al. (1987) *J. Immunol.* 17:887-892; Babcook et al. (1996) *Proc. Natl. Acad. Sci. USA* 93:7843-7848); gel microdroplet and flow cytometry (Powell et al. (1990) *Biotechnol.* 8:333-337; One Cell Systems, (Cambridge, Mass.).; Gray et al. (1995) *J. Imm. Meth.* 182:155-163; Kenny et al. (1995) *Bio/Technol.* 13:787-790); B-cell selection (Steenbakkers et al. (1994) *Molec. Biol. Reports* 19:125-134 (1994)). In particular, human antibodies against CFH may be derived, sequenced and characterized from peripheral human B lymphocytes using methods as described in Liao et al. (2013) *Immunity* 38(1): 176-186; Bonsignori et al. (2012) *J Virol* 86(21): 11521-11532; Moody et al. (2012) *J Virol* 86(14): 7496-7507; Gray et al. (2011) *J Virol* 85(15): 7719-7729; Morris et al. (2011) *PLoS ONE* 6(9): e23532; and Liao et al. (2009) *J Virol Methods* 158(1-2): 171-179.

An affinity matured antibody may be produced by any one of a number of procedures that are known in the art. For example, see Marks et al., *BioTechnology,* 10: 779-783 (1992) describes affinity maturation by VH and VL domain shuffling. Random mutagenesis of CDR and/or framework residues is described by Barbas et al., *Proc. Nat. Acad. Sci. USA,* 91: 3809-3813 (1994); Schier et al., *Gene,* 169: 147-155 (1995); Yelton et al., *J. Immunol.,* 155: 1994-2004 (1995); Jackson et al., *J. Immunol.,* 154(7): 3310-3319 (1995); Hawkins et al, *J. Mol. Biol.,* 226: 889-896 (1992). Selective mutation at selective mutagenesis positions and at contact or hypermutation positions with an activity enhancing amino acid residue is described in U.S. Pat. No. 6,914,128 B1.

Antibody variants of the present invention can also be prepared by delivering a polynucleotide encoding an antibody of this invention to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

Antibody variants also can be prepared by delivering a polynucleotide of this invention to provide transgenic plants and cultured plant cells (e.g., but not limited to tobacco, maize, and duckweed) that produce such antibodies, specified portions or variants in the plant parts or in cells cultured therefrom. For example, Cramer et al. (1999) *Curr. Top. Microbiol. Immunol.* 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al., *Adv. Exp. Med. Biol.* (1999) 464:127-147 and references cited therein. Antibody variants have also been produced in large amounts from transgenic plant seeds including antibody fragments, such as single chain antibodies (scFv's), including tobacco seeds and potato tubers. See, e.g., Conrad et al. (1998) *Plant Mol. Biol.* 38:101-109 and reference cited therein. Thus, antibodies of the present invention can also be produced using transgenic plants, according to known methods.

Antibody derivatives can be produced, for example, by adding exogenous sequences to modify immunogenicity or reduce, enhance, or modify binding, affinity, on-rate, off-rate, avidity, specificity, half-life, or any other suitable characteristic. Generally, part or all of the non-human or human CDR sequences are maintained while the non-human sequences of the variable and constant regions are replaced with human or other amino acids.

Small antibody fragments may be diabodies having two antigen-binding sites, wherein fragments comprise a heavy chain variable domain (VH) connected to a light chain variable domain (VL) in the same polypeptide chain (VH VL). See for example, EP 404,097; WO 93/11161; and Hollinger et al., (1993) *Proc. Natl. Acad. Sci. USA* 90:6444-6448. By using a linker that is too short to allow pairing between the two domains on the same chain, the domains are forced to pair with the complementary domains of another chain and create two antigen-binding sites. See also, U.S. Pat. No. 6,632,926 to Chen et al. which is hereby incorporated by reference in its entirety and discloses antibody variants that have one or more amino acids inserted into a hypervariable region of the parent antibody and a binding affinity for a target antigen which is at least about two fold stronger than the binding affinity of the parent antibody for the antigen.

The antibody may be a linear antibody. The procedure for making a linear antibody is known in the art and described in Zapata et al. (1995) *Protein Eng.* 8(10):1057-1062. Briefly, these antibodies comprise a pair of tandem Fd segments (VH-CH1-VH-CH1) which form a pair of antigen binding regions. Linear antibodies can be bispecific or monospecific.

The antibodies may be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

It may be useful to detectably or therapeutically label the antibody. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample. Antibodies can also be conjugated, for example, to a pharmaceutical agent, such as chemotherapeutic drug or a toxin. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (Ill) phthalocyanine tetrasulfonate, hematoporphyrin, and phthalocyanine; radionuclides, such as iodine-131 (131I), yttrium-90 (90Y), bismuth-212 (212Bi), bismuth-213 (213Bi), technetium-99m (99mTc), rhenium-186 (186Re), and rhenium-188 (188Re); antibiotics, such as doxorubicin, ADRIAMYCIN®, daunorubicin, methotrexate, daunomycin, neocarzinostatin, and carboplatin; bacterial, plant, and other toxins, such as diphtheria toxin, *Pseudomonas* exotoxin A, staphylococcal enterotoxin A, abrin-A toxin, ricin A (deglycosylated ricin A and native ricin A), TGF-alpha toxin, cytotoxin from chinese cobra (naja naja atra), and gelonin (a plant toxin); ribosome inactivating proteins from plants, bacteria and fungi, such as restrictocin (a ribosome inactivating protein produced by *Aspergillus restrictus*), saporin (a ribosome inactivating protein from *Saponaria officinalis*), and RNase; tyrosine kinase inhibitors; ly207702 (a difluorinated purine nucleoside); liposomes containing anti cystic agents (e.g., antisense oligonucleotides, plasmids which encode for toxins, methotrexate, etc.); and other antibodies or antibody fragments, such as F(ab).

The antibodies can be sequenced and replicated by recombinant or synthetic means. They also can be further sequenced down to the linear sequence of nucleotides that encode them. Accordingly, this invention provides these polynucleotides, alone or in combination with a carrier, vector or host cell as described above, that encode a sequence of an antibody of this invention.

Antibody production via the use of hybridoma technology, the selected lymphocyte antibody method (SLAM), transgenic animals, and recombinant antibody libraries is described in more detail below.

Anti-CFH Monoclonal Antibodies Using Hybridoma Technology

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, second edition, (Cold Spring Harbor Laboratory Press, Cold Spring Harbor, 1988); Hammerling, et al., In *Monoclonal Antibodies and T-Cell Hybridomas*, (Elsevier, N.Y., 1981). It is also noted that the term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

In an embodiment, the present invention provides methods of generating monoclonal antibodies as well as antibodies produced by the method. The method may comprise culturing a hybridoma cell secreting an antibody of the invention wherein, preferably, the hybridoma is generated by fusing splenocytes isolated from an animal, e.g., a rat or a mouse, immunized with CFH with myeloma cells and then screening the hybridomas resulting from the fusion for hybridoma clones that secrete an antibody able to bind a polypeptide, such as GPPPPIDNGDITSFP(GGGK-biotin) (SEQ ID NO:15). Briefly, rats can be immunized with a CFH antigen. In a preferred embodiment, the CFH antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks; however, a single administration of the polypeptide may also be used.

After immunization of an animal with a CFH antigen, antibodies and/or antibody-producing cells may be obtained from the animal. An anti-CFH antibody-containing serum is obtained from the animal by bleeding or sacrificing the animal. The serum may be used as it is obtained from the animal, an immunoglobulin fraction may be obtained from the serum, or the anti-CFH antibodies may be purified from the serum. Serum or immunoglobulins obtained in this manner are polyclonal, thus having a heterogeneous array of properties.

Once an immune response is detected, e.g., antibodies specific for the antigen CFH are detected in the rat serum, the rat spleen is harvested and splenocytes isolated. The splenocytes are then fused by well-known techniques to any suitable myeloma cells, for example, cells from cell line SP20 available from the American Type Culture Collection (ATCC, Manassas, Va., US). Hybridomas are selected and cloned by limited dilution. The hybridoma clones are then assayed by methods known in the art for cells that secrete antibodies capable of binding CFH. Ascites fluid, which generally contains high levels of antibodies, can be generated by immunizing rats with positive hybridoma clones.

In another embodiment, antibody-producing immortalized hybridomas may be prepared from the immunized animal. After immunization, the animal is sacrificed and the splenic B cells are fused to immortalized myeloma cells as is well known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using CFH, or a portion thereof, such as GPPP-PIDNGDITSFP(GGGK-biotin) (SEQ ID NO:15), or a cell expressing CFH. In a preferred embodiment, the initial screening is performed using an enzyme-linked immunosorbent assay (ELISA) or a radioimmunoassay (RIA), preferably an ELISA. An example of ELISA screening is provided in PCT Publication No. WO 00/37504.

Anti-CFH antibody-producing hybridomas are selected, cloned, and further screened for desirable characteristics, including robust hybridoma growth, high antibody production, and desirable antibody characteristics. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, hybridomas are rat hybridomas. In another embodiment, hybridomas are produced in a non-human, non-rat species such as mice, sheep, pigs, goats, cattle, rabbits, or horses. In yet another preferred embodiment, the hybridomas are human hybridomas, in which a human non-secretory myeloma is fused with a human cell expressing an anti-CFH antibody.

Antibody fragments that recognize specific epitopes may be generated by known techniques. For example, Fab and F(ab')$_2$ fragments of the invention may be produced by proteolytic cleavage of immunoglobulin molecules, using enzymes such as papain (to produce two identical Fab fragments) or pepsin (to produce an F(ab')$_2$ fragment). A F(ab')$_2$ fragment of an IgG molecule retains the two antigen-binding sites of the larger ("parent") IgG molecule, including both light chains (containing the variable light chain and constant light chain regions), the CH1 domains of the heavy chains, and a disulfide-forming hinge region of the parent IgG molecule. Accordingly, an F(ab')$_2$ fragment is still capable of crosslinking antigen molecules like the parent IgG molecule.

Anti-CFH Monoclonal Antibodies Using SLAM

In another aspect of the invention, recombinant antibodies are generated from single, isolated lymphocytes using a procedure referred to in the art as the selected lymphocyte antibody method (SLAM), as described in U.S. Pat. No. 5,627,052; PCT Publication No. WO 92/02551; and Babcook et al., *Proc. Natl. Acad. Sci. USA*, 93: 7843-7848 (1996). In this method, single cells secreting antibodies of interest, e.g., lymphocytes derived from any one of the immunized animals are screened using an antigen-specific hemolytic plaque assay, wherein the antigen CFH, a subunit of CFH, or a fragment thereof, is coupled to sheep red blood cells using a linker, such as biotin, and used to identify single cells that secrete antibodies with specificity for CFH. Following identification of antibody-secreting cells of interest, heavy- and light-chain variable region cDNAs are rescued from the cells by reverse transcriptase-PCR (RT-PCR) and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example, by panning the transfected cells to isolate cells expressing antibodies to CFH. The amplified immunoglobulin sequences further can be manipulated in vitro, such as by in vitro affinity maturation methods. See, for example, PCT Publication No. WO 97/29131 and PCT Publication No. WO 00/56772.

Anti-CFH Monoclonal Antibodies Using Transgenic Animals

In another embodiment of the invention, antibodies are produced by immunizing a non-human animal comprising some, or all, of the human immunoglobulin locus with a CFH antigen. In an embodiment, the non-human animal is a XENOMOUSE® transgenic mouse, an engineered mouse strain that comprises large fragments of the human immunoglobulin loci and is deficient in mouse antibody production. See, e.g., Green et al., *Nature Genetics*, 7: 13-21 (1994) and U.S. Pat. Nos. 5,916,771; 5,939,598; 5,985,615; 5,998, 209; 6,075,181; 6,091,001; 6,114,598; and 6,130,364. See also PCT Publication Nos. WO 91/10741; WO 94/02602; WO 96/34096; WO 96/33735; WO 98/16654; WO 98/24893; WO 98/50433; WO 99/45031; WO 99/53049; WO 00/09560; and WO 00/37504. The XENOMOUSE® transgenic mouse produces an adult-like human repertoire of fully human antibodies, and generates antigen-specific human monoclonal antibodies. The XENOMOUSE® transgenic mouse contains approximately 80% of the human antibody repertoire through introduction of megabase sized, germLine configuration YAC fragments of the human heavy chain loci and x light chain loci. See Mendez et al., *Nature Genetics*, 15: 146-156 (1997), Green and Jakobovits, *J. Exp. Med.*, 188: 483-495 (1998), the disclosures of which are hereby incorporated by reference.

Anti-CFH Monoclonal Antibodies Using Recombinant Antibody Libraries

In vitro methods also can be used to make the antibodies of the invention, wherein an antibody library is screened to identify an antibody having the desired CFH-binding specificity. Methods for such screening of recombinant antibody libraries are well known in the art and include methods described in, for example, U.S. Pat. No. 5,223,409 (Ladner et al.); PCT Publication No. WO 92/18619 (Kang et al.); PCT Publication No. WO 91/17271 (Dower et al.); PCT Publication No. WO 92/20791 (Winter et al.); PCT Publication No. WO 92/15679 (Markland et al.); PCT Publication No. WO 93/01288 (Breitling et al.); PCT Publication No. WO 92/01047 (McCafferty et al.); PCT Publication No. WO 92/09690 (Garrard et al.); Fuchs et al., *Bio/Technology*, 9: 1369-1372 (1991); Hay et al., *Hum. Antibod. Hybridomas*, 3: 81-85 (1992); Huse et al., *Science*, 246: 1275-1281 (1989); McCafferty et al., *Nature*, 348: 552-554 (1990); Griffiths et al., *EMBO J.*, 12: 725-734 (1993); Hawkins et al., *J. Mol. Biol.*, 226: 889-896 (1992); Clackson et al., *Nature*, 352: 624-628 (1991); Gram et al., *Proc. Natl. Acad. Sci. USA*, 89: 3576-3580 (1992); Garrard et al., *Bio/Technology*, 9: 1373-1377 (1991); Hoogenboom et al., *Nucl. Acids Res.*, 19: 4133-4137 (1991); Barbas et al., *Proc. Natl. Acad. Sci. USA*, 88: 7978-7982 (1991); US Patent Application Publication No. 2003/0186374; and PCT Publication No. WO 97/29131, the contents of each of which are incorporated herein by reference.

The recombinant antibody library may be from a subject immunized with CFH, or a portion of CFH. Alternatively, the recombinant antibody library may be from a naive subject, i.e., one who has not been immunized with CFH, such as a human antibody library from a human subject who has not been immunized with human CFH. Antibodies of the invention are selected by screening the recombinant antibody library with the peptide comprising human CFH to thereby select those antibodies that recognize CFH. Methods for conducting such screening and selection are well known in the art, such as described in the references in the preceding paragraph. To select antibodies of the invention having particular binding affinities for CFH, such as those that dissociate from human CFH with a particular Koff rate constant, the art-known method of surface plasmon resonance can be used to select antibodies having the desired Koff rate constant. To select antibodies of the invention having a particular neutralizing activity for hCFH, such as those with a particular $IC_{50}$, standard methods known in the art for assessing the inhibition of CFH activity may be used.

In one aspect, the invention pertains to an isolated antibody, or an antigen-binding portion thereof, that binds human CFH. Preferably, the antibody is a neutralizing antibody. In various embodiments, the antibody is a recombinant antibody or a monoclonal antibody.

For example, antibodies of the present invention can also be generated using various phage display methods known in the art. In phage display methods, functional antibody domains are displayed on the surface of phage particles which carry the polynucleotide sequences encoding them. Such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv, or disulfide stabilized Fv antibody domains recombinantly fused to either the phage gene III or gene VIII protein. Examples of phage display methods that can be used to make the antibodies of the present invention include those disclosed in Brinkmann et al., *J. Immunol. Methods*, 182: 41-50 (1995); Ames et al., *J. Immunol. Methods*, 184:177-186 (1995); Kettleborough et al., *Eur. J. Immunol.*, 24: 952-958 (1994); Persic et al., *Gene*, 187: 9-18 (1997); Burton et al., *Advances in Immunology*, 57: 191-280 (1994); PCT Publication No. WO 92/01047; PCT Publication Nos. WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; and 5,969,108.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab', and F(ab')$_2$ fragments can also be employed using methods known in the art such as those disclosed in PCT publication No. WO 92/22324; Mullinax et al., *BioTechniques*, 12(6): 864-869 (1992); Sawai et al., *Am. J. Reprod. Immunol.*, 34: 26-34 (1995); and Better et al., *Science*, 240: 1041-1043 (1988). Examples of techniques which can be used to produce single-chain Fvs and antibodies include those described in U.S. Pat. Nos. 4,946,778 and 5,258,498; Huston et al., Methods in Enzymology, 203: 46-88 (1991); Shu et al., *Proc. Natl. Acad. Sci. USA*, 90: 7995-7999 (1993); and Skerra et al., *Science*, 240: 1038-1041 (1988).

Alternative to screening of recombinant antibody libraries by phage display, other methodologies known in the art for screening large combinatorial libraries can be applied to the identification of antibodies of the invention. One type of alternative expression system is one in which the recombinant antibody library is expressed as RNA-protein fusions, as described in PCT Publication No. WO 98/31700 (Szostak and Roberts), and in Roberts and Szostak, *Proc. Natl. Acad. Sci. USA*, 94: 12297-12302 (1997). In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above. A preferred example of this methodology is PROfusion display technology.

In another approach, the antibodies of the present invention can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the antibodies of the present invention include those disclosed in U.S. Pat. No. 6,699,658 (Wittrup et al.) incorporated herein by reference.

Production of Recombinant CFH Antibodies

Antibodies of the present invention may be recombinant antibodies and may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection, and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody. The recombinant antibody may be a humanized antibody.

Exemplary mammalian host cells for expressing the recombinant antibodies of the invention include Chinese Hamster Ovary (CHO cells) (including dhfr-CHO cells, described in Urlaub and Chasin, *Proc. Natl. Acad. Sci. USA*, 77: 4216-4220 (1980), used with a DHFR selectable marker, e.g., as described in Kaufman and Sharp, *J. Mol. Biol.*, 159: 601-621 (1982), NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention (i.e., binds human CFH) and the other heavy and light chain are specific for an antigen other than human CFH by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells, and recover the antibody from the culture medium. Still further, the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

Humanized Antibody

The humanized antibody may be an antibody or a variant, derivative, analog or portion thereof which immunospecifically binds to an antigen of interest and which comprises a framework (FR) region having substantially the amino acid sequence of a human antibody and a complementary determining region (CDR) having substantially the amino acid sequence of a non-human antibody. The humanized antibody may be from a non-human species antibody that binds the desired antigen having one or more complementarity determining regions (CDRs) from the non-human species and framework regions from a human immunoglobulin molecule.

As used herein, the term "substantially" in the context of a CDR refers to a CDR having an amino acid sequence at least 90%, at least 95%, at least 98% or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. According to one aspect, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or of a heavy chain.

The humanized antibody can be selected from any class of immunoglobulins, including IgM, IgG, IgD, IgA and IgE, and any isotype, including without limitation IgG 1, IgG2, IgG3, and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In one embodiment, such mutations, however, will not be extensive. Usually, at least 90%, at least 95%, at least 98%, or at least 99% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, *From Genes to Clones* (Verlagsgesellschaft, Weinheim, Germany 1987)). In a family of immunoglobulins, each position in the consensus sequence is occupied by the amino acid occurring most frequently at that position in the family. If two amino acids occur equally frequently, either can be included in the consensus sequence.

The humanized antibody may be designed to minimize unwanted immunological response toward rodent anti-human antibodies, which limits the duration and effectiveness of therapeutic applications of those moieties in human recipients. The humanized antibody may have one or more amino acid residues introduced into it from a source that is non-human. These non-human residues are often referred to as "import" residues, which are typically taken from a variable domain. Humanization may be performed by substituting hypervariable region sequences for the corresponding sequences of a human antibody. Accordingly, such "humanized" antibodies are chimeric antibodies wherein substantially less than an intact human variable domain has been substituted by the corresponding sequence from a non-human species. For example, see U.S. Pat. No. 4,816,567, the contents of which are herein incorporated by reference. The humanized antibody may be a human antibody in which some hypervariable region residues, and possibly some FR residues are substituted by residues from analogous sites in rodent antibodies. Humanization or engineering of antibodies of the present invention can be performed using any known method, such as but not limited to those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

The humanized antibody may retain high affinity for CFH and other favorable biological properties. The humanized antibody may be prepared by a process of analysis of the parental sequences and various conceptual humanized products using three-dimensional models of the parental and humanized sequences. Three-dimensional immunoglobulin models are commonly available. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristics, such as increased affinity for CFH, is achieved. In general, the hypervariable region residues may be directly and most substantially involved in influencing antigen binding.

As an alternative to humanization, human antibodies (also referred to herein as "fully human antibodies") can be generated. For example, it is possible to isolate human antibodies from libraries via PROfusion and/or yeast related technologies. It is also possible to isolate antibody producing B cells from patients producing a relevant antibody, sequence, and then clone the immunoglobulin. It is also possible to produce transgenic animals (e.g., mice that are capable, upon immunization, of producing a full repertoire of human antibodies in the absence of endogenous immunoglobulin production. For example, the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. The humanized or fully human antibodies may be prepared according to the methods described in U.S. Pat. Nos. 5,770,429; 5,833,985; 5,837,243; 5,922,845; 6,017,517; 6,096,311; 6,111,166; 6,270,765; 6,303,755; 6,365,116; 6,410,690; 6,682,928; and 6,984,720, the contents each of which are herein incorporated by reference.

Small Molecules

A small molecule may be used as an inhibitor to target region of CFH to inhibit CFH binding to C3b. A small molecule may be a low molecular weight, for example, less than 800 Daltons, organic or inorganic compound that may serve as an enzyme substrate or regulator of biological processes. The small molecule may have a size of less than 1 nm. The small molecule may include ribo- or deoxyribonucleotides, dinucleotides, amino acids, peptides, monosaccharide, and disaccharides.

Pharmaceutical Compositions

The CFH inhibitor, such as the anti-CFH antibody, may be a component in a pharmaceutical composition. The pharmaceutical composition may also contain a pharmaceutically acceptable carrier. The pharmaceutical compositions comprising a CFH inhibitor of the invention are for use in, but not limited to, diagnosing, detecting, or monitoring a disorder, in preventing, treating, managing, or ameliorating of a disorder, or one or more symptoms thereof, and/or in research. In a specific embodiment, a composition comprises one or more CFH inhibitors of the invention. In another embodiment, the pharmaceutical composition comprises one or more CFH inhibitors of the invention and one or more prophylactic or therapeutic agents other than CFH inhibitors of the invention for treating a disorder in which activity of a targeted CFH is detrimental. In a further embodiment, the prophylactic or therapeutic agents are known to be useful for, or have been, or are currently being used in the prevention, treatment, management, or amelioration of a disorder, or one or more symptoms thereof. In accordance with these embodiments, the composition may further comprise of a carrier, diluent, or excipient.

The CFH inhibitor, such as the anti-CFH antibody, of the invention can be incorporated into pharmaceutical compositions suitable for administration to a subject. Typically, the pharmaceutical composition comprises a CFH inhibitor of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives, or buffers, which enhance the shelf life or effectiveness of the CFH inhibitor.

Various delivery systems are known and can be used to administer one or more CFH inhibitors of the invention or the combination of one or more CFH inhibitors of the invention and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the CFH inhibitor, receptor-mediated endocytosis (see, e.g., Wu and Wu, *J. Biol. Chem.* 262:4429-4432 (1987)), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO97/32572; WO97/44013; WO98/31346; and WO99/66903, each of which is incorporated herein by reference in their entireties. In one embodiment, a CFH inhibitor of the invention or a composition of the invention is administered using Alkermes AIR® pulmonary drug delivery technology (Alkermes, Inc., Cambridge, Mass.). In a specific embodiment, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the CFH inhibitors of the invention locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more CFH inhibitors of the invention is administered locally to the affected area to a subject to prevent, treat, manage, and/or ameliorate a disorder or a symptom thereof.

In another embodiment, the CFH inhibitors can be delivered in a controlled release or sustained release system. In one embodiment, a pump may be used to achieve controlled or sustained release (see Langer, supra; Sefton, 1987, *CRC Crit. Ref. Biomed. Eng.* 14:20; Buchwald et al., 1980, *Surgery* 88:507; Saudek et al., 1989, *N. Engl. J. Med.* 321:574). In another embodiment, polymeric materials can be used to achieve controlled or sustained release of the therapies of the invention (see e.g., Medical Applications of Controlled Release, Langer and Wise (eds.), CRC Pres., Boca Raton, Fla. (1974); *Controlled Drug Bioavailability*, Drug Product Design and Performance, Smolen and Ball (eds.), Wiley, New York (1984); Ranger and Peppas, 1983, *J., Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 7 1:105); U.S. Pat. Nos. 5,679,377; 5,916,597; 5,912,015; 5,989,463; 5,128,326; PCT Publication No. WO99/15154; and PCT Publication No. WO99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a particular embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, *Science* 249:1527-1533). Any technique known to one of skill in the art can be used to produce sustained release formulations comprising one or more CFH inhibitors of the invention. See, e.g., U.S. Pat. No. 4,526,938, PCT publication WO91/05548, PCT publication WO96/20698, Ning et al., 1996, "Intratumoral Radioimmunotherapy of a Human Colon Cancer Xenograft Using a Sustained-Release Gel," *Radiotherapy & Oncology* 39:179-189; Song et al., 1995, "Antibody Mediated Lung Targeting of Long-Circulating Emulsions," *PDA Journal of Pharmaceutical Science & Technology* 50:372-397; Cleek et al., 1997, "Biodegradable Polymeric Carriers for a bFGF Antibody for Cardiovascular Application," *Pro. Int'l. Symp. Control. Rel. Bioact. Mater.* 24:853-854; and Lam et al., 1997, "Microencapsulation of Recombinant Humanized Monoclonal Antibody for Local Delivery," *Proc. Int'l. Symp. Control Rel. Bioact. Mater.* 24:759-760, each of which is incorporated herein by reference in their entireties.

A pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

If the compositions of the invention are to be administered topically, the compositions can be formulated in the form of an ointment, cream, transdermal patch, lotion, gel, shampoo, spray, aerosol, solution, emulsion, or other form well-known to one of skill in the art. See, e.g., *Remington's Pharmaceutical Sciences* and *Introduction to Pharmaceutical Dosage Forms*, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, for example in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the method of the invention comprises intranasal administration of a composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebulizer, with the use of a suitable propellant (e.g., dichlorodifluoromethane, trichloro-fluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the method of the invention comprises oral administration, compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the invention may comprise pulmonary administration, e.g., by use of an inhaler or nebulizer, of a composition formulated with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference their entireties. In a specific embodiment, a CFH inhibitor of the invention and/or composition of the invention is administered using Alkermes AIR® pulmonary drug delivery technology (Alkermes, Inc., Cambridge, Mass.).

The method of the invention may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use. The methods of the invention may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the CFH inhibitors, or pharmaceutical compositions, of the invention is packaged in a hermetically sealed container such as an ampoule or sachette indicating the quantity of the CFH inhibitor. In one embodiment, one or more of the CFH inhibitors, or pharmaceutical compositions of the invention is supplied as a dry sterilized lyophilized powder or water free concentrate in a hermetically sealed container and can be reconstituted (e.g., with water or saline) to the appropriate concentration for administration to a subject. In one embodiment, one or more of the CFH inhibitors or pharmaceutical compositions of the invention is supplied as a dry sterile lyophilized powder in a hermetically sealed container at a unit dosage of at least 5 mg, for example at least 10 mg, at least 15 mg, at least 25 mg, at least 35 mg, at least 45 mg, at least 50 mg, at least 75 mg, or at least 100 mg. The lyophilized CFH inhibitors or pharmaceutical compositions of the invention should be stored at between 2° C. and 8° C. in its original container and the CFH inhibitors, or pharmaceutical compositions of the invention should be administered within 1 week, for example within 5 days, within 72 hours, within 48 hours, within 24 hours, within 12 hours, within 6 hours, within 5 hours, within 3 hours, or within 1 hour after being reconstituted. In an alternative embodiment, one or more of the CFH inhibitors or pharmaceutical compositions of the invention is supplied in liquid form in a hermetically sealed container indicating the quantity and concentration of the CFH inhibitor. In a further embodiment, the liquid form of the administered composition is supplied in a hermetically sealed container at least 0.25 mg/mL, for example at least 0.5 mg/mL, at least 1 mg/mL, at least 2.5 mg/mL, at least 5 mg/mL, at least 8 mg/mL, at least 10 mg/mL, at least 15 mg/mL, at least 25 mg/mL, at least 50 mg/mL, at least 75 mg/mL or at least 100 mg/mL. The liquid form should be stored at between 2° C. and 8° C. in its original container.

The CFH inhibitors of the invention can be incorporated into a pharmaceutical composition suitable for parenteral administration. In one aspect, CFH inhibitors will be prepared as an injectable solution containing 0.1-250 mg/mL CFH inhibitor. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the tonicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants. The pharmaceutical composition comprising the CFH inhibitors of the invention prepared as an injectable solution for parenteral administration, can further comprise an agent useful as an adjuvant, such as those used to increase the absorption, or dispersion of the CFH inhibitor. A particularly useful adjuvant is hyaluronidase, such as Hylenex® (recombinant human hyaluronidase). Addition of hyaluronidase in the injectable solution improves human bioavailability following parenteral administration, particularly subcutaneous administration. It also allows for greater injection site volumes (i.e., greater than 1 mL) with less pain and discomfort, and minimum incidence of injection site reactions. (See International Appln. Publication No. WO 04/078140 and U.S. Patent Appln. Publication No. US2006104968, incorporated herein by reference.)

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Compositions can be in the form of injectable or infusible solutions, such as compositions similar to those used for passive immunization of humans with other CFH inhibitors. In one embodiment, the CFH inhibitor is administered by intravenous infusion or injection. In another embodiment, the CFH inhibitor is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., a CFH inhibitor of the present invention) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, methods of preparation comprise vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The CFH inhibitors of the present invention can be administered by a variety of methods known in the art. For many therapeutic applications, the route/mode of administration may be subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, a CFH inhibitor of the invention may be orally administered, for example, with an inert diluent or an assimilable edible carrier. The CFH inhibitor (and other ingredients, if desired) may also be enclosed in a hard or soft shell gelatin capsule, compressed into tablets, or incorporated directly into the subject's diet. For oral therapeutic administration, the CFH inhibitor may be incorporated with excipients and used in the form of ingestible tablets, buccal tablets, troches, capsules, elixirs, suspensions, syrups, wafers, and the like. To administer a CFH inhibitor of the invention by other than parenteral administration, it may be necessary to coat the CFH inhibitor with, or co-administer the CFH inhibitor with, a material to prevent its inactivation.

In certain embodiments, a CFH inhibitor of the invention is linked to a half-life extending vehicle known in the art. Such vehicles include, but are not limited to, the Fc domain, polyethylene glycol, and dextran. Such vehicles are described, e.g., in U.S. application Ser. No. 09/428,082 and published PCT Application No. WO 99/25044, which are hereby incorporated by reference for any purpose.

The pharmaceutical compositions may include a "therapeutically effective amount" or a "prophylactically effective amount" of a CFH inhibitor. A "therapeutically effective amount" refers to an amount effective, at dosages and for periods of time necessary, to achieve the desired therapeutic result. A therapeutically effective amount of the CFH inhibitor may be determined by a person skilled in the art and may vary according to factors such as the disease state, age, sex, and weight of the individual, and the ability of the CFH inhibitor to elicit a desired response in the individual. A therapeutically effective amount is also one in which toxic or detrimental effects, if any, of the CFH inhibitor are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of the CFH inhibitor is a dose of between 0.1 and 200 mg/kg, for example between 0.1 and 10 mg/kg. The therapeutically or prophylactically effective amount of the CFH inhibitor may be between 1 and 200 mg/kg, 10 and 200 mg/kg, 20 and 200 mg/kg, 50 and 200 mg/kg, 75 and 200 mg/kg, 100 and 200 mg/kg, 150 and 200 mg/kg, 50 and 100 mg/kg, 5 and 10 mg/kg, or 1 and 10 mg/kg. It is to be noted that dosage values may vary with the type and severity of the condition to be alleviated. Further, the CFH inhibitor dose may be determined by a person skilled in the art and may vary according to factors such as the disease state, age, sex, and weight of the individual, and the ability of the CFH inhibitor to elicit a desired response in the individual. The dose is also one in which toxic or detrimental effects, if any, of the CFH inhibitor are outweighed by the therapeutically beneficial effects. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

CFH Detection

The present invention also is directed to a method of detecting and measuring CFH or the reduced form of CFH in a sample using the anti-CFH antibodies described above to bind to different CFH or the reduced form of CFH epitopes. The method includes contacting the sample with the isolated antibody or antibody fragment described above.

Immunoassay

CFH and the reduced form of CFH, and/or peptides or fragments thereof, i.e., CFH and reduced form of CFH fragments, may be analyzed using the antibodies described above in an immunoassay. The presence or amount of CFH or reduced form of CFH can be determined using antibodies and detecting specific binding to CFH or reduced form of CFH. For example, the antibody, or antibody fragment thereof, may specifically bind to CFH or reduced form of CFH. If desired, one or more of the antibodies can be used in combination with one or more commercially available monoclonal/polyclonal antibodies. Such antibodies are available from companies such as R&D Systems, Inc. (Minneapolis, MN) and Enzo Life Sciences International, Inc. (Plymouth Meeting, PA).

The presence or amount of CFH or reduced form of CFH present in a body sample may be readily determined using an immunoassay, such as sandwich immunoassay (e.g., monoclonal-polyclonal sandwich immunoassays, including radioisotope detection (radioimmunoassay (RIA)) and enzyme detection (enzyme immunoassay (EIA) or enzyme-linked immunosorbent assay (ELISA) (e.g., Quantikine ELISA assays, R&D Systems, Minneapolis, MN)). A chemiluminescent microparticle immunoassay, in particular one employing the ARCHITECT® automated analyzer (Abbott Laboratories, Abbott Park, IL), is an example of a preferred immunoassay. Other methods include, for example, mass spectrometry and immunohistochemistry (e.g., with sections from tissue biopsies) using CFH antibodies (monoclonal, polyclonal, chimeric, humanized, human etc.) or antibody fragments thereof against CFH. Other methods of detection include those described in, for example, U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. Specific immunological binding of the antibody to the CFH can be detected via direct labels, such as fluorescent or luminescent tags, metals and radionuclides attached to the antibody or via indirect labels, such as alkaline phosphatase or horseradish peroxidase.

Methods of Treating

Provided herein is a method of treating cancer in a subject. The method may include administering to the subject in need thereof an inhibitor of CFH, such as the anti-CFH antibody or small molecule described above. The CFH inhibitor may be administered in a therapeutically effective amount.

In general, the dosage of administered CFH inhibitor will vary depending upon such factors as the patient's age, weight, height, sex, general medical condition and previous medical history. Typically, it is desirable to provide the recipient with a dosage of CFH inhibitor component, immunoconjugate or fusion protein which is in the range of from about 1 pg/kg to 10 mg/kg (amount of agent/body weight of patient), although a lower or higher dosage also may be administered as circumstances dictate. Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be tested; each unit containing a predetermined quantity of active compound calculated to produce the desired therapeutic effect in association with the required pharmaceutical carrier. The specification for the dosage unit forms of the present invention are dictated by and directly dependent on (a) the unique characteristics of the active compound and the particular therapeutic or prophylactic effect to be achieved and (b) the limitations inherent in the art of compounding such an active compound for the treatment of sensitivity in individuals.

An exemplary, non-limiting range for a therapeutically or prophylactically effective amount of a CFH inhibitor of the invention is 0.1-20 mg/kg, more preferably 0.5-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Administration of CFH inhibitors to a patient can be intravenous, intraarterial, intraperitoneal, intramuscular, subcutaneous, intrapleural, intrathecal, intraocular, intravitreal, by perfusion through a regional catheter, or by direct intralesional injection. When administering therapeutic proteins by injection, the administration may be by continuous infusion or by single or multiple boluses. Intravenous injection provides a useful mode of administration due to the thoroughness of the circulation in rapidly distributing CFH inhibitors. The CFH inhibitor may be administered orally, for example, with an inert diluent or an assimilable edible carrier. The antibody and other ingredients, if desired, may be enclosed in a hard or soft shell gelatin capsule, compressed into tablets, buccal tablets, troches, capsules, elixirs, suspensions, syrups, wafers, and the like.

CFH inhibitors may be administered at low protein doses, such as 20 milligrams to 2 grams protein per dose, given once, or repeatedly, parenterally. Alternatively, the CFH inhibitors may be administered in doses of 20 to 1000 milligrams protein per dose, or 20 to 500 milligrams protein per dose, or 20 to 100 milligrams protein per dose.

The CFH inhibitors may be administered alone or they may be conjugated to liposomes, and can be formulated according to known methods to prepare pharmaceutically useful compositions, whereby the CFH inhibitors are combined in a mixture with a pharmaceutically acceptable carrier. A "pharmaceutically acceptable carrier" may be tolerated by a recipient patient. Sterile phosphate-buffered saline is one example of a pharmaceutically acceptable carrier. Other suitable carriers are well known to those in the art. See, for example, *REMINGTON'S PHARMACEUTICAL SCIENCES,* 19th Ed. (1995).

For purposes of therapy, CFH inhibitors are administered to a patient in a therapeutically effective amount in a pharmaceutically acceptable carrier. A "therapeutically effective amount" is one that is physiologically significant. The CFH inhibitor is physiologically significant if its presence results in a detectable change in the physiology of a recipient patient. In the present context, the CFH inhibitors may be physiologically significant if its presence results in, for example, increased complement dependent lysis of a cell, increased C3b deposition on a cell, and/or inhibition of CFH binding to C3b.

Additional treatment methods may be employed to control the duration of action of an antibody in a therapeutic application. Control release preparations can be prepared through the use of polymers to complex or adsorb the antibody. For example, biocompatible polymers include matrices of poly(ethylene-co-vinyl acetate) and matrices of a polyanhydride copolymer of a stearic acid dimer and sebacic acid. Sherwood et al., *Bio/Technology* 10:1446 (1992). The rate of release of an antibody from such a matrix depends upon the molecular weight of the protein, the amount of antibody within the matrix, and the size of dispersed particles. Saltzman et al., *Biophys. J.* 55:163 (1989); Sherwood et al., supra. Other solid dosage forms are described in *REMINGTON'S PHARMACEUTICAL SCIENCES,* 19th ed. (1995).

CFH Antibodies

The CFH antibodies described herein may interfere with CFH binding to tumor cells, such as lung cancer cells, and may be used to treat cancer in a subject. The interference of CFH binding to the tumor cells decreases the number of CFH on the tumor cells and enhances complement-dependent lysis of the tumor cells. The CFH antibodies may cause an increase in the deposition of C3b on lung cancer cells. C3b deposition is required for complement dependent cytotoxicity (CDC) and is frequently used as evidence for complement activation.

An effective amount of the CFH antibody or fragment thereof may be administered to the cell. For example, an effective amount between about 1 µg/mL to about 250 µg/mL, between about 10 µg/mL to about 250 µg/mL, between about 25 µg/mL to about 250 µg/mL, between about 40 µg/mL to about 250 µg/mL, between about 45 µg/mL to about 250 µg/mL, between about 50 µg/mL to about 250 µg/mL, between about 60 µg/mL to about 250 µg/mL, between about 75 µg/mL to about 250 µg/mL, between about 100 µg/mL to about 250 µg/mL, between about 10 µg/mL to about 200 µg/mL, between about 25 µg/mL to about 200 µg/mL, between about 40 µg/mL to about 200 µg/mL, between about 45 µg/mL to about 200 µg/mL, between about 50 µg/mL to about 200 µg/mL, between about 60 µg/mL to about 200 µg/mL, between about 75 µg/mL to about 200 µg/mL, between about 100 µg/mL to about 200 µg/mL, between about 10 µg/mL to about 150 µg/mL, between about 25 µg/mL to about 150 µg/mL, between about 40 µg/mL to about 150 µg/mL, between about 45 µg/mL to about 150 µg/mL, between about 50 µg/mL to about 150 µg/mL, between about 60 µg/mL to about 150 µg/mL, between about 75 µg/mL to about 150 µg/mL, between about 100 µg/mL to about 150 µg/mL, between about 10 µg/mL to about 120 µg/mL, between about 25 µg/mL to about 120 µg/mL, between about 40 µg/mL to about 120 µg/mL, between about 45 µg/mL to about 120 µg/mL, between about 50 µg/mL to about 120 µg/mL, between about 60 µg/mL to about 120 µg/mL, between about 75 µg/mL to about 120 µg/mL, between about 100 µg/mL to about 120 µg/mL, between about 10 µg/mL to about 100 µg/mL, between about 25 µg/mL to about 100 µg/mL, between about 40 µg/mL to about 100 µg/mL, between about 45 µg/mL to about 100 µg/mL, between about 50 µg/mL to about 100 µg/mL, between about 60 µg/mL to about 100 µg/mL, or between about 75 µg/mL to about 100 µg/mL of the CFH antibody or fragment thereof may be administered to the cell. The CFH antibodies may be Ab7960/293i or Ab7968.

Cancer

The method described herein may be used to treat a subject having any form of cancer. The method may include administering to the subject in need thereof an inhibitor of CFH, such as the anti-CFH antibody or small molecule described above. The cancer may be any cancer that uses CFH as a protective mechanism. The cancer may be Adrenocortical Carcinoma, Anal Cancer, Bladder Cancer, Brain Tumor, Breast Cancer, Carcinoid Tumor, Gastrointestinal, Carcinoma of Unknown Primary, Cervical Cancer, Colon Cancer, Endometrial Cancer, Esophageal Cancer, Extrahepatic Bile Duct Cancer, Ewings Family of Tumors (PNET), Extracranial Germ Cell Tumor, Intraocular Melanoma Eye Cancer, Gallbladder Cancer, Gastric Cancer (Stomach), Extragonadal Germ Cell Tumor, Gestational Trophoblastic Tumor, Head and Neck Cancer, Hypopharyngeal Cancer, Islet Cell Carcinoma, Kidney Cancer (renal cell cancer), Laryngeal Cancer, Acute Lymphoblastic Leukemia, Leukemia, Acute Myeloid, Chronic Lymphocytic Leukemia, Chronic Myelogenous Leukemia, Hairy Cell Leukemia, Lip and Oral Cavity Cancer, Liver Cancer, Non-Small Cell Lung Cancer, Small Cell Lung Cancer, AIDS-Related Lymphoma, Central Nervous System (Primary) Lymphoma, Cutaneous T-Cell Lymphoma, Hodgkin's Disease Lymphoma, Non-Hodgkin's Disease Lymphoma, Malignant Mesothelioma, Melanoma, Merkel Cell Carcinoma, Metasatic Squamous Neck Cancer with Occult Primary, Multiple Myeloma and Other Plasma Cell Neoplasms, Mycosis Fungoides, Myelodysplastic Syndrome, Myeloproliferative Disorders, Nasopharyngeal Cancer, euroblastoma, Oral Cancer, Oropharyngeal Cancer, Osteosarcoma, Ovarian Epithelial Cancer, Ovarian Germ Cell Tumor, Pancreatic Cancer, Exocrine, Pancreatic Cancer, Islet Cell Carcinoma, Paranasal Sinus and Nasal Cavity Cancer, Parathyroid Cancer, Penile Cancer, Pituitary Cancer, Plasma Cell Neoplasm, Prostate Cancer, Rhabdomyosarcoma, Rectal Cancer, Renal Cell Cancer (cancer of the kidney), Transitional Cell Renal Pelvis and Ureter, Salivary Gland Cancer, Sezary Syndrome, Skin Cancer, Small Intestine Cancer, Soft Tissue Sarcoma, Testicular Cancer, Malignant Thymoma, Thyroid Cancer, Urethral Cancer, Uterine Cancer, Unusual Cancer of Childhood, Vaginal Cancer, Vulvar Cancer, and Wilms' Tumor.

Lung Cancer

The method described herein can be used to treat a subject having lung cancer. The method may include administering to the subject in need thereof an inhibitor of CFH, such as the anti-CFH antibody or small molecule described above. The lung cancer may be small-cell lung cancer, also known as small-cell lung carcinoma and oat cell cancer, non-small-cell lung carcinoma ("NSCLC"), glandular tumors, carcinoid tumors and/or undifferentiated carcinomas.

Breast Cancer

The method described herein can be used to treat a subject having breast cancer. The method may include administering to the subject in need thereof an inhibitor of CFH, such as the anti-CFH antibody or small molecule described above. Breast cancer may be any cancer that starts in the tissues of the breast. The two main types of breast cancer are ductal carcinoma, which starts in the tubes (ducts) that move milk from the breast to the nipple, and lobular carcinoma, which starts in the parts of the breast, called lobules, that produce milk. Breast cancer may also start in other areas of the breast. Breast cancer may be invasive or noninvasive (in situ).

Combination Therapy

The methods described above may include a combination treatment of the CFH inhibitor with other drugs and/or other conventional cancer therapies.

Combination Drugs

The methods may further include administering an effective amount of at least one anti-cancer compound or chemotherapeutic agent. The CFH inhibitors may be used in conjunction with an anti-cancer drug or chemotherapeutic agent to increase tumor cell killing, i.e., enhance antibody-dependent cell-mediated cytotoxicity (ADCC) and cell mediated toxicity. Examples of anti-cancer compounds and chemotherapeutic agents include anthracyclines, such as doxorubicin (ADRIAMYCIN®, DOXIL®), epirubicin (ELLENCE®), and daunorubicin (CERUBIDINE®, DAUNOXOME®), capecitabine (XELODA®), carboplatin (PARAPLATIN®), cisplatin, cyclophosphamide (CYTOXAN®), eribulin (HALAVEN®), fluorouracil (also called 5-fluorouracil or 5-FU; ADRUCIL®), gemcitabine (GEMZAR®), ixabepilone (IXEMPRA®), methotrexate (Amethopterin, MEXATE®, FOLEX®), mitoxantrone (NOVANTRONE®), MUTAMYCIN® (Mitomycin), taxanes, such as paclitaxel (Taxol, ABRAXANE®), and docetaxel (TAXOTERE®), thiotepa (THIOPLEX®), vincristine (ONCOVIN®, Vincasar PES, VINCREX®), and vinorelbine (NAVELBINE®). Examples of targeted therapy include trastuzumab (HERCEPTIN®), lapatinib (TYKERB®), onartuzumab, rilotumumab (AMG102), ficlatuzumab (AV-299), bevacizumab (AVASTIN®), pertuzumab (PERJETA®), Rituximab, panatumamab, and everolimus (AFINITOR®). The CFH inhibitors may be used in conjunction with Cetuximab, PERJETA®, and HERCEPTIN®.

Conventional Cancer Therapies

Conventional cancer therapies may include surgery, radiation therapy, hormone therapy, and targeted therapy. Examples of surgery include open craniotomy with maximal excision, which may be followed by radiation therapy. Examples of radiation therapy include whole-brain irradiation, fractionated radiotherapy, and radiosurgery, such as stereotactic radiosurgery, e.g., Gamma Knife radiosurgery.

Subject

The subject may be a mammal, which may be a human. The subject may have, or be at risk of developing a cancer. The subject may have cancer. The subject may already be undergoing treatment for a cancer.

Methods of Increasing Complement Dependent Lysis of Cells

The methods described herein can also be used to increase complement-dependent lysis of a cell. The method described herein may include administering to the cell an inhibitor of CFH, such as the anti-CFH antibody or small molecule described above. The cell may be a tumor cell. For example, the tumor cell may be MCF7 breast cancer cell, SKBR3 breast cancer cell, MDA-MB-231 breast cancer cell, or A549 lung carcinoma cell.

As disclosed below, purified CFH antibodies had a statistically significant effect on both C3 deposition on A549 lung carcinoma cells and cytotoxicity by the alternative pathway. It should be noted that lung tumor cells, as well as other types of tumor cells, are protected from complement attack by other membrane bound inhibitors including MCP (CD46), CR1 (CD35), and DAF (CD55) in addition to CFH. Efficiency of cytotoxicity could conceivably be increased by combining patient antibodies to CFH with monoclonal antibodies to these proteins (See Example 2).

Methods of Inhibiting Complement Factor H Binding to C3b

The methods described herein can also be used to inhibit CFH binding to C3b in a subject or a cell. The method may include administering to the subject or the cell an inhibitor of CFH, such as the anti-CFH antibody or small molecule described above. The cell may be a tumor cell. For example, the tumor cell may be MCF7 breast cancer cell, SKBR3 breast cancer cell, MDA-MB-231 breast cancer cell, or A549 lung carcinoma cell.

Methods of Increasing C3b Deposition on Cells

The methods described herein can also be used to increase C3b deposition on a cell. The method may include administering to the subject or the cell an inhibitor of CFH, such as the anti-CFH antibody or small molecule described above. The cell may be a tumor cell. For example, the tumor cell may be MCF7 breast cancer cell, SKBR3 breast cancer cell, MDA-MB-231 breast cancer cell, or A549 lung carcinoma cell.

Methods of Inhibiting Tumor Growth

The methods described herein can also be used to inhibit tumor growth in a subject. The method may include may include administering to the subject or the cell an inhibitor of CFH, such as the anti-CFH antibody or small molecule described above. The tumor may be a solid tumor or a hematologic malignancy. For example, the tumor may be a lung tumor.

Mechanisms of Delivery

The CFH inhibitor may be formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the CFH inhibitor is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

Various delivery systems are known and can be used to administer one or more SERMs or the combination of one or more CFH inhibitors and a prophylactic agent or therapeutic agent useful for preventing, managing, treating, or ameliorating a disorder or one or more symptoms thereof, e.g., encapsulation in liposomes, microparticles, microcapsules, receptor-mediated endocytosis (see, e.g., Wu and Wu, *J. Biol. Chem.* 262:4429-4432 (1987)), etc. Methods of administering a prophylactic or therapeutic agent of the SERM include, but are not limited to, parenteral administration (e.g., intradermal, intramuscular, intraperitoneal, intravenous and subcutaneous), epidural administration, intratumoral administration, and mucosal administration (e.g., intranasal and oral routes).

Cell Types

The methods described herein may be utilized with a cell from a sample or subject. The cell may be a tumor or cancer cell. The cell may be a breast cancer cell or a lung cancer cell. For example, the cell may be MCF7 breast cancer cell, SKBR3 breast cancer cell, MDA-MB-231 breast cancer cell, A549 lung carcinoma cell, DMS79, or H226 cell lines.

Kit

Provided herein is a kit, which may be used for assaying a test sample for CFH or CFH fragment or reduced form of CFH or reduced form of CFH fragment. The kit comprises at least one component for assaying the test sample for CFH or reduced form of CFH and instructions for assaying the test sample for CFH or reduced form of CFH. For example, the kit can comprise instructions for assaying the test sample for CFH or reduced form of CFH by immunoassay, e.g., chemiluminescent microparticle immunoassay. Instructions included in kits can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

The component may include at least one composition comprising one or more isolated antibodies or antibody fragments thereof that specifically bind to CFH or reduced form of CFH. The antibody may be a CFH or reduced form of CFH capture antibody and/or a CFH or reduced form of CFH detection antibody. Preferably, the kit comprises all components, i.e., reagents, standards, buffers, diluents, etc., which are necessary to perform the assay. The kit may also include other drugs for treating cancer.

EXAMPLES

The present invention has multiple aspects, illustrated by the following non-limiting examples.

Example 1

Materials and Methods

Dot Blot for Domain Mapping. Dot blots, kindly supplied by Dr. Michael Pangburn, contained cloned, expressed, and purified overlapping protein domain subsets of CFH. These proteins were reduced with TCEP, as described below before spotting on nitrocellulose. The blots were probed with human NSCLC serum (1:2000) and anti-IgG gamma chain-HRP conjugate (Millipore, Temecula, CA; 1:5000), and then treated with a chemiluminescent substrate, exposed to film, and developed.

Purification of SCR19-20. A *Pichia pastoris* clone encoding human CFH short consensus repeat domains 19 and 20 (termed SCR19-20) in an integrated *P. pastoris* expression vector was obtained from Dr. Michael Pangburn (University of Texas Health Science Center, Tyler, TX). The protein was purified from the *P. pastoris* culture medium by sequential differential filtration using VIVACELL® 70 centrifugal units with 50,000 and 5,000 MW cutoffs (Sartorius, Goettingen, Germany) followed by HITRAP® SP FF cation exchange chromatography (GE Healthcare Life Sciences, Piscataway, NJ).

Purification of Human CFH Autoantibodies. An antibody purification strategy was developed to carry out functional studies on CFH autoantibodies. First, bulk immunoglobulin was purified from serum by Protein G chromatography. The specific antibody was then purified by affinity chromatography over N-hydroxysuccinimide ester-activated SEPHAROSE® 4 FF (GE Healthcare Life Sciences) conjugated according to the manufacturer's instructions with SCR19-20 reduced with TCEP, as described below. Immunoglobulin was loaded onto the SCR19-20 column, the column was washed, and bound anti-CFH antibody was recovered by elution with 3 M sodium thiocyanate, 20 mM Tris-HCl, pH 6.8. Elution buffer was exchanged by sequential steps of dilution with PBS plus 10% glycerol, followed by concentration in an AMICON® Ultra 4 spin device (30K MW cutoff), such that the initial buffer was diluted approximately 6000×. Recovery of anti-CFH antibody was confirmed by both ELISA and immunoblot.

CFH Autoantibody ELISA. Wells of a MAXISORP™ immunoplate (Nunc International, Rochester, NY) were coated with 500 ng native, reduced, denatured, or reduced and denatured CFH (Complement Technology, Inc., Tyler, TX). Reduction was carried out by incubating 1 mg/mL CFH with 10 mM Tris(2-carboxyethyl) phosphine (TCEP) for 30 min, then diluting the protein to 5 µg/mL with phosphate buffered saline (PBS) and dispensing 100 µL per well into the immunoplate. Denaturation was carried out with 7 M urea followed by dilution with PBS as above. Human NSCLC serum, CFH antibody-positive as assessed by immunoblot, was used as the primary antibody, and anti-IgG gamma chain-HRP (Millipore) was the secondary antibody-enzyme conjugate (1:2000). Plates were developed using 2,2'-azinobis [3-ethylbenzothiazoline-6-sulfonic acid (ABTS) and hydrogen peroxide and absorbance read at 405 nm in a plate reader (Tecan, San Jose, CA).

Epitope Mapping of Human CFH Autoantibodies. Epitope mapping was conducted by Pepscan (the Netherlands), as described in Slootstra et al., *Mol Divers* (1996) 1:87-96. Briefly, 15-mer peptides covering the complete amino acid sequence of SCR19-20 were synthesized with an overlap of 14 amino acids. Peptides were arrayed on a proprietary minicard and screened in an ELISA format using a purified human antibody as the primary antibody and an anti-human peroxidase conjugate as the secondary antibody. The minicards were developed using ABTS and hydrogen peroxide. The color development was quantified with a charge coupled device (CCD) camera and an image processing system. The values obtained from the CCD camera range from 0 to 3000 mAU.

Peptide Competition Experiments. A peptide containing the entire epitope of interest was synthesized by GenScript (Piscataway, NJ). For the immunoblot experiment, affinity purified autoantibodies (66.7 µg/mL) were incubated overnight at 4° C. with peptide (1.67 mg/mL) in PBS, or in PBS alone (final volume 6 µL). The next day, the autoantibodies with or without peptide were diluted to a final concentration of 2 µg/mL with PBS containing 0.1% (v/v) Tween-20 and 5% (w/v) non-fat dry milk and used to probe a blot containing full-length CFH and SCR19-20. Bound antibody was detected with anti-IgG gamma chain-HRP conjugate (1:5000) and a chemiluminescent substrate, followed by film exposure. Peptide competition of antibodies in cell-based assays is described below.

C3 Deposition on Lung Cancer Cells. A549 cells were used to determine whether CFH antibodies increase the deposition of C3 related fragments on the tumor cell surface under conditions favoring the alternative pathway. Normal human serum (NHS, Complement Technology, Inc.) at a 1:8 final dilution was used as a source of complement proteins. A549 cells were detached from culture dishes using VERSENE® (Life Technologies, Grand Island, NY), washed in Dulbecco's PBS (DPBS), and resuspended in veronal buffer containing $Mg^{2+}$ and EGTA (Boston Bioproducts, Ashland, MA). Cells ($2.5 \times 10^5$) were incubated for 30 min at 37° C. with NHS preincubated with purified C18 CFH antibody (0.1 mg/mL, SantaCruz Biotechnology, Inc., Santa Cruz, CA) or affinity purified CFH autoantibodies from patient E (0.2 mg/mL) for 30 min at 4° C. Cells were also incubated with heat-inactivated NHS (HI-NHS, prepared by heating NHS at 56° C. for 30 minutes) or NHS pre-incubated with pooled human IgG (0.2 mg/mL, Jackson Immunoresearch Laboratories Inc., West Grove, PA) for 30 min at 4° C. as negative controls. Following two washes in 1% (w/v) BSA in DPBS (DPBS-BSA), cells were incubated for 30 min at 4° C. with 0.5 µg of a fluorescein isothiocyanate (FITC)-conjugated mouse anti-human C3 antibody (Lifespan Biosciences, Seattle, WA). Following the C3-FITC antibody incubation, cells were washed three additional times in DPBS-BSA to remove excess C3 antibody. Flow cytometry was carried out using a FACSCANTO® II flow cytometer (BD Biosciences, San Jose, CA) at the Duke Cancer Center Core Facility. Mean fluorescence intensity on A549 cells, corresponding to C3 deposition on the cell surface, was determined using FLOWJO® software (Tree Star Inc., Ashland, OR).

For peptide competition, affinity purified autoantibodies (0.7 mg/mL) were preincubated overnight at room temperature with peptide (1.2 mg/mL). After addition to cells, the autoantibody concentration was 0.2 mg/mL and the peptide concentration was 0.34 mg/mL.

Complement Dependent Cytotoxicity of Lung Cancer Cells. The effect of CFH antibodies on the complement-mediated cytotoxicity of adenocarcinoma (A549) tumor cells was determined using assay conditions essentially identical to those used to determine C3 deposition as described above. Following the incubation of cells, serum, and antibodies, cells were washed three times with DPBS-BSA and then resuspended in 1 µg/mL propidium iodide (Biosource International, Camarillo, CA) in DPBS. Flow cytometry was carried out and the number of propidium iodide positive cells was determined. Peptide competition was performed as described for the C3 deposition assay.

Statistical Analysis. Data obtained from complement mediated cytotoxicity and C3 deposition experiments were analyzed using the Student's t-test. All experiments were completed in triplicate, and cytotoxicity and C3 deposition data are represented as mean±standard deviation.

Example 2

CFH Antibodies in NSCLC Patients are Specific for Reduced CFH

Antibodies to CFH in the sera of NSCLC patients, as described in Amornsiripanitch et al., Clin. Can. Res. (2010) 16:3226-3231, were used in an immunoblot in which CFH was reduced and/or denatured. As shown in FIG. 1, serum antibody recognition of CFH in an ELISA format was dependent on prior treatment of the CFH with a reducing agent, in this case TCEP. Reactivity was not dependent on prior denaturation of CFH.

As CFH is a ubiquitous and abundant serum protein, it was surprising to find antibodies directed against it at all. However, the antibodies present in the sera of NSCLC patients all have a distinct preference for the reduced form of CFH. Given that NSCLC patient antibodies recognize a reduced form of the CFH protein, the possibility that some patients with the autoantibodies may have a mutation in the CFH gene was examined. Such a mutation might create a structural mimic of the reduced form of the protein (such as a Cys to Ser mutation) or expose an epitope obscured in the wild type form, so that the altered protein was now antigenic. RT-PCR targeting the SCR19-20 domain was performed using RNA isolated from 10 patient tumor samples. All of the tested samples contained wild type sequence in this domain (data not shown).

Serum from 12 autoantibody-positive patients was tested against the CFH epitope peptide in an ELISA using secondary antibodies specific for IgG1, IgG2, IgG3, and IgG4. All the tested autoantibodies appear to be IgG3.

Example 3

CFH Autoantibodies Bind to an SCR19-20 Fragment of CFH

Initial domain mapping experiments were performed by incubating patient sera with "dot blots" containing cloned and purified subsets of SCR modules. CFH antibody-positive sera from three patients reacted with a fragment containing SCR19 and SCR20 (data not shown). A reduced SCR19-20 ELISA was developed and used to show that in a survey of 22 sera that recognized full length CFH on an immunoblot, 20 gave strong signals in the ELISA (data not shown).

Example 4

CFH Autoantibodies Epitope Map to SCR19

CFH antibodies from eight patients were purified using sequential Protein G and SCR19-20 affinity column chromatography steps. Three of the antibodies were epitope mapped on a library of overlapping peptides synthesized from the complete sequence of SCR19-20. A library was synthesized consisting of 115 overlapping peptides comprising all of SCR19-20 and screened with three autoantibodies; peptide ELISA signal data for one of them is shown. The beginning and ending amino acid residue number within CFH (UniProt P08603) are noted at the beginning and end of each peptide. The residues in bold are those that are present in all peptides giving the highest signal. Residues comprising only part of this epitope are in italics. The peptide binding data for one antibody are shown in Table 5, which shows the epitope mapping.

TABLE 5

| Peptide Sequence | SEQ ID NO: | ELISA Signal |
|---|---|---|
| 1105-EFGKCGPPP*PIDNGD*-1119 | 121 | 682 |
| 1106- FGKCGPPP*PIDNGDI*-1120 | 121 | 701 |
| 1107-GKCGPPPPIDNGDIT-1121 | 123 | 2886 |
| 1108-KCGPPPPIDNGDITS-1122 | 124 | 2898 |
| 1109-CGPPPPIDNGDITSF-1123 | 125 | 2853 |
| 1110-GPPPPIDNGDITSFP-1124 | 126 | 2844 |
| 1111-PPPPIDNGDITSFPL-1125 | 127 | 2888 |
| 1112-PPPIDNGDITSFPLS-1126 | 128 | 2675 |
| 1113-PPIDNGDITSFPLSV-1127 | 129 | 2900 |
| 1114-PIDNGDITSFPLSVY-1128 | 130 | 2440 |
| 1115-*IDNGDITSFPLSVYA*-1129 | 131 | 632 |
| 111 6-*DNGDITSFPLSVYAP*-1130 | 132 | 811 |

All three antibodies recognized the epitope PIDNGDIT (SEQ ID NO:3). This amino acid sequence corresponds to CFH 1114-1121, residues that are located in the binding interface with the C3d portion of C3b in the co-crystal structure of C3d-SCR19-20. C3d is a cleavage product of C3b that remains attached to the cell surface via a thioester domain. CFH D1119 is involved in the stability of the interface with C3d because a D1119G mutant of SCR19-20 abolished binding to C3d.

Figure 2:
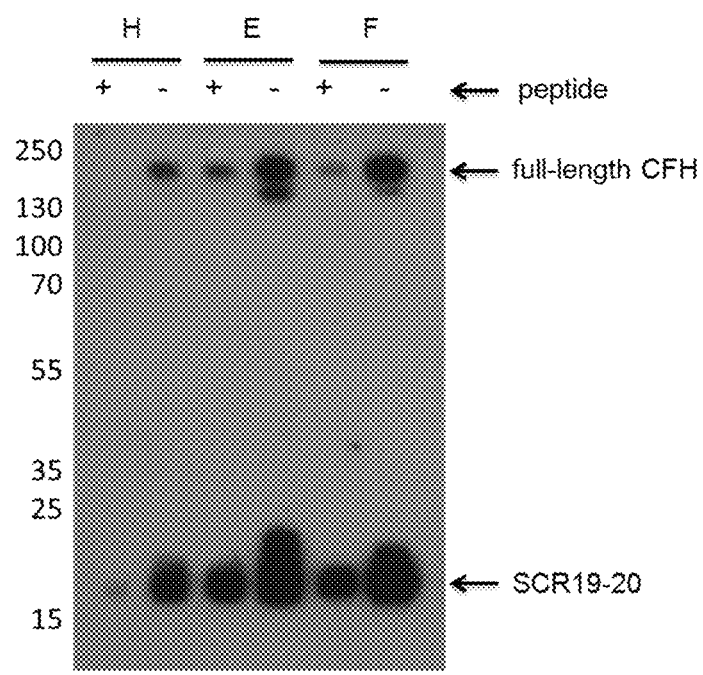
FIG. 2 shows the peptide competition of antibody binding to target. Autoantibodies (H, E, and F) were incubated overnight with (+) or without (−) peptide and were then used to probe a blot containing full-length CFH and SCR19-20, loaded in the same lane. Decreased immunoreactivity in the presence of peptide indicates interaction between the peptide and the autoantibody. Molecular weight standards, in kDa, are indicated to the left of the figure.

A peptide was synthesized with the sequence PIDNGDITGGGK-biotin (SEQ ID NO:120) and used as a competitor in immunoblots of CFH and SCR19-20 probed with each of the eight purified human CFH antibodies. Eight anti-CFH antibodies were affinity purified from patient sera and epitope mapped. Seven of the eight antibodies were competed by the peptide; competition is shown for three antibodies in FIG. 2. The common epitope recognized by these seven is located within a functional domain of CFH known to interact with C3b.

Example 5

Purified CHF Antibodies Increase Deposition of C3 on A549 Lung Carcinoma Cells

Figure 3:
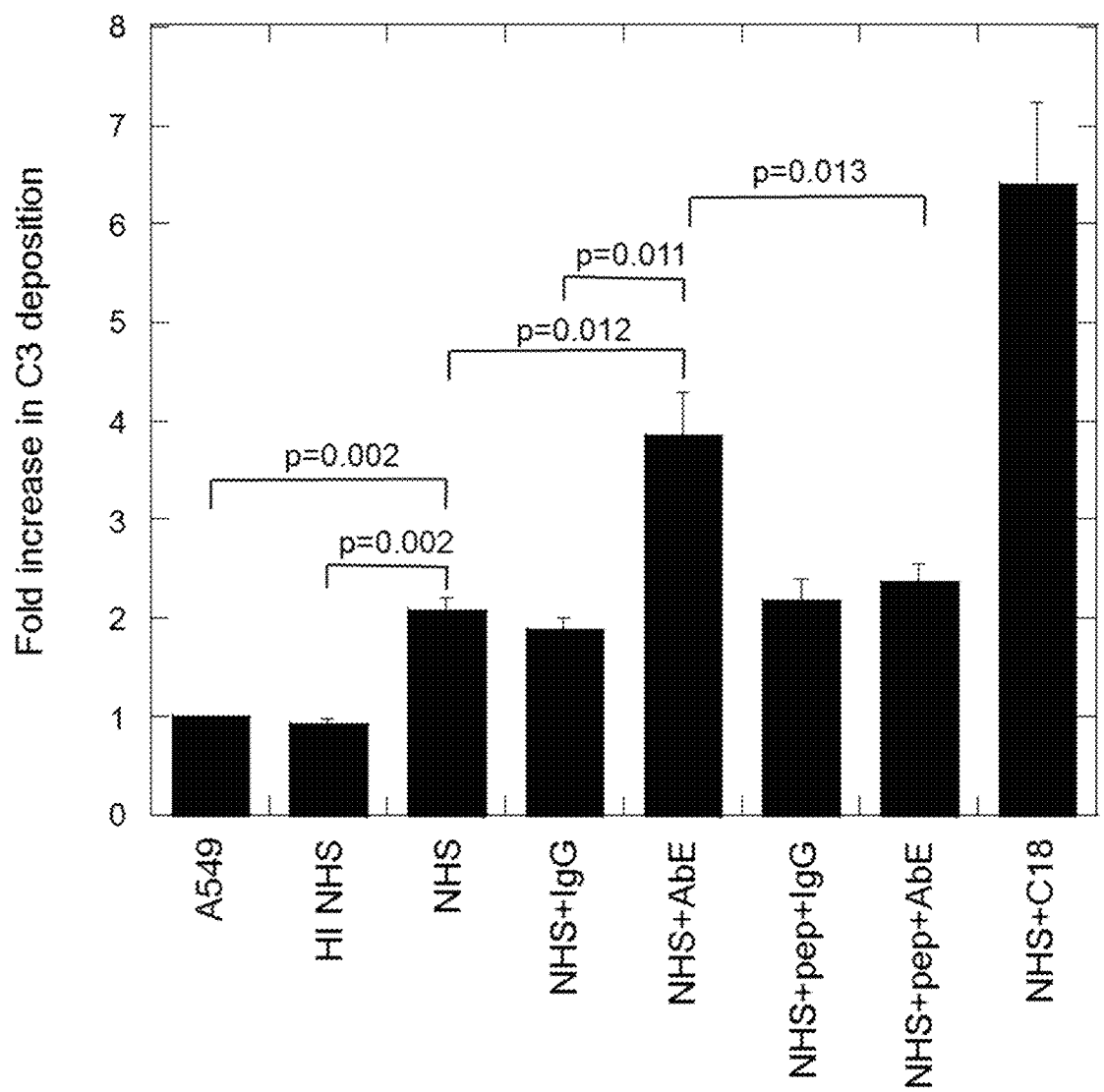
FIG. 3 shows the deposition of C3-related fragments on A549 lung cancer cells. Antibodies are control IgG pooled from normal human serum, human anti-CFH autoantibody from patient E (AbE) or mouse monoclonal antibody C18, tested with or without blocking peptide (pep), in the presence of normal human serum (NHS) or heat inactivated serum (HI NHS). Fold increase in C3 deposition is reported relative to the baseline observed in the absence of serum

Because most of the NSCLC patients' CFH autoantibodies appeared to interact with the region for the CFH-C3b interaction, the antibodies were tested to see if they could increase C3b deposition on lung tumor cells. Several purified CFH autoantibodies were incubated with A549 lung carcinoma cells and NHS as a source of complement proteins. Deposition of C3-related fragments was measured by flow cytometry using an FITC-conjugated mouse anti-human C3 antibody. Results for one of these antibodies, "Antibody E," are shown in FIG. 3. C3 deposition was dependent on the presence of complement proteins, as deposition increased when NHS was used in place of HI-NHS. A statistically significant increase in C3 deposition was seen in the presence of the NSCLC patient's CFH antibody over the IgG control (p=0.011). The peptide containing the epitope, i.e., PIDNGDITGGGK-biotin (SEQ ID NO:120), effectively neutralized the effect of the antibody demonstrating specificity of the antibody for CFH. Mouse monoclonal antibody C18, which binds SCR20 but does not bind to a reduced form of CFH (data not shown), was used as a positive control in these experiments. C18 also increased C3 deposition on tumor cells, consistent with its proposed interaction with a domain of CFH involved in both C3b and cell binding.

The clinical records of 26 CFH autoantibody-positive patients were examined for evidence of kidney disease, which may be indicative of a global attenuation of CFH activity causing glomerulonephritis, and thus a possible side effect of an autoantibody. The CFH antibody-positive patients showed no evidence of documented kidney disease, and, where recorded, BUN and creatinine levels were normal. These results suggest the absence of side effects of the CFH autoantibodies.

Example 6

Figure 4:
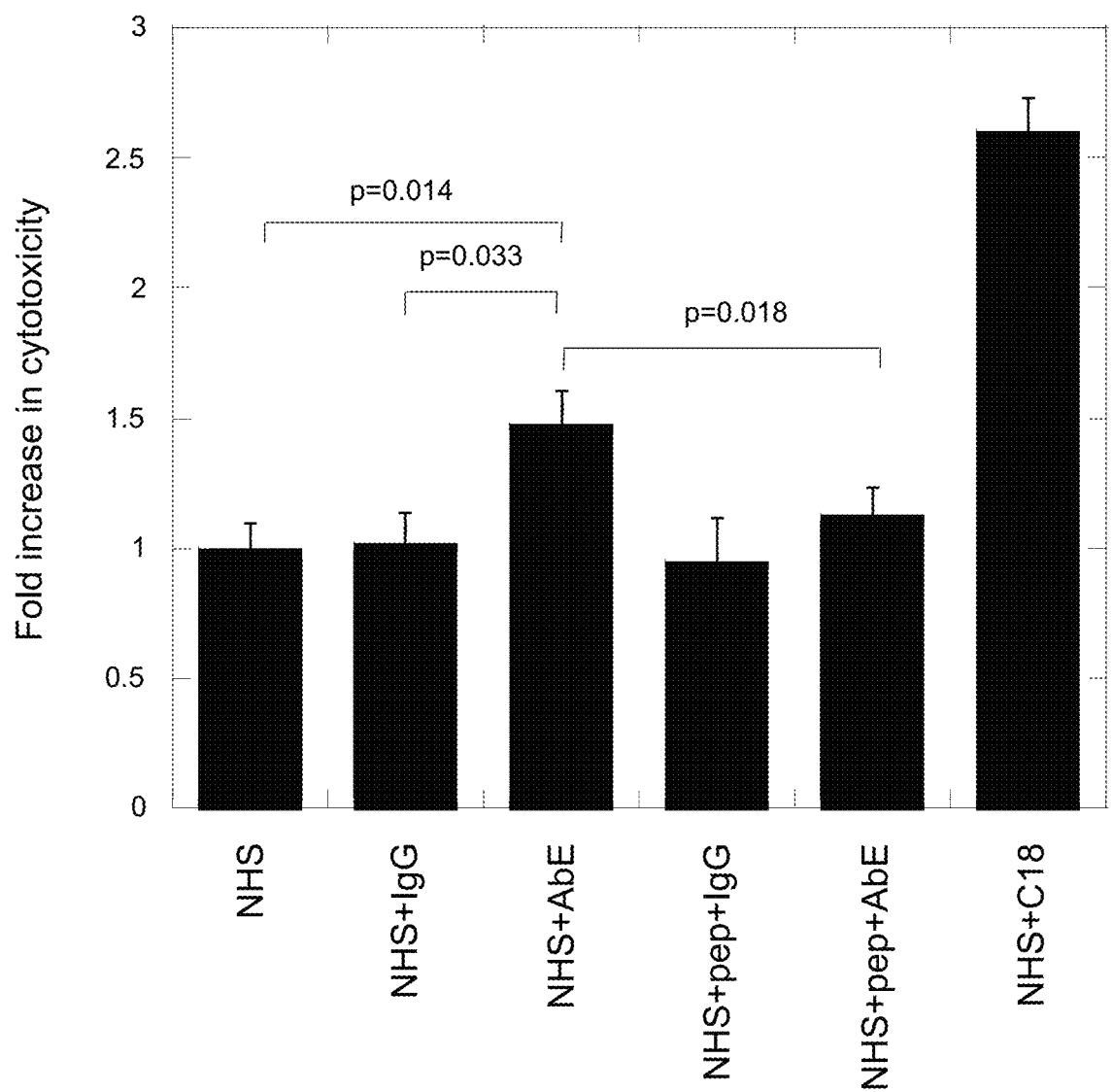
FIG. 4 shows the complement-dependent cytotoxicity of A549 lung cancer cells by the alternative pathway. Antibodies tested are mixed IgG, human anti-CFH autoantibody from patient E (AbE) or mouse monoclonal antibody C18, with or without blocking peptide (pep). Fold increase in cytotoxicity is reported relative to the baseline observed in the presence of normal human serum (NHS).

Purified CHF Antibodies Cause Increased Cytotoxicity of A549 Lung Carcinoma Cells Because C3 deposition should lead to cytotoxicity, NSCLC patients' antibodies were tested to determine if they could bring about cytotoxicity. Purified CFH antibodies were incubated with A549 lung carcinoma cells and NHS as a source of complement proteins under conditions promoting the alternative complement pathway. Cytotoxicity was measured in a propidium iodide-flow cytometry assay. The results for Antibody E are shown in FIG. 4. There was a statistically significant increase in cytotoxicity seen in the presence of the NSCLC patient CFH antibody over the IgG control (p=0.033) and again the peptide neutralized the effect of the antibody. Mouse monoclonal antibody C18 was used as a positive control as C18 had previously been shown to strongly inhibit binding of CFH to C3b and endothelial cells. As shown in FIG. 4, C18 causes an increased cytotoxicity of tumor cells, consistent with its ability to inhibit CFH.

Example 7

Materials and Methods

Monoclonal Antibody Production/Peptide Information and Sequencing. Human antibodies against CFH were derived from peripheral human B lymphocytes. The methods used to derive, sequence and characterize the antibodies were previously described. Liao et al. (2013) *Immunity* 38(1): 176-186; Bonsignori et al. (2012) *J Virol* 86(21): 11521-11532; Moody et al. (2012) *J Virol* 86(14): 7496-7507; Gray et al. (2011) *J Virol* 85(15): 7719-7729; Morris et al. (2011) *PLoS ONE* 6(9): e23532; Liao et al. (2009) *J Virol Methods* 158(1-2): 171-179. B cells from early stage cancer individuals that have CFH antibodies were collected and pooled. B cells producing CFH antibodies were single cell FACS sorted using a 15-mer peptide of GPPP-PIDNGDITSFP (SEQ ID NO:114) with a linker, specifically, a target peptide of GPPPPIDNGDITSFP(GGGK-biotin) (SEQ ID NO: 115) where the residues and biotin within the bracket represent a linker. A tetramer of the 15-mer peptide was used to FACs sort out double positive B cells. Once the B cells producing antibodies that recognized the target peptide were sorted, the immunoglobulin genes from each individual B cell were cloned. The immunoglobulin genes were expressed in mammalian cells to express the protein/antibody.

Immunoblotting: Full-length CFH and SCR19-20 were separated via SDS-PAGE under reducing or non-reducing conditions and blotted to polyvinylidene fluoride (PVDF) membrane (Millipore, Billerica, MA). The membrane was blocked with phosphate-buffered saline containing 0.1% (v/v) Tween-20 (PBST) and 5% (w/v) nonfat dry milk and probed with recombinant human monoclonal antibodies, each at 0.5 µg/mL. After a 2-hour incubation at room temperature, the membrane was washed in PBST and incubated for 1 hour with goat anti-human IgG-gamma horseradish peroxidase conjugate at a 1:10,000 dilution. After further washing, bound antibody was detected with chemiluminescent substrate and exposed to film.

ELISA vs. 15-mer peptide: Neutravidin (Thermo Scientific, Rockford, IL), a biotin-binding derivative of Protein A, was immobilized in the wells of a high-binding 96-well tray by overnight incubation at 4° C. After blocking the wells with PBS containing 1% (w/v) bovine serum albumin, biotinylated 15-mer peptide (SEQ ID NO: 115) at 2 µg/mL in PBST was added to half the wells; the remaining half received PBST alone for background determination. After washing, recombinant human monoclonal antibodies were added to the wells at 0.5 µg/mL and incubated for 2 hr at room temperature. The wells were washed and incubated with goat anti-human IgG-gamma horseradish peroxidase conjugate at a 1:1000 dilution. After further washing, bound antibody was detected with 2,2'-azino-bis (3-ethylbenzthiazoline-6-sulfonic acid)(ABTS)/hydrogen peroxide and the absorbance measured at 405 nm.

ELISA vs. SCR19-20: ELISA plates were coated with Neutravidin and blocked as previously described. Reduced or non-reduced SCR19-20-biotin were diluted to 2 µg/mL in PBST and incubated in the appropriate wells for 1 h. SCR19-20-biotin was reduced by incubation in 10 mM Tris(2-carboxyethyl) phosphine (TCEP, Sigma-Aldrich, St. Louis, MO) for 30 minutes; excess TCEP was removed with a size exclusion spin cartridge. After washing, recombinant human monoclonal antibodies were added to the wells at 0.2 µg/mL and incubated for 1 h at room temperature. The wells were washed and incubated with goat anti-human IgG-gamma horseradish peroxidase conjugate at a 1:1000 dilution. After further washing, bound antibody was detected with ABTS/hydrogen peroxide and the absorbance measured at 405 nm.

A549 LDH Cytotoxicity Assay: A549 cells were harvested, washed, counted, and plated in a 96 well plate at $5 \times 10^3$ cells/well in 100 µL RPMI 1640 media with 10% fetal bovine serum (FBS). Cells were incubated for 24 hours at 37° C. and 5% $CO_2$. The medium was then changed to RPMI 1640 and 1× veronal buffer (Lonza, Walkersville, MD). Normal human serum (NHS) at a 1:8 dilution was added to each experimental condition. Normal human serum was heat inactivated at 56° C. for 30 min (HINHS), and used at a 1:8 dilution as a negative control. In addition to NHS or HINHS, cells were treated with purified recombinant human monoclonal antibodies at 20, 60, or 120 µg/mL. All conditions were assayed in triplicate.

After 24 hours at 37° C. and 5% $CO_2$, cytotoxicity was determined using the CYTOTOX 96® Non-radioactive Cytotoxicity Assay (Promega, Madison, WI). Fifty microliters of supernatants were assayed for lactate dehydrogenase (LDH) activity following the manufacturer's protocol. Spontaneous LDH release and maximum LDH release were determined as recommended by the LDH protocol. The calculation of percent cytotoxicity for each condition was as follows:

$$\% \text{ Cytotoxicity} = \frac{\text{Experimental} - \text{Spontaneous}}{\text{Maximum} - \text{Spontaneous}} \times 100$$

Example 8

The cloned antibodies were tested using ELISA against the 15-mer peptide (i.e., the biotinylated 19-mer attached to immobilized Neutravidin) (FIG. 5) and using an immunoblot against reduced or non-reduced CFH and SCR19-20.

All antibodies recognizing CFH and SCR19-20 in the immunoblot showed enhanced binding to the reduced proteins. Complement Dependent Cytotoxicity (CDC) assays against breast cancer cells were performed using a pool of all positive antibodies.

Seventeen pairs of constructs expressing CFH-specific VH and VL regions were derived, as summarized in Table 6. As shown in Table 6, each pair of VH and VL constructs, designated IgH_ID and IgK_ID, expressed a CFH-specific monoclonal antibody comprising a heavy chain and a kappa light chain. All expressed monoclonal antibodies contain IgG1 constant regions. The isotypes of the antibodies extant in the donor B cells were either IgG3 (n=13) or IgM (n=2). Antibodies in three different clonal lineages are indicated by "*," "a," and "b." H007957, H007958, H007963 and H007982 have the identical sequences; K005991, K005992, K005998 and K006018 as well as K006004 have the identical sequences; H007960 and H007967 have the identical sequences; K005994 and K006002 have the identical sequence; H007961 and H007965 have the identical sequence; K006003 and K006000 have the identical sequence; and H007968 and H007971 have the identical sequence. The HCDR3 of heavy chain were determined (see Table 1, underlined residues for SEQ ID NOs 4-20.

TABLE 6

| Lung Cancer antigen reactive antibody Ig gene information | | | | | | | | | | | |
|---|---|---|---|---|---|---|---|---|---|---|---|
| Clone No. | IgH_ID | VH | DH | JH | Mut. Freq. | H_CDR3 length | Isotype | IgK_ID | VK | JK | Mut. Freq. | KCDR3 length |
| 1 | H007970 | 3~30 | 6~13 | 6 | 0.081 | 12 | G3 | K006004 | 4~1 | 1 | 0.063 | 9 |
| 2 | H007955 | 3~30 | 6~13 | 1 | 0.107 | 12 | G3 | K005989 | 4~1 | 1 | 0.054 | 9 |
| 3* | H007957 | 3~30 | 2~21 | 3 | 0.068 | 12 | G3 | K005991 | 4~1 | 1 | 0.063 | 9 |
| 4* | H007958 | 3~30 | 2~21 | 3 | 0.068 | 12 | G3 | K005992 | 4~1 | 1 | 0.063 | 9 |
| 5* | H007963 | 3~30 | 2~21 | 3 | 0.068 | 12 | G3 | K005998 | 4~1 | 1 | 0.063 | 9 |
| 6* | H007982 | 3~30 | 2~21 | 3 | 0.068 | 12 | G3 | K006018 | 4~1 | 1 | 0.063 | 9 |
| 7a | H007960 | 3~30 | 6~25 | 4 | 0.071 | 12 | G3 | K005994 | 4~1 | 1 | 0.041 | 9 |
| 8a | H007967 | 3~30 | 6~25 | 4 | 0.071 | 12 | G3 | K006002 | 4~1 | 1 | 0.041 | 9 |
| 9a | H007964 | 3~30 | 1~26 | 4 | 0.042 | 12 | G3 | K005999 | 4~1 | 1 | 0.035 | 9 |
| 10a | H007979 | 3~30 | 6~25 | 4 | 0.060 | 12 | G3 | K006015 | 4~1 | 1 | 0.033 | 9 |

TABLE 6-continued

Lung Cancer antigen reactive antibody Ig gene information

| Clone No. | IgH_ID | VH | DH | JH | Mut. Freq. | H_CDR3 length | Isotype | IgK_ID | VK | JK | Mut. Freq. | KCDR3 length |
|---|---|---|---|---|---|---|---|---|---|---|---|---|
| 11[a] | H007961 | 3~30 | 6~25 | 4 | 0.068 | 12 | G3 | K005995 | 4~1 | 1 | 0.030 | 9 |
| 12[a] | H007965 | 3~30 | 6~25 | 4 | 0.068 | 12 | G3 | K006000 | 4~1 | 1 | 0.030 | 9 |
| 13[b] | H007968 | 3~30 | 6~13 | 6 | 0.029 | 12 | G3 | K006003 | 4~1 | 1 | 0.043 | 9 |
| 14[b] | H007971 | 3~30 | 6~13 | 6 | 0.029 | 12 | G3 | K006005 | 4~1 | 1 | 0.043 | 9 |
| 15 | H007983 | 3~30 | 6~13 | 4 | 0.062 | 12 | G3 | K006019 | 4~1 | 4 | 0.076 | 9 |
| 16 | H007962 | 3~48 | 6~6 | 6 | 0.003 | 14 | M | K005996 | 4~1 | 4 | 0.049 | 9 |
| 17 | H007966 | 5~51 | 1~ IR1 | 6 | 0 | 17 | M | K006001 | 1~5 | 1 | 0 | 9 |

Figure 5:
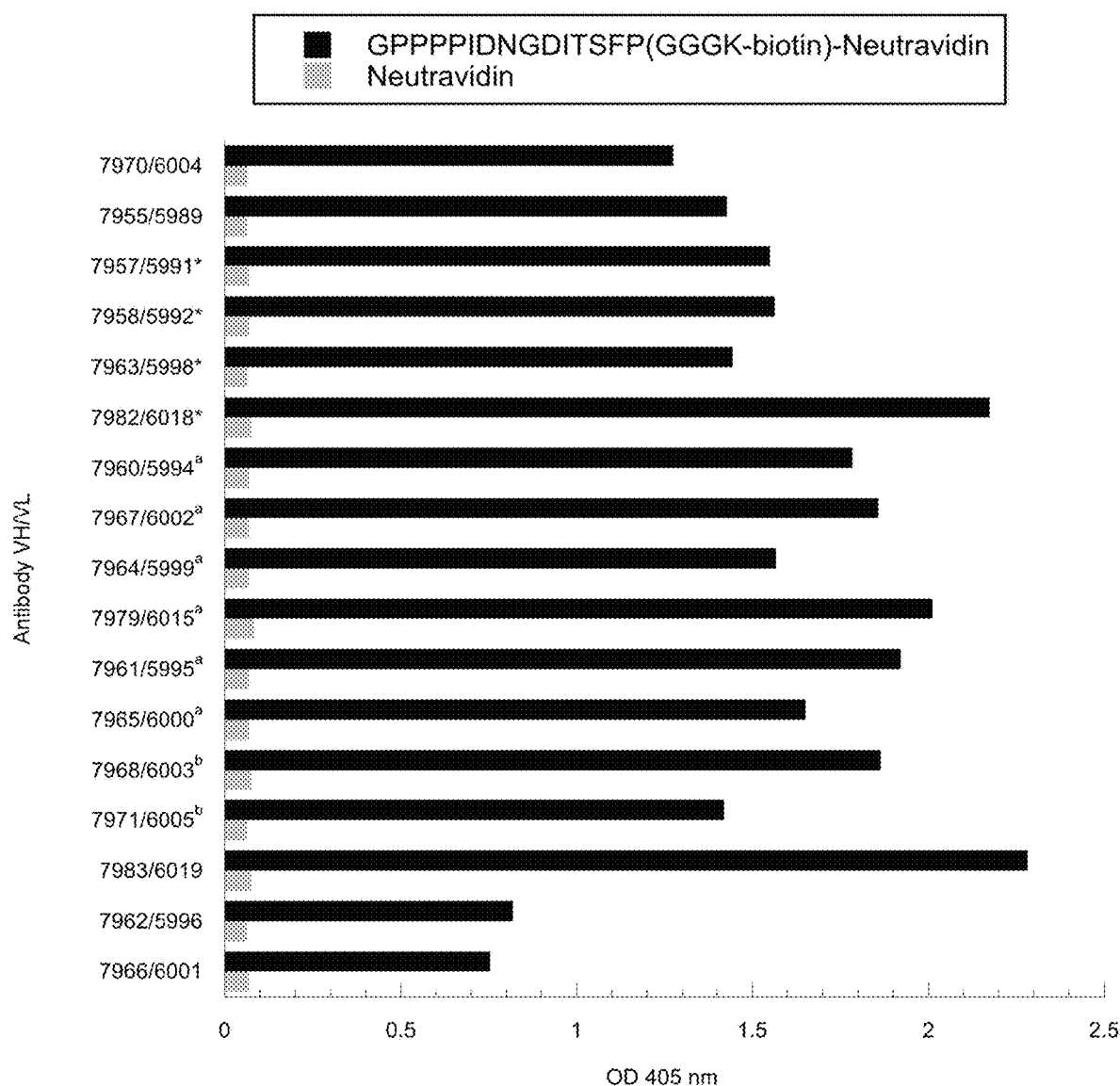
FIG. 5 shows an ELISA of the cloned human monoclonal antibodies versus the biotinylated 15-mer peptide antigen.

Table 7 identifies the SEQ ID NOs. corresponding to the VH and VL amino acid and nucleotide sequences determined for each clone described in Table 6. FIG. 5 shows ELISA data of the 17 purified antibodies.

TABLE 7

| Clone No. | VH ID. | Protein | Nucleotide | VL ID. | Protein | Nucleotide |
|---|---|---|---|---|---|---|
| 1 | H007970 | SEQ ID NO: 4 | SEQ ID NO: 38 | K006004 | SEQ ID NO: 21 | SEQ ID NO: 55 |
| 2 | H007955 | SEQ ID NO: 5 | SEQ ID NO: 39 | K005989 | SEQ ID NO: 22 | SEQ ID NO: 56 |
| 3 | H007957 | SEQ ID NO: 6 | SEQ ID NO: 40 | K005991 | SEQ ID NO: 23 | SEQ ID NO: 57 |
| 4 | H007958 | SEQ ID NO: 7 | SEQ ID NO: 41 | K005992 | SEQ ID NO: 24 | SEQ ID NO: 58 |
| 5 | H007963 | SEQ ID NO: 8 | SEQ ID NO: 42 | K005998 | SEQ ID NO: 25 | SEQ ID NO: 59 |
| 6 | H007982 | SEQ ID NO: 9 | SEQ ID NO: 43 | K006018 | SEQ ID NO: 26 | SEQ ID NO: 60 |
| 7 | H007960 | SEQ ID NO: 10 | SEQ ID NO: 44 | K005994 | SEQ ID NO: 27 | SEQ ID NO: 61 |
| 8 | H007967 | SEQ ID NO: 11 | SEQ ID NO: 45 | K006002 | SEQ ID NO: 28 | SEQ ID NO: 62 |
| 9 | H007964 | SEQ ID NO: 12 | SEQ ID NO: 46 | K005999 | SEQ ID NO: 29 | SEQ ID NO: 63 |
| 10 | H007979 | SEQ ID NO: 13 | SEQ ID NO: 47 | K006015 | SEQ ID NO: 30 | SEQ ID NO: 64 |
| 11 | H007961 | SEQ ID NO: 14 | SEQ ID NO: 48 | K005995 | SEQ ID NO: 31 | SEQ ID NO: 65 |
| 12 | H007965 | SEQ ID NO: 15 | SEQ ID NO: 49 | K006000 | SEQ ID NO: 32 | SEQ ID NO: 66 |
| 13 | H007968 | SEQ ID NO: 16 | SEQ ID NO: 50 | K006003 | SEQ ID NO: 33 | SEQ ID NO: 67 |
| 14 | H007971 | SEQ ID NO: 17 | SEQ ID NO: 51 | K006005 | SEQ ID NO: 34 | SEQ ID NO: 68 |
| 15 | H007983 | SEQ ID NO: 18 | SEQ ID NO: 52 | K006019 | SEQ ID NO: 35 | SEQ ID NO: 69 |
| 16 | H007962 | SEQ ID NO: 19 | SEQ ID NO: 53 | K005996 | SEQ ID NO: 36 | SEQ ID NO: 70 |
| 17 | H007966 | SEQ ID NO: 20 | SEQ ID NO: 54 | K006001 | SEQ ID NO: 37 | SEQ ID NO: 71 |

Example 9

Recombinant Antibodies

Table 8 shows 11 unique Ig VH and VK pairs used for production of recombinant antibodies using IgG1 heavy chain backbone and kappa light chain constant. Antibodies in three different clonal lineages are indicated by "*," "a," and "b."

TABLE 8

| Clone No. | IgH_ID | VH | DH | JH | Mutation Freq. | H_CDR3 length | Isotype | IgK_ID | VK | JK | Mutation Freq. | KCDR3 length |
|---|---|---|---|---|---|---|---|---|---|---|---|---|
| 18 | pH007970 | 3~30 | 6~13 | 6 | 0.081 | 12 | G3 | pK005991_6004 | 4~1 | 1 | 0.063 | 9 |
| 19 | pH007955 | 3~30 | 6~13 | 1 | 0.107 | 12 | G3 | pK005989 | 4~1 | 1 | 0.054 | 9 |
| 20* | pH007957 | 3~30 | 2~21 | 3 | 0.068 | 12 | G3 | pK005991_6004 | 4~1 | 1 | 0.063 | 9 |
| 21[a] | pH007960 | 3~30 | 6~25 | 4 | 0.071 | 12 | G3 | pK005994 | 4~1 | 1 | 0.041 | 9 |
| 22[a] | pH007964 | 3~30 | 1~26 | 4 | 0.042 | 12 | G3 | pK005999 | 4~1 | 1 | 0.035 | 9 |
| 23[a] | pH007979 | 3~30 | 6~25 | 4 | 0.060 | 12 | G3 | pK006015 | 4~1 | 1 | 0.033 | 9 |
| 24[a] | pH007961 | 3~30 | 6~25 | 4 | 0.068 | 12 | G3 | pK005995 | 4~1 | 1 | 0.030 | 9 |
| 25[b] | pH007968 | 3~30 | 6~13 | 6 | 0.029 | 12 | G3 | pK006003 | 4~1 | 1 | 0.043 | 9 |
| 26 | pH007983 | 3~30 | 6~13 | 4 | 0.062 | 12 | G3 | pK006019 | 4~1 | 4 | 0.076 | 9 |
| 27 | pH007962 | 3~48 | 6~6 | 6 | 0.003 | 14 | M | pK005996 | 4~1 | 4 | 0.049 | 9 |
| 28 | pH007966 | 5~51 | 1~IR1 | 6 | 0 | 17 | M | pK006001 | 1~5 | 1 | 0 | 9 |

Table 9 identifies the SEQ ID NOs corresponding to the VH and VL amino acid and nucleotide sequences determined for each clone described in Table 8. Table 2 shows the HCDR3 regions as the underlined residues for SEQ ID NOs. 72-82.

TABLE 9

| Clone No. (Antibody Name) | VH ID. | Protein | Nucleotide | VL ID. | Protein | Nucleotide |
|---|---|---|---|---|---|---|
| 18 | pH007970 | SEQ ID NO: 72 | SEQ ID NO: 93 | pK005991_6004 | SEQ ID NO: 83 | SEQ ID NO: 104 |
| 19 (Ab7955) | pH007955 | SEQ ID NO: 73 | SEQ ID NO: 94 | pK005989 | SEQ ID NO: 84 | SEQ ID NO: 105 |
| 20 (Ab7957/293i) | pH007957 | SEQ ID NO: 74 | SEQ ID NO: 95 | pK005991_6004 | SEQ ID NO: 83 | SEQ ID NO: 104 |
| 21 (Ab7960/293i) | pH007960 | SEQ ID NO: 75 | SEQ ID NO: 96 | pK005994 | SEQ ID NO: 85 | SEQ ID NO: 106 |
| 22 (Ab7964) | pH007964 | SEQ ID NO: 76 | SEQ ID NO: 97 | pK005999 | SEQ ID NO: 86 | SEQ ID NO: 107 |
| 23 (Ab7979) | pH007979 | SEQ ID NO: 77 | SEQ ID NO: 98 | pK006015 | SEQ ID NO: 87 | SEQ ID NO: 108 |
| 24 (Ab7961/293i) | pH007961 | SEQ ID NO: 78 | SEQ ID NO: 99 | pK005995 | SEQ ID NO: 88 | SEQ ID NO: 109 |
| 25 (Ab7968) | pH007968 | SEQ ID NO: 79 | SEQ ID NO: 100 | pK006003 | SEQ ID NO: 89 | SEQ ID NO: 110 |
| 26 | pH007983 | SEQ ID NO: 80 | SEQ ID NO: 101 | pK006019 | SEQ ID NO: 90 | SEQ ID NO: 111 |
| 27 (Ab7962/293i) | pH007962 | SEQ ID NO: 81 | SEQ ID NO: 102 | pK005996 | SEQ ID NO: 91 | SEQ ID NO: 112 |
| 28 (Ab7966) | pH007966 | SEQ ID NO: 82 | SEQ ID NO: 103 | pK006001 | SEQ ID NO: 92 | SEQ ID NO: 113 |

Figure 6:
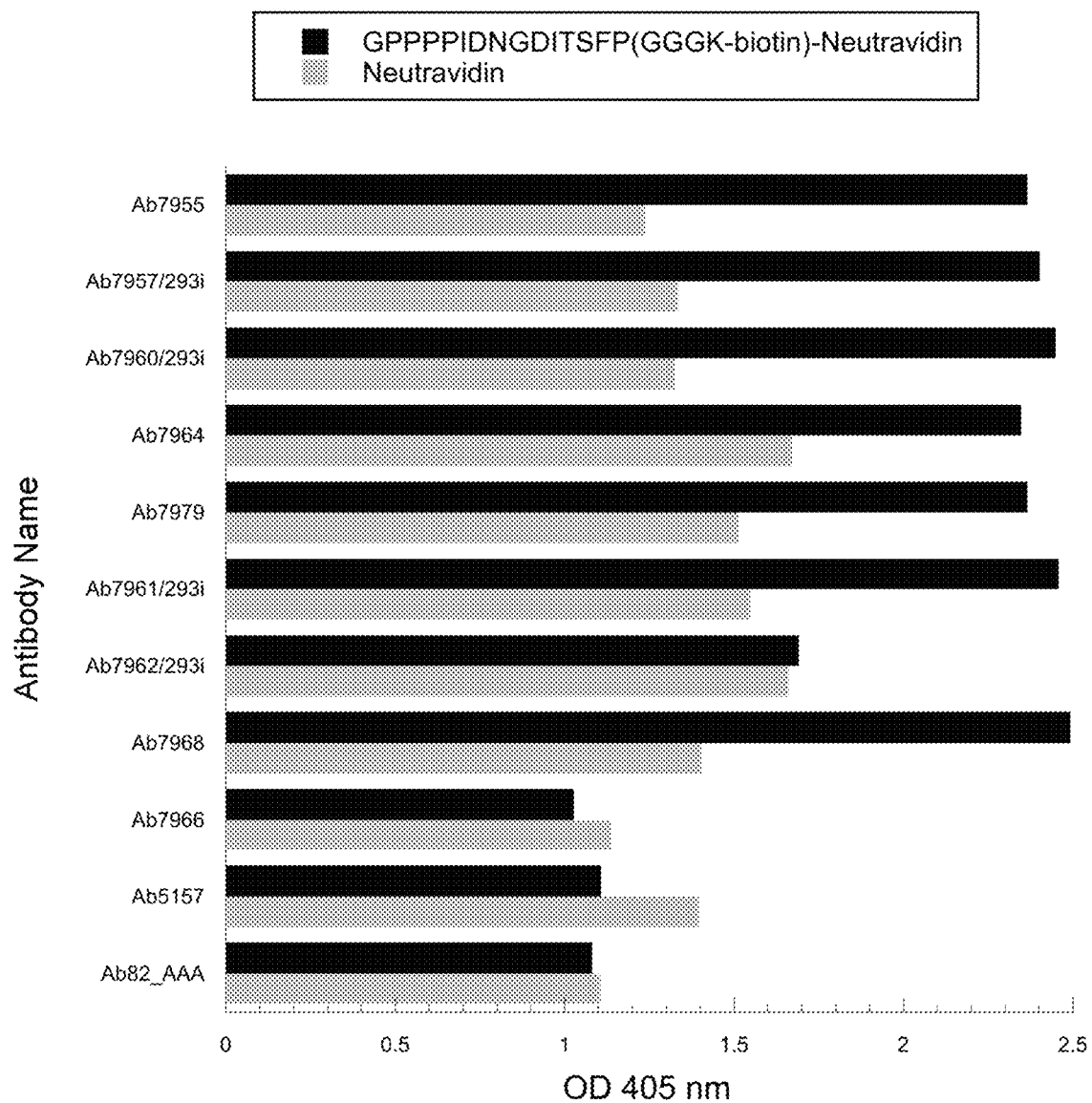
FIG. 6 shows an ELISA of the recombinant human monoclonal antibodies versus the biotinylated 15-mer peptide antigen
Figure 7:
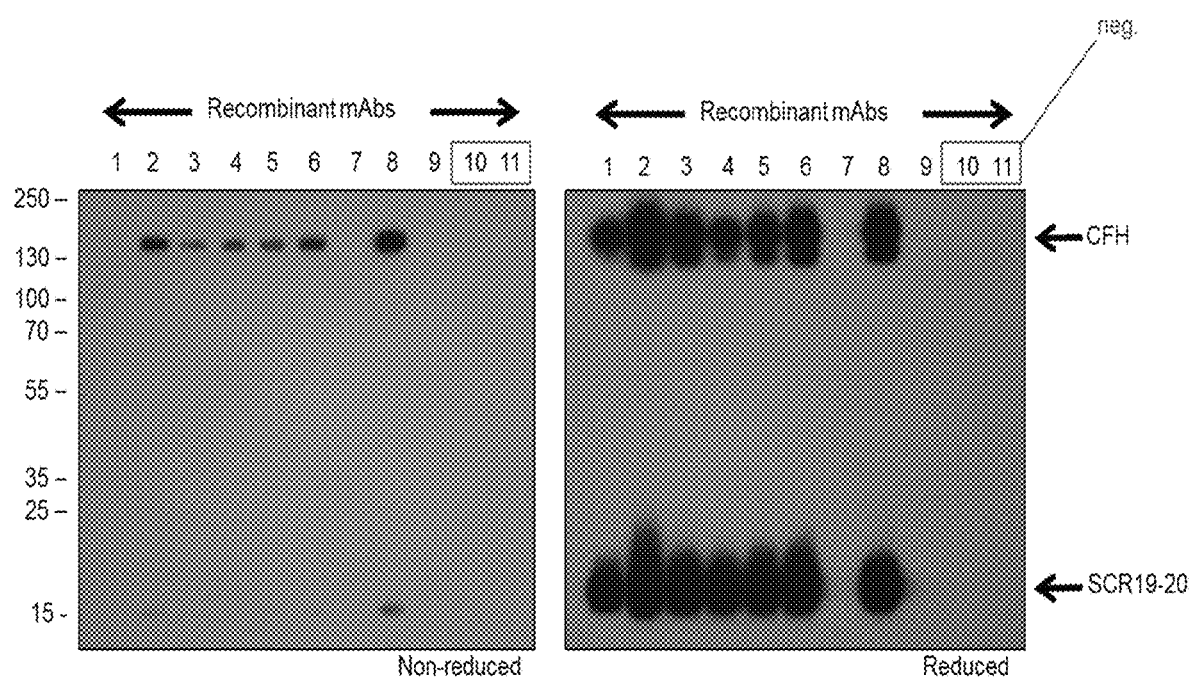
FIG. 7 shows an immunoblot of the recombinant human monoclonal antibodies versus the full-length CFH and SCR19-20 peptide under reducing and non-reducing conditions.
Figure 8:
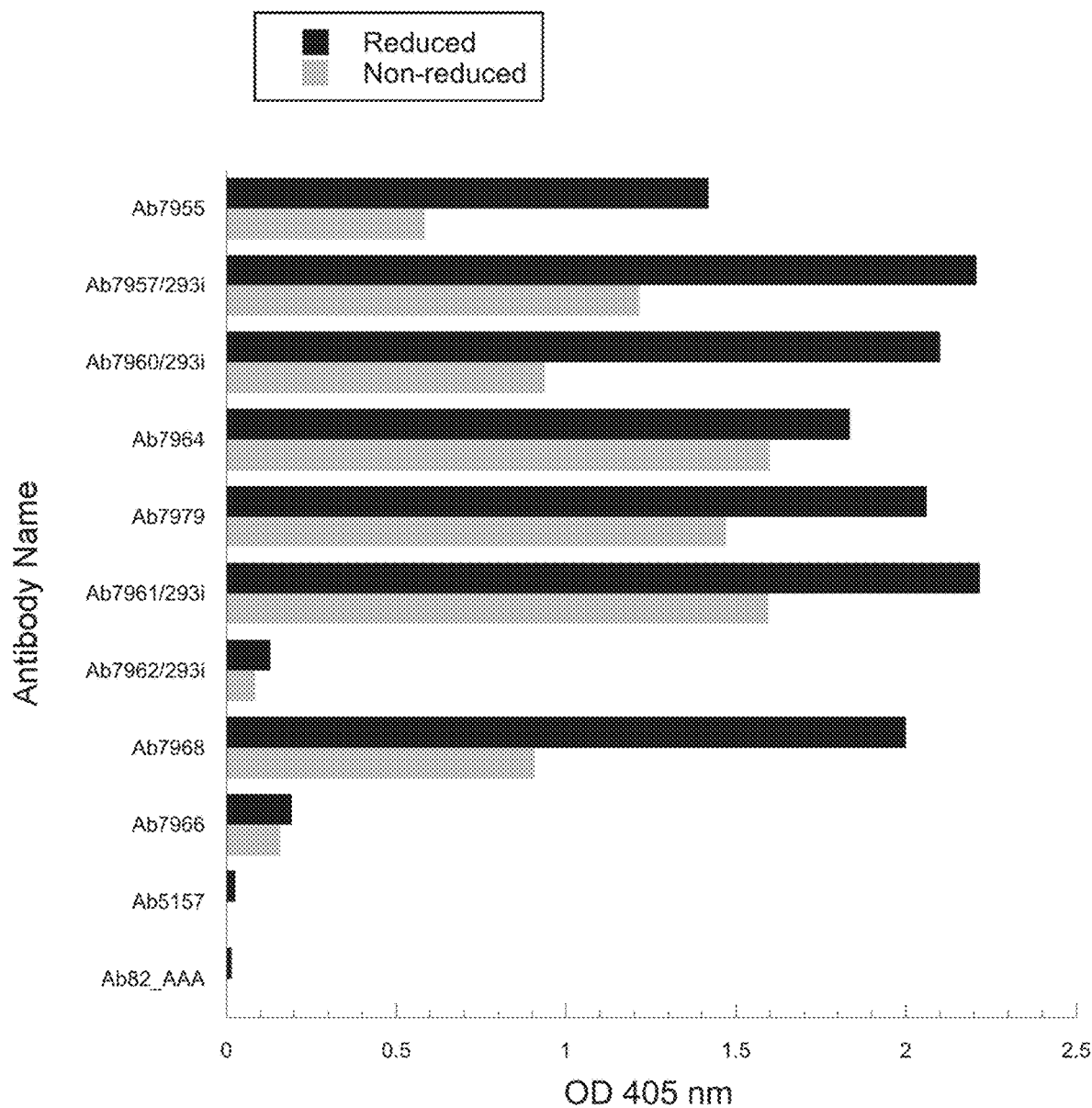
FIG. 8 shows an ELISA of the recombinant human monoclonal antibodies versus the SCR19-20-biotin peptide.

The recombinant antibodies were tested using ELISA against the 15-mer peptide (i.e., the biotinylated 19-mer attached to immobilized Neutravidin) (FIG. 6) and the SCR19-20-biotin peptide (FIG. 8). The recombinant antibodies were tested using an immunoblot against reduced or non-reduced CFH and SCR19-20 (Table 10; FIG. 7).

TABLE 10

| Tube # | Ab Name |
|---|---|
| 1 | Ab7955 |
| 2 | Ab7957/293i |
| 3 | Ab7960/293i |
| 4 | Ab7964 |
| 5 | Ab7979 |
| 6 | Ab7961/293i |
| 7 | Ab7962/293i |
| 8 | Ab7968 |
| 9 | Ab7966 |
| 10 | Ab5157 (neg) |
| 11 | Ab82 (neg) |

Figure 9:
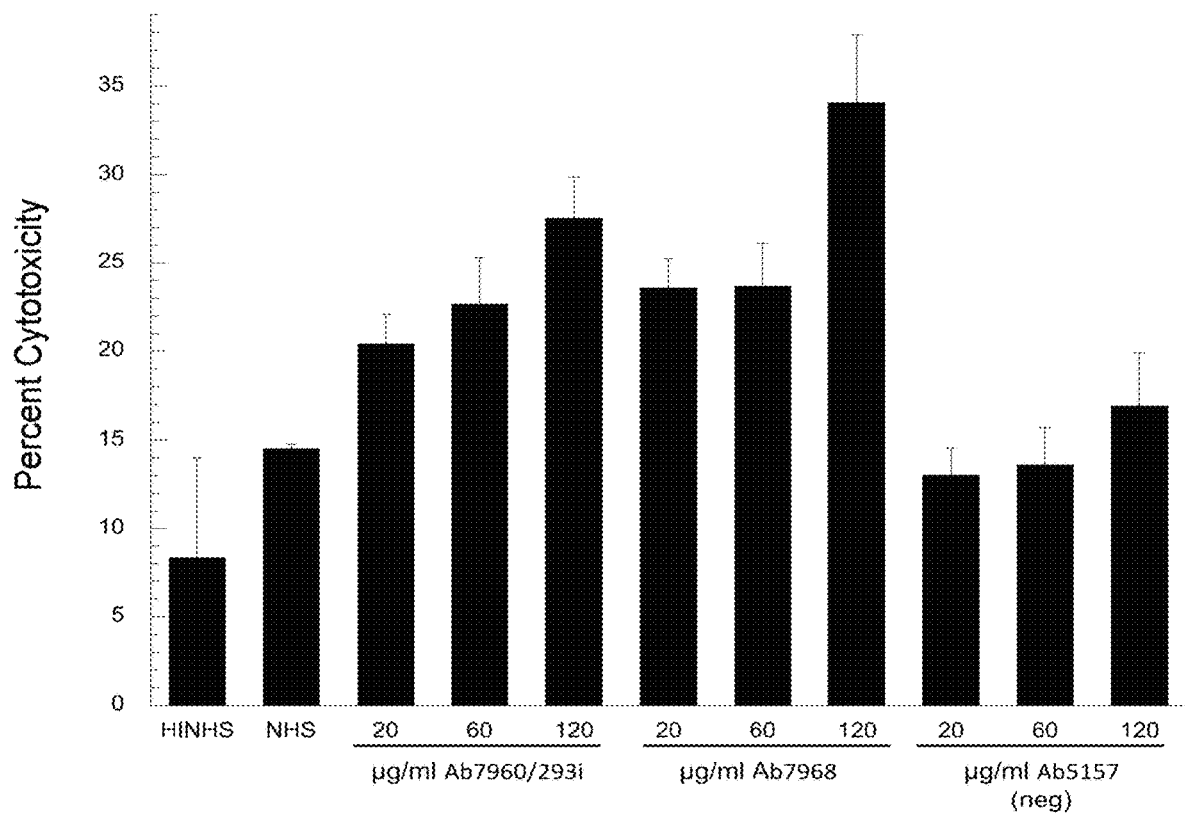
FIG. 9 shows an LDH Release Assay of the recombinant human monoclonal antibodies Ab7960/293i and Ab7968 versus the A549 cells.
Figure 10:
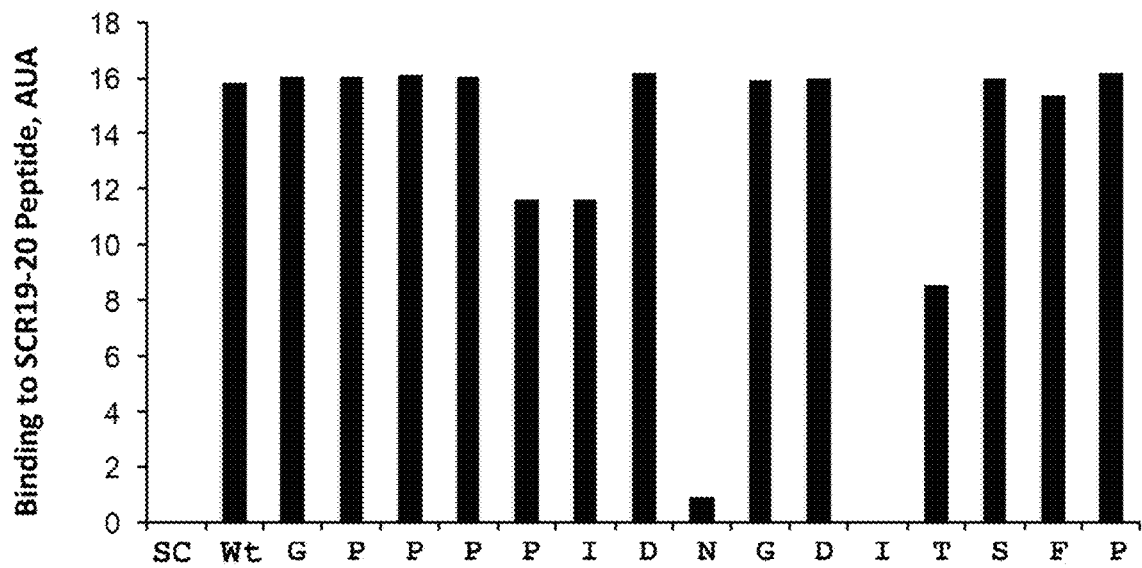
FIG. 10 shows the Epitope Mapping of Anti-Cancer mAb 7968.
Figure 11:
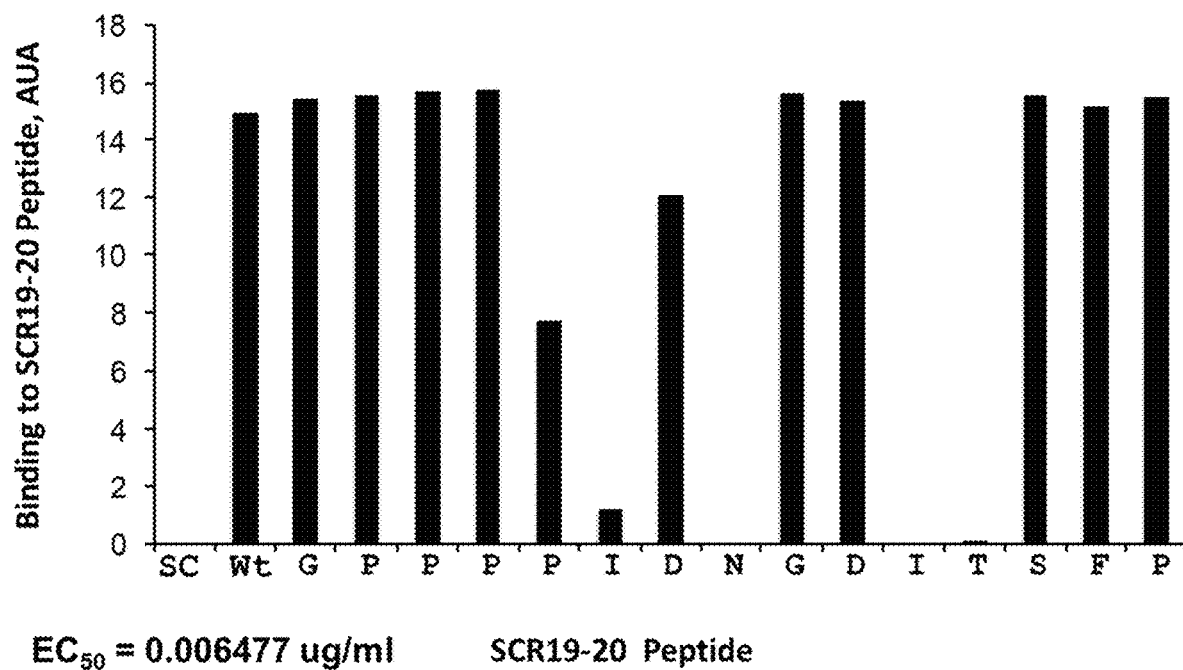
FIG. 11 shows the Epitope Mapping of Anti-Cancer mAb 7955.
Figure 12:
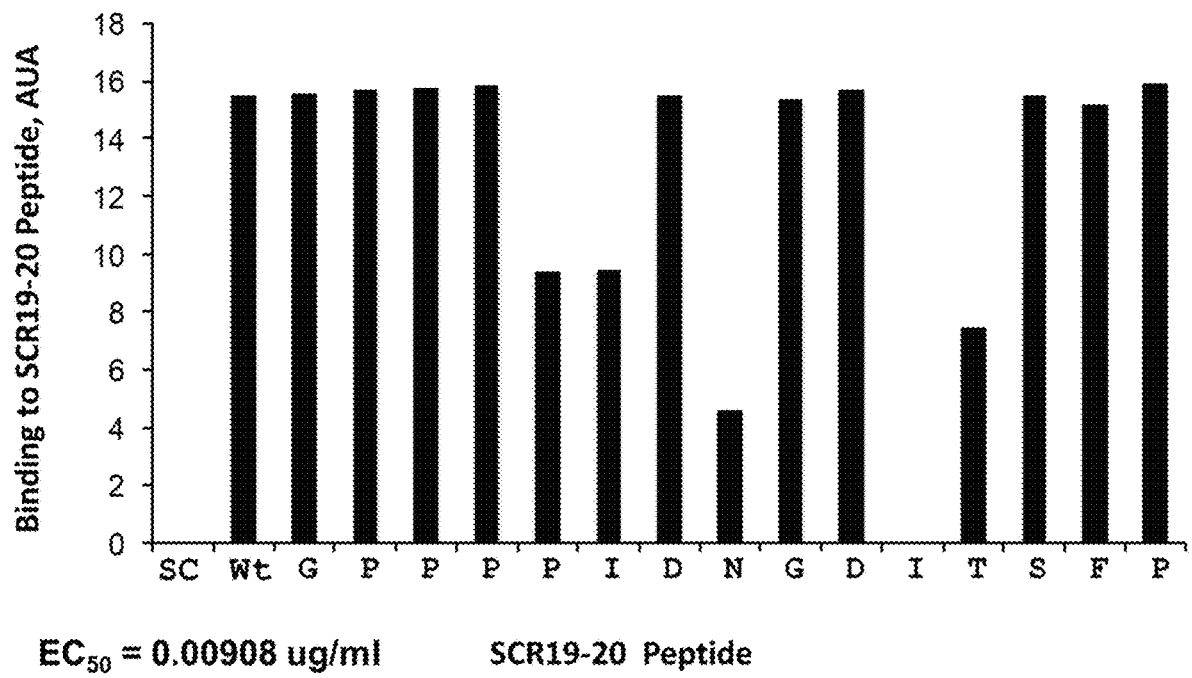
FIG. 12 shows the Epitope Mapping of Anti-Cancer mAb 7957.
Figure 13:
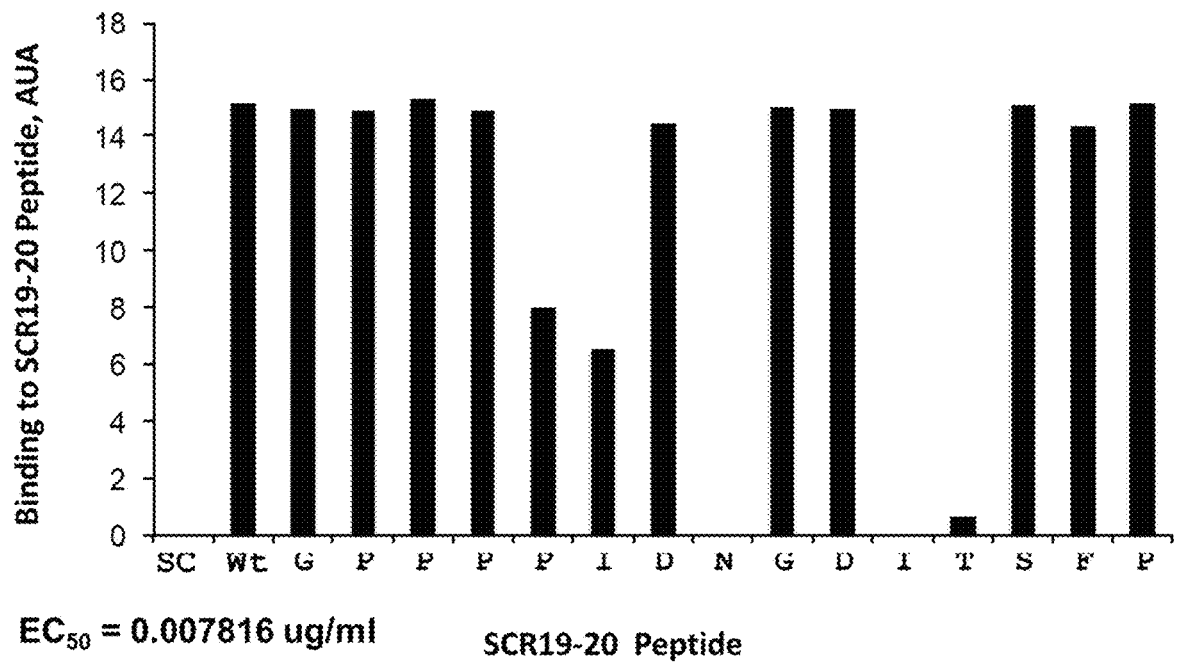
FIG. 13 shows the Epitope Mapping of Anti-Cancer mAb 7960.
Figure 14:
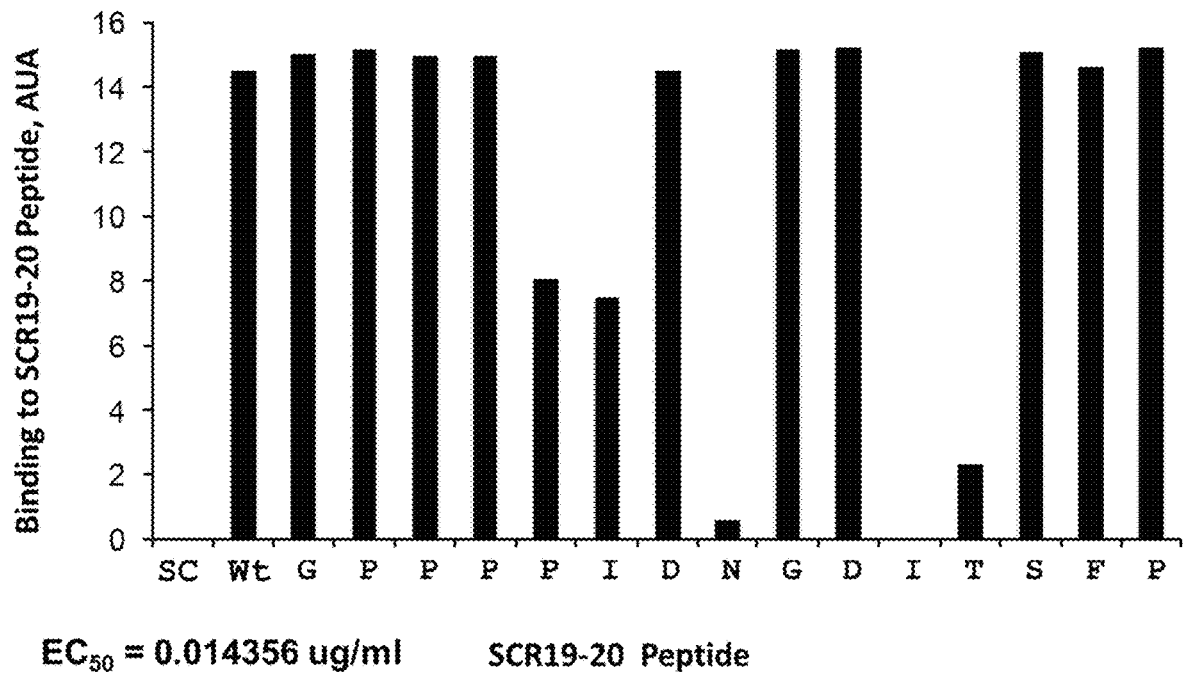
FIG. 14 shows the Epitope Mapping of Anti-Cancer mAb 7961.
Figure 15:
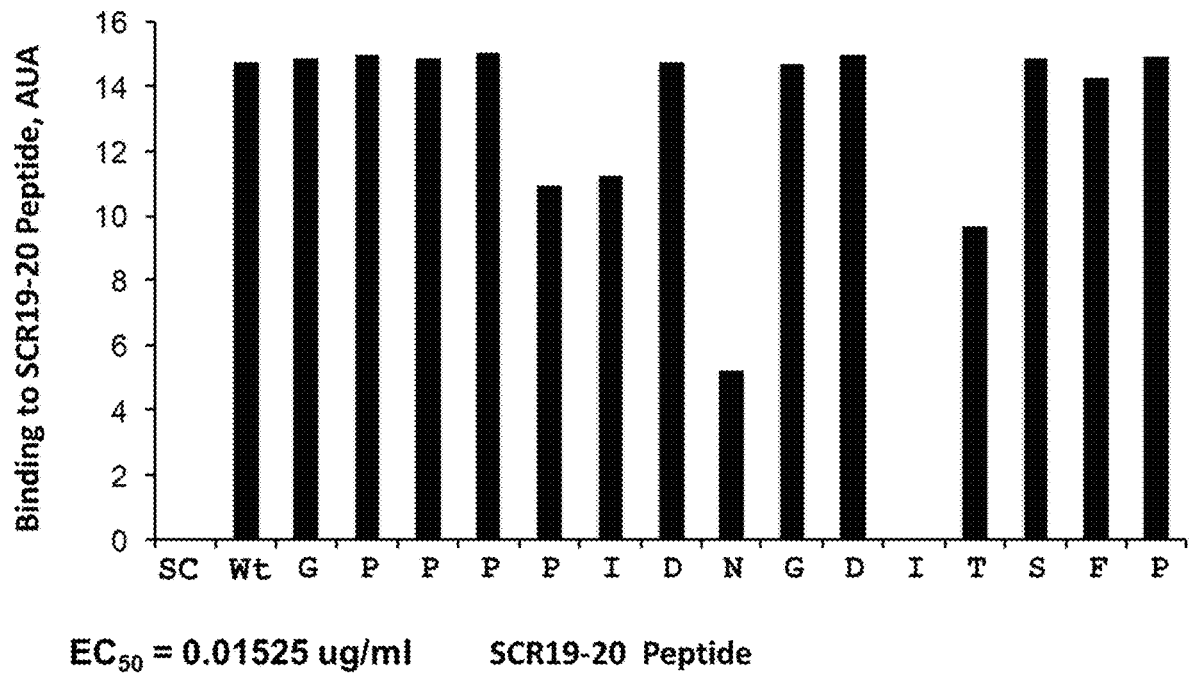
FIG. 15 shows the Epitope Mapping of Anti-Cancer mAb 7964.
Figure 16:
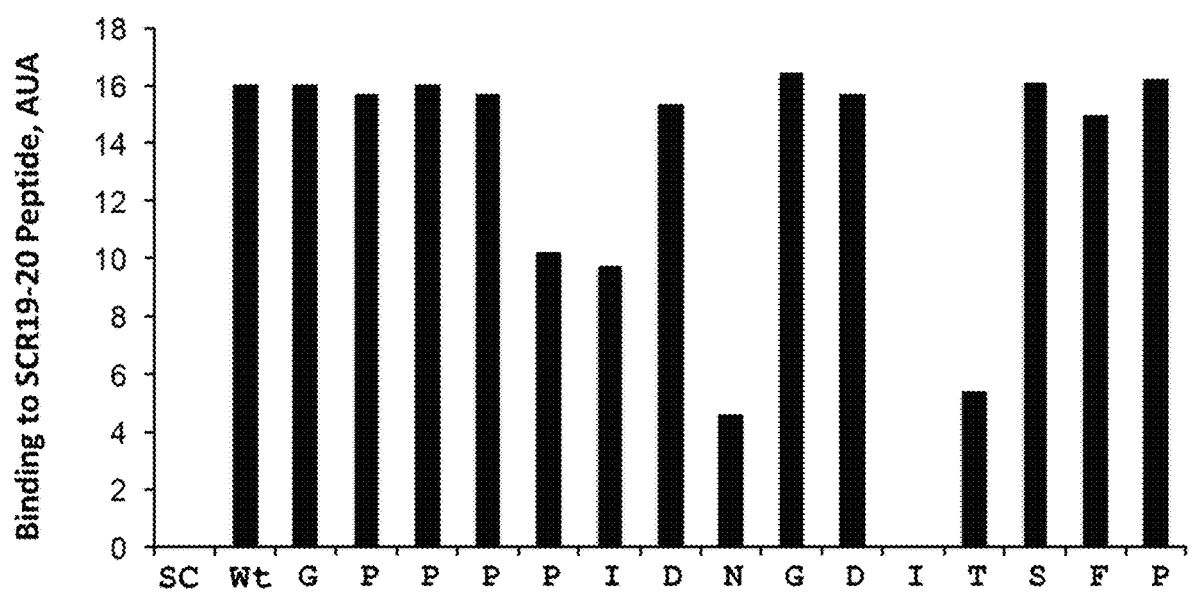
FIG. 16 shows the Epitope Mapping of Anti-Cancer mAb 7979.

The antibodies recognizing CFH and SCR19-20 in the immunoblot showed enhanced binding to the reduced proteins (FIG. 7). Complement Dependent Cytotoxicity (CDC) assays against breast cancer cells were performed using antibodies Ab7960/293i and Ab7968 (FIG. 9).

Example 10

Epitope Mapping

Alanine scanning was completed for all 7 CFH mAbs to identify the residues for CFH mAb binding identified. Surface plasmon resonance (SPR) was used to measure the binding affinity of each mAb against a panel of alanine-substituted 15-mer peptides of GPPPPIDNGDITSFP (SEQ ID NO: 114). The parent peptide consisted of the originally identified 8-mer epitope, i.e., PIDNGDIT (SEQ ID NO: 3) flanked by additional CFH residues. Alanine was substituted for the original residue at each position in the 15-mer to create a panel of 15 different peptides. Comparison of the binding affinity of each mAb for the parent peptide with that measured against the alanine-substituted peptide revealed residues important for mAb binding. This study revealed no important residues outside the original 8-mer epitope. Important residues within the 8-mer were similar overall among all 7 mAbs (FIGS. 10-16 and Table 11).

TABLE 11

| mAB ID | EC$_{50}$, µg/mL |
|---|---|
| Ab7968 | 0.007983 |
| Ab7955 | 0.006477 |
| Ab7957i | 0.00908 |
| Ab7960 | 0.007816 |
| Ab7961 | 0.014356 |
| Ab7964 | 0.01525 |
| Ab7979 | 0.012193 |

Example 11

Binding Affinities

The affinity of one of the CFH mAbs, Ab7968, was determined to be on the order of 2.5 pM. The binding affinity of the mAb was measured at 25, 50, or 100 nM against the immobilized 15-mer peptide of GPPPPIDNGDITSFP (SEQ ID NO:114) using SPR in a BIAcore instrument. This analysis revealed an off-rate ($k_d$) of $5.56 \times 10^{-7}$ s$^{-1}$; an on-rate ($k_a$) of $2.26 \times 10^5$ M$^{-1}$s$^{-1}$; and an affinity ($K_D$) of $2.46 \times 10^{-12}$ M.

Example 12

Cross-Reactivity Testing

All 7 mAbs were tested against the ATHENA MULTI-LYTE® panel of autoantigens. The ATHENA MULTI-LYTE® ANA test for a panel of nuclear antigens: systemic lupus erythematosus autoantigens SSA and SSB, sphingomyelin (Sm), ribonucleoprotein (RNP), sclerosis autoantigen (Scl-70), histidine-tRNA ligase (Jo-1), double-stranded DNA (dsDNA), centromere B (CentB), and histones. 4e10 (Anti HIV, NIH AIDS Reagent Program) and SYNAGIS® (anti-RSV monoclonal antibody palivizumab; "Synagis") were used as controls. Two of the mAbs demonstrated some cross-reactivity (see bolded numbers) and five showed no evidence for cross-reactivity (Table 12).

TABLE 12

Athena on Cancer antibodies

| Heavy chain | Light chain | Antibody ID | μg/mL | SSA | SSB | Sm | RNP | Scl 70 | Jo 1 | dsDNA | Cent B | Histone |
|---|---|---|---|---|---|---|---|---|---|---|---|---|
| | | 4e 10 | 50 | 92 | 184 | 11 | 18 | 3 | 149 | 14 | 12 | 20 |
| | | | 25 | 75 | 157 | 7 | 13 | 3 | 124 | 10 | 7 | 15 |
| | | Synagis | 50 | 0 | 5 | 4 | 1 | 1 | 1 | 3 | 1 | 2 |
| | | | 25 | 2 | 6 | 2 | 3 | 2 | 1 | 0 | 1 | 1 |
| H007955 | K005989 | Ab7955 | 50 | 92 | 83 | 10 | 13 | 8 | 39 | 26 | 85 | 90 |
| | | | 12.5 | 56 | 46 | 7 | 8 | 3 | 16 | 11 | 47 | 60 |
| | | | 6.25 | 32 | 26 | 5 | 4 | 2 | 11 | 3 | 29 | 44 |
| H007957 | K005991_6004 | Ab7957/293i | 50 | 11 | 11 | 4 | 6 | 2 | 5 | 2 | 4 | 15 |
| | | | 25 | 11 | 14 | 3 | 4 | 2 | 4 | 8 | 2 | 9 |
| | | | 12.5 | 9 | 11 | 1 | 3 | 2 | 3 | 4 | 2 | 8 |
| | | | 6.25 | 9 | 10 | 3 | 3 | 2 | 3 | 4 | 2 | 6 |
| H007960 | K005994 | Ab7960 | 50 | 6 | 8 | 2 | 4 | 3 | 5 | 8 | 12 | 31 |
| | | | 12.5 | 4 | 8 | 4 | 3 | 3 | 4 | 1 | 3 | 26 |
| | | | 6.25 | 2 | 7 | 2 | 2 | 1 | 2 | 4 | 3 | 18 |
| H007961 | K005995 | Ab7961/293i | 50 | 40 | 36 | 6 | 8 | 3 | 33 | 36 | 31 | 77 |
| | | | 25 | 31 | 37 | 5 | 8 | 3 | 22 | 32 | 25 | 77 |
| | | | 12.5 | 24 | 23 | 5 | 6 | 3 | 14 | 16 | 16 | 69 |
| | | | 6.25 | 18 | 19 | 4 | 7 | 2 | 10 | 21 | 13 | 62 |
| H007962 | K005996 | Ab7962/293i | 50 | 2 | 8 | 4 | 5 | 2 | 4 | 5 | 3 | 4 |
| | | | 12.5 | 2 | 5 | 3 | 3 | 2 | 5 | 2 | 2 | 1 |
| | | | 6.25 | 2 | 1 | 4 | 2 | 1 | 4 | 1 | 1 | 3 |
| H007964 | K005999 | Ab7964/293i | 50 | 162 | 162 | 137 | 62 | 45 | 120 | 172 | 105 | 133 |
| | | | 25 | 168 | 108 | 96 | 56 | 31 | 74 | 184 | 127 | 134 |
| | | | 12.5 | 132 | 80 | 67 | 51 | 22 | 44 | 147 | 133 | 115 |
| | | | 6.25 | 101 | 56 | 47 | 44 | 14 | 25 | 84 | 100 | 83 |
| H007966 | K006001 | Ab7966 | 50 | 91 | 18 | 3 | 14 | 2 | 133 | 11 | 10 | 42 |
| | | | 12.5 | 23 | 8 | 3 | 5 | 2 | 33 | 4 | 3 | 19 |
| | | | 6.25 | 10 | 6 | 3 | 3 | 2 | 13 | 4 | 3 | 11 |
| H007968 | K006003 | Ab7968 | 50 | 7 | 9 | 7 | 10 | 4 | 7 | 31 | 16 | 19 |
| | | | 25 | 8 | 8 | 5 | 8 | 3 | 3 | 14 | 8 | 10 |
| | | | 12.5 | 4 | 12 | 7 | 7 | 3 | 2 | 9 | 4 | 7 |
| | | | 6.25 | 4 | 7 | 4 | 7 | 3 | 4 | 9 | 3 | 5 |
| H007970 | K005991_6004 | Ab7970 | 28.3 | 165 | 126 | 22 | 56 | 11 | 123 | 148 | 146 | 131 |
| | | | 7.075 | 120 | 61 | 12 | 44 | 6 | 55 | 98 | 164 | 115 |
| | | | 3.538 | 84 | 40 | 10 | 34 | 6 | 32 | 74 | 129 | 86 |
| H007979 | K006015 | Ab7979/239i | 16.7 | 144 | 265 | 92 | 40 | 44 | 183 | 27 | 70 | 100 |
| | | | 8.35 | 146 | 253 | 77 | 38 | 39 | 165 | 58 | 84 | 114 |
| | | | 4.175 | 140 | 241 | 63 | 36 | 27 | 144 | 64 | 69 | 114 |
| | | | 2.088 | 119 | 180 | 45 | 29 | 19 | 106 | 67 | 49 | 93 |

Example 13

CFH mAb Dose-Dependent Increase in CDC

Figure 17:
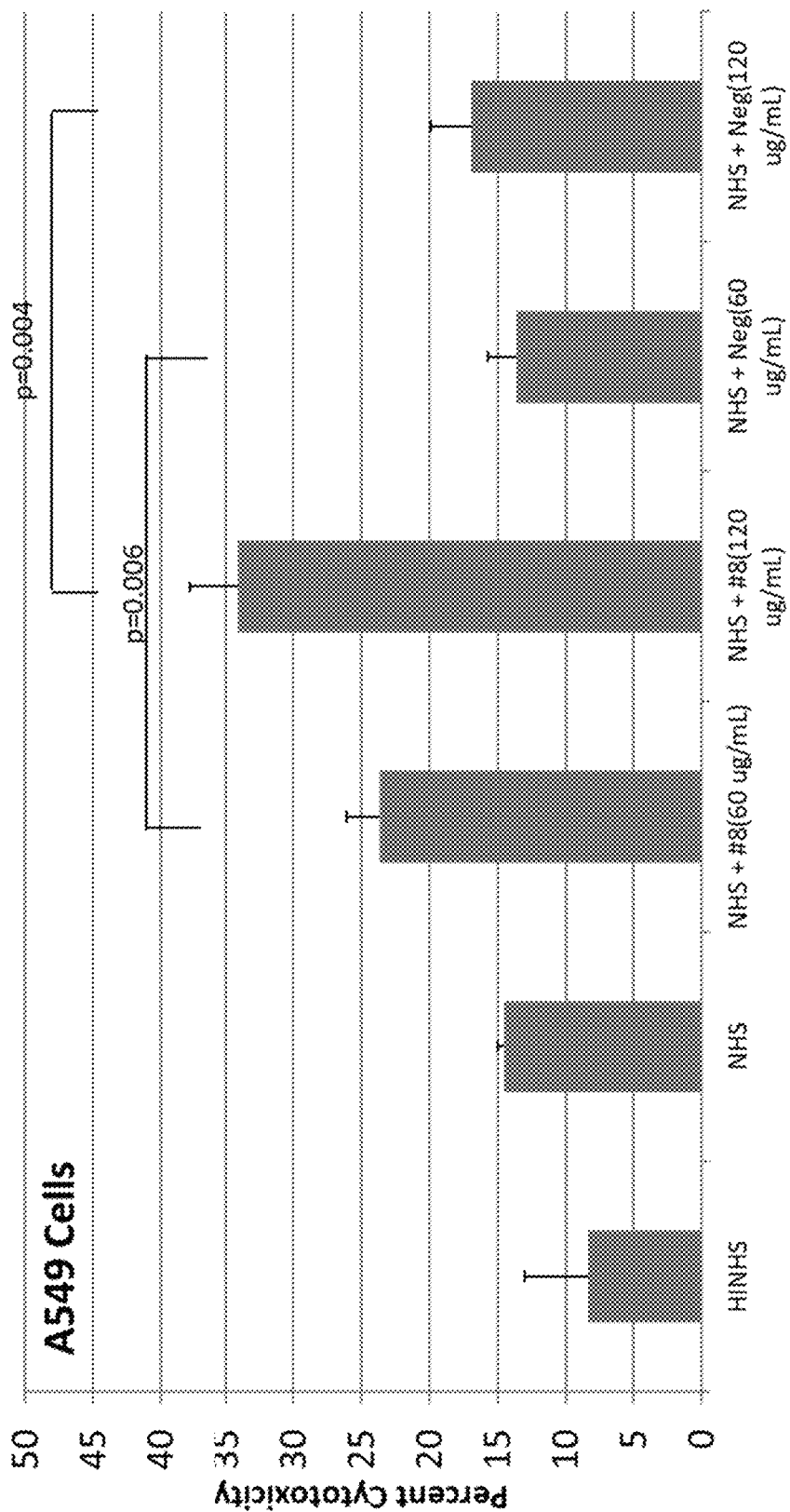
FIG. 17 shows that CFH mAbs cause a dose-dependent increase in CDC in lung cancer cells.
Figure 18:
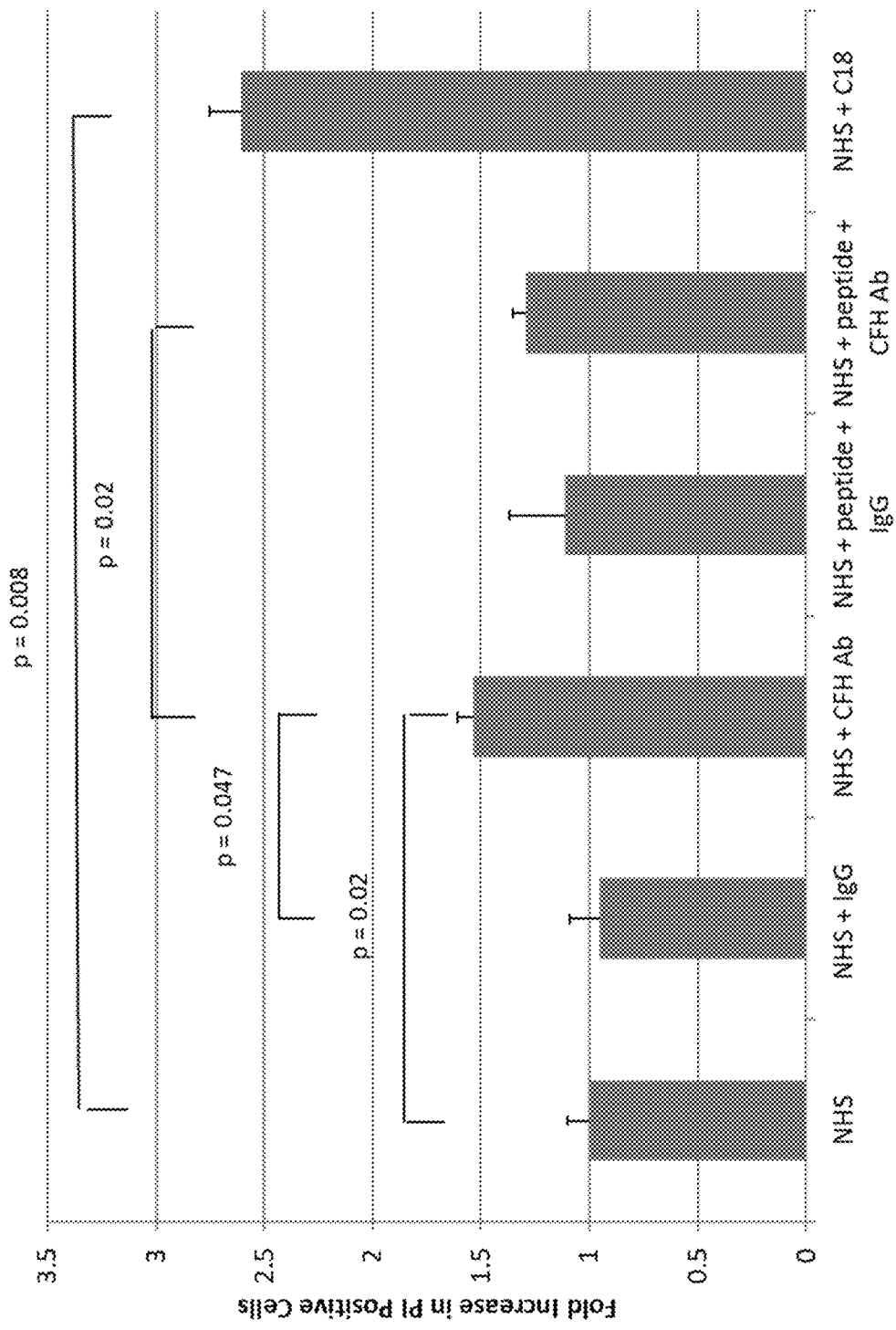
FIG. 18 shows that CFH antibody-induced CDC can be blocked with the epitope peptide.

CFH mAbs caused a dose-dependent increase in CDC in lung cancer cells. A549 lung cancer cells were incubated with CFH mAbs, mAb7968 or mAb7960, or negative control, IgG subclass-matched mAbs along with normal human serum (NHS) as a source of complement. The mAbs were tested at 60 or 120 μg/mL and measured cytotoxicity by an LDH-release ELISA (see e.g., FIG. 17). FIG. 17 shows that CFH mAb 7968 caused a statistically significant increase in CDC at 60 μg/mL (p=0.006) and 120 μg/mL (p=0.004).

Example 14

CFH Antibody-Induced CDC was Blocked with the Epitope Peptide

CFH antibody-induced CDC was blocked with the epitope peptide (SEQ ID NO: 3). The experiment was essentially the same as the CDC assay as described in the Dose Response Example except that a CFH antibody that had been affinity purified from patient serum was used and cell death was quantified using a propidium iodide flow cytometry assay, as described above. Before incubating A549 cells with CFH antibody or normal human IgG, the antibodies were incubated with the epitope peptide (SEQ ID NO: 3) overnight at RT with a 200 M excess of the peptide compared with the antibody. Peptide preincubation caused a statistically significant (p=0.02) decrease in CDC induced by the CFH antibody. The CDC observed may have been caused by binding of the CFH antibody to its target.

Example 15

CFH mAb-Induced CDC in Combination with Other Drugs

Figure 19:
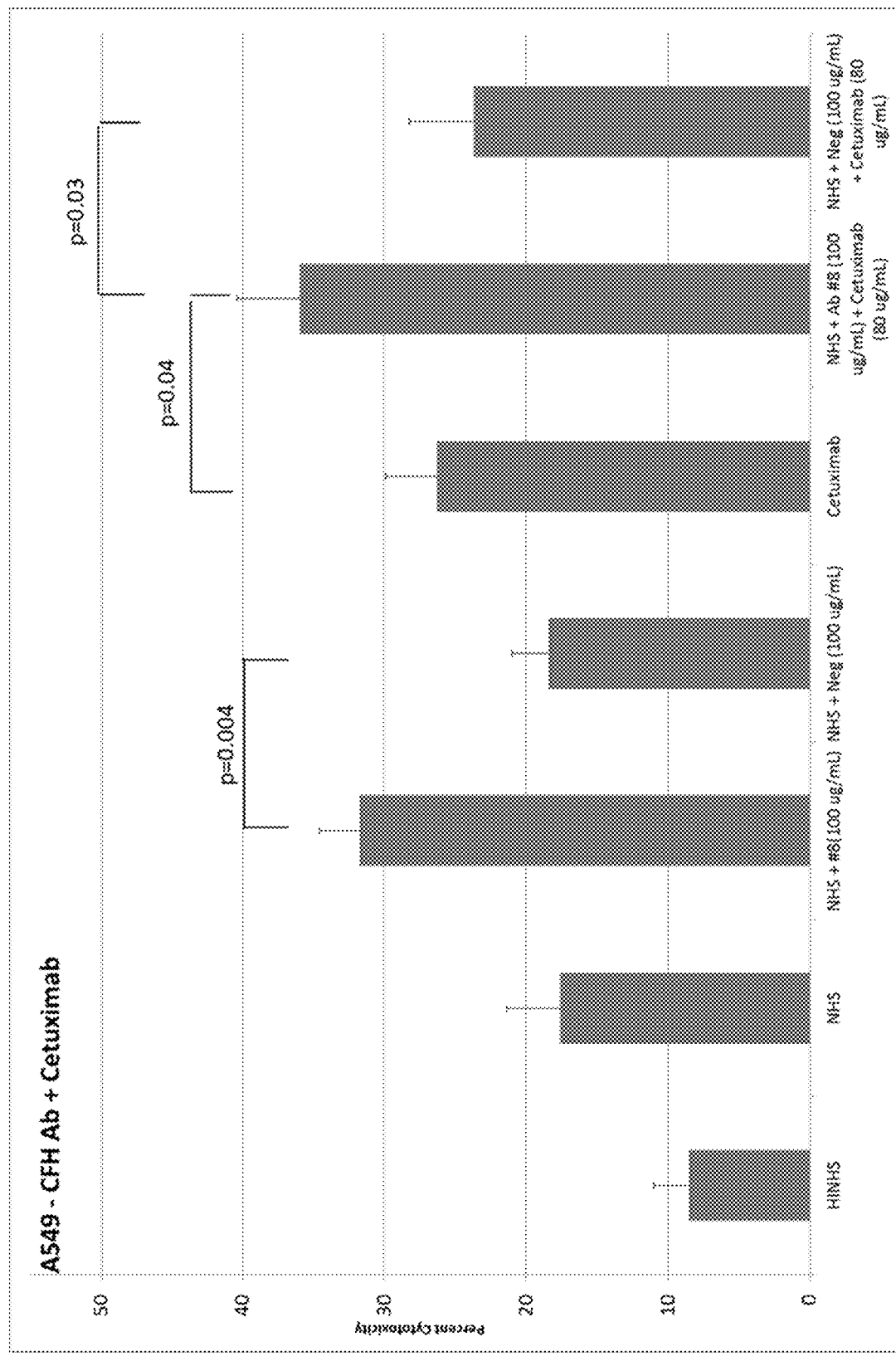
FIG. 19 shows that CFH mAb-induced CDC is additive with the effects of Cetuximab, PERJETA®, and HERCEPTIN®.

CFH mAb-induced CDC was additive with the effects of Cetuximab, PERJETA®, and HERCEPTIN®. The CFH mAbs may be used in conjunction with other anti-cancer drugs to increase tumor cell killing, i.e., enhance antibody-dependent cell-mediated cytotoxicity (ADCC) and cell mediated toxicity. Using the CDC assay as described in the Dose Response Example, A549 cells were incubated with Cetuximab at 80 μg/mL with or without CFH mAb 7968 at 100 μg/mL. The inclusion of mAb 7968 caused a statistically significant (p=0.04) increase in the level of CDC induced by Cetuximab alone (FIG. 19). Negative control mAb resulted in no increase in Cetuximab induced CDC.

Example 16

CFH mAbs Induction of CDC in Breast Cancer Cell Lines

Figure 20:
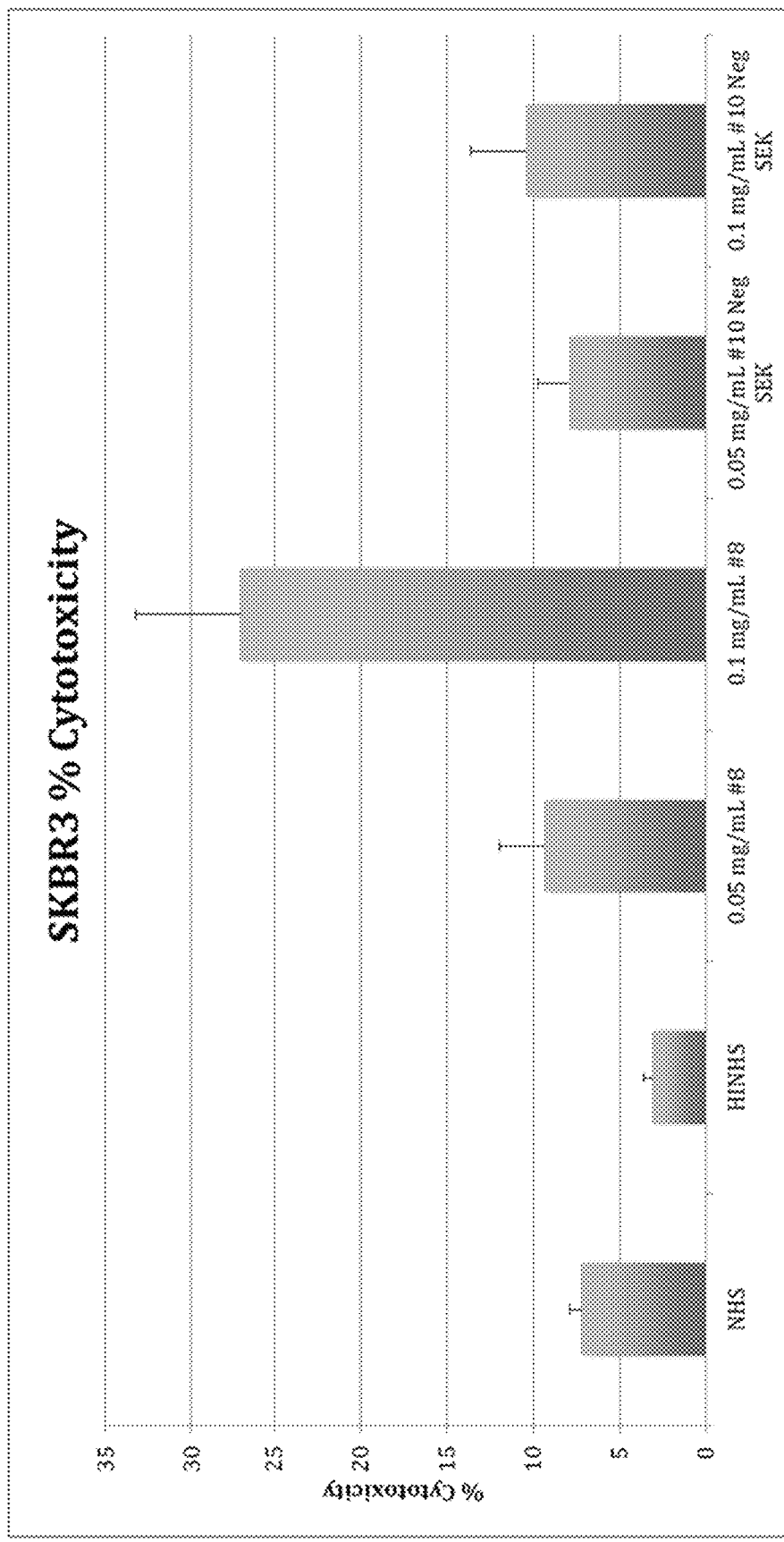
FIG. 20 shows that CFH mAbs are effective inducers of CDC in breast cancer cell lines.
Figure 21:
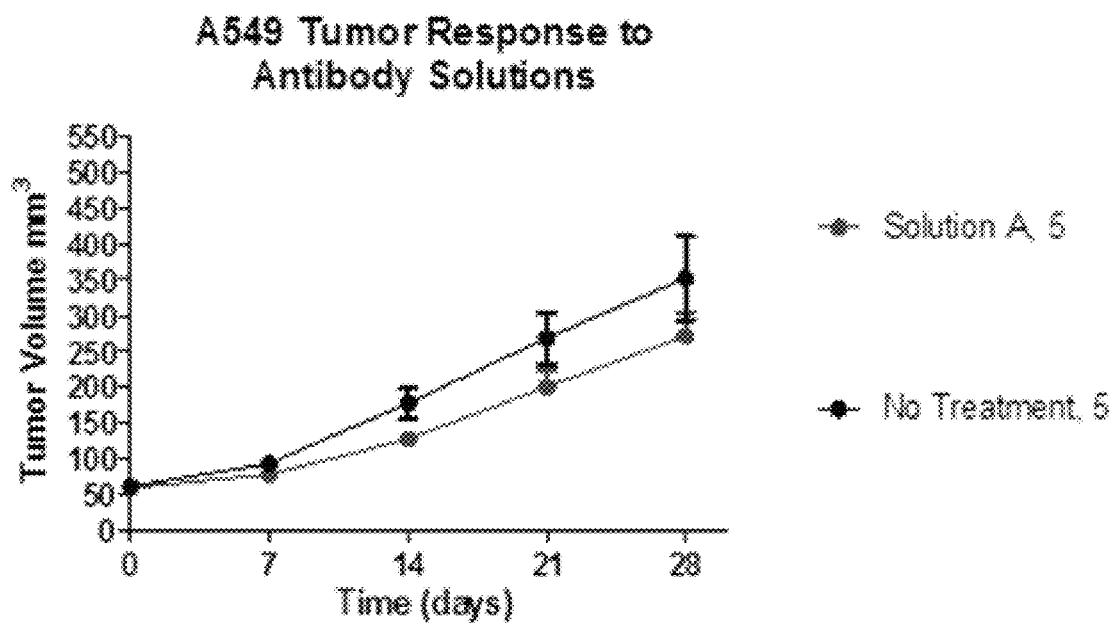
FIG. 21 shows the A549 tumor response to antibody solution A compared to no treatment.
Figure 22:
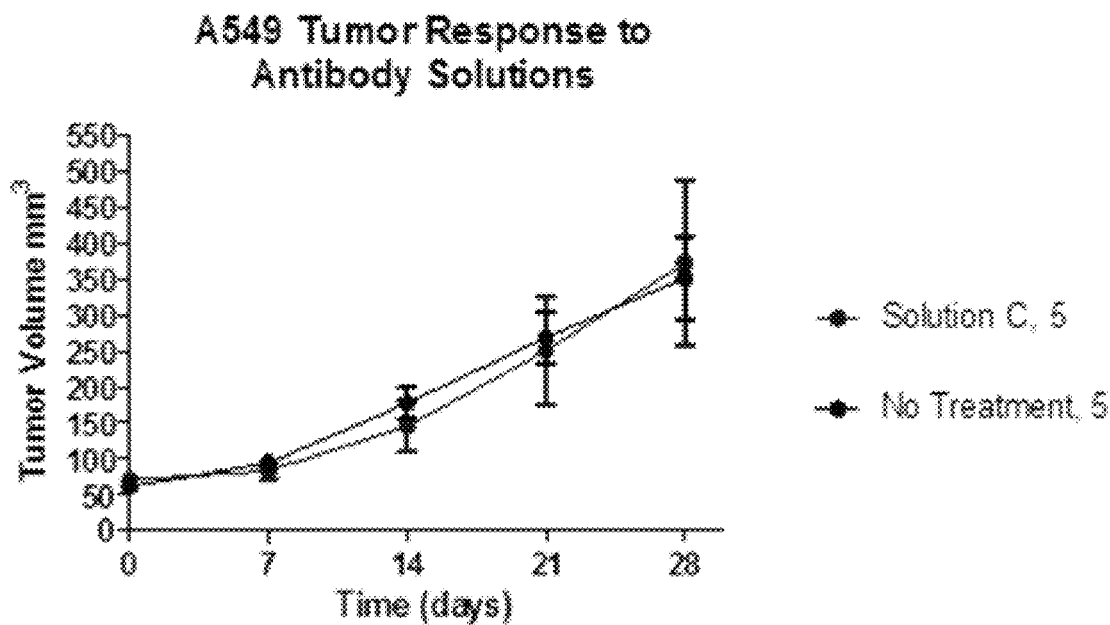
FIG. 22 shows the A549 tumor response to antibody solution C compared to no treatment.
Figure 23:
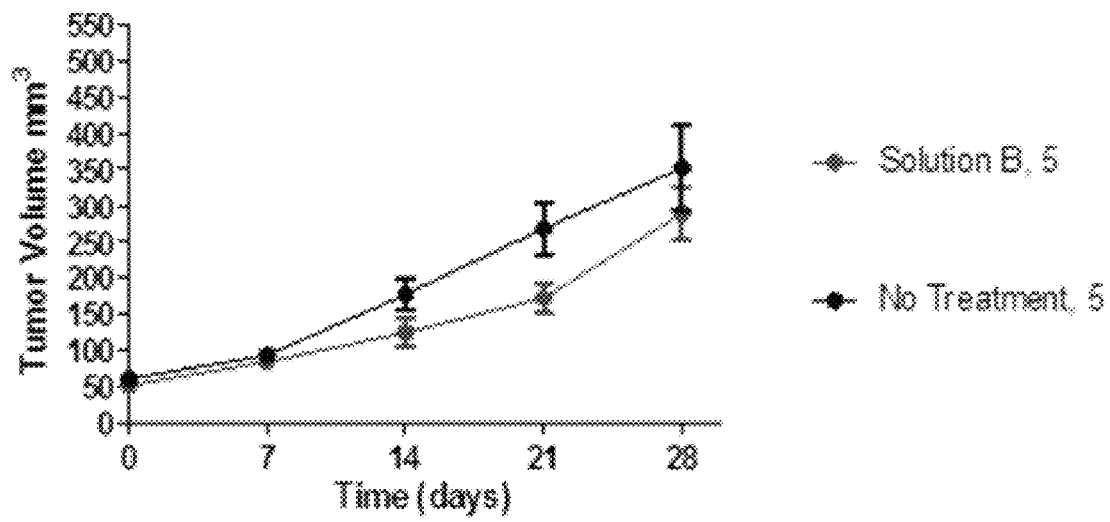
FIG. 23 shows the A549 tumor response to antibody solution B compared to no treatment.
Figure 24:
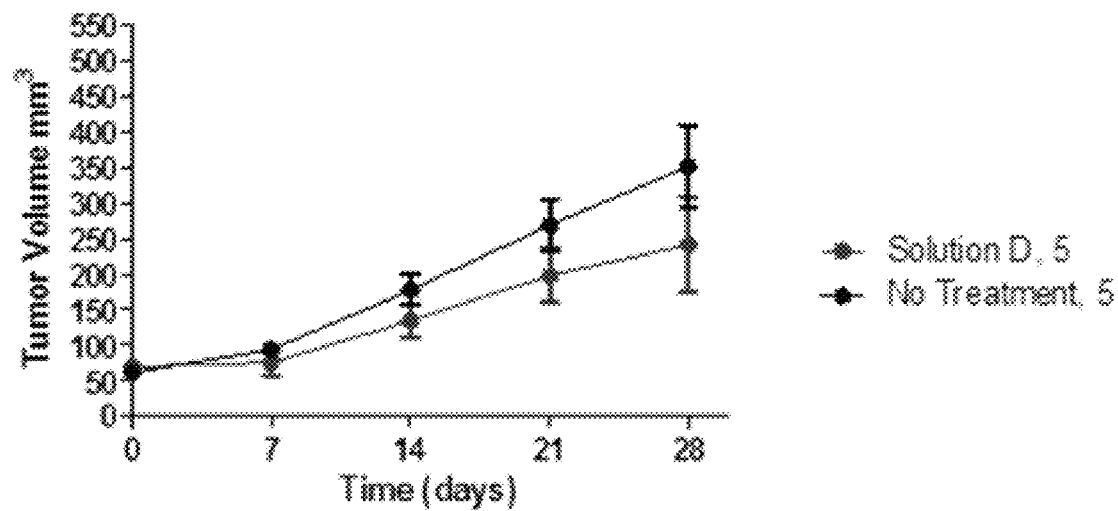
FIG. 24 shows the A549 tumor response to antibody solution D compared to no treatment.

CFH mAbs were effective inducers of CDC in breast cancer cell lines. CFH mAbs were effective inducers of CDC in the breast cancer cell lines MCF7, SKBR3, MDA-MB- 231 (FIG. 20). FIG. 20 shows a plot of CDC in the SKBR3 cell line using the CDC assay format as described in the Dose Response Example described above. SKBR3 breast cancer cells, which overexpress the HER2/c-erb-2 gene product, were susceptible to CFH mAb 7968-induced CDC. CDC in SKBR3 cells was induced by mAb 7968 at 50 or 100 μg/mL.

Example 17

Tumor Growth—Animal Studies

The ability of one of the CFH mAbs (CFH mAb 7968) to inhibit lung tumor xenograft growth was investigated in athymic nude mice. The antibodies were administered at 20 or 200 μg/dose, two doses per animal per week, for 5 weeks.

Lung tumor xenografts in female athymic nude mice were induced by the subcutaneous injection of 2 million A549 cells suspended in 100 μL of a 50:50 mix of Hank's buffered saline/2% (v/v) FBS and MATRIGEL® (BD Biosciences catalog number 354234). When the tumors reached 50-75 mm³ in volume, the mice were randomized into 5 cohorts of 5 mice per cohort. Twice per week, the mice were injected with one of the following: 20 μg CFH mAb 7968, 200 μg CFH mAb 7968, 20 μg subclass-matched negative control IgG, or 200 μg negative control IgG. One cohort received no treatment. All antibodies were injected intraperitoneally in a volume of 150 μL phosphate buffered saline. Tumor volumes were measured with calipers every 7 days and the volume calculated using the formula V=W2×L/2 (FIG. 21-24). There was some dose dependent difference at 14 days, but no statistically significant growth inhibition was observed compared to a negative control antibody at 28 days (consistent with prior CFH siRNA studies).

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed:

1. A method for inhibiting complement factor H (CFH) protein in a subject by administering a therapeutically effective amount of an isolated antibody or antibody fragment thereof which immunospecifically binds to Complement Factor H (CFH) protein, wherein the isolated antibody or antibody fragment thereof binds to an epitope of PIDNGDIT (SEQ ID NO: 3) within short consensus repeat (SCR) 19 of CFH protein, wherein the antibody comprises:
   (a) a variable heavy domain comprising the amino acid sequence of SEQ ID NO: 73 and a variable light domain region comprising the amino acid sequence of SEQ ID NO: 84;
   (b) a variable heavy domain comprising the amino acid sequence of SEQ ID NO: 74 and a variable light domain region comprising the amino acid sequence of SEQ ID NO: 83;
   (c) a variable heavy domain comprising the amino acid sequence of SEQ ID NO: 75 and a variable light domain region comprising the amino acid sequence of SEQ ID NO: 85;
   (d) a variable heavy domain comprising the amino acid sequence of SEQ ID NO: 78 and a variable light domain region comprising the amino acid sequence of SEQ ID NO: 88;
   (e) a variable heavy domain comprising the amino acid sequence of SEQ ID NO: 79 and a variable light domain region comprising the amino acid sequence of SEQ ID NO: 89;
   (f) a variable heavy domain comprising the amino acid sequence of SEQ ID NO: 76 and a variable light domain region comprising the amino acid sequence of SEQ ID NO: 86; or
   (g) a variable heavy domain comprising the amino acid sequence of SEQ ID NO: 77 and a variable light domain region comprising the amino acid sequence of SEQ ID NO: 87.

2. The method of claim 1, wherein the isolated antibody or antibody fragment thereof comprises a variable heavy domain comprising the amino acid sequence of SEQ ID NO: 79 and a variable light domain region comprising the amino acid sequence of SEQ ID NO: 89.

3. The method of claim 1, wherein the isolated antibody or antibody fragment thereof is selected from the group consisting of a human antibody, an immunoglobulin molecule, a disulfide linked Fv, a monoclonal antibody, an affinity matured, a scFv, a chimeric antibody, a single domain antibody, a CDR-grafted antibody, a diabody, a humanized antibody, a multispecific antibody, a Fab, a dual specific antibody, a DVD, a TVD, a Fab', a bispecific antibody, a F(ab')$_2$, and a Fv.

4. The method of claim 1, wherein the isolated antibody or antibody fragment thereof comprises a heavy chain immunoglobulin constant domain selected from the group consisting of a human IgM constant domain, a human IgG4 constant domain, a human IgG1 constant domain, a human IgE constant domain, a human IgG2 constant domain, a human IgG3 constant domain, and a human IgA constant domain.

5. The method of claim 1, wherein the subject has cancer.

6. The method of claim 1, wherein the subject has a cancer that uses CFH as a protective mechanism.

7. The method of claim 1, wherein the subject has lung cancer or breast cancer.

8. The method of claim 1, wherein the subject has non-small cell lung carcinoma.

9. The method of claim 1, wherein the method further comprises administering a therapeutically effective amount of one or more of doxorubicin, epirubicin, daunorubicin, capecitabine, carboplatin, cisplatin, cyclophosphamide, eribulin, fluorouracil, gemcitabine, ixabepilone, methotrexate, mitoxantrone, mitomycin, paclitaxel, docetaxel, thiotepa, vincristine, vinorelbine, lapatinib, onartuzumab, rilotumumab, ficlatuzumab, bevacizumab, rituximab, panatumamab, cetuximab, pertuzumab, or trastuzumab.

10. A method for increasing complement dependent lysis of a cell, the method comprising administering to a cell a therapeutically effective amount of an isolated antibody or antibody fragment thereof which immunospecifically binds to Complement Factor H (CFH) protein, wherein the isolated antibody or antibody fragment thereof binds to an epitope of PIDNGDIT (SEQ ID NO: 3) within short consensus repeat (SCR) 19 of CFH protein, wherein the antibody comprises:
(a) a variable heavy domain comprising the amino acid sequence of SEQ ID NO: 73 and a variable light domain region comprising the amino acid sequence of SEQ ID NO: 84;
(b) a variable heavy domain comprising the amino acid sequence of SEQ ID NO: 74 and a variable light domain region comprising the amino acid sequence of SEQ ID NO: 83;
(c) a variable heavy domain comprising the amino acid sequence of SEQ ID NO: 75 and a variable light domain region comprising the amino acid sequence of SEQ ID NO: 85;
(d) a variable heavy domain comprising the amino acid sequence of SEQ ID NO: 78 and a variable light domain region comprising the amino acid sequence of SEQ ID NO: 88;
(e) a variable heavy domain comprising the amino acid sequence of SEQ ID NO: 79 and a variable light domain region comprising the amino acid sequence of SEQ ID NO: 89;
(f) a variable heavy domain comprising the amino acid sequence of SEQ ID NO: 76 and a variable light domain region comprising the amino acid sequence of SEQ ID NO: 86; or
(g) a variable heavy domain comprising the amino acid sequence of SEQ ID NO: 77 and a variable light domain region comprising the amino acid sequence of SEQ ID NO: 87.

11. The method of claim 10, wherein the isolated antibody or antibody fragment thereof comprises a variable heavy domain comprising the amino acid sequence of SEQ ID NO: 79 and a variable light domain region comprising the amino acid sequence of SEQ ID NO: 89.

12. The method of claim 10, wherein the isolated antibody or antibody fragment thereof is selected from the group consisting of a human antibody, an immunoglobulin molecule, a disulfide linked Fv, a monoclonal antibody, an affinity matured, a scFv, a chimeric antibody, a single domain antibody, a CDR-grafted antibody, a diabody, a humanized antibody, a multispecific antibody, a Fab, a dual specific antibody, a DVD, a TVD, a Fab', a bispecific antibody, a F(ab')$_2$, and a Fv.

13. The method of claim 10, wherein the isolated antibody or antibody fragment thereof comprises a heavy chain immunoglobulin constant domain selected from the group consisting of a human IgM constant domain, a human IgG4 constant domain, a human IgG1 constant domain, a human IgE constant domain, a human IgG2 constant domain, a human IgG3 constant domain, and a human IgA constant domain.

14. The method of claim 10, wherein the cell is a cancer cell.

15. The method of claim 10, wherein the cell is a cancer cell that uses CFH as a protective mechanism.

16. The method of claim 10, wherein the cell is a lung cancer cell or breast cancer cell.

17. The method of claim 10, wherein the cell is non-small cell lung carcinoma cell.

* * * * *

SEQUENCE LISTING

```
<160> NUMBER OF SEQ ID NOS: 132

<210> SEQ ID NO 1
<211> LENGTH: 1231
<212> TYPE: PRT
<213> ORGANISM: Homo sapiens

<400> SEQUENCE: 1

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Val Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205
```

-continued

```
Ser Cys Lys Ser Pro Asp Val Ile Asn Gly Ser Pro Ile Ser Gln Lys
    210                 215                 220
Ile Ile Tyr Lys Glu Asn Glu Arg Phe Gln Tyr Lys Cys Asn Met Gly
225                 230                 235                 240
Tyr Glu Tyr Ser Glu Arg Gly Asp Ala Val Cys Thr Glu Ser Gly Trp
                245                 250                 255
Arg Pro Leu Pro Ser Cys Glu Lys Ser Cys Asp Asn Pro Tyr Ile
            260                 265                 270
Pro Asn Gly Asp Tyr Ser Pro Leu Arg Ile Lys His Arg Thr Gly Asp
                275                 280                 285
Glu Ile Thr Tyr Gln Cys Arg Asn Gly Phe Tyr Pro Ala Thr Arg Gly
    290                 295                 300
Asn Thr Ala Lys Cys Thr Ser Thr Gly Trp Ile Pro Ala Pro Arg Cys
305                 310                 315                 320
Thr Leu Lys Pro Cys Asp Tyr Pro Asp Ile Lys His Gly Gly Leu Tyr
                325                 330                 335
His Glu Asn Met Arg Arg Pro Tyr Phe Pro Val Ala Val Gly Lys Tyr
                340                 345                 350
Tyr Ser Tyr Tyr Cys Asp Glu His Phe Glu Thr Pro Ser Gly Ser Tyr
            355                 360                 365
Trp Asp His Ile His Cys Thr Gln Asp Gly Trp Ser Pro Ala Val Pro
    370                 375                 380
Cys Leu Arg Lys Cys Tyr Phe Pro Tyr Leu Glu Asn Gly Tyr Asn Gln
385                 390                 395                 400
Asn Tyr Gly Arg Lys Phe Val Gln Gly Lys Ser Ile Asp Val Ala Cys
                405                 410                 415
His Pro Gly Tyr Ala Leu Pro Lys Ala Gln Thr Thr Val Thr Cys Met
            420                 425                 430
Glu Asn Gly Trp Ser Pro Thr Pro Arg Cys Ile Arg Val Lys Thr Cys
    435                 440                 445
Ser Lys Ser Ser Ile Asp Ile Glu Asn Gly Phe Ile Ser Glu Ser Gln
450                 455                 460
Tyr Thr Tyr Ala Leu Lys Glu Lys Ala Lys Tyr Gln Cys Lys Leu Gly
465                 470                 475                 480
Tyr Val Thr Ala Asp Gly Glu Thr Ser Gly Ser Ile Thr Cys Gly Lys
                485                 490                 495
Asp Gly Trp Ser Ala Gln Pro Thr Cys Ile Lys Ser Cys Asp Ile Pro
            500                 505                 510
Val Phe Met Asn Ala Arg Thr Lys Asn Asp Phe Thr Trp Phe Lys Leu
    515                 520                 525
Asn Asp Thr Leu Asp Tyr Glu Cys His Asp Gly Tyr Glu Ser Asn Thr
530                 535                 540
Gly Ser Thr Thr Gly Ser Ile Val Cys Gly Tyr Asn Gly Trp Ser Asp
545                 550                 555                 560
Leu Pro Ile Cys Tyr Glu Arg Glu Cys Glu Leu Pro Lys Ile Asp Val
                565                 570                 575
His Leu Val Pro Asp Arg Lys Lys Asp Gln Tyr Lys Val Gly Glu Val
            580                 585                 590
Leu Lys Phe Ser Cys Lys Pro Gly Phe Thr Ile Val Gly Pro Asn Ser
    595                 600                 605
Val Gln Cys Tyr His Phe Gly Leu Ser Pro Asp Leu Pro Ile Cys Lys
610                 615                 620
Glu Gln Val Gln Ser Cys Gly Pro Pro Pro Glu Leu Leu Asn Gly Asn
```

```
       625                 630                 635                 640
Val Lys Glu Lys Thr Lys Glu Glu Tyr Gly His Ser Glu Val Val Glu
                    645                 650                 655

Tyr Tyr Cys Asn Pro Arg Phe Leu Met Lys Gly Pro Asn Lys Ile Gln
                660                 665                 670

Cys Val Asp Gly Glu Trp Thr Thr Leu Pro Val Cys Ile Val Glu Glu
            675                 680                 685

Ser Thr Cys Gly Asp Ile Pro Glu Leu Glu His Gly Trp Ala Gln Leu
        690                 695                 700

Ser Ser Pro Pro Tyr Tyr Gly Asp Ser Val Glu Phe Asn Cys Ser
705                 710                 715                 720

Glu Ser Phe Thr Met Ile Gly His Arg Ser Ile Thr Cys Ile His Gly
                725                 730                 735

Val Trp Thr Gln Leu Pro Gln Cys Val Ala Ile Asp Lys Leu Lys Lys
                740                 745                 750

Cys Lys Ser Ser Asn Leu Ile Ile Leu Glu Glu His Leu Lys Asn Lys
                755                 760                 765

Lys Glu Phe Asp His Asn Ser Asn Ile Arg Tyr Arg Cys Arg Gly Lys
                770                 775                 780

Glu Gly Trp Ile His Thr Val Cys Ile Asn Gly Arg Trp Asp Pro Glu
785                 790                 795                 800

Val Asn Cys Ser Met Ala Gln Ile Gln Leu Cys Pro Pro Pro Gln
                805                 810                 815

Ile Pro Asn Ser His Asn Met Thr Thr Thr Leu Asn Tyr Arg Asp Gly
                820                 825                 830

Glu Lys Val Ser Val Leu Cys Gln Glu Asn Tyr Leu Ile Gln Glu Gly
                835                 840                 845

Glu Glu Ile Thr Cys Lys Asp Gly Arg Trp Gln Ser Ile Pro Leu Cys
                850                 855                 860

Val Glu Lys Ile Pro Cys Ser Gln Pro Pro Gln Ile Glu His Gly Thr
865                 870                 875                 880

Ile Asn Ser Ser Arg Ser Ser Gln Glu Ser Tyr Ala His Gly Thr Lys
                885                 890                 895

Leu Ser Tyr Thr Cys Glu Gly Gly Phe Arg Ile Ser Glu Glu Asn Glu
                900                 905                 910

Thr Thr Cys Tyr Met Gly Lys Trp Ser Ser Pro Pro Gln Cys Glu Gly
                915                 920                 925

Leu Pro Cys Lys Ser Pro Pro Glu Ile Ser His Gly Val Val Ala His
                930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975

Lys Trp Ser His Pro Pro Ser Cys Ile Lys Thr Asp Cys Leu Ser Leu
                980                 985                 990

Pro Ser Phe Glu Asn Ala Ile Pro  Met Gly Glu Lys Lys Asp Val Tyr
                995                 1000                1005

Lys Ala Gly Glu Gln Val Thr  Tyr Thr Cys Ala Thr  Tyr Tyr Lys
        1010                1015                1020

Met Asp Gly Ala Ser Asn Val  Thr Cys Ile Asn Ser  Arg Trp Thr
        1025                1030                1035

Gly Arg Pro Thr Cys Arg Asp  Thr Ser Cys Val Asn  Pro Pro Thr
        1040                1045                1050
```

Val Gln Asn Ala Tyr Ile Val Ser Arg Gln Met Ser Lys Tyr Pro
    1055                1060                1065

Ser Gly Glu Arg Val Arg Tyr Gln Cys Arg Ser Pro Tyr Glu Met
    1070                1075                1080

Phe Gly Asp Glu Glu Val Met Cys Leu Asn Gly Asn Trp Thr Glu
    1085                1090                1095

Pro Pro Gln Cys Lys Asp Ser Thr Gly Lys Cys Gly Pro Pro Pro
    1100                1105                1110

Pro Ile Asp Asn Gly Asp Ile Thr Ser Phe Pro Leu Ser Val Tyr
    1115                1120                1125

Ala Pro Ala Ser Ser Val Glu Tyr Gln Cys Gln Asn Leu Tyr Gln
    1130                1135                1140

Leu Glu Gly Asn Lys Arg Ile Thr Cys Arg Asn Gly Gln Trp Ser
    1145                1150                1155

Glu Pro Pro Lys Cys Leu His Pro Cys Val Ile Ser Arg Glu Ile
    1160                1165                1170

Met Glu Asn Tyr Asn Ile Ala Leu Arg Trp Thr Ala Lys Gln Lys
    1175                1180                1185

Leu Tyr Ser Arg Thr Gly Glu Ser Val Glu Phe Val Cys Lys Arg
    1190                1195                1200

Gly Tyr Arg Leu Ser Ser Arg Ser His Thr Leu Arg Thr Thr Cys
    1205                1210                1215

Trp Asp Gly Lys Leu Glu Tyr Pro Thr Cys Ala Lys Arg
    1220                1225                1230

<210> SEQ ID NO 2
<211> LENGTH: 59
<212> TYPE: PRT
<213> ORGANISM: Homo sapiens

<400> SEQUENCE: 2

Gly Lys Cys Gly Pro Pro Pro Ile Asp Asn Gly Asp Ile Thr Ser
1               5                   10                  15

Phe Pro Leu Ser Val Tyr Ala Pro Ala Ser Ser Val Glu Tyr Gln Cys
            20                  25                  30

Gln Asn Leu Tyr Gln Leu Glu Gly Asn Lys Arg Ile Thr Cys Arg Asn
        35                  40                  45

Gly Gln Trp Ser Glu Pro Pro Lys Cys Leu His
    50                  55

<210> SEQ ID NO 3
<211> LENGTH: 8
<212> TYPE: PRT
<213> ORGANISM: Homo sapiens

<400> SEQUENCE: 3

Pro Ile Asp Asn Gly Asp Ile Thr
1               5

<210> SEQ ID NO 4
<211> LENGTH: 120
<212> TYPE: PRT
<213> ORGANISM: Artificial Sequence
<220> FEATURE:
<223> OTHER INFORMATION: Description of Artificial Sequence:
      Synthetic polypeptide

<400> SEQUENCE: 4

-continued

```
Leu Val Glu Ser Gly Gly Gly Val Val Gln Pro Gly Arg Ser Leu Arg
1               5                   10                  15

Leu Ser Cys Ala Ala Ser Gly Leu Thr Phe Ser Phe Tyr Asn Phe His
            20                  25                  30

Trp Val Arg Gln Thr Pro Gly Lys Gly Leu Glu Trp Val Ala Gly Ile
        35                  40                  45

Ser Tyr Asp Ala Thr Arg Thr Asn Tyr Ala Gly Ser Val Thr Gly Arg
    50                  55                  60

Phe Thr Ile Ser Arg Asp Asn Ser Lys Lys Met Leu Tyr Leu Gln Met
65                  70                  75                  80

Ser Ser Leu Gly Pro Gln Asp Thr Ala Val Tyr His Cys Ala Arg Asp
                85                  90                  95

Arg Ser Asp Gly Gln Leu His Lys Val Ala Phe Asp Ser Trp Gly Gln
            100                 105                 110

Gly Ala Leu Val Thr Val Ser Ser
            115                 120
```

<210> SEQ ID NO 5
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Leu Val Glu Ser Gly Gly Gly Val Val Arg Pro Gly Arg Ser Leu Arg
1               5                   10                  15

Leu Ser Cys Val Ala Ser Gly Phe Thr Phe Asn Ala Tyr Gly Met His
            20                  25                  30

Trp Val Arg Gln Gly Pro Gly Lys Gly Leu Glu Trp Leu Ala Val Ile
        35                  40                  45

Ser Tyr Glu Gly Lys Thr Val Tyr Tyr Ala Asp Ser Val Lys Asp Arg
    50                  55                  60

Phe Thr Ile Ser Arg Asp Asn Ser Arg Asn Thr Val Ser Leu His Leu
65                  70                  75                  80

Asn Asn Leu Arg Gly Glu Asp Thr Ala Val Tyr Tyr Cys Ala Lys Gly
                85                  90                  95

Ser Ala Ser Ala Ala Val Leu Gln His Trp Gly Gln Gly Thr Leu Val
            100                 105                 110

Ser Val Thr Ser
        115
```

<210> SEQ ID NO 6
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Leu Val Glu Ser Gly Gly Gly Val Val Pro Pro Gly Lys Ser Leu Arg
1               5                   10                  15

Leu Ser Cys Ala Ala Ser Gly Phe Thr Phe Ser Leu Tyr Gly Ile His
            20                  25                  30

Trp Val Arg Gln Ala Pro Gly Lys Gly Leu Glu Trp Val Ala Val Ile
        35                  40                  45
```

```
Ser Tyr Asp Gly Asn Thr Lys Tyr Tyr Thr Asp Ser Val Lys Gly Arg
    50                  55                  60

Phe Thr Ile Ser Arg Asp Asn Ala Lys Asn Thr Ile Tyr Leu Gln Met
 65                  70                  75                  80

Asn Ser Leu Arg Leu Asp Asp Thr Ala Val Tyr Tyr Cys Ala Lys Gly
                 85                  90                  95

Ala Ala Asn Ser Ala Thr Phe Asp Phe Trp Gly Arg Gly Thr Met Val
            100                 105                 110

Thr Val Ser Ser
        115

<210> SEQ ID NO 7
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Leu Val Glu Ser Gly Gly Gly Val Val Pro Pro Gly Lys Ser Leu Arg
 1               5                  10                  15

Leu Ser Cys Ala Ala Ser Gly Phe Thr Phe Ser Leu Tyr Gly Ile His
             20                  25                  30

Trp Val Arg Gln Ala Pro Gly Lys Gly Leu Glu Trp Val Ala Val Ile
         35                  40                  45

Ser Tyr Asp Gly Asn Thr Lys Tyr Tyr Thr Asp Ser Val Lys Gly Arg
    50                  55                  60

Phe Thr Ile Ser Arg Asp Asn Ala Lys Asn Thr Ile Tyr Leu Gln Met
 65                  70                  75                  80

Asn Ser Leu Arg Leu Asp Asp Thr Ala Val Tyr Tyr Cys Ala Lys Gly
                 85                  90                  95

Ala Ala Asn Ser Ala Thr Phe Asp Phe Trp Gly Arg Gly Thr Met Val
            100                 105                 110

Thr Val Ser Ser
        115

<210> SEQ ID NO 8
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Leu Val Glu Ser Gly Gly Gly Val Val Pro Pro Gly Lys Ser Leu Arg
 1               5                  10                  15

Leu Ser Cys Ala Ala Ser Gly Phe Thr Phe Ser Leu Tyr Gly Ile His
             20                  25                  30

Trp Val Arg Gln Ala Pro Gly Lys Gly Leu Glu Trp Val Ala Val Ile
         35                  40                  45

Ser Tyr Asp Gly Asn Thr Lys Tyr Tyr Thr Asp Ser Val Lys Gly Arg
    50                  55                  60

Phe Thr Ile Ser Arg Asp Asn Ala Lys Asn Thr Ile Tyr Leu Gln Met
 65                  70                  75                  80

Asn Ser Leu Arg Leu Asp Asp Thr Ala Val Tyr Tyr Cys Ala Lys Gly
                 85                  90                  95
```

```
Ala Ala Asn Ser Ala Thr Phe Asp Phe Trp Gly Arg Gly Thr Met Val
            100                 105                 110

Thr Val Ser Ser
        115

<210> SEQ ID NO 9
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Leu Val Glu Ser Gly Gly Gly Val Val Pro Pro Gly Lys Ser Leu Arg
1               5                   10                  15

Leu Ser Cys Ala Ala Ser Gly Phe Thr Phe Ser Leu Tyr Gly Ile His
            20                  25                  30

Trp Val Arg Gln Ala Pro Gly Lys Gly Leu Glu Trp Val Ala Val Ile
        35                  40                  45

Ser Tyr Asp Gly Asn Thr Lys Tyr Tyr Thr Asp Ser Val Lys Gly Arg
    50                  55                  60

Phe Thr Ile Ser Arg Asp Asn Ala Lys Asn Thr Ile Tyr Leu Gln Met
65                  70                  75                  80

Asn Ser Leu Arg Leu Asp Asp Thr Ala Val Tyr Tyr Cys Ala Lys Gly
                85                  90                  95

Ala Ala Asn Ser Ala Thr Phe Asp Phe Trp Gly Arg Gly Thr Met Val
            100                 105                 110

Thr Val Ser Ser
        115

<210> SEQ ID NO 10
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Leu Val Glu Ser Gly Gly Gly Val Val Gln Pro Gly Lys Ser Leu Arg
1               5                   10                  15

Leu Ser Cys Val Ala Ser Gly Phe Ser Phe Ser Thr Tyr Gly Met His
            20                  25                  30

Trp Val Arg Gln Ala Pro Gly Lys Gly Leu Glu Trp Val Ala Val Met
        35                  40                  45

Ser Phe Asp Gly Lys Thr Lys Tyr Tyr Ala Asp Ser Val Lys Gly Arg
    50                  55                  60

Phe Thr Ile Ser Arg Asp Asn Pro Lys Asn Thr Leu Tyr Leu Gln Met
65                  70                  75                  80

Asn Ser Leu Arg Ser Glu Asp Thr Ala Val Tyr Tyr Cys Ala Lys Gly
                85                  90                  95

Gly Ala Ala Ala Ala Val Phe Asp Ser Trp Gly Pro Gly Ile Leu Leu
            100                 105                 110

Thr Val Ser Ser
        115

<210> SEQ ID NO 11
<211> LENGTH: 116
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Leu Val Glu Ser Gly Gly Gly Val Val Gln Pro Gly Lys Ser Leu Arg
1               5                   10                  15

Leu Ser Cys Val Ala Ser Gly Phe Ser Phe Ser Thr Tyr Gly Met His
            20                  25                  30

Trp Val Arg Gln Ala Pro Gly Lys Gly Leu Glu Trp Val Ala Val Met
        35                  40                  45

Ser Phe Asp Gly Lys Thr Lys Tyr Tyr Ala Asp Ser Val Lys Gly Arg
50                  55                  60

Phe Thr Ile Ser Arg Asp Asn Pro Lys Asn Thr Leu Tyr Leu Gln Met
65                  70                  75                  80

Asn Ser Leu Arg Ser Glu Asp Thr Ala Val Tyr Tyr Cys Ala Lys Gly
                85                  90                  95

Gly Ala Ala Ala Val Phe Asp Ser Trp Gly Pro Gly Ile Leu Leu
            100                 105                 110

Thr Val Ser Ser
        115

<210> SEQ ID NO 12
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Leu Val Glu Ser Gly Gly Gly Val Val Gln Pro Gly Arg Ser Leu Arg
1               5                   10                  15

Leu Ser Cys Ala Ala Ser Gly Val Thr Phe Ser Arg Tyr Gly Met His
            20                  25                  30

Trp Val Arg Gln Ala Pro Gly Lys Gly Leu Glu Trp Val Ala Val Ile
        35                  40                  45

Ser Tyr Asp Glu Lys Thr Lys Tyr Tyr Ala Asp Ser Val Lys Gly Arg
50                  55                  60

Phe Thr Ile Ser Arg Asp Asn Ser Lys Asn Thr Leu Phe Leu His Met
65                  70                  75                  80

Asn Arg Leu Arg Tyr Glu Asp Thr Ala Val Tyr Tyr Cys Ala Lys Gly
                85                  90                  95

Ala Ser Ser Gly Ala Tyr Phe Asp Tyr Trp Gly Gln Gly Thr Leu Val
            100                 105                 110

Thr Val Ser Ser
        115

<210> SEQ ID NO 13
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Leu Val Glu Ser Gly Gly Gly Val Val Gln Pro Gly Lys Ser Leu Arg

```
                1               5                  10                 15
Leu Ser Cys Val Ala Ser Gly Phe Thr Phe Ser Thr Tyr Gly Met His
                20                 25                 30

Trp Val Arg Gln Ala Pro Gly Lys Gly Leu Glu Trp Val Ala Val Met
                35                 40                 45

Ser Phe Asp Gly Lys Thr Lys Tyr Tyr Ala Asp Ser Val Lys Gly Arg
                50                 55                 60

Phe Thr Ile Ser Arg Asp Asn Pro Lys Asn Thr Leu Tyr Leu Gln Met
65                  70                 75                 80

Asn Ser Leu Arg Ser Glu Asp Thr Ala Val Tyr Tyr Cys Ala Lys Gly
                85                 90                 95

Gly Ala Ala Ala Val Phe Asp Ser Trp Gly Gln Gly Ile Leu Leu
                100                105                110

Thr Val Ser Ser
        115

<210> SEQ ID NO 14
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Leu Val Glu Ser Gly Gly Gly Val Val Gln Pro Gly Lys Ser Leu Arg
1               5                  10                 15

Leu Ser Cys Val Ala Ser Gly Phe Thr Phe Ser Ser Tyr Gly Met His
                20                 25                 30

Trp Val Arg Gln Ala Pro Gly Lys Gly Leu Glu Trp Val Ala Val Met
                35                 40                 45

Ser Phe Asp Gly Lys Thr Lys Tyr Tyr Ala Asp Ser Val Lys Gly Arg
                50                 55                 60

Phe Thr Ile Ser Arg Asp Asn Pro Lys Asn Thr Leu Tyr Leu Gln Met
65                  70                 75                 80

Asn Ser Leu Arg Ser Glu Asp Thr Ala Val Tyr Tyr Cys Ala Lys Gly
                85                 90                 95

Gly Ala Ala Ala Val Phe Asp Ser Trp Gly Gln Gly Ile Leu Leu
                100                105                110

Thr Val Ser Ser
        115

<210> SEQ ID NO 15
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Leu Val Glu Ser Gly Gly Gly Val Val Gln Pro Gly Lys Ser Leu Arg
1               5                  10                 15

Leu Ser Cys Val Ala Ser Gly Phe Thr Phe Ser Ser Tyr Gly Met His
                20                 25                 30

Trp Val Arg Gln Ala Pro Gly Lys Gly Leu Glu Trp Val Ala Val Met
                35                 40                 45

Ser Phe Asp Gly Lys Thr Lys Tyr Tyr Ala Asp Ser Val Lys Gly Arg
```

```
                 50                  55                  60
Phe Thr Ile Ser Arg Asp Asn Pro Lys Asn Thr Leu Tyr Leu Gln Met
 65                  70                  75                  80

Asn Ser Leu Arg Ser Glu Asp Thr Ala Val Tyr Tyr Cys Ala Lys Gly
                 85                  90                  95

Gly Ala Ala Ala Ala Val Phe Asp Ser Trp Gly Gln Gly Ile Leu Leu
                100                 105                 110

Thr Val Ser Ser
        115

<210> SEQ ID NO 16
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Leu Val Glu Ser Gly Gly Gly Val Val Gln Pro Gly Arg Ser Leu Arg
  1               5                  10                  15

Leu Ser Cys Ala Ala Ser Gly Phe Thr Phe Ser Arg Tyr Gly Met His
                 20                  25                  30

Trp Val Arg Gln Ala Pro Gly Lys Gly Leu Glu Trp Val Ala Val Met
             35                  40                  45

Ser Tyr Asp Gly Ser Thr Lys Tyr Tyr Ala Asp Ser Val Lys Gly Arg
         50                  55                  60

Phe Ala Ile Ser Arg Asp Asn Pro Lys Asn Thr Leu Phe Leu Gln Met
 65                  70                  75                  80

Asn Ser Leu Arg Pro Asp Asp Thr Ala Val Tyr Tyr Cys Ala Lys Gly
                 85                  90                  95

Gly Ala Ala Ala Ala Val Met Asp Val Trp Gly Lys Gly Thr Thr Val
                100                 105                 110

Thr Val Ser Ser
        115

<210> SEQ ID NO 17
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Leu Val Glu Ser Gly Gly Gly Val Val Gln Pro Gly Arg Ser Leu Arg
  1               5                  10                  15

Leu Ser Cys Ala Ala Ser Gly Phe Thr Phe Ser Arg Tyr Gly Met His
                 20                  25                  30

Trp Val Arg Gln Ala Pro Gly Lys Gly Leu Glu Trp Val Ala Val Met
             35                  40                  45

Ser Tyr Asp Gly Ser Thr Lys Tyr Tyr Ala Asp Ser Val Lys Gly Arg
         50                  55                  60

Phe Ala Ile Ser Arg Asp Asn Pro Lys Asn Thr Leu Phe Leu Gln Met
 65                  70                  75                  80

Asn Ser Leu Arg Pro Asp Asp Thr Ala Val Tyr Tyr Cys Ala Lys Gly
                 85                  90                  95

Gly Ala Ala Ala Ala Val Met Asp Val Trp Gly Lys Gly Thr Thr Val
```

-continued

```
                100                 105                 110

Thr Val Ser Ser
        115

<210> SEQ ID NO 18
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Arg Phe
            20                  25                  30

Gly Met His Trp Val Arg Gln Arg Val Pro Gly Lys Gly Leu Glu
        35                  40                  45

Trp Val Ala Val Ile Ser Tyr Asp Asp Asn Thr Lys Tyr Tyr Ala Asp
    50                  55                  60

Ser Val Lys Gly Arg Phe Thr Ile Ser Arg Asp Asn Asn Lys Ser Thr
65                  70                  75                  80

Leu Tyr Leu Gln Met Ser Ser Leu Arg Val Glu Asp Thr Ala Val Tyr
                85                  90                  95

Phe Cys Ala Lys Gly Ser Thr Ala Ala Val Leu Asp Tyr Trp Gly
            100                 105                 110

Gln Gly Thr Leu Val Thr Val Ser Ser
        115                 120

<210> SEQ ID NO 19
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Leu Val Glu Ser Gly Gly Gly Leu Val Gln Pro Gly Gly Ser Leu Arg
1               5                   10                  15

Leu Ser Cys Ala Ala Ser Gly Phe Thr Phe Ser Ser Tyr Glu Met Asn
            20                  25                  30

Trp Val Arg Gln Ala Pro Gly Lys Gly Leu Glu Trp Val Ser Tyr Ile
        35                  40                  45

Ser Ser Ser Gly Ser Thr Ile Tyr Tyr Ala Asp Ser Val Lys Gly Arg
    50                  55                  60

Phe Thr Ile Ser Arg Asp Asn Ala Lys Asn Ser Leu Tyr Leu Gln Met
65                  70                  75                  80

Asn Ser Leu Arg Ala Glu Asp Thr Ala Val Tyr Tyr Cys Ala Arg Val
                85                  90                  95

Glu Gln Leu Ala Pro Ser Pro Tyr Met Asp Val Trp Gly Lys Gly Thr
            100                 105                 110

Thr Val Thr Val Ser Ser
        115

<210> SEQ ID NO 20
<211> LENGTH: 124
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Gly Leu Arg Gly Ala Tyr Tyr Tyr Tyr Gly Met Asp
            100                 105                 110

Val Trp Gly Gln Gly Thr Thr Val Thr Val Ser Ser
        115                 120

<210> SEQ ID NO 21
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Thr Gln Ser Pro Asp Ser Leu Thr Leu Ser Leu Gly Glu Arg Ala
1               5                   10                  15

Thr Ile Asn Cys Arg Ser Ser Arg Thr Val Leu Tyr Arg Ser Asn Asn
            20                  25                  30

Lys Asn Tyr Leu Ala Trp Tyr Gln His Lys Pro Gly Gln Pro Pro Lys
        35                  40                  45

Leu Leu Met Ser Trp Ala Ser Thr Arg Glu Thr Gly Val Pro Asp Arg
    50                  55                  60

Phe Ser Gly Ser Gly Ser Gly Thr His Phe Thr Leu Thr Ile Thr Ser
65                  70                  75                  80

Leu Gln Pro Glu Asp Val Ala Val Tyr Tyr Cys Gln Gln Tyr Tyr Ser
                85                  90                  95

Pro Pro Trp Thr Phe Gly Gln Gly Thr Lys Val Glu Ile Arg
            100                 105                 110

<210> SEQ ID NO 22
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Thr Gln Ser Pro Gly Ser Leu Ala Val Ser Leu Gly Ser Arg Ala
1               5                   10                  15

Thr Ile Asn Cys Lys Ser Ser Arg Ser Leu Leu Tyr Arg Ser Asn Asn
            20                  25                  30

Lys Asn Tyr Leu Ala Trp Tyr Gln Gln Lys Pro Gly Gln Ser Pro Arg
            35                  40                  45

Leu Leu Ile Tyr Trp Ala Ser Ser Arg Glu Ser Gly Val Pro Asp Arg
 50                  55                  60

Phe Ser Gly Gly Ser Gly Thr Ser Phe Thr Leu Thr Ile Ser Ser
65                  70                  75                  80

Leu Gln Ala Glu Asp Val Ala Val Tyr Tyr Cys Gln Gln Tyr Phe Asn
                85                  90                  95

Pro Pro Trp Thr Phe Gly Gln Gly Thr Lys Val Glu Ile Lys
            100                 105                 110

<210> SEQ ID NO 23
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Thr Gln Ser Pro Asp Ser Leu Thr Leu Ser Leu Gly Glu Arg Ala
1               5                   10                  15

Thr Ile Asn Cys Arg Ser Ser Arg Thr Val Leu Tyr Arg Ser Asn Asn
            20                  25                  30

Lys Asn Tyr Leu Ala Trp Tyr Gln His Lys Pro Gly Gln Pro Pro Lys
            35                  40                  45

Leu Leu Met Ser Trp Ala Ser Thr Arg Glu Thr Gly Val Pro Asp Arg
 50                  55                  60

Phe Ser Gly Ser Gly Ser Gly Thr His Phe Thr Leu Thr Ile Thr Ser
65                  70                  75                  80

Leu Gln Pro Glu Asp Val Ala Val Tyr Tyr Cys Gln Gln Tyr Tyr Ser
                85                  90                  95

Pro Pro Trp Thr Phe Gly Gln Gly Thr Lys Val Glu Ile Arg
            100                 105                 110

<210> SEQ ID NO 24
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Thr Gln Ser Pro Asp Ser Leu Thr Leu Ser Leu Gly Glu Arg Ala
1               5                   10                  15

Thr Ile Asn Cys Arg Ser Ser Arg Thr Val Leu Tyr Arg Ser Asn Asn
            20                  25                  30

Lys Asn Tyr Leu Ala Trp Tyr Gln His Lys Pro Gly Gln Pro Pro Lys
            35                  40                  45

Leu Leu Met Ser Trp Ala Ser Thr Arg Glu Thr Gly Val Pro Asp Arg
 50                  55                  60

Phe Ser Gly Ser Gly Ser Gly Thr His Phe Thr Leu Thr Ile Thr Ser
65                  70                  75                  80

Leu Gln Pro Glu Asp Val Ala Val Tyr Tyr Cys Gln Gln Tyr Tyr Ser
                85                  90                  95

Pro Pro Trp Thr Phe Gly Gln Gly Thr Lys Val Glu Ile Arg
            100                 105                 110

<210> SEQ ID NO 25
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Thr Gln Ser Pro Asp Ser Leu Thr Leu Ser Leu Gly Glu Arg Ala
1               5                   10                  15

Thr Ile Asn Cys Arg Ser Ser Arg Thr Val Leu Tyr Arg Ser Asn Asn
            20                  25                  30

Lys Asn Tyr Leu Ala Trp Tyr Gln His Lys Pro Gly Gln Pro Pro Lys
        35                  40                  45

Leu Leu Met Ser Trp Ala Ser Thr Arg Glu Thr Gly Val Pro Asp Arg
    50                  55                  60

Phe Ser Gly Ser Gly Ser Gly Thr His Phe Thr Leu Thr Ile Thr Ser
65                  70                  75                  80

Leu Gln Pro Glu Asp Val Ala Val Tyr Tyr Cys Gln Gln Tyr Tyr Ser
                85                  90                  95

Pro Pro Trp Thr Phe Gly Gln Gly Thr Lys Val Glu Ile Arg
            100                 105                 110

<210> SEQ ID NO 26
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Thr Gln Ser Pro Asp Ser Leu Thr Leu Ser Leu Gly Glu Arg Ala
1               5                   10                  15

Thr Ile Asn Cys Arg Ser Ser Arg Thr Val Leu Tyr Arg Ser Asn Asn
            20                  25                  30

Lys Asn Tyr Leu Ala Trp Tyr Gln His Lys Pro Gly Gln Pro Pro Lys
        35                  40                  45

Leu Leu Met Ser Trp Ala Ser Thr Arg Glu Thr Gly Val Pro Asp Arg
    50                  55                  60

Phe Ser Gly Ser Gly Ser Gly Thr His Phe Thr Leu Thr Ile Thr Ser
65                  70                  75                  80

Leu Gln Pro Glu Asp Val Ala Val Tyr Tyr Cys Gln Gln Tyr Tyr Ser
                85                  90                  95

Pro Pro Trp Thr Phe Gly Gln Gly Thr Lys Val Glu Ile Arg
            100                 105                 110

<210> SEQ ID NO 27
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Thr Gln Ser Pro Asn Ser Leu Ala Val Ser Leu Gly Gly Arg Ala
1               5                   10                  15

```
Thr Ile Asn Cys Lys Ala Ser Gln Ser Ile Leu Tyr Arg Ser Asn Asn
             20                  25                  30

Lys Asn Tyr Leu Ala Trp Tyr Gln His Lys Ala Gly Gln Pro Pro Lys
         35                  40                  45

Leu Leu Ile Tyr Trp Ala Ser Thr Arg Glu Ser Gly Val Pro Glu Arg
     50                  55                  60

Phe Ser Gly Ser Gly Ser Arg Thr Asp Phe Thr Leu Thr Ile Asn Gly
 65                  70                  75                  80

Leu Gln Ala Glu Asp Val Ala Val Tyr Tyr Cys Gln Gln Tyr Tyr Asn
                 85                  90                  95

Pro Pro Trp Thr Phe Gly Gln Gly Thr Lys Val Glu Ile Lys
            100                 105                 110

<210> SEQ ID NO 28
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Thr Gln Ser Pro Asn Ser Leu Ala Val Ser Leu Gly Gly Arg Ala
 1               5                  10                  15

Thr Ile Asn Cys Lys Ala Ser Gln Ser Ile Leu Tyr Arg Ser Asn Asn
             20                  25                  30

Lys Asn Tyr Leu Ala Trp Tyr Gln His Lys Ala Gly Gln Pro Pro Lys
         35                  40                  45

Leu Leu Ile Tyr Trp Ala Ser Thr Arg Glu Ser Gly Val Pro Glu Arg
     50                  55                  60

Phe Ser Gly Ser Gly Ser Arg Thr Asp Phe Thr Leu Thr Ile Asn Gly
 65                  70                  75                  80

Leu Gln Ala Glu Asp Val Ala Val Tyr Tyr Cys Gln Gln Tyr Tyr Asn
                 85                  90                  95

Pro Pro Trp Thr Phe Gly Gln Gly Thr Lys Val Glu Ile Lys
            100                 105                 110

<210> SEQ ID NO 29
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Thr Gln Ser Pro Asp Ser Leu Ala Val Ser Leu Gly Glu Arg Ala
 1               5                  10                  15

Thr Ile Lys Cys Lys Ser Ser Gln Ser Val Leu Tyr Ser Ser Asn Asn
             20                  25                  30

Lys Asn Tyr Leu Ala Trp Tyr Gln His Lys Pro Gly Gln Pro Pro Lys
         35                  40                  45

Val Leu Val Tyr Trp Ala Ser Thr Arg Glu Ser Gly Val Pro Asp Arg
     50                  55                  60

Phe Ser Gly Ser Gly Ser Gly Thr Asp Phe Thr Leu Thr Ile Ser Ser
 65                  70                  75                  80

Leu Gln Ala Glu Asp Val Ala Val Tyr Tyr Cys Gln Gln Tyr Tyr Asn
                 85                  90                  95
```

-continued

Pro Pro Trp Thr Phe Gly Gln Gly Thr Lys Val Ala Ile Lys
            100                 105                 110

<210> SEQ ID NO 30
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Thr Gln Ser Pro Asn Ser Leu Ala Val Ser Leu Gly Gly Arg Ala
1               5                   10                  15

Thr Ile Asn Cys Lys Thr Ser Gln Ser Ile Leu Tyr Arg Ser Asn Asn
            20                  25                  30

Lys Asn Tyr Leu Ala Trp Tyr Gln His Lys Pro Gly Gln Pro Pro Lys
        35                  40                  45

Leu Leu Ile Tyr Trp Ala Ser Thr Arg Glu Ser Arg Val Pro Asp Arg
    50                  55                  60

Phe Ser Gly Ser Gly Ser Arg Thr Asp Phe Thr Leu Thr Ile Ser Gly
65                  70                  75                  80

Leu Gln Ala Glu Asp Val Ala Val Tyr Tyr Cys Gln Gln Tyr Tyr Asn
                85                  90                  95

Pro Pro Trp Thr Phe Gly Gln Gly Thr Lys Val Glu Ile Lys
            100                 105                 110

<210> SEQ ID NO 31
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Thr Gln Ser Pro Asn Ser Leu Ala Val Ser Leu Gly Gly Arg Ala
1               5                   10                  15

Thr Ile Asn Cys Lys Thr Ser Gln Ser Ile Leu Tyr Arg Ser Asn Asn
            20                  25                  30

Lys Asn Tyr Leu Ala Trp Tyr Gln His Lys Ser Gly Gln Pro Pro Lys
        35                  40                  45

Leu Leu Ile Tyr Trp Ala Ser Thr Arg Glu Ser Gly Val Pro Asp Arg
    50                  55                  60

Phe Ser Gly Ser Gly Ser Arg Thr Asp Phe Thr Leu Thr Ile Ser Gly
65                  70                  75                  80

Leu Gln Ala Glu Asp Val Ala Val Tyr Tyr Cys Gln Gln Tyr Tyr Asn
                85                  90                  95

Pro Pro Trp Thr Phe Gly Gln Gly Thr Lys Val Glu Ile Lys
            100                 105                 110

<210> SEQ ID NO 32
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Thr Gln Ser Pro Asn Ser Leu Ala Val Ser Leu Gly Gly Arg Ala

```
                1               5                   10                  15
Thr Ile Asn Cys Lys Thr Ser Gln Ser Ile Leu Tyr Arg Ser Asn Asn
                20                  25                  30

Lys Asn Tyr Leu Ala Trp Tyr Gln His Lys Ser Gly Gln Pro Pro Lys
            35                  40                  45

Leu Leu Ile Tyr Trp Ala Ser Thr Arg Glu Ser Gly Val Pro Asp Arg
        50                  55                  60

Phe Ser Gly Ser Gly Ser Arg Thr Asp Phe Thr Leu Thr Ile Ser Gly
65                  70                  75                  80

Leu Gln Ala Glu Asp Val Ala Val Tyr Tyr Cys Gln Gln Tyr Tyr Asn
                85                  90                  95

Pro Pro Trp Thr Phe Gly Gln Gly Thr Lys Val Glu Ile Lys
            100                 105                 110

<210> SEQ ID NO 33
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Thr Gln Ser Pro Asp Ser Leu Thr Val Ser Leu Gly Glu Arg Ala
1               5                   10                  15

Thr Ile Ser Cys Lys Ser Ser Gln Arg Leu Leu Tyr Ser Ser Asn Asn
                20                  25                  30

Lys Asn Tyr Leu Ala Trp Tyr Gln Gln Lys Pro Gly Gln Pro Pro Lys
            35                  40                  45

Leu Leu Met Tyr Trp Ala Ser Thr Arg Glu Ser Gly Val Pro Asp Arg
        50                  55                  60

Phe Ser Gly Ser Gly Ser Gly Thr Asp Phe Ser Leu Thr Ile Ser Ser
65                  70                  75                  80

Leu Gln Ala Glu Asp Val Ala Val Tyr Tyr Cys Gln Gln Tyr Tyr Asn
                85                  90                  95

Pro Pro Trp Thr Phe Gly Gln Gly Thr Lys Val Glu Val Lys
            100                 105                 110

<210> SEQ ID NO 34
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Thr Gln Ser Pro Asp Ser Leu Thr Val Ser Leu Gly Glu Arg Ala
1               5                   10                  15

Thr Ile Ser Cys Lys Ser Ser Gln Arg Leu Leu Tyr Ser Ser Asn Asn
                20                  25                  30

Lys Asn Tyr Leu Ala Trp Tyr Gln Gln Lys Pro Gly Gln Pro Pro Lys
            35                  40                  45

Leu Leu Met Tyr Trp Ala Ser Thr Arg Glu Ser Gly Val Pro Asp Arg
        50                  55                  60

Phe Ser Gly Ser Gly Ser Gly Thr Asp Phe Ser Leu Thr Ile Ser Ser
65                  70                  75                  80

Leu Gln Ala Glu Asp Val Ala Val Tyr Tyr Cys Gln Gln Tyr Tyr Asn
```

```
                    85                  90                  95

Pro Pro Trp Thr Phe Gly Gln Gly Thr Lys Val Glu Val Lys
                100                 105                 110

<210> SEQ ID NO 35
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Ile Val Met Thr Gln Ser Pro Asp Ser Leu Thr Leu Ser Leu Gly
1               5                   10                  15

Glu Arg Ala Thr Ile Asn Cys Lys Ser Ser Gln Ser Leu Phe Tyr Arg
            20                  25                  30

Ser Asn Asn Lys Ser Tyr Leu Ala Trp Tyr Gln Gln Lys Pro Gly Gln
        35                  40                  45

Pro Pro Lys Leu Leu Ile Tyr Trp Ala Ser Val Arg Glu Ser Gly Val
    50                  55                  60

Pro Asp Arg Phe Thr Gly Ser Gly Ser Val Thr Asp Phe Thr Leu Thr
65                  70                  75                  80

Ile Ser Ser Leu Arg Ala Glu Asp Val Ala Val Tyr Tyr Cys Gln Gln
                85                  90                  95

Tyr Phe Thr Thr Pro Leu Thr Phe Gly Gly Gly Thr Lys Val Ala Ile
                100                 105                 110

Lys

<210> SEQ ID NO 36
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Thr Gln Ser Leu Asp Ser Leu Thr Val Ser Leu Gly Glu Arg Ala
1               5                   10                  15

Thr Ile Asn Cys Lys Ser Ser Gln Ser Leu Leu Tyr Thr Ser Asn Asn
            20                  25                  30

Lys Asn Tyr Leu Ala Trp Tyr Gln Gln Lys Ser Gly Gln Pro Pro Lys
        35                  40                  45

Leu Leu Ile Tyr Trp Ala Ser Ile Arg Asp Ser Gly Val Pro Asp Arg
    50                  55                  60

Phe Ser Gly Ser Gly Ser Ala Thr Asp Phe Thr Leu Thr Ile Asn Asn
65                  70                  75                  80

Leu Gln Ala Glu Asp Val Ala Val Tyr Phe Cys Gln Gln Tyr Tyr Lys
                85                  90                  95

Thr Pro Leu Thr Phe Gly Gly Gly Thr Lys Val Glu Val Arg
                100                 105                 110

<210> SEQ ID NO 37
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (4)..(4)
<223> OTHER INFORMATION: Any amino acid

<400> SEQUENCE: 37

Asp Ile Gln Xaa Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Trp
                85                  90                  95

Thr Phe Gly Gln Gly Thr Lys Val Glu Ile Lys
            100                 105

<210> SEQ ID NO 38
<211> LENGTH: 368
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
gaggtgcagc tggtggagtc tgggggaggc gtggtccagc ctgggaggtc cctgagactc    60
tcctgcgcag cctctggact caccttcagt ttctataatt tccactgggt ccgccagact   120
ccaggcaagg ggctggagtg gtggcaggc atctcatacg atgcaaccag gacgaactac    180
gcaggctcgt cacgggccga ttcaccattt ccagagacaa ttccaagaaa atgctgtatc   240
tgcaaatgag cagcctggga cctcaagaca cggctgtata tcattgtgcg agagatcgtt   300
ctgacgggca actgcataaa gtggcttttg actcctgggg ccaggagcc ctggtcaccg    360 tctcatca                                                           368

<210> SEQ ID NO 39
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
gaggtgcagc tggtggagtc tgggggaggc gtggtccggc ctgggcggtc cctgagactc    60
tcctgtgttg cctctggttt caccttcaat gcttatggca tgcattgggt ccgccagggt   120
ccaggcaagg gccttgagtg gctggcggtc atttcatatg aaggaaagac tgtttattat   180
gcagattccg ttaaggaccg tttcaccatc tccagagaca attccaggaa cacggtgtct   240
ctacatctga caacctgag aggtgaggac acggctgtct attactgtgc gaaggggtcg    300
gcttcagcag cagtcctcca acactggggt cagggcaccc tggtcagcgt cacgtca     357

<210> SEQ ID NO 40
<211> LENGTH: 357
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
gaggtgcagc tggtggagtc tgggggaggc gtggtcccgc ctgggaagtc cctgagactc      60
tcctgtgcag cctctggatt caccttcagt ctctatggca tacactgggt ccgccaggct     120
cccggcaagg gactggagtg ggtggcagtt atctcatatg atggaaatac taaatactat     180
acagactctg taaagggtcg attcaccatc tccagagaca atgccaagaa cacaatttat     240
ctgcaaatga acagtctaag acttgacgac acggctgttt attactgtgc gaaaggagcg     300
gcgaatagcg ctacttttga tttctggggc cgagggacaa tggtcaccgt ctcttca        357

<210> SEQ ID NO 41
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
gaggtgcagc tggtggagtc tgggggaggc gtggtcccgc ctgggaagtc cctgagactc      60
tcctgtgcag cctctggatt caccttcagt ctctatggca tacactgggt ccgccaggct     120
cccggcaagg gactggagtg ggtggcagtt atctcatatg atggaaatac taaatactat     180
acagactctg taaagggtcg attcaccatc tccagagaca atgccaagaa cacaatttat     240
ctgcaaatga acagtctaag acttgacgac acggctgttt attactgtgc gaaaggagcg     300
gcgaatagcg ctacttttga tttctggggc cgagggacaa tggtcaccgt ctcttca        357

<210> SEQ ID NO 42
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
gaggtgcagc tggtggagtc tgggggaggc gtggtcccgc ctgggaagtc cctgagactc      60
tcctgtgcag cctctggatt caccttcagt ctctatggca tacactgggt ccgccaggct     120
cccggcaagg gactggagtg ggtggcagtt atctcatatg atggaaatac taaatactat     180
acagactctg taaagggtcg attcaccatc tccagagaca atgccaagaa cacaatttat     240
ctgcaaatga acagtctaag acttgacgac acggctgttt attactgtgc gaaaggagcg     300
gcgaatagcg ctacttttga tttctggggc cgagggacaa tggtcaccgt ctcttca        357

<210> SEQ ID NO 43
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
gaggtgcagc tggtggagtc tgggggaggc gtggtcccgc ctgggaagtc cctgagactc      60
```

```
tcctgtgcag cctctggatt caccttcagt ctctatggca tacactgggt ccgccaggct    120
cccggcaagg gactggagtg ggtggcagtt atctcatatg atggaaatac taaatactat   180
acagactctg taaagggtcg attcaccatc tccagagaca atgccaagaa cacaatttat   240
ctgcaaatga acagtctaag acttgacgac acggctgttt attactgtgc gaaaggagcg   300
gcgaatagcg ctacttttga tttctggggc cgagggacaa tggtcaccgt ctcttca      357
```

<210> SEQ ID NO 44
<211> LENGTH: 246
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 44

```
gaggtgcagc tggtggagtc tgggggaggc gtggtccagc ctggaaagtc tctgagactc   60
tcctgtgtag cctctggatt cagcttcagt acttatggca tgcactgggt ccgccaggct   120
ccaggcaagg ggctggagtg ggtggcggtt atgtcatttg atggaaagac taaatactat   180
gcagactccg tgaagggccg attcaccatc tccagagaca atcccaagaa cacactatat   240
ctgcaa                                                              246
```

<210> SEQ ID NO 45
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 45

```
gaggtgcagc tggtggagtc tgggggaggc gtggtccagc ctggaaagtc tctgagactc   60
tcctgtgtag cctctggatt cagcttcagt acttatggca tgcactgggt ccgccaggct   120
ccaggcaagg ggctggagtg ggtggcggtt atgtcatttg atggaaagac taaatactat   180
gcagactccg tgaagggccg attcaccatc tccagagaca atcccaagaa cacactatat   240
ctgcaaatga acagcctgag aagcgaagac acggctgtgt attattgtgc gaaggggggt   300
gcagcagcgg ccgtctttga ctcctggggc cgggaatac tgctcaccgt ctcctca      357
```

<210> SEQ ID NO 46
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 46

```
gaggtgcagc tggtggagtc tgggggaggc gtggtccagc ctgggaggtc cctaagactc   60
tcctgtgcag cctctggagt caccttcagt agatatggca tgcactgggt ccgccaggct   120
ccaggcaagg ggctggagtg ggtggcagtt atatcatatg atgaaaagac taaatactat   180
gcagactccg tgaagggccg attcaccatc tccagagaca attccaagaa cacactgttt   240
ctgcacatga acagactgag atatgaggac acggctgtat attattgtgc gaaggggggcc   300 agtagcggtg cgtactttga ctactggggc cagggtaccc tggtcaccgt ctcctca     357
```

<210> SEQ ID NO 47

<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 47

```
gaggtgcagc tggtggagtc tgggggaggc gtggtccagc ctggaaagtc tctgagactc      60
tcctgtgtag cctctggatt caccttcagt acttatggca tgcactgggt ccgccaggct     120
ccaggcaagg ggctggagtg ggtggcagtt atgtcatttg atggaaagac taaatactat     180
gcagactccg tgaagggccg attcaccatc tccagagaca atcccaagaa cacactatat     240
ctgcaaatga acagcctgag aagcgaagac acggctgtgt attattgtgc gaaggggggt     300
gcagcagcgg ccgtctttga ctcctggggc cagggaatac tgctcaccgt ctcctca        357
```

<210> SEQ ID NO 48
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 48

```
gaggtgcagc tggtggagtc tgggggaggc gtggtccagc ctggaaagtc tctgagactc      60
tcctgtgtag cctctggatt caccttcagt agttatggca tgcactgggt ccgccaggct     120
ccgggcaagg ggctggagtg ggtggcggtt atgtcatttg atggaaagac taaatactat     180
gcagactccg tgaagggccg attcaccatc tccagagaca accccaagaa cacactatat     240
ctgcaaatga acagcctgag aagcgaagac acggctgtct attattgtgc gaaggggggt     300
gcagcagcgg ccgtctttga ctcctggggc cagggaatac tgctcaccgt ctcctca        357
```

<210> SEQ ID NO 49
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 49

```
gaggtgcagc tggtggagtc tgggggaggc gtggtccagc ctggaaagtc tctgagactc      60
tcctgtgtag cctctggatt caccttcagt agttatggca tgcactgggt ccgccaggct     120
ccgggcaagg ggctggagtg ggtggcggtt atgtcatttg atggaaagac taaatactat     180
gcagactccg tgaagggccg attcaccatc tccagagaca accccaagaa cacactatat     240
ctgcaaatga acagcctgag aagcgaagac acggctgtct attattgtgc gaaggggggt     300
gcagcagcgg ccgtctttga ctcctggggc cagggaatac tgctcaccgt ctcctca        357
```

<210> SEQ ID NO 50
<211> LENGTH: 356
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 50

```
gaggtgcagc tggtggagtc tgggggaggc gtggtccagc ctgggaggtc cctgagactc      60
```

```
tcctgtgcag cctctggatt caccttcagt agatatggca tgcactgggt ccgccaggct    120
ccaggcaagg ggctggagtg ggtggcagtt atgtcatatg atggaagtac taaatactat    180
gcagactccg tgaagggccg cttcgccatc tccagagaca atcccaagaa cacgctattt    240
ctgcaaatga acagcctgag acctgacgac acggctgtat attactgtgc gaaaggggg     300 gcggcacagc tgtcatggac gtctgggca aagggaccac ggtcaccgtc tcctca         356

<210> SEQ ID NO 51
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
gaggtgcagc tggtggagtc tgggggaggc gtggtccagc ctgggaggtc cctgagactc    60
tcctgtgcag cctctggatt caccttcagt agatatggca tgcactgggt ccgccaggct    120
ccaggcaagg ggctggagtg ggtggcagtt atgtcatatg atggaagtac taaatactat    180
gcagactccg tgaagggccg cttcgccatc tccagagaca atcccaagaa cacgctattt    240
ctgcaaatga acagcctgag acctgacgac acggctgtat attactgtgc gaaaggggg     300 gcggcagcag ctgtcatgga cgtctgggc aaagggacca cggtcaccgt ctcctca        357

<210> SEQ ID NO 52
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
gaggtgcagc tggtggagtc tgggggaggc gtggtccagc ctgggaggtc cctgagactc    60
tcctgtgcag cctctggatt caccttcaat aggtttggca tgcactgggt ccgccagcgc    120
caggttccag gcaaggggct ggagtgggtg gcagttatct catatgacga acacactaaa    180
tattatgcgg actccgtgaa gggccgtttc accatctcca gagacaataa caagagcact    240
ctctatctgc aaatgagcag cctgagagtt gaggacacgg ctgtctattt ctgtgcgaag    300
gggtcgacag cggcagctgt tcttgactac tggggccagg gaacccttgt caccgtctcc    360
tca                                                                 363

<210> SEQ ID NO 53
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
gaggtgcagc tggtggagtc tgggggaggc ttggtacagc ctggagggtc cctgagactc    60
tcctgtgcag cctctggatt caccttcagt agttatgaaa tgaactgggt ccgccaggct    120
ccagggaagg ggctggagtg ggtttcatac attagtagta gtggtagtac catatactac    180
gcagactctg tgaagggccg attcaccatc tccagagaca acgccaagaa ctcactgtat    240
ctgcaaatga acagcctgag agccgaggac acggctgttt attactgtgc gagagtagag    300
```

```
cagctcgccc cctcccccta catggacgtc tggggcaaag ggaccacggt caccgtctcc    360
tca                                                                  363

<210> SEQ ID NO 54
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
caggtgcagc tggtgcagtc tggggcagag gtgaaaaagc ccggggagtc tctgaagatc     60
tcctgtaagg gttctggata cagctttacc agctactgga tcggctgggt gcgccagatg    120
cccgggaaag gcctggagtg gatggggatc atctatcctg gtgactctga taccagatac    180
agcccgtcct tccaaggcca ggtcaccatc tcagccgaca gtccatcag caccgcctac     240 ctgcagtgga gcagcctgaa ggcctcggac accgccatgt attactgtgc gagacggggt    300
cttcgagggg cctactacta ctactacggt atggacgtct ggggccaagg gaccacggtc    360
accgtctcct ca                                                        372

<210> SEQ ID NO 55
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
gacatcgtga tgacccagtc tccagactcc ctgactctgt ctctgggcga gagggccacc     60
atcaactgca gatccagccg gactgtttta tacaggtcca acaataaaaa ttacttagct    120
tggtatcaac ataaaccagg acagcctcct aagttgctca tgtcctgggc atctacccgg    180
gaaaccgggg tccctgaccg attcagtggc agcggttctg ggacacattt cactctcacc    240
atcaccagcc tgcagcctga agatgtggca gtttattact gtcaacagta ttatagtcct    300
ccgtggacgt tcggccaagg gaccaaggtg gaaatcaga                           339

<210> SEQ ID NO 56
<211> LENGTH: 246
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
gacatcgtga tgacccagtc tccaggctcc ctggctgtgt ctctgggctc gagggccacc     60
atcaactgca gtccagccg gagtctttta caggtcca acaataagaa ttatttagct       120
tggtatcaac agaaaccagg acagtctcct cggcttctca tttattgggc atcttcccgg    180
gaatccgggg tccctgaccg attcagtggc ggcgggtctg ggacaagttt cactctcacc    240
atcagc                                                               246

<210> SEQ ID NO 57
<211> LENGTH: 339
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 57
gacatcgtga tgacccagtc tccagactcc ctgactctgt ctctgggcga gagggccacc    60
atcaactgca gatccagccg gactgtttta tacaggtcca acaataaaaa ttacttagct   120
tggtatcaac ataaaccagg acagcctcct aagttgctca tgtcctgggc atctacccgg   180
gaaaccgggg tccctgaccg attcagtggc agcggttctg ggacacattt cactctcacc   240
atcaccagcc tgcagcctga agatgtggca gtttattact gtcaacagta ttatagtcct   300
ccgtggacgt tcggccaagg gaccaaggtg gaaatcaga                          339

<210> SEQ ID NO 58
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
gacatcgtga tgacccagtc tccagactcc ctgactctgt ctctgggcga gagggccacc    60
atcaactgca gatccagccg gactgtttta tacaggtcca acaataaaaa ttacttagct   120
tggtatcaac ataaaccagg acagcctcct aagttgctca tgtcctgggc atctacccgg   180
gaaaccgggg tccctgaccg attcagtggc agcggttctg ggacacattt cactctcacc   240
atcaccagcc tgcagcctga agatgtggca gtttattact gtcaacagta ttatagtcct   300
ccgtggacgt tcggccaagg gaccaaggtg gaaatcaga                          339

<210> SEQ ID NO 59
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
gacatcgtga tgacccagtc tccagactcc ctgactctgt ctctgggcga gagggccacc    60
atcaactgca gatccagccg gactgtttta tacaggtcca acaataaaaa ttacttagct   120
tggtatcaac ataaaccagg acagcctcct aagttgctca tgtcctgggc atctacccgg   180
gaaaccgggg tccctgaccg attcagtggc agcggttctg ggacacattt cactctcacc   240
atcaccagcc tgcagcctga agatgtggca gtttattact gtcaacagta ttatagtcct   300
ccgtggacgt tcggccaagg gaccaaggtg gaaatcaga                          339

<210> SEQ ID NO 60
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
gacatcgtga tgacccagtc tccagactcc ctgactctgt ctctgggcga gagggccacc    60
atcaactgca gatccagccg gactgtttta tacaggtcca acaataaaaa ttacttagct   120
```

| | |
|---|---|
| tggtatcaac ataaaccagg acagcctcct aagttgctca tgtcctgggc atctacccgg | 180 |
| gaaaccgggg tccctgaccg attcagtggc agcggttctg ggacacattt cactctcacc | 240 |
| atcaccagcc tgcagcctga agatgtggca gtttattact gtcaacagta ttatagtcct | 300 |
| ccgtggacgt tcggccaagg gaccaaggtg gaaatcaga | 339 |

<210> SEQ ID NO 61
<211> LENGTH: 339
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 61

| | |
|---|---|
| gacatcgtga tgacccagtc tccaaactcc ctggctgtgt ctctgggcgg agggccacc | 60 |
| atcaactgca aggccagcca gagtatttta tacaggtcca acaataagaa ctatttagct | 120 |
| tggtaccaac ataaagcagg acagcctccc aagctgctca tttactgggc atctacccgg | 180 |
| gaatccgggg tccctgagcg attcagtggc agcgggtcta ggacagattt cactctcacc | 240 |
| atcaacggcc tgcaggctga agatgtggca gtttattact gtcagcaata ttataatcct | 300 |
| ccgtggacgt tcggccaagg gaccaaggtg gaaatcaaa | 339 |

<210> SEQ ID NO 62
<211> LENGTH: 339
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 62

| | |
|---|---|
| gacatcgtga tgacccagtc tccaaactcc ctggctgtgt ctctgggcgg agggccacc | 60 |
| atcaactgca aggccagcca gagtatttta tacaggtcca acaataagaa ctatttagct | 120 |
| tggtaccaac ataaagcagg acagcctccc aagctgctca tttactgggc atctacccgg | 180 |
| gaatccgggg tccctgagcg attcagtggc agcgggtcta ggacagattt cactctcacc | 240 |
| atcaacggcc tgcaggctga agatgtggca gtttattact gtcagcaata ttataatcct | 300 |
| ccgtggacgt tcggccaagg gaccaaggtg gaaatcaaa | 339 |

<210> SEQ ID NO 63
<211> LENGTH: 339
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 63

| | |
|---|---|
| gacatcgtga tgacccagtc tccagactcc ctggctgtgt ctctgggcga gagggccacc | 60 |
| atcaagtgca agtccagcca gagtgtcttg tacagctcca acaataagaa ctacttagct | 120 |
| tggtaccagc ataaaccagg acagcctcct aaggtactcg tttactgggc atccacccgg | 180 |
| gaatccgggg tccctgaccg attcagtggc agcgggtctg ggacagattt cactctcacc | 240 |
| atcagcagcc tgcaggctga agatgtggca gtttattact gtcaacaata ttataatcct | 300 |
| ccgtggacgt tcggccaagg gaccaaggta gcaatcaag | 339 |

<210> SEQ ID NO 64

```
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
gacatcgtga tgacccagtc tccaaactcc ctggctgtgt ctctgggcgg gagggccacc      60
atcaactgca agaccagcca gagtatttta tacaggtcca acaataagaa ctacttagct     120
tggtaccagc ataaaccagg acagcctccc aagctgctca tttactgggc atctacccgg     180
gaatccaggg tccctgaccg attcagtggc agcgggtcta ggacagattt cactctcacc     240
atcagcggcc tgcaggctga agatgtggca gtttattact gtcagcaata ttataatcct     300
ccgtggacgt tcggccaggg gaccaaggtg gaaatcaaa                            339

<210> SEQ ID NO 65
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
gacatcgtga tgacccagtc tccaaactcc ctggctgtgt ctctgggcgg gagggccacc      60
atcaactgca agaccagcca gagtatttta tacaggtcca acaataagaa ctacttagct     120
tggtaccagc ataaatcagg acagcctccc aagctgctca tttactgggc atctacccgg     180
gaatccgggg tccctgaccg attcagtggc agcgggtcta ggacagattt cactctcacc     240
atcagcggcc tgcaggctga agatgtggca gtttattact gtcagcaata ttataatcct     300
ccgtggacgt tcggccaagg gaccaaggtg gaaatcaaa                            339

<210> SEQ ID NO 66
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
gacatcgtga tgacccagtc tccaaactcc ctggctgtgt ctctgggcgg gagggccacc      60
atcaactgca agaccagcca gagtatttta tacaggtcca acaataagaa ctacttagct     120
tggtaccagc ataaatcagg acagcctccc aagctgctca tttactgggc atctacccgg     180
gaatccgggg tccctgaccg attcagtggc agcgggtcta ggacagattt cactctcacc     240
atcagcggcc tgcaggctga agatgtggca gtttattact gtcagcaata ttataatcct     300
ccgtggacgt tcggccaagg gaccaaggtg gaaatcaaa                            339

<210> SEQ ID NO 67
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
gacatcgtga tgacccagtc tccggactcc ctgactgtgt ctctgggcga gagggccacc      60
```

```
atcagctgca agtccagcca gcgtcttttg tatagttcca acaataagaa ctacttagct    120
tggtaccagc agaaacctgg acagcctcct aaactgctca tgtactgggc gtccacccgg    180
gaatccgggg tccctgaccg attcagtggc agcgggtctg ggacagattt ctctctcacc    240
atcagcagcc tgcaggctga agatgtggca gtttattact gtcagcaata ttataatcct    300
ccctggacgt tcggccaagg gaccaaggtg gaagtcaaa                           339
```

<210> SEQ ID NO 68
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68

```
gacatcgtga tgacccagtc tccggactcc ctgactgtgt ctctgggcga gagggccacc    60
atcagctgca agtccagcca gcgtcttttg tatagttcca acaataagaa ctacttagct    120
tggtaccagc agaaacctgg acagcctcct aaactgctca tgtactgggc gtccacccgg    180
gaatccgggg tccctgaccg attcagtggc agcgggtctg ggacagattt ctctctcacc    240
atcagcagcc tgcaggctga agatgtggca gtttattact gtcagcaata ttataatcct    300
ccctggacgt tcggccaagg gaccaaggtg gaagtcaaa                           339
```

<210> SEQ ID NO 69
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69

```
gacatcgtga tgacccagtc tccagattcc ctgactctgt ctctgggcga gagggccacc    60
atcaactgca agtccagcca gagtctgttt tacaggtcca acaataagag ctacttagct    120
tggtatcagc aaaaaccagg gcagcctcct aaactgctca tttactgggc ctctgtccgg    180
gaatccgggg tccctgaccg attcactggc agcgggtctg taacagattt cactctcacc    240
atcagcagcc tgcgggctga ggatgtggct gtttattatt gtcaacagta ttttactact    300
cctctcactt tcggcggggg gaccaaggtg gcgatcaaa                           339
```

<210> SEQ ID NO 70
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70

```
gacatcgtga tgacccagtc tctagactcc ctgactgtgt ctctgggcga gagggccacc    60
atcaactgca agtccagcca gagtctttta tacacctcca acaataagaa ttacttagct    120
tggtaccagc agaaatcagg acagcctcct aagttactca tttactgggc gtctattcgg    180
gattccgggg tccctgaccg attcagtggc agcgggtctg cgacagattt cactctcacc    240
atcaacaacc tgcaggctga agatgtggca gtttacttct gtcagcaata ttacaagact    300
cctctcactt tcggcggggg gaccaaggtg gaggtcaga                           339
```

-continued

```
<210> SEQ ID NO 71
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
gacatccagw tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataatagtt attcttggac gttcggccaa   300
gggaccaagg tggaaatcaa a                                             321

<210> SEQ ID NO 72
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Leu Val Glu Ser Gly Gly Gly Val Val Gln Pro Gly Arg Ser Leu Arg
1               5                   10                  15

Leu Ser Cys Ala Ala Ser Gly Leu Thr Phe Ser Phe Tyr Asn Phe His
                20                  25                  30

Trp Val Arg Gln Thr Pro Gly Lys Gly Leu Glu Trp Val Ala Gly Ile
            35                  40                  45

Ser Tyr Asp Ala Thr Arg Thr Asn Tyr Ala Gly Ser Val Thr Gly Arg
        50                  55                  60

Phe Thr Ile Ser Arg Asp Asn Ser Lys Lys Met Leu Tyr Leu Gln Met
65                  70                  75                  80

Ser Ser Leu Gly Pro Gln Asp Thr Ala Val Tyr His Cys Ala Arg Asp
                85                  90                  95

Arg Ser Asp Gly Gln Leu His Lys Val Ala Phe Asp Ser Trp Gly Gln
            100                 105                 110

Gly Ala Leu Val Thr Val Ser Ser
        115                 120

<210> SEQ ID NO 73
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Leu Val Glu Ser Gly Gly Gly Val Val Arg Pro Gly Arg Ser Leu Arg
1               5                   10                  15

Leu Ser Cys Val Ala Ser Gly Phe Thr Phe Asn Ala Tyr Gly Met His
                20                  25                  30

Trp Val Arg Gln Gly Pro Gly Lys Gly Leu Glu Trp Leu Ala Val Ile
            35                  40                  45
```

```
Ser Tyr Glu Gly Lys Thr Val Tyr Tyr Ala Asp Ser Val Lys Asp Arg
        50                  55                  60

Phe Thr Ile Ser Arg Asp Asn Ser Arg Asn Thr Val Ser Leu His Leu
65                  70                  75                  80

Asn Asn Leu Arg Gly Glu Asp Thr Ala Val Tyr Tyr Cys Ala Lys Gly
                85                  90                  95

Ser Ala Ser Ala Ala Val Leu Gln His Trp Gly Gln Gly Thr Leu Val
            100                 105                 110

Ser Val Thr Ser
        115

<210> SEQ ID NO 74
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Leu Val Glu Ser Gly Gly Gly Val Val Pro Gly Lys Ser Leu Arg
1               5                   10                  15

Leu Ser Cys Ala Ala Ser Gly Phe Thr Phe Ser Leu Tyr Gly Ile His
                20                  25                  30

Trp Val Arg Gln Ala Pro Gly Lys Gly Leu Glu Trp Val Ala Val Ile
            35                  40                  45

Ser Tyr Asp Gly Asn Thr Lys Tyr Tyr Thr Asp Ser Val Lys Gly Arg
        50                  55                  60

Phe Thr Ile Ser Arg Asp Asn Ala Lys Asn Thr Ile Tyr Leu Gln Met
65                  70                  75                  80

Asn Ser Leu Arg Leu Asp Asp Thr Ala Val Tyr Tyr Cys Ala Lys Gly
                85                  90                  95

Ala Ala Asn Ser Ala Thr Phe Asp Phe Trp Gly Arg Gly Thr Met Val
            100                 105                 110

Thr Val Ser Ser
        115

<210> SEQ ID NO 75
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Leu Val Glu Ser Gly Gly Gly Val Val Gln Pro Gly Lys Ser Leu Arg
1               5                   10                  15

Leu Ser Cys Val Ala Ser Gly Phe Ser Phe Ser Thr Tyr Gly Met His
                20                  25                  30

Trp Val Arg Gln Ala Pro Gly Lys Gly Leu Glu Trp Val Ala Val Met
            35                  40                  45

Ser Phe Asp Gly Lys Thr Lys Tyr Tyr Ala Asp Ser Val Lys Gly Arg
        50                  55                  60

Phe Thr Ile Ser Arg Asp Asn Pro Lys Asn Thr Leu Tyr Leu Gln Met
65                  70                  75                  80

Asn Ser Leu Arg Ser Glu Asp Thr Ala Val Tyr Tyr Cys Ala Lys Gly
                85                  90                  95
```

Gly Ala Ala Ala Ala Val Phe Asp Ser Trp Gly Pro Gly Ile Leu Leu
            100                 105                 110

Thr Val Ser Ser
        115

<210> SEQ ID NO 76
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Leu Val Glu Ser Gly Gly Gly Val Val Gln Pro Gly Arg Ser Leu Arg
1               5                   10                  15

Leu Ser Cys Ala Ala Ser Gly Val Thr Phe Ser Arg Tyr Gly Met His
            20                  25                  30

Trp Val Arg Gln Ala Pro Gly Lys Gly Leu Glu Trp Val Ala Val Ile
        35                  40                  45

Ser Tyr Asp Glu Lys Thr Lys Tyr Tyr Ala Asp Ser Val Lys Gly Arg
    50                  55                  60

Phe Thr Ile Ser Arg Asp Asn Ser Lys Asn Thr Leu Phe Leu His Met
65                  70                  75                  80

Asn Arg Leu Arg Tyr Glu Asp Thr Ala Val Tyr Tyr Cys Ala Lys Gly
                85                  90                  95

Ala Ser Ser Gly Ala Tyr Phe Asp Tyr Trp Gly Gln Gly Thr Leu Val
            100                 105                 110

Thr Val Ser Ser
        115

<210> SEQ ID NO 77
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Leu Val Glu Ser Gly Gly Gly Val Val Gln Pro Gly Lys Ser Leu Arg
1               5                   10                  15

Leu Ser Cys Val Ala Ser Gly Phe Thr Phe Ser Thr Tyr Gly Met His
            20                  25                  30

Trp Val Arg Gln Ala Pro Gly Lys Gly Leu Glu Trp Val Ala Val Met
        35                  40                  45

Ser Phe Asp Gly Lys Thr Lys Tyr Tyr Ala Asp Ser Val Lys Gly Arg
    50                  55                  60

Phe Thr Ile Ser Arg Asp Asn Pro Lys Asn Thr Leu Tyr Leu Gln Met
65                  70                  75                  80

Asn Ser Leu Arg Ser Glu Asp Thr Ala Val Tyr Tyr Cys Ala Lys Gly
                85                  90                  95

Gly Ala Ala Ala Ala Val Phe Asp Ser Trp Gly Gln Gly Ile Leu Leu
            100                 105                 110

Thr Val Ser Ser
        115

<210> SEQ ID NO 78
<211> LENGTH: 116

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Leu Val Glu Ser Gly Gly Gly Val Val Gln Pro Gly Lys Ser Leu Arg
1               5                   10                  15

Leu Ser Cys Val Ala Ser Gly Phe Thr Phe Ser Ser Tyr Gly Met His
            20                  25                  30

Trp Val Arg Gln Ala Pro Gly Lys Gly Leu Glu Trp Val Ala Val Met
        35                  40                  45

Ser Phe Asp Gly Lys Thr Lys Tyr Tyr Ala Asp Ser Val Lys Gly Arg
    50                  55                  60

Phe Thr Ile Ser Arg Asp Asn Pro Lys Asn Thr Leu Tyr Leu Gln Met
65                  70                  75                  80

Asn Ser Leu Arg Ser Glu Asp Thr Ala Val Tyr Tyr Cys Ala Lys Gly
                85                  90                  95

Gly Ala Ala Ala Val Phe Asp Ser Trp Gly Gln Gly Ile Leu Leu
            100                 105                 110

Thr Val Ser Ser
        115

<210> SEQ ID NO 79
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Leu Val Glu Ser Gly Gly Gly Val Val Gln Pro Gly Arg Ser Leu Arg
1               5                   10                  15

Leu Ser Cys Ala Ala Ser Gly Phe Thr Phe Ser Arg Tyr Gly Met His
            20                  25                  30

Trp Val Arg Gln Ala Pro Gly Lys Gly Leu Glu Trp Val Ala Val Met
        35                  40                  45

Ser Tyr Asp Gly Ser Thr Lys Tyr Tyr Ala Asp Ser Val Lys Gly Arg
    50                  55                  60

Phe Ala Ile Ser Arg Asp Asn Pro Lys Asn Thr Leu Phe Leu Gln Met
65                  70                  75                  80

Asn Ser Leu Arg Pro Asp Asp Thr Ala Val Tyr Tyr Cys Ala Lys Gly
                85                  90                  95

Gly Ala Ala Ala Val Met Asp Val Trp Gly Lys Gly Thr Thr Val
            100                 105                 110

Thr Val Ser Ser
        115

<210> SEQ ID NO 80
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Val Gln Leu Val Glu Ser Gly Gly Gly Val Val Gln Pro Gly Arg
```

```
 1               5                   10                  15
Ser Leu Arg Leu Ser Cys Ala Ala Ser Gly Phe Thr Phe Asn Arg Phe
            20                  25                  30

Gly Met His Trp Val Arg Gln Arg Gln Val Pro Gly Lys Gly Leu Glu
            35                  40                  45

Trp Val Ala Val Ile Ser Tyr Asp Asp Asn Thr Lys Tyr Tyr Ala Asp
    50                  55                  60

Ser Val Lys Gly Arg Phe Thr Ile Ser Arg Asp Asn Asn Lys Ser Thr
65                  70                  75                  80

Leu Tyr Leu Gln Met Ser Ser Leu Arg Val Glu Asp Thr Ala Val Tyr
                85                  90                  95

Phe Cys Ala Lys Gly Ser Thr Ala Ala Ala Val Leu Asp Tyr Trp Gly
            100                 105                 110

Gln Gly Thr Leu Val Thr Val Ser Ser
            115                 120
```

<210> SEQ ID NO 81
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

```
Leu Val Glu Ser Gly Gly Gly Leu Val Gln Pro Gly Gly Ser Leu Arg
1               5                   10                  15

Leu Ser Cys Ala Ala Ser Gly Phe Thr Phe Ser Ser Tyr Glu Met Asn
            20                  25                  30

Trp Val Arg Gln Ala Pro Gly Lys Gly Leu Glu Trp Val Ser Tyr Ile
            35                  40                  45

Ser Ser Ser Gly Ser Thr Ile Tyr Tyr Ala Asp Ser Val Lys Gly Arg
    50                  55                  60

Phe Thr Ile Ser Arg Asp Asn Ala Lys Asn Ser Leu Tyr Leu Gln Met
65                  70                  75                  80

Asn Ser Leu Arg Ala Glu Asp Thr Ala Val Tyr Tyr Cys Ala Arg Val
                85                  90                  95

Glu Gln Leu Ala Pro Ser Pro Tyr Met Asp Val Trp Gly Lys Gly Thr
            100                 105                 110

Thr Val Thr Val Ser Ser
            115
```

<210> SEQ ID NO 82
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
```

```
              50                  55                  60
Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Arg Gly Leu Arg Gly Ala Tyr Tyr Tyr Tyr Gly Met Asp
            100                 105                 110

Val Trp Gly Gln Gly Thr Thr Val Thr Val Ser Ser
            115                 120

<210> SEQ ID NO 83
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Met Thr Gln Ser Pro Asp Ser Leu Thr Leu Ser Leu Gly Glu Arg Ala
 1               5                  10                  15

Thr Ile Asn Cys Arg Ser Ser Arg Thr Val Leu Tyr Arg Ser Asn Asn
             20                  25                  30

Lys Asn Tyr Leu Ala Trp Tyr Gln His Lys Pro Gly Gln Pro Pro Lys
         35                  40                  45

Leu Leu Met Ser Trp Ala Ser Thr Arg Glu Thr Gly Val Pro Asp Arg
     50                  55                  60

Phe Ser Gly Ser Gly Ser Gly Thr His Phe Thr Leu Thr Ile Thr Ser
 65                  70                  75                  80

Leu Gln Pro Glu Asp Val Ala Val Tyr Tyr Cys Gln Gln Tyr Tyr Ser
                 85                  90                  95

Pro Pro Trp Thr Phe Gly Gln Gly Thr Lys Val Glu Ile Arg
            100                 105                 110

<210> SEQ ID NO 84
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Met Thr Gln Ser Pro Gly Ser Leu Ala Val Ser Leu Gly Ser Arg Ala
 1               5                  10                  15

Thr Ile Asn Cys Lys Ser Ser Arg Ser Leu Leu Tyr Arg Ser Asn Asn
             20                  25                  30

Lys Asn Tyr Leu Ala Trp Tyr Gln Gln Lys Pro Gly Gln Ser Pro Arg
         35                  40                  45

Leu Leu Ile Tyr Trp Ala Ser Ser Arg Glu Ser Gly Val Pro Asp Arg
     50                  55                  60

Phe Ser Gly Gly Gly Ser Gly Thr Ser Phe Thr Leu Thr Ile Ser Ser
 65                  70                  75                  80

Leu Gln Ala Glu Asp Val Ala Val Tyr Tyr Cys Gln Gln Tyr Phe Asn
                 85                  90                  95

Pro Pro Trp Thr Phe Gly Gln Gly Thr Lys Val Glu Ile Lys
            100                 105                 110
```

```
<210> SEQ ID NO 85
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Met Thr Gln Ser Pro Asn Ser Leu Ala Val Ser Leu Gly Gly Arg Ala
1               5                   10                  15

Thr Ile Asn Cys Lys Ala Ser Gln Ser Ile Leu Tyr Arg Ser Asn Asn
            20                  25                  30

Lys Asn Tyr Leu Ala Trp Tyr Gln His Lys Ala Gly Gln Pro Pro Lys
        35                  40                  45

Leu Leu Ile Tyr Trp Ala Ser Thr Arg Glu Ser Gly Val Pro Glu Arg
    50                  55                  60

Phe Ser Gly Ser Gly Ser Arg Thr Asp Phe Thr Leu Thr Ile Asn Gly
65                  70                  75                  80

Leu Gln Ala Glu Asp Val Ala Val Tyr Tyr Cys Gln Gln Tyr Tyr Asn
                85                  90                  95

Pro Pro Trp Thr Phe Gly Gln Gly Thr Lys Val Glu Ile Lys
            100                 105                 110

<210> SEQ ID NO 86
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Met Thr Gln Ser Pro Asp Ser Leu Ala Val Ser Leu Gly Glu Arg Ala
1               5                   10                  15

Thr Ile Lys Cys Lys Ser Ser Gln Ser Val Leu Tyr Ser Ser Asn Asn
            20                  25                  30

Lys Asn Tyr Leu Ala Trp Tyr Gln His Lys Pro Gly Gln Pro Pro Lys
        35                  40                  45

Val Leu Val Tyr Trp Ala Ser Thr Arg Glu Ser Gly Val Pro Asp Arg
    50                  55                  60

Phe Ser Gly Ser Gly Ser Gly Thr Asp Phe Thr Leu Thr Ile Ser Ser
65                  70                  75                  80

Leu Gln Ala Glu Asp Val Ala Val Tyr Tyr Cys Gln Gln Tyr Tyr Asn
                85                  90                  95

Pro Pro Trp Thr Phe Gly Gln Gly Thr Lys Val Ala Ile Lys
            100                 105                 110

<210> SEQ ID NO 87
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Met Thr Gln Ser Pro Asn Ser Leu Ala Val Ser Leu Gly Gly Arg Ala
1               5                   10                  15

Thr Ile Asn Cys Lys Thr Ser Gln Ser Ile Leu Tyr Arg Ser Asn Asn
            20                  25                  30
```

```
Lys Asn Tyr Leu Ala Trp Tyr Gln His Lys Pro Gly Gln Pro Pro Lys
            35                  40                  45

Leu Leu Ile Tyr Trp Ala Ser Thr Arg Glu Ser Arg Val Pro Asp Arg
50                  55                  60

Phe Ser Gly Ser Gly Ser Arg Thr Asp Phe Thr Leu Thr Ile Ser Gly
65                  70                  75                  80

Leu Gln Ala Glu Asp Val Ala Val Tyr Tyr Cys Gln Gln Tyr Tyr Asn
                85                  90                  95

Pro Pro Trp Thr Phe Gly Gln Gly Thr Lys Val Glu Ile Lys
            100                 105                 110

<210> SEQ ID NO 88
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Thr Gln Ser Pro Asn Ser Leu Ala Val Ser Leu Gly Gly Arg Ala
1               5                   10                  15

Thr Ile Asn Cys Lys Thr Ser Gln Ser Ile Leu Tyr Arg Ser Asn Asn
            20                  25                  30

Lys Asn Tyr Leu Ala Trp Tyr Gln His Lys Ser Gly Gln Pro Pro Lys
            35                  40                  45

Leu Leu Ile Tyr Trp Ala Ser Thr Arg Glu Ser Gly Val Pro Asp Arg
50                  55                  60

Phe Ser Gly Ser Gly Ser Arg Thr Asp Phe Thr Leu Thr Ile Ser Gly
65                  70                  75                  80

Leu Gln Ala Glu Asp Val Ala Val Tyr Tyr Cys Gln Gln Tyr Tyr Asn
                85                  90                  95

Pro Pro Trp Thr Phe Gly Gln Gly Thr Lys Val Glu Ile Lys
            100                 105                 110

<210> SEQ ID NO 89
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Met Thr Gln Ser Pro Asp Ser Leu Thr Val Ser Leu Gly Glu Arg Ala
1               5                   10                  15

Thr Ile Ser Cys Lys Ser Ser Gln Arg Leu Leu Tyr Ser Ser Asn Asn
            20                  25                  30

Lys Asn Tyr Leu Ala Trp Tyr Gln Gln Lys Pro Gly Gln Pro Pro Lys
            35                  40                  45

Leu Leu Met Tyr Trp Ala Ser Thr Arg Glu Ser Gly Val Pro Asp Arg
50                  55                  60

Phe Ser Gly Ser Gly Ser Gly Thr Asp Phe Ser Leu Thr Ile Ser Ser
65                  70                  75                  80

Leu Gln Ala Glu Asp Val Ala Val Tyr Tyr Cys Gln Gln Tyr Tyr Asn
                85                  90                  95

Pro Pro Trp Thr Phe Gly Gln Gly Thr Lys Val Glu Val Lys
            100                 105                 110
```

<210> SEQ ID NO 90
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Asp Ile Val Met Thr Gln Ser Pro Asp Ser Leu Thr Leu Ser Leu Gly
1               5                   10                  15

Glu Arg Ala Thr Ile Asn Cys Lys Ser Ser Gln Ser Leu Phe Tyr Arg
            20                  25                  30

Ser Asn Asn Lys Ser Tyr Leu Ala Trp Tyr Gln Gln Lys Pro Gly Gln
        35                  40                  45

Pro Pro Lys Leu Leu Ile Tyr Trp Ala Ser Val Arg Glu Ser Gly Val
    50                  55                  60

Pro Asp Arg Phe Thr Gly Ser Gly Ser Val Thr Asp Phe Thr Leu Thr
65                  70                  75                  80

Ile Ser Ser Leu Arg Ala Glu Asp Val Ala Val Tyr Tyr Cys Gln Gln
                85                  90                  95

Tyr Phe Thr Thr Pro Leu Thr Phe Gly Gly Gly Thr Lys Val Ala Ile
            100                 105                 110

Lys

<210> SEQ ID NO 91
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Met Thr Gln Ser Leu Asp Ser Leu Thr Val Ser Leu Gly Glu Arg Ala
1               5                   10                  15

Thr Ile Asn Cys Lys Ser Ser Gln Ser Leu Leu Tyr Thr Ser Asn Asn
            20                  25                  30

Lys Asn Tyr Leu Ala Trp Tyr Gln Gln Lys Ser Gly Gln Pro Pro Lys
        35                  40                  45

Leu Leu Ile Tyr Trp Ala Ser Ile Arg Asp Ser Gly Val Pro Asp Arg
    50                  55                  60

Phe Ser Gly Ser Gly Ser Ala Thr Asp Phe Thr Leu Thr Ile Asn Asn
65                  70                  75                  80

Leu Gln Ala Glu Asp Val Ala Val Tyr Phe Cys Gln Gln Tyr Tyr Lys
                85                  90                  95

Thr Pro Leu Thr Phe Gly Gly Gly Thr Lys Val Glu Val Arg
            100                 105                 110

<210> SEQ ID NO 92
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any amino acid

<400> SEQUENCE: 92

Asp Ile Gln Xaa Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Trp
                85                  90                  95

Thr Phe Gly Gln Gly Thr Lys Val Glu Ile Lys
            100                 105

<210> SEQ ID NO 93
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
gaggtgcagc tggtggagtc tgggggaggc gtggtccagc ctgggaggtc cctgagactc      60
tcctgcgcag cctctggact caccttcagt ttctataatt ccactgggt ccgccagact      120 ccaggcaagg gctggagtg gtggcaggc atctcatacg atgcaaccag gacgaactac       180
gcaggctccg tgacgggccg attcaccatt tccagagaca attccaagaa aatgctgtat     240
ctgcaaatga gcagcctggg acctcaagac acggctgtat atcattgtgc gagagatcgt    300
tctgacgggc aactgcataa agtggctttt gactcctggg gccagggagc cctggtcacc    360
gtctcatca                                                              369

<210> SEQ ID NO 94
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
gaggtgcagc tggtggagtc tgggggaggc gtggtccggc ctgggcggtc cctgagactc      60
tcctgtgttg cctctggttt caccttcaat gcttatggca tgcattgggt ccgccagggt    120
ccaggcaagg gccttgagtg gctggcggtc atttcatatg aaggaaagac tgttttattat    180 gcagattccg ttaaggaccg tttcaccatc tccagagaca attccaggaa cacggtgtct    240
ctacatctga caacctgag aggtgaggac acggctgtct attactgtgc gaaggggtcg    300
gcttcagcag cagtcctcca acactgggt cagggcaccc tggtcagcgt cacgtca       357

<210> SEQ ID NO 95
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 95

```
gaggtgcagc tggtggagtc tggggggaggc gtggtcccgc ctgggaagtc cctgagactc    60
tcctgtgcag cctctggatt caccttcagt ctctatggca tacactgggt ccgccaggct   120
cccggcaagg gactggagtg ggtggcagtt atctcatatg atggaaatac taaatactat   180
acagactctg taaagggtcg attcaccatc tccagagaca atgccaagaa cacaatttat   240
ctgcaaatga acagtctaag acttgacgac acggctgttt attactgtgc gaaaggagcg   300
gcgaatagcg ctacttttga tttctggggc cgagggacaa tggtcaccgt ctcttca      357
```

<210> SEQ ID NO 96
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96

```
gaggtgcagc tggtggagtc tggggggaggc gtggtccagc ctggaaagtc tctgagactc    60
tcctgtgtag cctctggatt cagcttcagt acttatggca tgcactgggt ccgccaggct   120
ccaggcaagg ggctggagtg ggtggcggtt atgtcatttg atggaaagac taaatactat   180
gcagactccg tgaagggccg attcaccatc tccagagaca atcccaagaa cacactatat   240
ctgcaaatga acagcctgag aagcgaagac acggctgtgt attattgtgc gaaggggggt   300
gcagcagcgg ccgtctcttga ctcctggggc ccgggaatac tgctcaccgt ctcctca     357
```

<210> SEQ ID NO 97
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97

```
gaggtgcagc tggtggagtc tggggggaggc gtggtccagc ctgggaggtc cctaagactc    60
tcctgtgcag cctctggagt caccttcagt agatatggca tgcactgggt ccgccaggct   120
ccaggcaagg ggctggagtg ggtggcagtt atatcatatg atgaaaagac taaatactat   180
gcagactccg tgaagggccg attcaccatc tccagagaca attccaagaa cacactgttt   240
ctgcacatga acagactgag atatgaggac acggctgtat attattgtgc gaaaggggcc   300
agtagcggtg cgtactttga ctactggggc caggtaccc tggtcaccgt ctcctca      357
```

<210> SEQ ID NO 98
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98

```
gaggtgcagc tggtggagtc tggggggaggc gtggtccagc ctggaaagtc tctgagactc    60
tcctgtgtag cctctggatt caccttcagt acttatggca tgcactgggt ccgccaggct   120
ccaggcaagg ggctggagtg ggtggcagtt atgtcatttg atggaaagac taaatactat   180
```
gcagactccg tgaagggccg attcaccatc tccagagaca atcccaagaa cacactatat    240
ctgcaaatga acagcctgag aagcgaagac acggctgtgt attattgtgc gaagggggt     300 gcagcagcgg ccgtctttga ctcctggggc cagggaatac tgctcaccgt ctcctca       357

<210> SEQ ID NO 99
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99
gaggtgcagc tggtggagtc tgggggaggc gtggtccagc ctggaaagtc tctgagactc    60
tcctgtgtag cctctggatt caccttcagt agttatggca tgcactgggt ccgccaggct    120
ccgggcaagg ggctggagtg ggtggcggtt atgtcatttg atggaaagac taaatactat    180
gcagactccg tgaagggccg attcaccatc tccagagaca accccaagaa cacactatat    240
ctgcaaatga acagcctgag aagcgaagac acggctgtct attattgtgc gaagggggt    300 gcagcagcgg ccgtctttga ctcctggggc cagggaatac tgctcaccgt ctcctca      357

<210> SEQ ID NO 100
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
gaggtgcagc tggtggagtc tgggggaggc gtggtccagc ctgggaggtc cctgagactc    60
tcctgtgcag cctctggatt caccttcagt agatatggca tgcactgggt ccgccaggct    120
ccaggcaagg ggctggagtg ggtggcagtt atgtcatatg atggaagtac taaatactat    180
gcagactccg tgaagggccg cttcgccatc tccagagaca atcccaagaa cacgctattt    240
ctgcaaatga acagcctgag acctgacgac acggctgtat attactgtgc gaaggggg     300 gcggcagcag ctgtcatgga cgtctggggc aaagggacca cggtcaccgt ctcctca      357

<210> SEQ ID NO 101
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
gaggtgcagc tggtggagtc tgggggaggc gtggtccagc ctgggaggtc cctgagactc    60
tcctgtgcag cctctggatt caccttcaat aggtttggca tgcactgggt ccgccagcgc    120
caggttccag gcaaggggct ggagtgggtg gcagttatct catatgacga aacactaaa    180 tattatgcgg actccgtgaa gggccgtttc accatctcca gagacaataa caagagcact    240
ctctatctgc aaatgagcag cctgagagtt gaggacacgc tgtctatttt ctgtgcgaag    300
gggtcgacag cggcagctgt tcttgactac tggggccagg gaacccttgt caccgtctcc    360
tca                                                                  363

<210> SEQ ID NO 102

```
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
gaggtgcagc tggtggagtc tgggggaggc ttggtacagc ctggagggtc cctgagactc      60
tcctgtgcag cctctggatt caccttcagt agttatgaaa tgaactgggt ccgccaggct     120
ccagggaagg ggctggagtg ggtttcatac attagtagta gtggtagtac catatactac     180
gcagactctg tgaagggccg attcaccatc tccagagaca acgccaagaa ctcactgtat     240
ctgcaaatga acagcctgag agccgaggac acggctgttt attactgtgc gagagtagag     300
cagctcgccc cctcccccta catggacgtc tggggcaaag ggaccacggt caccgtctcc     360
tca                                                                    363

<210> SEQ ID NO 103
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
caggtgcagc tggtgcagtc tggggcagag gtgaaaaagc ccggggagtc tctgaagatc      60
tcctgtaagg gttctggata cagctttacc agctactgga tcggctgggt gcgccagatg     120
cccgggaaag gcctggagtg gatggggatc atctatcctg gtgactctga taccagatac     180
agcccgtcct tccaaggcca ggtcaccatc tcagccgaca gtccatcagc accgcctac     240 ctgcagtgga gcagcctgaa ggcctcggac accgccatgt attactgtgc gagacggggt     300
cttcgagggg cctactacta ctactacggt atggacgtct ggggccaagg gaccacggtc     360
accgtctcct ca                                                          372

<210> SEQ ID NO 104
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104
gacatcgtga tgacccagtc tccagactcc ctgactctgt ctctgggcga gagggccacc      60
atcaactgca gatccagccg gactgtttta tacaggtcca acaataaaaa ttacttagct     120
tggtatcaac ataaaccagg acagcctcct aagttgctca tgtcctgggc atctacccgg     180
gaaaccgggg tccctgaccg attcagtggc agcggttctg ggacagattt cactctcacc     240
atcaccagcc tgcagcctga agatgtggca gtttattact gtcaacagta ttatagtcct     300
ccgtggacgt tcggccaagg gaccaaggtg gaaatcaga                             339

<210> SEQ ID NO 105
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 105

```
gacatcgtga tgacccagtc tccaggctcc ctggctgtgt ctctgggctc gagggccacc      60
atcaactgca agtccagccg gagtctttta tacaggtcca acaataagaa ttatttagct     120
tggtatcaac agaaaccagg acagtctcct cggcttctca tttattgggc atcttcccgg     180
gaatccgggg tccctgaccg attcagtggc ggcgggtctg ggacaagttt cactctcacc     240
atcagcagcc tgcaggctga agatgtggca gtttattact gtcagcaata ttttaatcct     300
ccgtggacgt tcggccaagg gaccaaggtg gagatcaaa                            339
```

<210> SEQ ID NO 106
<211> LENGTH: 339
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 106

```
gacatcgtga tgacccagtc tccaaactcc ctggctgtgt ctctgggcgg gagggccacc      60
atcaactgca aggccagcca gagtatttta tacaggtcca acaataagaa ctatttagct     120
tggtaccaac ataaagcagg acagcctccc aagctgctca tttactgggc atctacccgg     180
gaatccgggg tccctgagcg attcagtggc agcgggtcta ggacagattt cactctcacc     240
atcaacggcc tgcaggctga agatgtggca gtttattact gtcagcaata ttataatcct     300
ccgtggacgt tcggccaagg gaccaaggtg gaaatcaaa                            339
```

<210> SEQ ID NO 107
<211> LENGTH: 339
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 107

```
gacatcgtga tgacccagtc tccagactcc ctggctgtgt ctctgggcga gagggccacc      60
atcaagtgca agtccagcca gagtgtcttg tacagctcca acaataagaa ctacttagct     120
tggtaccagc ataaaccagg acagcctcct aaggtactcg tttactgggc atccacccgg     180
gaatccgggg tccctgaccg attcagtggc agcgggtctg ggacagattt cactctcacc     240
atcagcagcc tgcaggctga agatgtggca gtttattact gtcaacaata ttataatcct     300
ccgtggacgt tcggccaagg gaccaaggta gcaatcaag                            339
```

<210> SEQ ID NO 108
<211> LENGTH: 339
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 108

```
gacatcgtga tgacccagtc tccaaactcc ctggctgtgt ctctgggcgg gagggccacc      60
atcaactgca agaccagcca gagtatttta tacaggtcca acaataagaa ctacttagct     120
tggtaccagc ataaaccagg acagcctccc aagctgctca tttactgggc atctacccgg     180
gaatccaggg tccctgaccg attcagtggc agcgggtcta ggacagattt cactctcacc     240
```

```
atcagcggcc tgcaggctga agatgtggca gtttattact gtcagcaata ttataatcct    300
ccgtggacgt tcggccaggg gaccaaggtg gaaatcaaa                           339
```

<210> SEQ ID NO 109
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109

```
gacatcgtga tgacccagtc tccaaactcc ctggctgtgt ctctgggcgg gagggccacc    60
atcaactgca agaccagcca gagtatttta tacaggtcca acaataagaa ctacttagct    120
tggtaccagc ataaatcagg acagcctccc aagctgctca tttactgggc atctacccgg    180
gaatccgggg tccctgaccg attcagtggc agcgggtcta ggacagattt cactctcacc    240
atcagcggcc tgcaggctga agatgtggca gtttattact gtcagcaata ttataatcct    300
ccgtggacgt tcggccaagg gaccaaggtg gaaatcaaa                           339
```

<210> SEQ ID NO 110
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110

```
gacatcgtga tgacccagtc tccggactcc ctgactgtgt ctctgggcga gagggccacc    60
atcagctgca agtccagcca gcgtcttttg tatagttcca acaataagaa ctacttagct    120
tggtaccagc agaaacctgg acagcctcct aaactgctca tgtactgggc gtccacccgg    180
gaatccgggg tccctgaccg attcagtggc agcgggtctg ggacagattt ctctctcacc    240
atcagcagcc tgcaggctga agatgtggca gtttattact gtcagcaata ttataatcct    300
ccctggacgt tcggccaagg gaccaaggtg gaagtcaaa                           339
```

<210> SEQ ID NO 111
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111

```
gacatcgtga tgacccagtc tccagattcc ctgactctgt ctctgggcga gagggccacc    60
atcaactgca agtccagcca gagtctgttt tacaggtcca acaataagag ctacttagct    120
tggtatcagc aaaaaccagg gcagcctcct aaactgctca tttactgggc ctctgtccgg    180
gaatccgggg tccctgaccg attcactggc agcgggtctg taacagattt cactctcacc    240
atcagcagcc tgcgggctga ggatgtggct gtttattatt gtcaacagta ttttactact    300
cctctcactt tcggcggggg gaccaaggtg gcgatcaaa                           339
```

<210> SEQ ID NO 112
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112
gacatcgtga tgacccagtc tctagactcc ctgactgtgt ctctgggcga gagggccacc    60
atcaactgca agtccagcca gagtctttta tacacctcca acaataagaa ttacttagct   120
tggtaccagc agaaatcagg acagcctcct aagttactca tttactgggc gtctattcgg   180
gattccgggg tccctgaccg attcagtggc agcgggtctg cgacagattt cactctcacc   240
atcaacaacc tgcaggctga agatgtggca gtttacttct gtcagcaata ttacaagact   300
cctctcactt tcggcggggg gaccaaggtg gaggtcaga                          339

<210> SEQ ID NO 113
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113
gacatccagw tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataatagtt attcttggac gttcggccaa   300
gggaccaagg tggaaatcaa a                                             321

<210> SEQ ID NO 114
<211> LENGTH: 15
<212> TYPE: PRT
<213> ORGANISM: Homo sapiens

<400> SEQUENCE: 114

Gly Pro Pro Pro Pro Ile Asp Asn Gly Asp Ile Thr Ser Phe Pro
1               5                   10                  15

<210> SEQ ID NO 115
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (19)..(19)
<223> OTHER INFORMATION: C-term Biotin

<400> SEQUENCE: 115

Gly Pro Pro Pro Pro Ile Asp Asn Gly Asp Ile Thr Ser Phe Pro Gly
1               5                   10                  15

Gly Gly Lys

<210> SEQ ID NO 116
<211> LENGTH: 6
<212> TYPE: PRT
<213> ORGANISM: Artificial Sequence
<220> FEATURE:
<223> OTHER INFORMATION: Description of Artificial Sequence: Synthetic

```
      6xHis tag

<400> SEQUENCE: 116

His His His His His His
1               5

<210> SEQ ID NO 117
<211> LENGTH: 5
<212> TYPE: PRT
<213> ORGANISM: Artificial Sequence
<220> FEATURE:
<223> OTHER INFORMATION: Description of Unknown: Enterokinase cleavage
      site sequence

<400> SEQUENCE: 117

Asp Asp Asp Asp Lys
1               5

<210> SEQ ID NO 118
<211> LENGTH: 6
<212> TYPE: PRT
<213> ORGANISM: Artificial Sequence
<220> FEATURE:
<223> OTHER INFORMATION: Description of Unknown: Enterokinase cleavage
      site sequence

<400> SEQUENCE: 118

Ala Asp Asp Asp Asp Lys
1               5

<210> SEQ ID NO 119

<400> SEQUENCE: 119

000

<210> SEQ ID NO 120
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (12)..(12)
<223> OTHER INFORMATION: C-term Biotin

<400> SEQUENCE: 120

Pro Ile Asp Asn Gly Asp Ile Thr Gly Gly Gly Lys
1               5                   10

<210> SEQ ID NO 121
<211> LENGTH: 15
<212> TYPE: PRT
<213> ORGANISM: Homo sapiens

<400> SEQUENCE: 121

Glu Phe Gly Lys Cys Gly Pro Pro Pro Ile Asp Asn Gly Asp
1               5                   10                  15

<210> SEQ ID NO 122
<211> LENGTH: 15
<212> TYPE: PRT
<213> ORGANISM: Homo sapiens

<400> SEQUENCE: 122
```

Phe Gly Lys Cys Gly Pro Pro Pro Ile Asp Asn Gly Asp Ile
1               5                   10                  15

<210> SEQ ID NO 123
<211> LENGTH: 15
<212> TYPE: PRT
<213> ORGANISM: Homo sapiens

<400> SEQUENCE: 123

Gly Lys Cys Gly Pro Pro Pro Ile Asp Asn Gly Asp Ile Thr
1               5                   10                  15

<210> SEQ ID NO 124
<211> LENGTH: 15
<212> TYPE: PRT
<213> ORGANISM: Homo sapiens

<400> SEQUENCE: 124

Lys Cys Gly Pro Pro Pro Ile Asp Asn Gly Asp Ile Thr Ser
1               5                   10                  15

<210> SEQ ID NO 125
<211> LENGTH: 15
<212> TYPE: PRT
<213> ORGANISM: Homo sapiens

<400> SEQUENCE: 125

Cys Gly Pro Pro Pro Ile Asp Asn Gly Asp Ile Thr Ser Phe
1               5                   10                  15

<210> SEQ ID NO 126
<211> LENGTH: 15
<212> TYPE: PRT
<213> ORGANISM: Homo sapiens

<400> SEQUENCE: 126

Gly Pro Pro Pro Ile Asp Asn Gly Asp Ile Thr Ser Phe Pro
1               5                   10                  15

<210> SEQ ID NO 127
<211> LENGTH: 15
<212> TYPE: PRT
<213> ORGANISM: Homo sapiens

<400> SEQUENCE: 127

Pro Pro Pro Ile Asp Asn Gly Asp Ile Thr Ser Phe Pro Leu
1               5                   10                  15

<210> SEQ ID NO 128
<211> LENGTH: 15
<212> TYPE: PRT
<213> ORGANISM: Homo sapiens

<400> SEQUENCE: 128

Pro Pro Ile Asp Asn Gly Asp Ile Thr Ser Phe Pro Leu Ser
1               5                   10                  15

<210> SEQ ID NO 129
<211> LENGTH: 15
<212> TYPE: PRT
<213> ORGANISM: Homo sapiens

<400> SEQUENCE: 129

Pro Ile Asp Asn Gly Asp Ile Thr Ser Phe Pro Leu Ser Val
1               5                   10                  15

```
<210> SEQ ID NO 130
<211> LENGTH: 15
<212> TYPE: PRT
<213> ORGANISM: Homo sapiens

<400> SEQUENCE: 130

Pro Ile Asp Asn Gly Asp Ile Thr Ser Phe Pro Leu Ser Val Tyr
1               5                   10                  15

<210> SEQ ID NO 131
<211> LENGTH: 15
<212> TYPE: PRT
<213> ORGANISM: Homo sapiens

<400> SEQUENCE: 131

Ile Asp Asn Gly Asp Ile Thr Ser Phe Pro Leu Ser Val Tyr Ala
1               5                   10                  15

<210> SEQ ID NO 132
<211> LENGTH: 15
<212> TYPE: PRT
<213> ORGANISM: Homo sapiens

<400> SEQUENCE: 132

Asp Asn Gly Asp Ile Thr Ser Phe Pro Leu Ser Val Tyr Ala Pro
1               5                   10                  15
```